(12) United States Patent
Carlson

(10) Patent No.: US 7,960,311 B2
(45) Date of Patent: *Jun. 14, 2011

(54) METHODS EMPLOYING COMBINATORIAL ARTIFICIAL RECEPTORS

(75) Inventor: Robert E. Carlson, Minnetonka, MN (US)

(73) Assignee: Receptors LLC, Chaska, MN (US)

( * ) Notice: Subject to any disclaimer, the term of this patent is extended or adjusted under 35 U.S.C. 154(b) by 1529 days.

This patent is subject to a terminal disclaimer.

(21) Appl. No.: 10/934,977

(22) Filed: Sep. 3, 2004

(65) Prior Publication Data

US 2005/0118617 A1    Jun. 2, 2005

Related U.S. Application Data

(63) Continuation-in-part of application No. 10/813,612, filed on Mar. 29, 2004, now abandoned, and a continuation-in-part of application No. 10/813,568, filed on Mar. 29, 2004, and a continuation-in-part of application No. 10/812,850, filed on Mar. 29, 2004, now abandoned, and a continuation-in-part of application No. 10/244,727, filed on Sep. 16, 2002, now Pat. No. 7,504,364.

(60) Provisional application No. 60/527,190, filed on Dec. 2, 2003, provisional application No. 60/526,708, filed on Dec. 2, 2003, provisional application No. 60/526,703, filed on Dec. 2, 2003, provisional application No. 60/526,699, filed on Dec. 2, 2003, provisional application No. 60/526,511, filed on Dec. 2, 2003, provisional application No. 60/499,975, filed on Sep. 3, 2003, provisional application No. 60/499,965, filed on Sep. 3, 2003, provisional application No. 60/499,867, filed on Sep. 3, 2003, provisional application No. 60/499,776, filed on Sep. 3, 2003, provisional application No. 60/500,081, filed on Sep. 3, 2003, provisional application No. 60/499,752, filed on Sep. 3, 2003.

(30) Foreign Application Priority Data

Feb. 19, 2003  (WO) .............................. WO 03/05328
Mar. 29, 2004  (WO) .............................. WO 04/09649

(51) Int. Cl.
C40B 40/00    (2006.01)

(52) U.S. Cl. .................................. 506/13; 506/7; 506/23

(58) Field of Classification Search ........................ None
See application file for complete search history.

(56) References Cited

U.S. PATENT DOCUMENTS

| | | |
|---|---|---|
| 4,344,438 A | 8/1982 | Schultz |
| 5,159,656 A | 10/1992 | Goldstein |
| 5,178,673 A | 1/1993 | Caster et al. |
| 5,225,374 A | 7/1993 | Fare et al. |
| 5,281,539 A | 1/1994 | Schramm |
| 5,324,633 A | 6/1994 | Fodor et al. |
| 5,340,474 A | 8/1994 | Kauvar |
| 5,453,533 A | 9/1995 | Luo et al. |
| 5,475,100 A | 12/1995 | Hashino et al. |
| 5,508,164 A | 4/1996 | Kausch et al. |
| 5,512,435 A | 4/1996 | Renschler et al. |
| 5,632,957 A | 5/1997 | Heller et al. |
| 5,677,196 A | 10/1997 | Herron et al. |
| 5,677,441 A | 10/1997 | Waldman et al. |
| 5,690,894 A | 11/1997 | Pinkel et al. |
| 5,770,380 A | 6/1998 | Hamilton et al. |
| 5,804,563 A | 9/1998 | Still et al. |
| 5,925,529 A | 7/1999 | Coughlin et al. |
| 5,942,393 A | 8/1999 | Nobori et al. |
| 5,990,163 A | 11/1999 | Evans et al. |
| 5,993,653 A * | 11/1999 | Ahmed et al. .............. 210/198.2 |
| 5,998,594 A | 12/1999 | Goodman et al. |
| 6,030,782 A | 2/2000 | Anderson et al. |
| 6,030,917 A | 2/2000 | Weinberg et al. |
| 6,061,636 A | 5/2000 | Horlbeck |
| 6,066,448 A | 5/2000 | Wohlstadter et al. |
| 6,083,758 A | 7/2000 | Imperiali et al. |
| 6,083,763 A | 7/2000 | Balch |
| 6,096,551 A | 8/2000 | Barbas et al. |
| 6,111,123 A | 8/2000 | Coucouvanis et al. |
| 6,153,743 A | 11/2000 | Hubbell et al. |
| 6,168,912 B1 | 1/2001 | Chen |
| 6,207,369 B1 | 3/2001 | Wohlstadter et al. |
| 6,225,047 B1 | 5/2001 | Hutchens et al. |
| 6,251,864 B1 | 6/2001 | Dower et al. |
| 6,261,776 B1 | 7/2001 | Pirrung et al. |
| 6,287,765 B1 | 9/2001 | Cubicciotti |

(Continued)

FOREIGN PATENT DOCUMENTS

DE    197 40 263    5/1998

(Continued)

OTHER PUBLICATIONS

International Search Report mailed May 4, 2006.

(Continued)

*Primary Examiner* — Jeffrey S. Lundgren
(74) *Attorney, Agent, or Firm* — Merchant & Gould P.C.

(57) ABSTRACT

The present invention relates to methods employing artificial receptors, such as combinatorial artificial receptor arrays. The present receptors include heterogeneous and immobilized combinations of building block molecules. In certain embodiments, combinations of 2, 3, 4, or 5 distinct building block molecules immobilized near one another on a support provide molecular structures that can be employed in the present methods. The present methods can develop artificial receptors that can then be employed to detect the receptor's ligand. The present methods can find compounds that disrupt one or more binding interactions.

53 Claims, 59 Drawing Sheets

U.S. PATENT DOCUMENTS

| | | |
|---|---|---|
| 6,297,059 B1 | 10/2001 | Song et al. |
| 6,310,191 B1 | 10/2001 | Collins et al. |
| 6,312,664 B1 | 11/2001 | Brasch et al. |
| 6,316,268 B1 | 11/2001 | Yang et al. |
| 6,316,616 B1 | 11/2001 | Jacobsen et al. |
| 6,331,441 B1 | 12/2001 | Balch et al. |
| 6,344,272 B1 | 2/2002 | Oldenburg et al. |
| 6,346,413 B1 | 2/2002 | Fodor et al. |
| 6,346,423 B1 | 2/2002 | Schembri |
| 6,361,944 B1 | 3/2002 | Mirkin et al. |
| 6,372,907 B1 | 4/2002 | Lee et al. |
| 6,410,585 B1 | 6/2002 | Larsen et al. |
| 6,419,881 B1 | 7/2002 | Weinberg et al. |
| 6,428,811 B1 | 8/2002 | West et al. |
| 6,489,093 B1 | 12/2002 | Jacobsen et al. |
| 6,528,020 B1 | 3/2003 | Dai et al. |
| 6,543,936 B2 | 4/2003 | Feldman |
| 6,562,566 B1 | 5/2003 | Hoheisel |
| 6,627,396 B1 | 9/2003 | Swanson et al. |
| 6,645,517 B2 | 11/2003 | West et al. |
| 6,649,356 B2 | 11/2003 | Bryan et al. |
| 6,652,835 B1 | 11/2003 | Lauffer et al. |
| 6,667,159 B1 | 12/2003 | Walt et al. |
| 6,673,533 B1 | 1/2004 | Wohlstadter et al. |
| 6,698,201 B1 | 3/2004 | Sarkar et al. |
| 6,699,501 B1 | 3/2004 | Neu et al. |
| 6,699,719 B2 | 3/2004 | Yamazaki et al. |
| 6,767,194 B2 | 7/2004 | Jeon et al. |
| 6,767,706 B2 | 7/2004 | Quake et al. |
| 6,844,165 B2 | 1/2005 | Hutchens et al. |
| 6,872,574 B2 | 3/2005 | Cravatt et al. |
| 6,875,620 B1 | 4/2005 | Schembri |
| 7,018,792 B2 | 3/2006 | Swanson et al. |
| 7,160,734 B2 | 1/2007 | Hutchens et al. |
| 2002/0019015 A1 | 2/2002 | Lahiri et al. |
| 2002/0090728 A1 | 7/2002 | Shair et al. |
| 2002/0187197 A1 | 12/2002 | Caruso et al. |
| 2002/0187347 A1 | 12/2002 | Halas et al. |
| 2002/0187509 A1 | 12/2002 | Shao et al. |
| 2003/0083235 A1 | 5/2003 | Danishefsky et al. |
| 2003/0104360 A1 | 6/2003 | Still et al. |
| 2003/0138853 A1 | 7/2003 | Lahiri et al. |
| 2003/0143756 A1 | 7/2003 | Fisher et al. |
| 2003/0156991 A1 | 8/2003 | Halas et al. |
| 2003/0175517 A1 | 9/2003 | Voigt et al. |
| 2003/0219384 A1 | 11/2003 | Donath et al. |
| 2003/0228605 A1 | 12/2003 | Slootstra et al. |
| 2004/0010126 A1 | 1/2004 | Lubman et al. |
| 2004/0013721 A1 | 1/2004 | Antipov et al. |
| 2004/0076681 A1 | 4/2004 | Dennis et al. |
| 2004/0077102 A1 | 4/2004 | Coute et al. |
| 2004/0102607 A1 | 5/2004 | Danishefsky et al. |
| 2004/0137526 A1 | 7/2004 | Hanash et al. |
| 2004/0151733 A1 | 8/2004 | Livingston et al. |
| 2004/0185473 A1 | 9/2004 | Cuppoletti et al. |
| 2004/0203049 A1 | 10/2004 | Schembri |
| 2004/0208884 A1 | 10/2004 | Danishefsky et al. |
| 2006/0051802 A1 | 3/2006 | Carlson |

FOREIGN PATENT DOCUMENTS

| | | |
|---|---|---|
| EP | 0482727 A2 | 4/1992 |
| EP | 1143252 A1 | 10/2001 |
| EP | 1310794 A2 | 5/2003 |
| GB | 2 319 838 A | 6/1998 |
| JP | 7-188278 | 7/1995 |
| JP | 11-509736 | 8/1999 |
| WO | WO 93/25910 | 12/1993 |
| WO | WO 95/02566 | 1/1995 |
| WO | WO 98/12156 | 3/1998 |
| WO | WO 99/25384 | 5/1999 |
| WO | WO 00/13016 | 3/2000 |
| WO | WO 00/13017 | 3/2000 |
| WO | WO 00/16733 | 3/2000 |
| WO | WO 00/66790 | 11/2000 |
| WO | WO 00/79008 A2 | 12/2000 |
| WO | WO 01/01140 A1 | 1/2001 |
| WO | WO 01/02839 A1 | 1/2001 |
| WO | WO 01/18545 A2 | 3/2001 |
| WO | WO 01/46698 A2 | 6/2001 |
| WO | WO 02/08154 | 1/2002 |
| WO | WO 02/42775 A2 | 5/2002 |
| WO | WO 03/012390 A2 | 2/2003 |
| WO | WO 03/031975 A1 | 4/2003 |
| WO | WO 03/033674 A2 | 4/2003 |
| WO | WO 03/043684 A1 | 5/2003 |
| WO | WO 03/074990 A2 | 9/2003 |
| WO | WO 2004/011476 | 2/2004 |
| WO | WO 2006/017180 | 2/2006 |
| WO | WO 2006/061207 A1 | 6/2006 |

OTHER PUBLICATIONS

Alluri, P. et al., "Isolation of Protein Ligands from Large Peptoid Libraries," *J. Am. Chem. Soc.*, vol. 125, pp. 13995-14004 (2003).

Korbel, G. et al., "Reaction Microarrays: A Method for Rapidly Determining the Enantiomeric Excess of Thousands of Samples," *J. Am. Chem. Soc.*, vol. 123, No. 2, pp. 361-362 (2001).

Olivos, H. et al., "Quantum Dots as a Visual Aid for Screening Bead-Bound Combinatorial Libraries", Center for Biomedical inventions and the Departments of Internal Medicine and Molecular Biology, University of Texas Southwestern Medical Center, Dallas, Texas, preprint received by Sep. 2005.

"Introducing Human Cancer OligoArray™", Sigma Genosys, 1 page (2002).

Various Search Reports, 109 pages (2001-2002).

Aguilar, Z. et al., "Self-Contained Microelectrochemical Immunoassay for Small Volumes Using Mouse IgG as a Model System," *Anal. Chem.*, vol. 74, No. 14, pp. 3321-3329 (Jul. 15, 2002).

Ainsworth, S., "Nanotech IP: As nanometer-scale materials start making money, intellectual property issues are heating up," *Chemical & Engineering News*, vol. 82, No. 15, pp. 17-22 (Apr. 12, 2004).

Albert, K. et al., "Cross-Reactive Chemical Sensor Arrays," *Chemical Reviews*, vol. 100, No. 7, opp. 2595-2626 (2000).

Aziz, H., "Route to Carbon Nanotube Solubilization and Applications," *Dept. of Chem., Duke University, for Chem 110*, pp. 1-15, Submitted Nov. 25, 2003.

Bakker, E., "Electrochemical Sensors," *Anal. Chem.*, vol. 76, No. 12, pp. 3285-3298 (Jun. 15, 2004).

Ball, P., "Yarn spun from nanotubes," *Nature*, http://www.nature.com/nsu/040308/040308-10.html, (Mar. 12, 2004).

Basabe-Desmonts, L. et al., "A Simple Approach to Sensor Discovery and Fabrication on Self-Assembled Monolayers on Glass," *J. Am. Chem. Soc.*, vol. 126, No. 23, pp. 7293-7299 (2004).

Buchanan, J. et al., "Practical synthesis of fully-substituted peptide thiazoles," *Tetrahedron Letters*, vol. 40, pp. 3985-3988 (1999).

Caswell, K. et al., "Preferential End-to-End Assembly of Gold Nanorods by Biotin-Streptavidin Connectors," *J. Am. Chem. Soc.*, vol. 125, No. 46, pp. 13914-13915 (2003).

Chen, J. et al., "Biased Combinatorial Libraries: Novel Ligands for the SH3 Domain of Phosphatidylinositol 3-Kinase," *J. Am. Chem. Soc.*, vol. 115, No. 26, pp. 12591-12592 (1993).

International Search Report dated Feb. 9, 2006.

International Search Report mailed Mar. 14, 2006.

Dai, Z. et al., "Reagentless Amperometric Immunosensors Based on Direct Electrochemistry of Horseradish Peroxidase for Determination of Carcinoma Antigen-125," *Anal. Chem.*, vol. 75, No. 20, pp. 5429-5434 (Oct. 15, 2003).

Developing Nano, http://www.nanosysinc.com/technology.html, pp. 1-12 (May 3, 2004).

Diamond, D., "Internet-Scale Sensing," *Analytical Chemistry*, vol. 76, No. 15, pp. 279A-286A (Aug. 1, 2004).

Ellman, J. et al., "Combinatorial thinking in chemistry and biology," *Proc. Natl. Acad. Sci. USA*, vol. 94, pp. 2779-2782 (Apr. 1997).

Feder, B., "Bashful vs. Brash in the New Field of Nanotech," *The New York Times*, 5 pages, http://www.nytimes.com/2004/03/15/technology/15nano.html?ei=1&en=873c8a6f53eb2287&ex=1080357865&adxnnl..., (Mar. 15, 2004).

Furlan, R. et al., "A New Cyclic Pseudopeptide Receptor for Li$^+$ from a Dynamic Combinatorial Library," *J. Am. Chem. Soc.*, vol. 123, No. 36, pp. 8876-8877 (2001).

Grabar, K. et al., "Two-Dimensional Arrays of Colloidal Gold Particles: A Flexible Approach to Macroscopic Metal Surfaces", Langmuir, 12:2353-2361 (1996).

Grant, S. et al., "Labeless and reversible immunosensor assay based upon an electrochemical current-transient protocol," *Analytica Chimica Acta*, vol. 495, pp. 21-32 (2003).

Grennan, K. et al., "Atrazine analysis using an amperometric immunosensor based on single-chain antibody fragments and regeneration-free multi-calibrant measurement," *Analytica Chimica Acta*, vol. 500, pp. 287-298 (2003).

Gwynne, P. et al., "Proteomics 3: Probing Proteins' Structures," *Drug Discovery and Biotechnology Trends*, pp. 689-699 (Jul. 30, 2004).

Jacoby, M., "Chiral Catalysis at Surfaces," *C & EN*, pp. 37-41 (Mar. 15, 2004).

Kimura, M. et al., "Construction of Regulated Nanospace around a Porphyrin Core," *J. Am. Chem. Soc.*, vol. 123, No. 24, pp. 5636-5642 (2001).

Kojima, K. et al., "Electrochemical Protein Chip with Arrayed Immunosensors with Antibodies Immobilized in a Plasma-Polymerized Film," *Anal. Chem.*, vol. 75, No. 5, pp. 1116-1122 (Mar. 1, 2003).

Lavigne, J. et al., "Sensing a Paradigm Shift in the Field of Molecular Recognition: From Selective to Differential Receptors," *Angew. Chem. Int. Ed.*, vol. 40, pp. 3118-3130 (2001).

Morgenthaler, S. et al., "Surfaces with a Hydrophobicity Gradient: Possible Applications in Biological Testing", European Cells and Materials, 6(1):69 (2001).

Naffin, J. et al., "Immobilized Peptides as High-Affinity Capture Agents for Self-Associating Proteins", Chemistry & Biology, 10:251-259 (2003).

Reid et al., "Conformationally Constrained Macrocycles that Mimic Tripeptide b-Strands in Water and Aprotic Solvents," J. Am. Chem. Soc., vol. 124, pp. 5673-5683 (May 22, 2002).

Ruardy, T. et al., "Preparation and characterization of chemical gradient surfaces and their application for the study of cellular interaction phenomena", Surface Science Reports, 29:1-30 (1997).

Sadik, O. et al., "Differential Impedance Spectroscopy for Monitoring Protein Immobilization and Antibody-Antigen Reactions," *Anal. Chem.*, vol. 74, No. 13, pp. 3142-3150 (Jul. 1, 2002).

Tsuda, M. et al., "Suberedamines A and B, New Bromotyrosine Alkaloids from a Sponge Suberea Species," J. Nat. Prod., vol. 64, pp. 980-982 (2001).

Wolfbeis, O., "Fiber-Optic Chemical Sensors and Biosensors," *Anal. Chem.*, vol. 76, No. 12, pp. 3269-3283 (Jun. 15, 2004).

Worsley, K. et al., "Long-Range Periodicity in Carbon Nanotube Sidewall Functionalization," *Nano Letters*, vol. 4, No. 8, pp. 1541-1546 (2004).

Wu, Z. et al., "Transparent, Conductive Carbon Nanotube Films," *Science*, vol. 305, pp. 1273-1276 (Aug. 27, 2004).

Zhang, Z. et al., "Self-Assembly of Patchy Particles," *Nano Letters*, vol. 4, No. 8, pp. 1407-1413 (2004).

U.S. Appl. No. 10/703,876 Office Action Nov. 15, 2007.
U.S. Appl. No. 10/727,059 Office Action Nov. 15, 2007.
International Search Report mailed Mar. 8, 2006.
Angers et al., Proc. Natl. Acad. Sci. USA (Mar. 28, 2000), vol. 97(7), pp. 3684-3689.
European Search Report, Application No. 03709250.9 dated May 7, 2007.

Iorio et al., "Highly Sequence Selective Nonmacrocyclic Two-armed Receptors for Peptides," Bioorganic & Medicinal Chemistry Letters, Oxford, GB, vol. 9, No. 15, Aug. 2, 1999, pp. 2145-2150.

Iorio et al., "Sequence-Selective Peptide Detection by Small Synthetic Chemosensors Selected from an Encoded Combinatorial Chemosensor Library," Bioorganic & Medicinal Chemistry Letters, Oxford, GB, vol. 11, No. 13, Jul. 9, 2001, pp. 1635-1638.

Nestler et al., "Combinatorial Libraries: Studies in Molecular Recognition," Combinatorial Chemistry and High Throughput Screening, Hilversum, NL, vol. 1, No. 3, Oct. 1998, pp. 113-126.

Still, "Discovery of Sequence-selective Peptide Binding by Synthetic Receptors Using Encoded Combinatorial Libraries," Accounts of Chemical Research, ACS, Washington, DC, US, vol. 29, 1996, pp. 155-163.

U.S. Appl. No. 10/244,727 Office Action Jan. 25, 2006.
U.S. Appl. No. 10/244,727 Office Action Feb. 8, 2006.
U.S. Appl. No. 10/244,727 Office Action Feb. 12, 2007.
U.S. Appl. No. 10/244,727 Office Action May 17, 2005.
U.S. Appl. No. 10/244,727 Office Action May 17, 2007.
U.S. Appl. No. 10/244,727 Office Action Aug. 10, 2005.
U.S. Appl. No. 10/244,727 Office Action Aug. 11, 2006.
U.S. Appl. No. 10/244,727 Office Action Dec. 29, 2006.
U.S. Appl. No. 10/703,660 Office Action Mar. 8, 2007.
U.S. Appl. No. 10/703,660 Office Action Jun. 22, 2006.
U.S. Appl. No. 10/703,779 Office Action Mar. 12, 2007.
U.S. Appl. No. 10/703,779 Office Action Jun. 29, 2006.
U.S. Appl. No. 10/703,876 Office Action Mar. 2, 2007.
U.S. Appl. No. 10/703,876 Office Action Jun. 29, 2006.
U.S. Appl. No. 10/706,505 Office Action Feb. 15, 2007.
U.S. Appl. No. 10/706,505 Office Action Jun. 29, 2006.
U.S. Appl. No. 10/706,573 Office Action Jan. 31, 2007.
U.S. Appl. No. 10/706,573 Office Action Jun. 30, 2006.
U.S. Appl. No. 10/706,573 Office Action Oct. 18, 2007.
U.S. Appl. No. 10/727,059 Office Action Oct. 5, 2006.
U.S. Appl. No. 10/813,568 Office Action Feb. 15, 2007.
U.S. Appl. No. 10/813,568 Office Action Oct. 5, 2006.
U.S. Appl. No. 10/813,568 Office Action Jul. 27, 2007.
U.S. Appl. No. 10/813,612 Office Action Feb. 15, 2007.
U.S. Appl. No. 10/813,612 Office Action Oct. 6, 2006.
U.S. Appl. No. 10/813,612 Office Action Aug. 7, 2007.
U.S. Appl. No. 10/934,193 Office Action Jul. 27, 2007.
U.S. Appl. No. 10/934,865 Office Action Aug. 2, 2007.

Adams et al., "Oligosaccharide and Glycoprotein Micorarrays as Tools in HIV Glycobiology: Glycan-Dependent gp120/Protein Interactions," *Chemistry & Biology*, vol. 11, 875-881, Jun. 2004.

Bryan et al., "Saccharide Display on Microtiter Plates," *Chemistry & Biology*, vol. 9, 713-720, Jun. 2002.

Bryan et al., "Covalent Display of Oligosaccharide Arrays in Microtiter Plates," *J. Am Chem. Soc.* 2004, 126, 8640-8641.

Cho et al., "Pin-Printed Chemical Sensor Arrays for Simultaneous Multianalyte Quantification," *Anal. Chem.* 2002, 74, 1462-1466.

Collins et al., "Cell Surface Biology Mediated by Low Affinity Multivalent Protein-Glycan Interactions," *Current Opinion in Chemical Biology*, 2004,8:617-625.

Disney et al., "Aminoglycoside Microarrays to Study Antibiotic Resistance," *Angew. Chem. Int. Ed.* 2004, 43, 1591-1594.

Disney et al., "Aminoglycisde Microarrays to Explore Interactions of Antibiotics with RNAs and Proteins," *Chem. Eur J.*, 2004, 10, 3308-3314.

Disney et al., "The Use of Carbohydrate Microarrays to Study Carbohydrate-Cell Interactions and to Detect Pathogens," *Chemistry & Biology*, vol. 11, 1701-1707, Dec. 2004.

Fukui et al., "Oligosaccharrdie Microarrays for High-Throughput Detection and Specificity Assignmetns of Carbohydrate-Protein Interactions," *Nature Biotechnology*, Oct. 2002, vol. 20, 1011-1017.

Houseman et al., "Carbohydrate Arrays for the Evaluation of Protein Binding and Enzymatic Modification," *Chemistry & Biology*, vol. 9, 443-454, Apr. 2002.

Kuruvilla et al., "Dissecting Glucose Signalling with Diversity-Oriented Synthesis and Small-Molecule Microarrays," *Nature*, vol. 416, Apr. 2002, 653-657.

Mahal, "Catching Bacteria with Sugar," *Chemistry & Biology*, vol. 11, Dec. 2004.

Mellet et al., "Carbohydrate Microarrays," *ChemBioChem*, 2002, 3, 819-822.

Michael et al., "Randomly Ordered Addressable High-Density Optical Sensor Arrays," *Anal. Chem.*, 1998, 70, 1242-1248.

Ni et al., "Synthesis of Maleimide-Activated Carbohydrates as Chemoselective Tags for Site-Specific Glycosylation of Peptides and Proteins," *Bioconjugate Chem.*, 2003, 14, 232-238.

Nimrichter et al., "Intact Cell Adhesion to Glycan Microarrays," *Glycobiology*, vol. 14, No. 2, pp. 197-203, 2004.

Ratner et al., "Probing Protein-Carbohydrate Interactions with Microarrays of Synthetic Oligosaccharides," *ChemBioChem*, 2004, 5, 379-383.

Sasmai et al., "Facile Purification of Rare Cucurbiturils by Affinity Chromatography," *Organic Letters*, 2004, vol. 6, No. 8, 1225-1228.

Park, H. et al., "Modulation of protein-protein interactions by synthetic receptors: Design of molecules that disrupt serine protease-proteinaceous inhibitor interaction", *PNAS*, 99(8):5105-5109 (2002).
Alberti, P. et al., "DNA duplex-quadruplex exchange as the basis for a nanomolecular machine," *PNAS*, vol. 100, No. 4, pp. 1569-1573 (Feb. 18, 2003).
Noji, H. et al. "Direct observation of the rotation of $F_1$-ATPase," *Nature*, vol. 386, pp. 299-302 (Mar. 1997).
Yurke, B. et al., "A DNA-fuelled molecular machine made of DNA," *Nature*, vol. 406, pp. 605-608 (Aug. 10, 2000).
International Search Report dated Mar. 7, 2005.
International Search Report dated Mar. 10, 2005.
Barbaro, A. et al., "CHEMFET Devices for Biomedical and Environmental Applications", *Advanced Materials*, 4(6):402-408 (1992).
International Search Report dated Apr. 28, 2005.
International Search Report dated May 3, 2005.
DeLong, S. et al., "Covalently immobilized gradients of bFGF on hydrogel scaffolds for directed cell migration", *Biomaterials*, 26:3227-3234 (2005).
Dertinger, S. et al., "Gradients of substrate-bound laminin orient axonal specification of neurons", *PNAS*, 99(20):12542-12547 (2002).
Hypolite, C. et al., "Formation of Microscale Gradients of Protein Using Heterobifunctional Photolinkers", *Bioconjugate Chem.*, 8:658-663 (1997).
Kramer, S. et al., "Preparation of Protein Gradients through the Controlled Deposition of Protein-Nanoparticle Conjugates onto Functionalized Surfaces", *J. Am. Chem. Soc.*, 126:5388-5395 (2004).
International Search Report dated Sep. 8, 2005.
Sila et al., "Topological Templates as Tool in Molecular Recognition and Peptide Mimicry: Synthesis of a TASK Library," Journal of Molecular Recognition, vol. 8, 2-34 (1995).
U.S. Appl. No. 10/244,727 Notice of Allowance Jan. 9, 2009.
U.S. Appl. No. 10/703,876 Office Action Oct. 20, 2008.
U.S. Appl. No. 10/934,193 Notice of Allowance Oct. 6, 2008.
U.S. Appl. No. 10/934,865 Office Action Apr. 8, 2009.
U.S. Appl. No. 10/934,879 Office Action Oct. 16, 2008.
U.S. Appl. No. 11/219,338 Office Action Mar. 2, 2009.
U.S. Appl. No. 11/219,515 Notice of Allowance Jan. 9, 2009.
U.S. Appl. No. 11/223,463 Office Action Mar. 11, 2009.
U.S. Appl. No. 11/709,696 Office Action Oct. 16, 2008.
Non-proprietary Summary dated Nov. 29, 2001 that may have been sent to the Department of Defense and the National Institutes of Health.
U.S. Appl. No. 10/934,193 Office Action May 16, 2008.
U.S. Appl. No. 11/004,593 Office Action Apr. 14, 2008.
U.S. Appl. No. 11/217,384 Office Action Apr. 29, 2008.
U.S. Appl. No. 11/219,515 Office Action Apr. 30, 2008.
U.S. Appl. No. 10/244,727 Office Action Jul. 2, 2008.
U.S. Appl. No. 10/706,573 Office Action Jul. 28, 2008.
"Various Search Reports," 73 pages (2004).
Bachhawat-Sikder, K. et al., "Mixed-Element Capture Agents: A simple Strategy for the Construction of Synthetic, High Affinity Protein Capture Ligands", *J. Am. Chem. Soc.*, 125:9550-9551 (2003).
Blackwell, H. et al., "Exploiting Site—Site Interactions on Solid Support to Generate Dimeric Molecules," *Organic Letters*, vol. 3, No. 8, pp. 1185-1188 (2001).
Bluhm, L. et al., "An Alternative Procedure to Screen Mixture Combinatorial Libraries for Selectors for Chiral Chromatography," *Analytical Chemistry*, vol. 72, No. 21, pp. 5201-5205 (Nov. 1, 2000).
Borchardt, A. et al., "Synthetic Receptor Binding Elucidated with an Encoded Combinatorial Library," *J. Am. Chem. Soc.*, vol. 116, No. 1, pp. 373-374 (1994).
Boyce, R. et al., "Peptidosteroidal Receptors for Opioid Peptides, Sequence-Selective Binding Using a Synthetic Receptor Library," *J. Am. Chem. Soc.*, vol. 116, No. 17, pp. 7955-7956 (1994).
Brennan, M., "Protein Interactions: Putting on the Brakes. Antibody Mimics that Bind to Protein Surface Block Protein-Protein Interactions," *C & EN*, pp. 65-66 (Jan. 22, 2001).

Breslow, R. et al., "Sequence Selective Binding of Peptides by Artificial Receptors in Aqueous Solution," *J. Am. Chem. Soc.*, vol. 120, No. 14, pp. 3536-3537 (1998).
Bunin, B. et al., "A General and Expedient Method for the Solid-Phase Synthesis of 1,4-Benzodiazepine Derivatives," *J. Am. Chem. Soc.*, vol. 114, pp. 10997-10998 (1992).
Burns, C. et al., "Components for Tethered Bilayer Membranes: Synthesis of Hydrophilically Substituted Phytanol Derivatives", *Aust. J. Chem.*, vol. 54, pp. 431-438 (2001).
CARA presented Sep. 10, 2003.
Cha, X. et al., "Molecular Recognition of Aqueous Dipeptides by Noncovalently Aligned Oligoglycine Units at the Air/Water Interface," *J. Am. Chem. Soc.*, vol. 117, No. 48, pp. 11833-11838 (1995).
Chambers, R. et al., "High-level generation of polyclonal antibodies by genetic immunization", *Nature Biotechnology*, 21(9):1088-1092 (Sep. 2003).
Cheng, Y. et al., "Sequence-Selective Peptide Bonding with a Peptido-A,B-trans-steroidal Receptor Selected from an Encoded Combinatorial Receptor Library," *J. Am. Chem. Soc.*, vol. 118, No. 7, pp. 1813-1814 (1996).
Cousins, G. et al., "Molecular Evolution: Dynamic Combinatorial Libraries, Autocatalytic Networks and the Quest for Molecular Function," *Current Opinion in Chemical Biology*, vol. 4, pp. 270-279 (2000).
Deng, Q. et al., "Retention and Separation of Adenosine and Analogues by Affinity Chromatography with an Aptamer Stationary Phaase," *Anal. Chem.*, vol. 73, No. 22, pp. 5415-5421 (Nov. 15, 2001).
Fiammengo, R. et al., "Synthetic Self-Assembled Models with Biomimetic Functions," *Current Opinion in Chemical Biology*, vol. 5, pp. 660-673 (2001).
Francis, M. et al., "Combinatorial Approach to the Discovery of Novel Coordination Complexes", *J. Am. Chem. Soc.*, vol. 37, No. 118, pp. 8983-8984 (1996).
Freemantle, M., "Amplification of the Fittest. Dynamic Combinatorial Library Strategy Leads to Discovery and Synthesis of New Compounds", *C & EN*, pp. 31-33 (Sep. 2, 2002).
Goodman, M. et al., "A Combinatorial Library Approach to Artificial Receptor Design", *J. Am. Chem. Soc.*, vol. 117, No. 46, pp. 11610-11611 (1995).
Halter, M. et al., "Engineered Lipids That Cross-Link the Inner and Outer Leaflets of Lipid Bilayers", *Langmuir*, vol. 20, No. 6, pp. 2416-2423 (2004).
Hamilton, A. et al., "Model Systems Artificial Models of Protein Function," *Current Opinion in Chemical Biology*, vol. 5, pp. 623-625 (2001).
Hamuro, Y. et al., "A Calixarene with Four Peptide Loops: An Antibody Mimic for Recognition of Protein Surfaces," *Angew. Chem. Int. Ed. Engl.*, vol. 36, No. 23, pp. 2680-2683 (1997).
Hamuro, Y. et al., "Functionalized Oligoanthranilamides: Molecular and Conformationally Controlled Scaffolds," *Bioorganic & Medicinal Chemistry*, vol. 9, 2355-2363 (2001).
Haupt, K. et al., "Molecularly Imprinted Polymers and Their Use in Biomimetic Sensors," *Chem. Rev.*, vol. 100, No. 7, pp. 2495-2504 (2000).
Hergenrother, P. et al., "Small-Molecule Microarrays: Covalent Attachment and Screening of Alcohol-Containing Small Molecules on Glass Slides," *J. Am. Chem. Soc.*, vol. 122, No. 32, pp. 7849-7850 (2000).
Hubbard, R. et al., "Highly Substituted *ter*-Cyclopentanes as Receptors for Lipid A," *J. Am. Chem. Soc.*, vol. 123, No. 24, pp. 5810-5811 (2001).
Huc, I. et al., "Virtual Combinatorial Libraries: Dynamic Generation of Molecular and Supramolecular Diversity by Self-Assembly," *Proc. Natl. Acad. Sci. USA*, vol. 94, pp. 2106-2110 (Mar. 1997).
Jain, R. et al., "Protein Surface Recognition by Synthetic Receptors Based on a Tetraphenylporphyrin Scaffold," *Organic Letters*, vol. 2, No. 12, pp. 1721-1723 (2000).
Kasher, R. et al., "Design and Synthesis of Peptides that Bind α-Bungarotoxin with High Affinity," *Chemistry & Biology*, vol. 8, pp. 147-155 (2001).

Kick, E. et al., "Structure-Based Design and Combinatorial Chemistry Yield Low Nanomolar Inhibitors of Cathepsin D," *Chemistry & Biology*, vol. 4, No. 4, pp. 297-307 (Apr. 1997).
Kodadek, T., "Development of Protein-Detecting Microarrays and Related Devices," *TRENDS in Biochemical Sciences*, vol. 27, No. 6, pp. 295-300 (Jun. 2002).
Kodadek, T., "Protein microarrays: prospects and problems", *Chemistry & Biology*, 8:105-115 (2001).
Korbel, G. et al., "A Method for Rapidly Determining the Enantiomeric Excess of Thousands of Samples", *J. Am. Chem. Soc.*, 123:361-362 (2001).
Lam, K. et al., "The 'One-Bead-One Compound' Combinatorial Library Method," *Chemical Reviews*, vol, 97, No. 2, pp. 411-448 (1997).
Lee, D. et al., "Pairwise Use of Complexity-Generating Reactions in Diversity-Oriented Organic Synthesis," *Organic Letters*, vol, 2, No. 5, pp. 709-712 (2000).
Lehn, J et al., "Dynamic Combinatorial Chemistry," *Science*, vol. 291, pp, 2331-2332 (Mar. 23, 2001).
Leigh, D., "Summing Up Ligand Binding Interactions", *Chemistry & Biology*, vol. 10, pp. 1143-1144 (Dec. 2003).
Li, S. et al., "Artificial Receptor-Facilitated Solid-Phase Microextraction of Barbiturates," *Anal. Chem.*, vol. 71, No. 11, pp. 2146-2151 (Jun. 1, 1999).
Lindsley, C. et al., "Solid-Phase Biomimetic Synthesis of Carpanone-like Molecules", *J. Am. Chem. Soc.*, 122:422-423 (2000).
Linton, B. et al., "Host-guest chemistry: combinatorial receptors", *Current Opinion in Chemical Biology*, 3:307-312 (1999).
MacBeath, G. et al., "Printing Proteins as Microarrays for High-Throughput Function Determination," *Science*, vol. 289, pp. 1760-1763 (Sep. 8, 2000).
MacBeath, G. et al., "Printing Small Molecules as Microarrays and Detecting Protein-Ligand Interactions en Masse" *J. Am. Chem. Soc.*, vol. 121, No. 34, pp. 7967-7968 (1999).
Malin, R. et al, "Identification of Technetium-99m Binding Peptides Using Combinatorial Cellulose-Bound Peptide Libraries", *J. Am. Chem. Soc.*, vol. 117, No. 47, pp. 118821-118822 (1995).
Maly, D. et al., "Combinatorial Target-Guided Ligand Assembly: Identification of Potent Subtype-Selective c-Src Inhibitors," *PNAS*, vol. 97, No. 6, pp. 2419-2424 (Mar. 14, 2000).
McDonald, D. et al., "Application of Free Energy Perturbation Calculations to the Enantioselective Binding of Peptides to $C_3$-Symmetric Synthetic Receptors," *J. Am. Chem. Soc.*, vol. 118, No. 8, pp. 2073-2077 (1996).
Moore, J. et al., "'Masterpiece' Copolymer Sequences by Targeted Equilibruim-Shifting," *Organic Letters*, vol. 2, No. 7, pp. 915-918 (2000).
Mosbach, K. et al., "Generation of New Enzyme Inhibitors Using Imprinted Binding Sites: The Anti-Idiotypic Approach, a Step Toward the Next Generation of Molecular Imprinting," *J. Am. Chem. Soc* ., vol. 123, No. 49, pp. 12420-12421 (2001).
Ogoshi, H. et al., "Novel Approaches to Molecular Recognition Using Porphyrins," *Current Opinion in Chemical Biology*, vol. 3, pp. 736-739 (1999).
Olivos, H. et al., "Microwave-Assisted Solid-Phase Synthesis of Peptoids", *Organic Letters*, 4(23):4057-4059 (2002).
Opatz, T. et al., "A Selectively Deprotectable Triazacyclophane Scaffold for the Construction of Artificial Receptors," *Organic Letters*, vol. 3, No. 22, pp. 3499-3502 (2001).
Oprea, T. et al., "Chemography: The Art of Navigating in Chemical Space," *J. Comb. Chem.*, vol. 3, No. 2, pp. 157-166 (2001).
Park, H. et al., "Protein Surface Recognition by Synthetic Receptors: A Route to Novel Submicromolar Inhibitors for α-Chymotrypsin," *J. Am. Chem. Soc.*, vol. 121, No. 1, pp. 8-13 (1999).
Pattarawarapan, M. et al., "A Linker Scaffold to Present Dimers of Pharmacophores Prepared by Solid-Phase Syntheses," *Angew. Chem. Int. Ed.*, vol. 39, No. 23, pp. 4299-4301 (2000).
Peezuh, M. et al., "Peptide and Protein Recognition by Designed Molecules," *Chem. Rev.*, vol. 100, No. 7, pp. 2479-2494 (2000).
Pickens, J. et al., "Anchor-Based Design of Improved Cholera Toxin and *E. coli* Heat-Labile Enterotoxin Receptor Binding Antagonists that Display Multiple Binding Modes", *Chemistry & Biology*, 9:215-224 (2002).

Pirrung, M., "Spatially Addressable Combinatorial Libraries," *Chemical Reviews*, vol. 97, No. 2, pp. 473-488 (1997).
Quaglia, M. et al., "Target Analogue Imprinted Polymers with Affinity for Folic Acid and Related Compounds," *J. Am. Chem. Soc.*, vol. 123, No. 10, pp. 2146-2154 (2001).
Ramström, O. et al., "Synthesis and Catalysis by Molecularly Imprinted Materials," *Current Opinion in Chemical Biology*, vol. 3, pp. 759-764 (1999).
Rodriguez, M. et al., "An Oriented Peptide Array Library (OPAL) Strategy to Study Protein-Protein Interactions", *The Journal of Biological Chemistry*, 279(10):8802-8807 (2004).
Sasaki, D., "Control of Membrane Structure and Organization Through Chemical Recognition", *Cell Biochemistry and Biophysics*, vol. 39, pp. 145-161 (2003).
Sasaki, D. et al., "Crown Ether Functionalized Lipid Membranes: Lead Ion Recognition and Molecular Reorganization", *Langmuir*, 18:3714-3721 (2002).
Shao, Y. et al., "Sequence-Selective Receptors of Peptides, A Simple Molecular Design for Construction of Large Combinatorial Libraries of Receptors," *J. Org. Chem.* vol. 61, No. 18, pp. 6086-6087 (1996).
Shellenberger, K. et al., "Effect of Molecular Scale Roughness of Glass Beads on Colloidal and Bacterial Deposition," *Environ. Sci. Technol.*, vol. 36, No. 2, pp. 184-189 (2002).
Shinoda, S. et al., "Ester-Armed Cyclens Having Quadruplicated Helical Geometry: Remarkable Stable and Selective Encapsulation of $Na^+$ Ion," *J. Org. Chem.*, vol. 66, No. 18, pp. 6104-6108 (2001).
Song, X, "Direct, Ultrasensitive, and Selective Optical Detection of Protein Toxins Using Multivalent Interactions", *Anal. Chem.*, vol. 71, No. 11, pp. 2097-2107 (Jun. 1, 1999).
Srinivasan, N. et al., "Combinatorial approaches to synthetic receptors", *Current Opinion in Chemical Biology*, 8:305-310 (2004).
Sternson, et al., "Split-Pool Synthesis of 1,3-Dioxanes Leading to Arrayed Stock Solutions of Single Compounds Sufficient for Multiple Phenotypic and Protein-Binding Assays," *J. Am. Chem. Soc.*, vol. 123, No. 8, pp. 1740-1747.
Tomalia, D., "Birth of a New Macromolecular Architecture: Dendrimers as Quantized Building Blocks for Nanoscale Synthetic Organic Chemistry", *Aldrichimica ACTA*, 37(2): 39-57 (2004).
Wang, Y. et al., "Identification of Chiral Selectors from a 200-Member Parallel Combinatorial Library," *Anal. Chem.*, vol. 72, No. 21, pp. 5459-5465 (Nov. 1, 2000).
Way, J., "Covalent Modifications as a Strategy to Block Protein-Protein Interactions with Small-Molecule Drugs," *Current Opinion in Chemical Biology*, vol. 4, pp. 40-46 (2000).
Winssinger, N. et al., "From Split-Pool Libraries to Spatially Addressable Microarrays and its Application to Functional Proteomic Profiling," *Angew. Chem. Int. Ed.*, vol. 40, No. 17, pp. 3152-3155 (2001).
Xu, R. et al., "Combinatorial Library Approach for the Identification of Synthetic Receptors Targeting Vancomycin-Resistant Bacteria," *J. Am. Chem. Soc.*, vol, 121, No. 20, pp. 4898-4899 (1999).
Yan, B. et al , "Crucial Factors Regulating Site Interactions in Resin Supports Determined by Single Bead IR," *J. Org. Chem.*, vol. 63, No. 1, pp. 55-58 (1998).
Zhu, H. et al., "Protein Arrays and Microarrays," *Current Opinion in Chemical Biology*, vol. 5, pp. 40-45 (2001).
Zhuravlev, N. et al., "Surface Coverages of Bonded-Phase Ligands on Silica: A Computational Study," *Anal Chem.*, vol. 73, No. 16, pp. 4006-4011 (Aug. 15, 2001).
Zimmerman, S. et al., "Model Systems," *Current Opinion in Chemical Biology*, vol. 3, pp. 711-713 (1999).
International Search Report dated May 27, 2004.
International Search Report and Written Opinion mailed May 15, 2009.
U.S. Appl. No. 10/703,779 Office Action dated Aug. 5, 2009.
U.S. Appl. No. 10/703,779 Office Action dated Feb. 19, 2010.
U.S. Appl. No. 10/703,876 Office Action dated Jul. 23, 2009.
U.S. Appl. No. 10/703,876 Office Action dated Apr. 1, 2010.
U.S. Appl. No. 10/706,573 Office Action dated Sep. 2, 2009.
U.S. Appl. No. 10/813,568 Office Action dated Jul. 22, 2009.
U.S. Appl. No. 10/813,612 Office Action dated Jul. 8, 2009.
U.S. Appl. No. 10/813,612 Office Action dated Mar. 22, 2010.
U.S. Appl. No. 10/934,865 Office Action dated Jan. 22, 2010.
U.S. Appl. No. 10/934,879 Office Action dated Apr. 5, 2010.

U.S. Appl. No. 11/004,593 Office Action dated Sep. 15, 2009.
U.S. Appl. No. 11/217,384 Office Action dated Aug. 17, 2009.
U.S. Appl. No. 11/219,338 Office Action dated Dec. 28, 2009.
U.S. Appl. No. 11/219,338 Notice of Allowance dated Sep. 27, 2010.
U.S. Appl. No. 11/223,463 Office Action dated May 11, 2010.
U.S. Appl. No. 11/709,696 Office Action dated Apr. 6, 2010.
U.S. Appl. No. 12/261,508 Office Action dated Sep. 15, 2010.

* cited by examiner

FIG.2
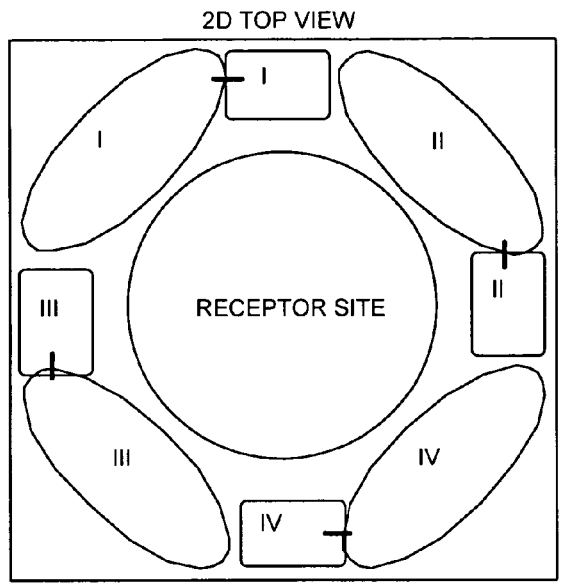
2D TOP VIEW
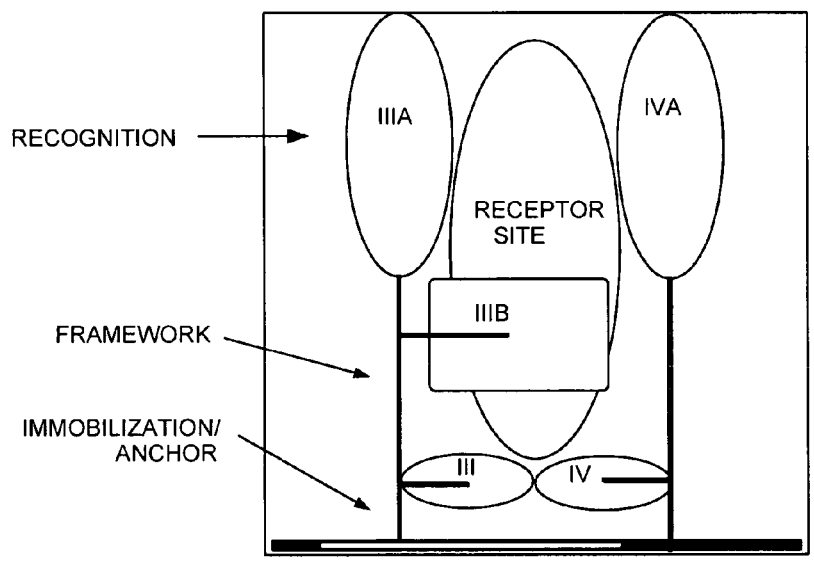
2D SIDE VIEW
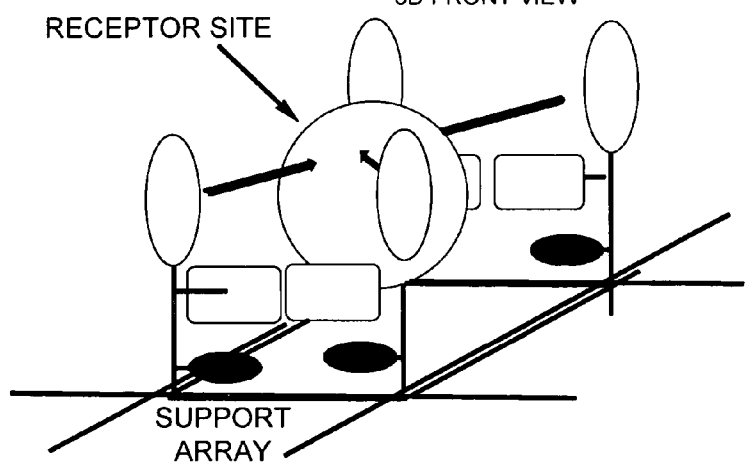
3D FRONT VIEW

Origin   = 28, 140 pixels
         (0.28,  1.4 mm)
Size     = 2032 x 1888 pixels
         (20.32 x 18.88 mm)
Scaling  = 10 µm/pixel
Scanner  = GenePix 4100A 01 [92896]
No averaging.
PMT Gain = 940
Laser Power = 100%
Normalization Factor = 1
Focus Position = 0

Origin = 4, 0 pixels
(0.04, 0 mm)
Size = 2180 x 1368 pixels
(21.8 x 13.68 mm)
Scaling = 10μm/pixel
Scanner = GenePix 4100A 01 [92896]
No averaging.
PMT Gain = 600
Laser Power = 100%
Normalization Factor = 1
Filter = 670DF40
Focus Position = 0

Origin = 4, 0 pixels
(0.04, 0 mm)
Size = 2180 x 1068 pixels
(21.8 x 10.68 mm)
Scaling = 10µm/pixel
Scanner = GenePix 4100A 01 [92896]
No averaging.
PMT Gain = 600
Laser Power = 100%
Normalization Factor = 1
Filter = 670DF40
Focus Position = 0

Origin = 4, 0 pixels
(0.04, 0 mm)
Size = 2180 x 1368 pixels
(21.8 x 13.68 mm)
Scaling = 10µm/pixel
Scanner = GenePix 4100A 01 [92896]
No averaging.
PMT Gain = 600
Laser Power = 100%
Normalization Factor = 1
Filter = 670DF40
Focus Position = 0

Origin = 4, 0 pixels
(0.04, 0 mm)
Size = 2180 x 1368 pixels
(21.8 x 13.68 mm)
Scaling = 10μm/pixel
Scanner = GenePix 4100A 01 [92896]
No averaging.
PMT Gain = 560
Laser Power = 100%
Normalization Factor = 1
Filter = 670DF40
Focus Position = 0

METHODS EMPLOYING COMBINATORIAL ARTIFICIAL RECEPTORS

CROSS REFERENCE TO RELATED APPLICATIONS

The present application claims priority to U.S. Provisional Patent Application Nos. 60/499,752 and 60/500,081, each filed Sep. 3, 2003, and 60/526,511, filed Dec. 2, 2003, each entitled "ARTIFICIAL RECEPTORS, BUILDING BLOCKS, AND METHODS"; is a continuation in part of copending U.S. patent application Ser. No. 10/244,727, filed Sep. 16, 2002, (which claims priority to U.S. Provisional Patent Application No. 60/360,980 filed Mar. 1, 2002; 60/362,600, filed Mar. 8, 2002; 60/375,655, filed Apr. 26, 2002; and 60/400,605, filed Aug. 2, 2002), Ser. No. 10/813,568, filed Mar. 29, 2004, and Application No. PCT/US03/05328, filed Feb. 19, 2003, each entitled "ARTIFICIAL RECEPTORS, BUILDING BLOCKS, AND METHODS"; is a continuation in part of U.S. patent application Ser. Nos. 10/812,850 and 10/813,612, and application No. PCT/U.S. 2004/009649, each filed Mar. 29, 2004 and each entitled "ARTIFICIAL RECEPTORS INCLUDING REVERSIBLY IMMOBILIZED BUILDING BLOCKS, THE BUILDING BLOCKS, AND METHODS"; and claims priority to U.S. Provisional Patent Application Nos. 60/499,776, 60/499,867, 60/499,965, 60/499,975, and 60/500,081, each filed Sep. 3, 2003, and 60/526,511 60/526,699, 60/526,703, 60/526,708, and 60/527,190 each filed Dec. 2, 2003. Each of these patent applications is incorporated herein by reference in its entirety.

FIELD OF THE INVENTION

The present invention relates to methods employing artificial receptors, such as combinatorial artificial receptor arrays. The present receptors include heterogeneous and immobilized combinations of building block molecules. In certain embodiments, combinations of 2, 3, 4, or 5 distinct building block molecules immobilized near one another on a support provide molecular structures that can be employed in the present methods. The present methods can develop artificial receptors that can then be employed to detect the receptor's ligand. The present methods can find compounds that disrupt one or more binding interactions.

BACKGROUND

The preparation of artificial receptors that bind ligands like proteins, peptides, carbohydrates, microbes, pollutants, pharmaceuticals, and the like with high sensitivity and specificity is an active area of research. None of the conventional approaches has been particularly successful; achieving only modest sensitivity and specificity mainly due to low binding affinity.

Antibodies, enzymes, and natural receptors generally have binding constants in the $10^8$-$10^{12}$ range, which results in both nanomolar sensitivity and targeted specificity. By contrast, conventional artificial receptors typically have binding constants of about $10^3$ to $10^5$, with the predictable result of millimolar sensitivity and limited specificity.

Several conventional approaches are being pursued in attempts to achieve highly sensitive and specific artificial receptors. These approaches include, for example, affinity isolation, molecular imprinting, and rational and/or combinatorial design and synthesis of synthetic or semi-synthetic receptors.

Such rational or combinatorial approaches have been limited by the relatively small number of receptors which are evaluated and/or by their reliance on a design strategy which focuses on only one building block, the homogeneous design strategy. Common combinatorial approaches form microarrays that include 10,000 or 100,000 distinct spots on a standard microscope slide. However, such conventional methods for combinatorial synthesis provide a single molecule per spot. Employing a single building block in each spot provides only a single possible receptor per spot. Synthesis of thousands of building blocks would be required to make thousands of possible receptors.

Further, these conventional approaches are hampered by the currently limited understanding of the principals which lead to efficient binding and the large number of possible structures for receptors, which makes such an approach problematic.

There remains a need for methods for detecting ligands and for detecting compounds that disrupt one or more binding interactions.

SUMMARY

The present invention relates to methods employing artificial receptors, such as combinatorial artificial receptor arrays. The present receptors include heterogeneous and immobilized combinations of building block molecules. In certain embodiments, combinations of 2, 3, 4, or 5 distinct building block molecules immobilized near one another on a support provide molecular structures that can be employed in the present methods. The present methods can develop artificial receptors that can then be employed to detect the receptor's ligand. The present methods can find compounds that disrupt one or more binding interactions.

The present invention includes methods for making an artificial receptor for binding a test ligand. In an embodiment, the method of the present invention can include contacting at least one candidate artificial receptor with a test ligand, detecting binding of the test ligand to at least one candidate artificial receptor, and selecting at least one candidate artificial receptor for which test ligand binding was detected as a working artificial receptor for the test ligand. The candidate artificial receptor can include a plurality of building blocks coupled to a region of a support.

The present invention includes methods for detecting a test ligand. In an embodiment, a method of the invention can include contacting at least one working artificial receptor with a sample suspected of containing the test ligand and monitoring for binding to the at least one working artificial receptor, wherein binding to the at least one working artificial receptor indicates the presence of the test ligand in the sample. The working artificial receptor can include a plurality of building blocks coupled to a region of a support. In an embodiment, the at least one working artificial receptor is known to bind the test ligand. In an embodiment, the at least one working artificial receptor can include a plurality of artificial receptors.

In an embodiment, a method of the present invention can include contacting a plurality of candidate artificial receptors with a first test ligand; detecting binding of the first test ligand to at least one candidate artificial receptor; and cataloging location or composition of the at least one artificial receptor that bound the first test ligand. Each candidate artificial receptor independently can include a plurality of building blocks coupled to a region of a support.

The present invention includes methods for detecting a compound that disrupts an interaction of a test ligand. This method can include contacting at least one working artificial receptor with a test ligand and a candidate disrupter. Contacting can be simultaneous, contacting with test ligand can come before contacting with candidate disrupter, or contacting with candidate disrupter ligand can come before contacting with test ligand. In an embodiment, the method can include contacting at least one working artificial receptor with a mixture comprising the test ligand and a candidate disrupter. The method can also include monitoring for those candidate disruptors that decrease binding of the test ligand to the at least one working artificial receptor, wherein decreased binding indicates that the candidate disrupter is a lead disrupter. The working artificial receptor can include a plurality of building blocks coupled to a region of a support. In an embodiment, the at least one working artificial receptor is known to bind the test ligand.

The present invention includes methods for making an affinity support for a test ligand. In an embodiment, a method of the invention can include contacting at least one candidate artificial receptor with the test ligand; detecting binding of the test ligand to at least one candidate artificial receptor; selecting at least one candidate artificial receptor for which test ligand binding was detected as a working artificial receptor for the test ligand; and coupling the working artificial receptor to a second support to form an affinity support. The candidate artificial receptor can include a plurality of building blocks coupled to a region of a first support.

The present invention includes methods for isolating a test ligand. In an embodiment, a method of the invention can include contacting a sample containing the test ligand with a working artificial receptor. The working artificial receptor can include a plurality of building blocks coupled to a region of a support. In an embodiment, the working artificial receptor is known to bind the test ligand.

The present invention includes methods for making a reaction support for a reactant. In an embodiment, a method of the invention can include contacting at least one candidate artificial receptor with the reactant; detecting binding of the test ligand to at least one candidate artificial receptor; selecting at least one candidate artificial receptor for which test ligand binding was detected as a working artificial receptor for the test ligand; contacting at least one working artificial receptor with the reactant and monitoring for a reaction of the reactant; selecting a working artificial receptor for which the reaction was observed as a reaction artificial receptor; and coupling the reaction artificial receptor to a second support to form a reaction support. The candidate artificial receptor can include a plurality of building blocks coupled to a region of a first support. In an embodiment, the method can include contacting at least one working artificial receptor with a second reactant.

The present invention includes methods for reacting a reactant. In an embodiment, a method of the invention can include contacting a sample containing the reactant with a working artificial receptor. The working artificial receptor can include a plurality of building blocks coupled to a region of a support. In an embodiment, the working artificial receptor is known to bind the test ligand. In an embodiment, the method can include contacting the working artificial receptor with a second reactant.

The present invention includes methods of making a catalytic support for a reactant. In an embodiment, a method of the present invention can include contacting at least one candidate artificial receptor with the reactant; detecting catalysis of a reaction of the reactant in the presence of the at least one candidate artificial receptor; selecting at least one candidate artificial receptor for which catalysis was detected as a working artificial receptor for the test ligand; and coupling the working receptor to a second support to form a catalytic support. The candidate artificial receptor can include a plurality of building blocks coupled to a region of a first support. In an embodiment, the method can include contacting at least one working artificial receptor with a second reactant.

The present invention includes methods of catalyzing a reaction. In an embodiment, a method of the invention can include contacting a sample containing a reactant with a working artificial receptor. The working artificial receptor can include a plurality of building blocks coupled to a region of a support. In an embodiment, the working artificial receptor is known to bind the test ligand and catalyze the reaction.

The present invention includes methods of making a surface that does not bind a test ligand. In an embodiment, a method of the invention can include contacting at least one candidate artificial receptor with the test ligand; detecting lack of binding of the test ligand to at least one candidate artificial receptor; and selecting at least one candidate artificial receptor for which test lack of ligand binding was detected as a nonbinding surface for the test ligand. The candidate artificial receptor can include a plurality of building blocks coupled to a region of a support. In an embodiment, the test ligand comprises a plurality of test ligands.

The present invention includes methods for detecting a compound that disrupts an interaction of a test ligand with a second ligand. In an embodiment, a method of the invention can include binding the test ligand to at least one working artificial receptor. This method can include contacting at least one working artificial receptor with a second ligand and a candidate disruptor. Contacting can be simultaneous, contacting with second ligand can come before contacting with candidate disruptor, or contacting with candidate disruptor ligand can come before contacting with second ligand. In an embodiment, the method can include monitoring for those candidate disruptors that decrease binding of the second ligand to the test ligand wherein decreased binding indicates that the candidate disruptor is a lead disruptor. The working artificial receptor can include a plurality of building blocks coupled to a region of a support. In an embodiment, the at least one working artificial receptor is known to bind the test ligand.

BRIEF DESCRIPTION OF THE FIGURES

FIG. 2 schematically illustrates two and three dimensional representations of an embodiment of a molecular configuration of 4 building blocks, each building block including a recognition element, a framework, and a linker coupled to a support (immobilization/anchor).

DETAILED DESCRIPTION

Definitions

Figure 1:
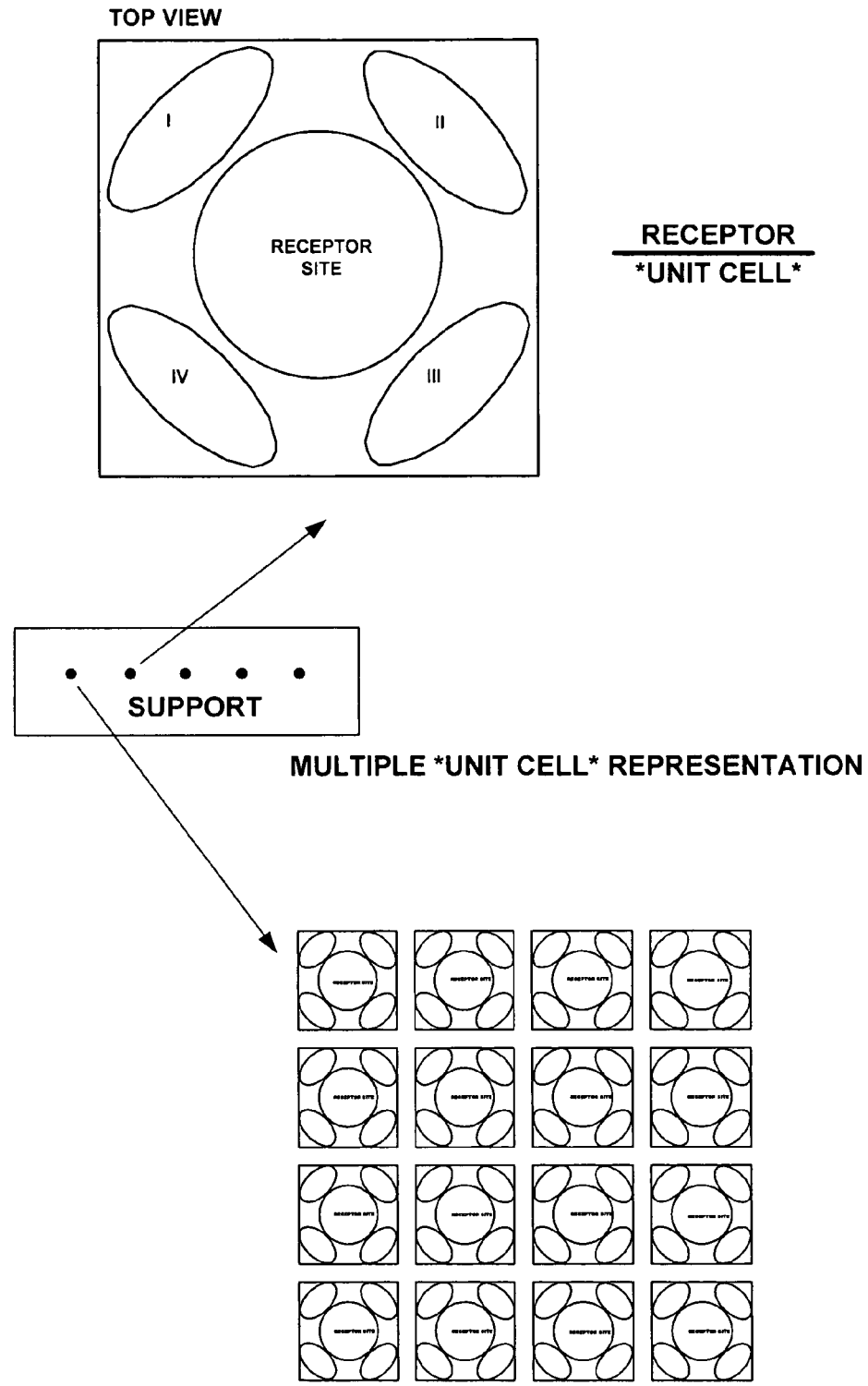
FIG. 1 schematically illustrates two dimensional representations of an embodiment of a receptor according to the present invention that employs 4 different building blocks to make a ligand binding site.

As used herein, the term "peptide" refers to a compound including two or more amino acid residues joined by amide bond(s).

As used herein, the terms "polypeptide" and "protein" refer to a peptide including more than about 20 amino acid residues connected by peptide linkages.

As used herein, the term "proteome" refers to the expression profile of the proteins of an organism, tissue, organ, or cell. The proteome can be specific to a particular status (e.g., development, health, etc.) of the organism, tissue, organ, or cell.

Reversibly immobilizing building blocks on a support couples the building blocks to the support through a mechanism that allows the building blocks to be uncoupled from the support without destroying or unacceptably degrading the building block or the support. That is, immobilization can be reversed without destroying or unacceptably degrading the building block or the support. In an embodiment, immobilization can be reversed with only negligible or ineffective levels of degradation of the building block or the support. Reversible immobilization can employ readily reversible covalent bonding or noncovalent interactions. Suitable noncovalent interactions include interactions between ions, hydrogen bonding, van der Waals interactions, and the like. Readily reversible covalent bonding refers to covalent bonds that can be formed and broken under conditions that do not destroy or unacceptably degrade the building block or the support.

A combination of building blocks immobilized on, for example, a support can be a candidate artificial receptor, a lead artificial receptor, or a working artificial receptor. That is, a heterogeneous building block spot on a slide or a plurality of building blocks coated on a tube or well can be a candidate artificial receptor, a lead artificial receptor, or a working artificial receptor. A candidate artificial receptor can become a lead artificial receptor, which can become a working artificial receptor.

As used herein the phrase "candidate artificial receptor" refers to an immobilized combination of building blocks that can be tested to determine whether or not a particular test ligand binds to that combination. In an embodiment, the combination includes one or more reversibly immobilized building blocks. In an embodiment, the candidate artificial receptor can be a heterogeneous building block spot on a slide or a plurality of building blocks coated on a tube or well.

As used herein the phrase "lead artificial receptor" refers to an immobilized combination of building blocks that binds a test ligand at a predetermined concentration of test ligand, for example at 10, 1, 0.1, or 0.01 µg/ml, or at 1, 0.1, or 0.01 ng/ml. In an embodiment, the combination includes one or more reversibly immobilized building blocks. In an embodiment, the lead artificial receptor can be a heterogeneous building block spot on a slide or a plurality of building blocks coated on a tube or well.

As used herein the phrase "working artificial receptor" refers to a combination of building blocks that binds a test ligand with a selectivity and/or sensitivity effective for categorizing or identifying the test ligand. That is, binding to that combination of building blocks describes the test ligand as belonging to a category of test ligands or as being a particular test ligand. A working artificial receptor can, for example, bind the ligand at a concentration of, for example, 100, 10, 1, 0.1, 0.01, or 0.001 ng/ml. In an embodiment, the combination includes one or more reversibly immobilized building blocks. In an embodiment, the working artificial receptor can be a heterogeneous building block spot on a slide or a plurality of building blocks coated on a tube, well, slide, or other support or on a scaffold.

As used herein the phrase "working artificial receptor complex" refers to a plurality of artificial receptors, each a combination of building blocks, that binds a test ligand with a pattern of selectivity and/or sensitivity effective for categorizing or identifying the test ligand. That is, binding to the several receptors of the complex describes the test ligand as belonging to a category of test ligands or as being a particular test ligand. The individual receptors in the complex can each bind the ligand at different concentrations or with different affinities. For example, the individual receptors in the complex each bind the ligand at concentrations of 100, 10, 1, 0.1, 0.01 or 0.001 ng/ml. In an embodiment, the combination includes one or more reversibly immobilized building blocks. In an embodiment, the working artificial receptor complex can be a plurality of heterogeneous building block spots or regions on a slide; a plurality of wells, each coated with a different combination of building blocks; or a plurality of tubes, each coated with a different combination of building blocks.

As used herein, the phrase "significant number of candidate artificial receptors" refers to sufficient candidate artificial receptors to provide an opportunity to find a working artificial receptor, working artificial receptor complex, or lead artificial receptor. As few as about 100 to about 200 candidate artificial receptors can be a significant number for finding working artificial receptor complexes suitable for distinguishing two proteins (e.g., cholera toxin and phycoerythrin). In other embodiments, a significant number of candidate artificial receptors can include about 1,000 candidate artificial receptors, about 10,000 candidate artificial receptors, about 100,000 candidate artificial receptors, or more.

Although not limiting to the present invention, it is believed that the significant number of candidate artificial receptors required to provide an opportunity to find a working artificial receptor may be larger than the significant number required to find a working artificial receptor complex. Although not limiting to the present invention, it is believed that the significant number of candidate artificial receptors required to provide an opportunity to find a lead artificial receptor may be larger than the significant number required to find a working artificial receptor. Although not limiting to the present invention, it is believed that the significant number of candidate artificial receptors required to provide an opportunity to find a working artificial receptor for a test ligand with few features may be more than for a test ligand with many features.

As used herein, the term "building block" refers to a molecular component of an artificial receptor including portions that can be envisioned as or that include one or more linkers, one or more frameworks, and one or more recognition elements. In an embodiment, the building block includes a linker, a framework, and one or more recognition elements. In an embodiment, the linker includes a moiety suitable for reversibly immobilizing the building block, for example, on a support, surface or lawn. The building block interacts with the ligand.

As used herein, the term "linker" refers to a portion of or functional group on a building block that can be employed to or that does (e.g., reversibly) couple the building block to a support, for example, through covalent link, ionic interaction, electrostatic interaction, or hydrophobic interaction.

As used herein, the term "framework" refers to a portion of a building block including the linker or to which the linker is coupled and to which one or more recognition elements are coupled.

As used herein, the term "recognition element" refers to a portion of a building block coupled to the framework but not covalently coupled to the support. Although not limiting to the present invention, the recognition element can provide or form one or more groups, surfaces, or spaces for interacting with the ligand.

As used herein, the phrase "plurality of building blocks" refers to two or more building blocks of different structure in a mixture, in a kit, or on a support or scaffold. Each building block has a particular structure, and use of building blocks in the plural, or of a plurality of building blocks, refers to more than one of these particular structures. Building blocks or plurality of building blocks does not refer to a plurality of molecules each having the same structure.

As used herein, the phrase "combination of building blocks" refers to a plurality of building blocks that together are in a spot, region, or a candidate, lead, or working artificial receptor. A combination of building blocks can be a subset of a set of building blocks. For example, a combination of building blocks can be one of the possible combinations of 2, 3, 4, 5, or 6 building blocks from a set of N (e.g., N=10-200) building blocks.

As used herein, the phrases "homogenous immobilized building block" and "homogenous immobilized building blocks" refer to a support or spot having immobilized on or within it only a single building block.

As used herein, the phrase "activated building block" refers to a building block activated to make it ready to form a covalent bond to a functional group, for example, on a support. A building block including a carboxyl group can be converted to a building block including an activated ester group, which is an activated building block. An activated building block including an activated ester group can react, for example, with an amine to form a covalent bond.

As used herein, the term "naïve" used with respect to one or more building blocks refers to a building block that has not previously been determined or known to bind to a test ligand of interest. For example, the recognition element(s) on a naïve building block has not previously been determined or known to bind to a test ligand of interest. A building block that is or includes a known ligand (e.g., GM1) for a particular protein (test ligand) of interest (e.g., cholera toxin) is not naïve with respect to that protein (test ligand).

As used herein, the term "immobilized" used with respect to building blocks coupled to a support refers to building blocks being stably oriented on the support so that they do not migrate on the support or release from the support. Building blocks can be immobilized by covalent coupling, by ionic interactions, by electrostatic interactions, such as ion pairing, or by hydrophobic interactions, such as van der Waals interactions.

As used herein a "region" of a support, tube, well, or surface refers to a contiguous portion of the support, tube, well, or surface. Building blocks coupled to a region can refer to building blocks in proximity to one another in that region.

As used herein, a "bulky" group on a molecule is larger than a moiety including 7 or 8 carbon atoms.

As used herein, a "small" group on a molecule is hydrogen, methyl, or another group smaller than a moiety including 4 carbon atoms.

As used herein, the term "lawn" refers to a layer, spot, or region of functional groups on a support, for example, at a density sufficient to place coupled building blocks in proximity to one another. The functional groups can include groups capable of forming covalent, ionic, electrostatic, or hydrophobic interactions with building blocks.

As used herein, the term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{12}$ for straight chain, $C_1$-$C_6$ for branched chain). Likewise, cycloalkyls can have from 3-10 carbon atoms in their ring structure, for example, 5, 6 or 7 carbons in the ring structure.

The term "alkyl" as used herein refers to both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl alkyl, or an aromatic or heteroaromatic moiety. The moieties substituted on the hydrocarbon chain can themselves be substituted, if appropriate. For example, the substituents of a substituted alkyl can include substituted and unsubstituted forms of the groups listed above.

The phrase "aryl alkyl", as used herein, refers to an alkyl group substituted with an aryl group (e.g., an aromatic or heteroaromatic group).

As used herein, the terms "alkenyl" and "alkynyl" refer to unsaturated aliphatic groups analogous in length and optional substitution to the alkyls groups described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents such as those described above for alkyl groups. The term "aryl" also includes polycyclic ring systems having two or more cyclic rings in which two or more carbons are common to two adjoining rings (the rings are "fused rings") wherein at least one of the rings is aromatic, e.g., the other cyclic ring(s) can be cycloalkyls, cycloalkenyls, cycloalkynyls, aryls and/or heterocyclyls.

As used herein, the terms "heterocycle" or "heterocyclic group" refer to 3- to 12-membered ring structures, e.g., 3- to 7-membered rings, whose ring structures include one to four heteroatoms. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents such as those described for alkyl groups.

As used herein, the term "heteroatom" as used herein means an atom of any element other than carbon or hydrogen, such as nitrogen, oxygen, sulfur and phosphorous.

Overview of the Artificial Receptor

FIG. 1 schematically illustrates an embodiment employing 4 distinct building blocks in a spot on a microarray to make a ligand binding site. This Figure illustrates a group of 4 building blocks at the corners of a square forming a unit cell. A group of four building blocks can be envisioned as the vertices on any quadrilateral. FIG. 1 illustrates that spots or regions of building blocks can be envisioned as multiple unit cells, in this illustration square unit cells. Groups of unit cells of four building blocks in the shape of other quadrilaterals can also be formed on a support.

Each immobilized building block molecule can provide one or more "arms" extending from a "framework" and each can include groups that interact with a ligand or with portions of another immobilized building block. FIG. 2 illustrates that combinations of four building blocks, each including a framework with two arms (called "recognition elements"), provides a molecular configuration of building blocks that form a site for binding a ligand. Such a site formed by building blocks such as those exemplified below can bind a small molecule, such as a drug, metabolite, pollutant, or the like, and/or can bind a larger ligand such as a macromolecule or microbe.

The present artificial receptors can include building blocks reversibly immobilized on a support or surface. Reversing immobilization of the building blocks can allow movement of building blocks to a different location on the support or surface, or exchange of building blocks onto and off of the surface. For example, the combinations of building blocks can bind a ligand when reversibly coupled to or immobilized on the support. Reversing the coupling or immobilization of the building blocks provides opportunity for rearranging the building blocks, which can improve binding of the ligand. Further, the present invention can allow for adding additional or different building blocks, which can further improve binding of a ligand.

Figure 3:
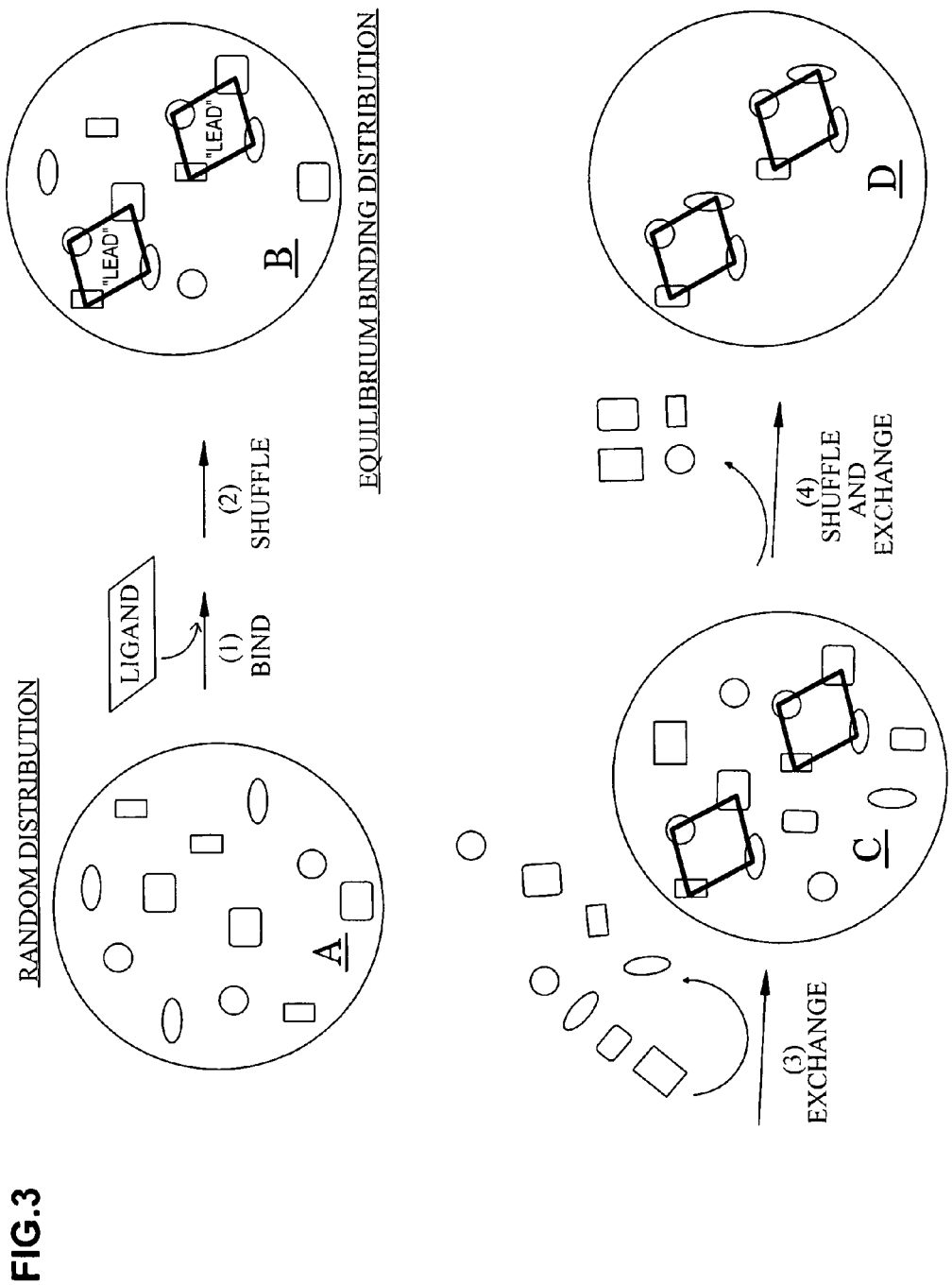
FIG. 3 schematically illustrates an embodiment of the present methods and artificial receptors employing shuffling and exchanging building blocks.

FIG. 3 schematically illustrates an embodiment employing an initial artificial receptor surface (A) with four different building blocks on the surface, which are represented by shaded shapes. This initial artificial receptor surface (A) undergoes (1) binding of a ligand to an artificial receptor and (2) shuffling the building blocks on the receptor surface to yield a lead artificial receptor (B). Shuffling refers to reversing the coupling or immobilization of the building blocks and allowing their rearrangement on the receptor surface. After forming a lead artificial receptor, additional building blocks can be (3) exchanged onto and/or off of the receptor surface (C). Exchanging refers to building blocks leaving the surface and entering a solution contacting the surface and/or building blocks leaving a solution contacting the surface and becoming part of the artificial receptor. The additional building blocks can be selected for structural diversity (e.g., randomly) or selected based on the structure of the building blocks in the lead artificial receptor to provide additional avenues for improving binding. The original and additional building blocks can then be (4) shuffled and exchanged to provide higher affinity artificial receptors on the surface (D).

Methods Employing the Artificial Receptors

Working artificial receptors can be generated to be specific to a given test ligand or specific to a particular part of a given test ligand. Heterogeneous and immobilized combinations of building block molecules form the working artificial receptors. For example, combinations of 2, 3, 4, or 5 distinct building block molecules immobilized in proximity to one another on a support provide molecular structures that serve as candidate and working artificial receptors. The building blocks can be naïve to the test ligand. Once a plurality of candidate artificial receptors are generated, they can be tested to determine which are specific or useful for a given ligand.

The specific or working artificial receptor or receptor complex can then be used in a variety of different methods and systems. For example, the receptors can be employed in methods and/or devices for binding or detecting a test ligand. By way of further example, the receptors can be employed in methods and/or devices for chemical synthesis. Methods and systems for chemical synthesis can include methods and systems for regiospecific and stereospecific chemical synthesis. The receptors can also be employed for developing compounds that disrupt or model binding interactions. Methods and systems for developing therapeutic agents can include methods and systems for pharmaceutical and vaccine development.

In an embodiment, methods and systems of the present invention can be employed for detecting a plurality of ligands of interest. For example, an unknown biological sample can be characterized by the presence of a combination of specific ligands. Such a method can be useful in assays for detecting specific pathogens or disease states. By way of further example, such an embodiment can be used for determining the genetic profile of a subject. For example, cancerous tissue can be detected or a genetic disposition to cancer can be detected.

The present artificial receptors can be part of products used in: analyzing a genome and/or proteome (protein isolation and characterization); pharmaceutical development (such as identification of sequence specific small molecule leads, characterization of protein to protein interactions); detectors for a test ligand; drug of abuse diagnostics or therapy (such as clinical or field analysis of cocaine or other drugs of abuse); hazardous waste analysis or remediation; chemical exposure alert or intervention; disease diagnostics or therapy; cancer diagnostics or therapy (such as clinical analysis of prostate specific antigen); biological agent alert or intervention; food chain contamination analysis or remediation and clinical analysis of food contaminants; and the like.

Methods of Binding or Detecting Test Ligands

In an embodiment, the invention can include methods and/or devices for binding or detecting a test ligand. For example, the present artificial receptors can be used for a variety of assays that presently employ an antibody. The present artificial receptors can be specific for a given ligand, such as an antigen or an immunogen. Thus, the present artificial receptors can be used in formats analogous to enzyme immunoassay, enzyme-linked immunoassay, immunodiffusion, immunoelectrophoresis, latex agglutination, and the like. Test ligands that can be detected in such a method include a drug of abuse, a biological agent (such as a hazardous agent), a marker for a biological agent, a marker for a disease state, etc. Methods and systems for detection can include methods and systems for clinical chemistry, environmental analysis, and diagnostic assays of all types.

For example, the artificial receptor can be contacted with a sample including or suspected of including at least one test ligand. The building blocks making up the artificial receptors can be naïve to the test ligand. Then, binding of one or more of the test ligands to the artificial receptors can be detected. Next, the binding results can be interpreted to provide information about the sample. In an embodiment, the invention includes a method for detecting a test ligand in a sample including contacting an artificial receptor specific to the test ligand with a sample suspected of containing the test ligand. The method can also include detecting or quantitating binding of the test ligand to the artificial receptor. For example, an artificial receptor that binds (e.g., tightly) the molecule, cell, or microbe under appropriate conditions can be employed in a format where binding itself is sufficient to indicate presence of the molecule or organism. Such a format can also include artificial receptors to be probed with positive and control samples.

Figure 4:
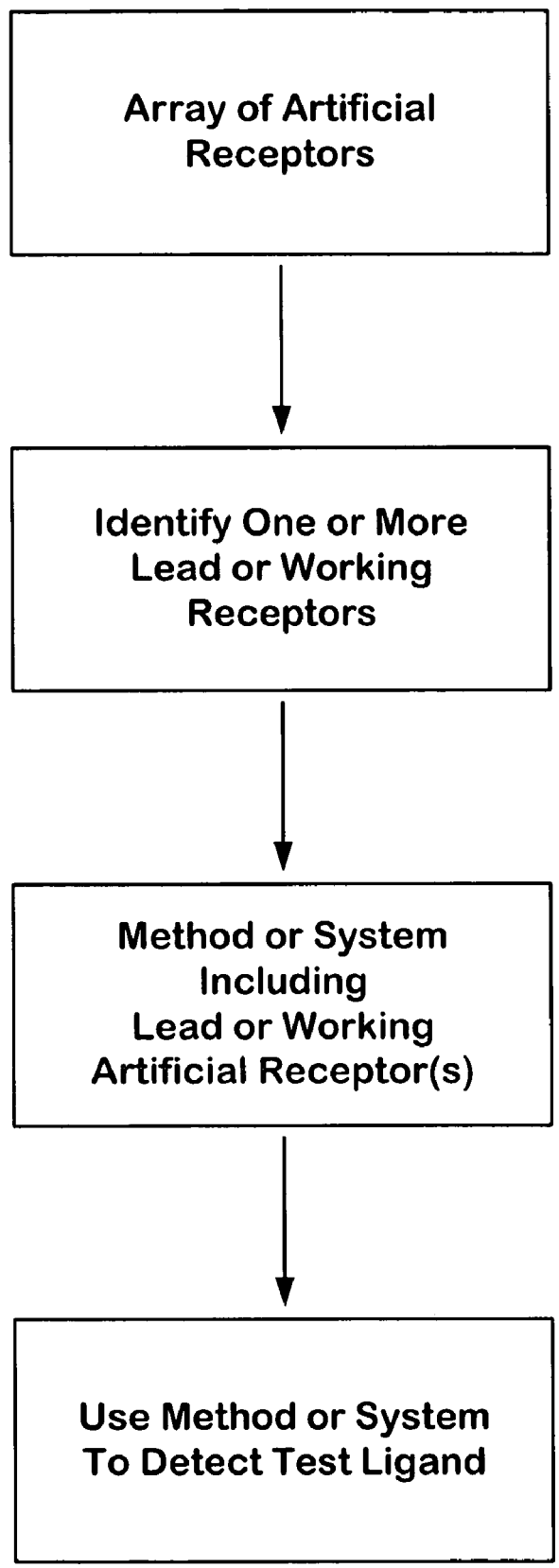
FIG. 4 schematically illustrates an embodiment of a method for evaluating candidate artificial receptors for binding to a test ligand, such as a molecule or cell.

FIG. 4 schematically illustrates an embodiment of a method for evaluating candidate artificial receptors for binding to a test ligand, such as a molecule or cell. The method can include making an array of candidate artificial receptors. Working artificial receptors can be identified by contacting the array with test ligand and identifying which receptors bind the test ligand. The building blocks making up the artificial receptors can be naïve to the test ligand. Such a method can employ a labeled test ligand. The method can include producing an array or device including the working artificial receptor or receptor complex. In an embodiment, the method can include employing the array or device for detecting or characterizing the test ligand in a sample, such as a biological, laboratory, or environmental sample.

Figure 5:
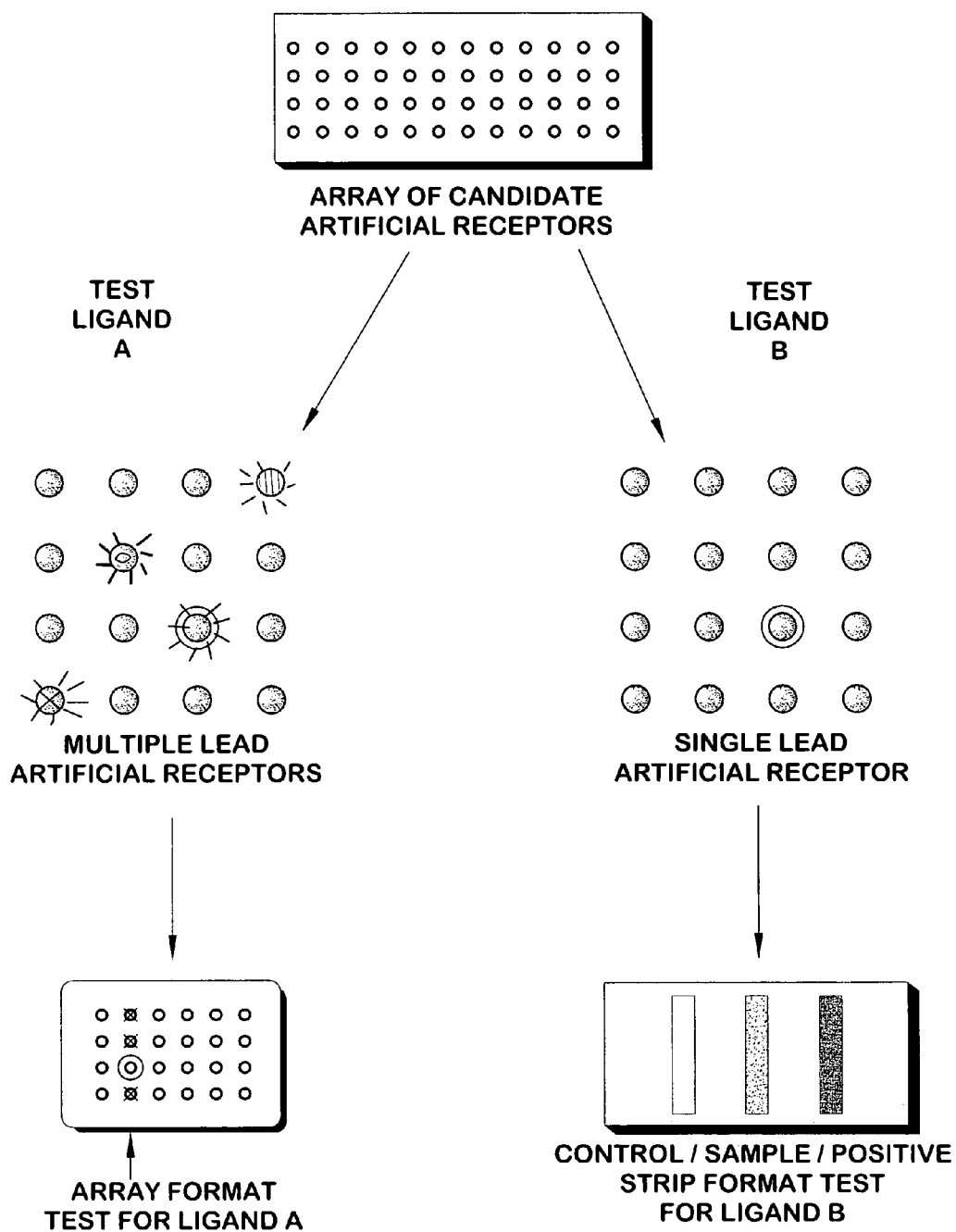
FIG. 5 schematically illustrates an embodiment of the present method employing an array of candidate artificial receptors.

FIG. 5 schematically illustrates an embodiment of the present method employing an array of candidate artificial receptors. This embodiment of the method can employ an array including a significant number of the present artificial receptors to produce an assay or system for characterizing or detecting a test ligand. The method can include evaluating an array including a significant number of candidate artificial receptors for binding to a test ligand, e.g., a molecule or cell. The building blocks making up the artificial receptors can be naïve to the test ligand. The molecule or cell can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the molecule or cell.

As illustrated in FIG. 5, a test ligand can be identified by a method employing a single or a plurality of lead or working artificial receptors. The plurality of lead or working artificial receptors suitable for identifying a test ligand can be employed in an array format test. A single lead or working artificial receptor can be configured on a support as a strip together with positive and/or negative control receptors, which can also be configured as strips.

In an embodiment, the method can include producing or employing the selected working artificial receptor or receptor complex on a substrate. The substrate can include working artificial receptors for a single test ligand or working artificial receptors for a plurality of test ligands. For example, a method can include contacting the artificial receptors with a sample. A substrate including working artificial receptors for a single test ligand can be employed in a method or system for detecting that test ligand. Binding to the working artificial receptors indicates that the sample includes the test ligand. A substrate including working artificial receptors for a plurality of test ligands can be employed in a method or system for detecting one, several, or all of the test ligands. Binding to the working artificial receptors for a particular test ligand or ligands indicates that the sample includes such test ligand or ligands.

Figure 6:
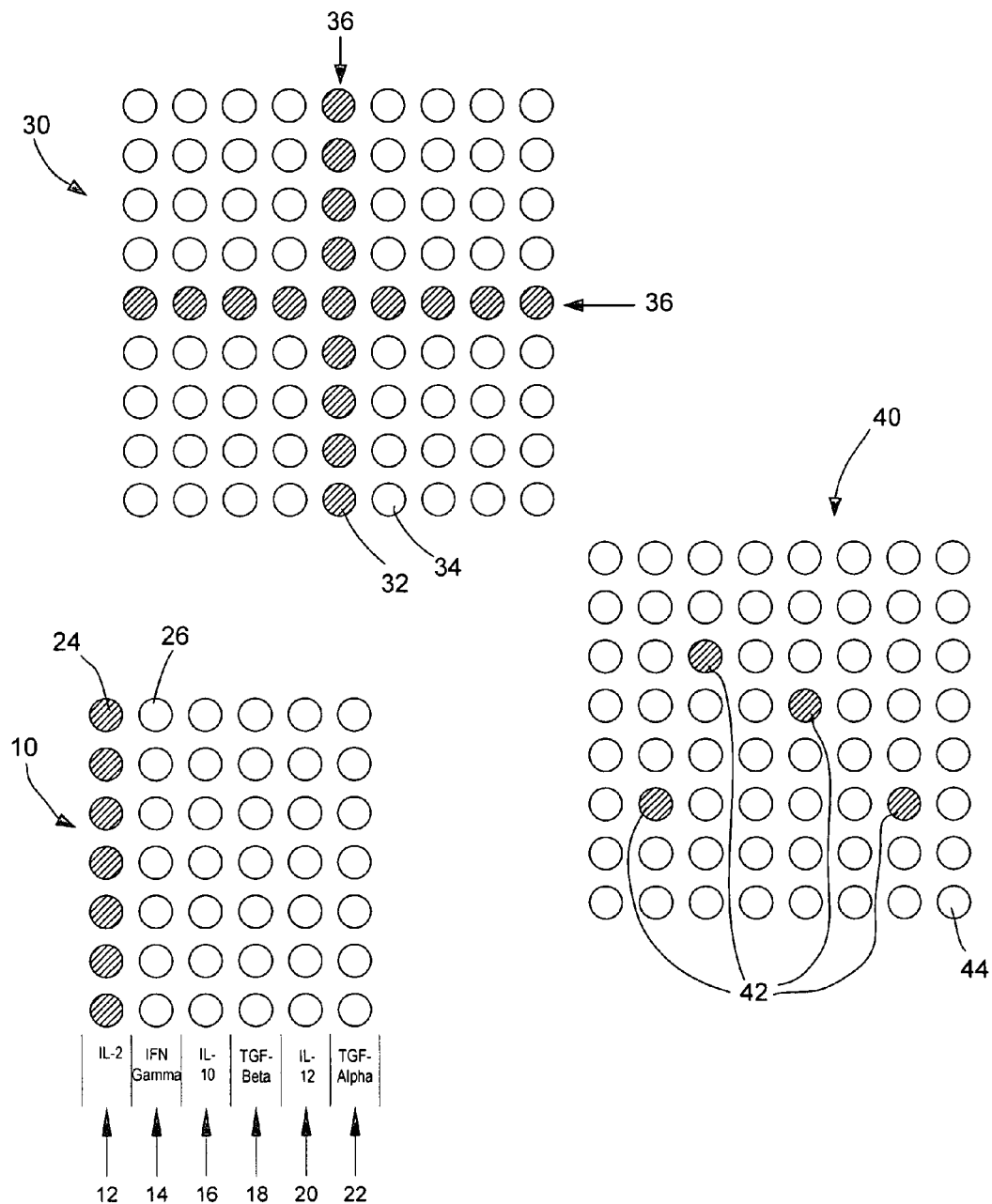
FIG. 6 schematically illustrates certain binding patterns on an array of working artificial receptors.

The working artificial receptors or receptor complexes can be configured to provide a pattern indicative of the presence of one or more of the test ligands. The method can include detecting the binding pattern of the sample and comparing it with binding patterns from known samples. FIG. 6 schematically illustrates certain binding patterns on an array of working artificial receptors. In an embodiment, all artificial receptors for one test ligand can be arranged in a line across the substrate. Referring to FIG. 6, receptors that are specific for IL-2 are in a line 12 on the array 10 of working artificial receptor complexes. Working artificial receptors that have bound a test ligand (e.g., IL-2) are indicated as shaded 24. Working artificial receptors that have not bound a test ligand are illustrated as open circles 26.

A method employing the illustrated array can include detecting binding on line 12 of working artificial receptors through fluorescence or another means described herein. In the illustrated embodiment, detecting binding on line 12 of working artificial receptors indicates that the sample contains IL-2. Further, lack of signal from the other working artificial receptors in array 10 indicates that the sample does not contain IFN-gamma, IL-10, TGF-beta, IL-12, or TGF-alpha. Thus, a method employing such an array can determine whether a sample is a particular type of biological sample or contains a particular type of molecule or cell.

When designed for use with a field assay kit, the device 30 can have spots arranged such that a positive result creates an easily recognizable pattern 36, such as a plus sign. The readily recognizable pattern can thus indicate that a particular test ligand is present in the sample. Alternatively, the artificial receptors or spots for a particular target 42 can be arranged randomly on third array 40. In this manner, when the detection device or array is used, the results of the test may not be immediately apparent to an observer but will be readily read by a machine which can be programmed to correlate binding to receptors or spots in different positions with the identity of a particular biological sample, molecule, or cell.

In an embodiment, the invention includes a method for detecting or characterizing a biological sample, a molecule, or cell. This embodiment of the method can include selecting an artificial receptor that binds the biological sample, molecule, or cell from an array of artificial receptors, contacting the artificial receptor with a test composition, and detecting binding of the artificial receptor to the test composition. In such an embodiment, binding indicates the presence of the biological sample, molecule, or cell in the test composition.

In an embodiment, the invention includes a method for detecting or characterizing a biological sample, molecule, or cell. This embodiment of the method can include contacting an array of artificial receptors with a test composition and detecting binding to the artificial receptors. Binding indicates the presence of the biological sample, molecule, or cell in the test composition.

The present method can develop or employ a plurality of working receptors specific for a particular test ligand, e.g., biological sample, molecule, or cell. That is, the working receptors can be specific for a particular test ligand, but different receptors can interact with different distinct antigens (e.g., proteins or carbohydrates), ligands, functional groups, or structural features of the test ligand. Such a method can provide a robust test for the presence of a test ligand. For example, such a robust test can reduce the chances of a false-positive or false-negative result in comparison with an assay that relies upon a single unique receptor to detect a given test ligand. Further, this embodiment of the method can develop or employ working receptors that demonstrate higher binding affinity due to interaction with multiple antigens or ligands on the same test ligand (e.g., multivalent binding).

In an embodiment, the method can employ an array including a significant number of the present artificial receptors to produce an assay or system for characterizing or detecting a polynucleotide, e.g., DNA or RNA. The method can include evaluating an array including a significant number of candidate artificial receptors for binding to the polynucleotide, e.g., DNA or RNA. The building blocks making up the artificial receptors can be naïve to the DNA or RNA. The polynucleotide, e.g., DNA or RNA, can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the polynucleotide, e.g., DNA or RNA.

In an embodiment, the method can employ an array including a significant number of the present artificial receptors to produce an assay or system for characterizing or detecting a polypeptide or peptide. The method can include evaluating an array including a significant number of candidate artificial receptors for binding to the polypeptide or peptide. The building blocks making up the artificial receptors can be naïve to the polypeptide or peptide. The polypeptide or peptide can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the polypeptide or peptide.

In an embodiment, the method can employ an array including a significant number of the present artificial receptors to produce an assay or system for characterizing or detecting a oligo- or polysaccharide. The method can include evaluating an array including a significant number of candidate artificial receptors for binding to the oligo- or polysaccharide. The building blocks making up the artificial receptors can be naïve to the oligo- or polysaccharide. The oligo- or polysaccharide can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the oligo- or polysaccharide.

In an embodiment, the method can employ an array including a significant number of the present artificial receptors to produce an assay or system for characterizing or detecting a cell, e.g., a hepatocyte. The method can include evaluating an array including a significant number of candidate artificial receptors for binding to the cell, e.g., a hepatocyte. The building blocks making up the artificial receptors can be naïve to the cell. The cell, e.g., a hepatocyte, can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the cell, e.g., a hepatocyte.

Methods of Binding or Detecting Drugs of Abuse

In an embodiment, the invention can include methods and/or devices for binding or detecting a drug of abuse. Methods and systems for detection can include methods and systems for clinical chemistry, field analysis, and diagnostic assays of all types. For example, the artificial receptor can be contacted with a sample including or suspected of including at least one drug of abuse. Then, binding of one or more of the drugs of abuse to the artificial receptors can be detected. Next, the binding results can be interpreted to provide information about the sample. In an embodiment, the invention includes a method for detecting a drug of abuse in a sample including contacting an artificial receptor specific to the drug of abuse with a sample suspected of containing the drug of abuse. The method can also include detecting or quantitating binding of the drug of abuse to the artificial receptor.

FIG. 4 schematically illustrates an embodiment of a method for evaluating candidate artificial receptors for binding to a test ligand. This embodiment of the present method can be employed for detecting a test ligand such as a drug of abuse. The method can include making an array of candidate artificial receptors. The building blocks making up the artificial receptors can be naïve to the test ligand. Working artificial receptors can be identified by contacting the array with a drug of abuse and identifying which receptors bind the drug of abuse. The method can include producing an array or device including the working artificial receptor or receptor complex. In an embodiment, the method can include employing the array or device for detecting or characterizing the drug of abuse in a sample, such as a biological, laboratory, or evidence sample.

FIG. 5 schematically illustrates an embodiment of the present method employing an array of candidate artificial receptors. This embodiment of the method can employ an array including a significant number of the present artificial receptors to produce an assay or system for characterizing or detecting a drug of abuse. The method can include evaluating an array including a significant number of candidate artificial receptors for binding to a drug of abuse. The building blocks making up the artificial receptors can be naïve to the drug of abuse. The drug of abuse can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological or field sample, or characterizing or detecting the drug of abuse.

In an embodiment, the method can include producing or employing the selected working artificial receptor or receptor complex on a substrate. The substrate can include working artificial receptors for a single drug of abuse or working artificial receptors for a plurality of drugs of abuse. For example, a method can include contacting the artificial receptors with a sample. A substrate including working artificial receptors for a single drug of abuse can be employed in a method or system for detecting that drug of abuse. Binding to the working artificial receptors indicates that the sample includes the drug of abuse. A substrate including working artificial receptors for a plurality of drugs of abuse can be employed in a method or system for detecting one, several, or all of the drugs of abuse. Binding to the working artificial receptors for a particular drug of abuse or drugs of abuse indicates that the sample includes such a drug of abuse or drugs of abuse.

The working artificial receptors or receptor complexes can be configured to provide a pattern indicative of the presence of one or more of the drugs of abuse. The method can include detecting the binding pattern of the sample and comparing it with binding patterns from known samples. FIG. 6 schematically illustrates binding patterns on an array of working artificial receptors. Such patterns and schemes can be employed for identifying a variety of test ligands including drugs of abuse.

The present method can develop or employ a plurality of working receptors specific for a particular drug of abuse or feature on the drug of abuse. That is, the working receptors can be specific for a particular drug of abuse, but different receptors can interact with different distinct ligands, functional groups, or structural features of the drug of abuse. Such a method can provide a robust test for the presence of a drug of abuse. For example, such a robust test can reduce the chances of a false-positive or false-negative result in comparison with an assay that relies upon a single unique receptor to detect a given drug of abuse. Further, this embodiment of the method can develop or employ working receptors that demonstrate higher binding affinity due to interaction with multiple ligands or features on the same drug of abuse (e.g., multivalent binding).

Suitable drugs of abuse include cannabinoids (e.g., hashish and marijuana), depressants (e.g., barbiturates, benzodiazepines, gamma-hydroxy butyrate, methaqualone), dissociative anesthetics (e.g., ketamine, PCP, and PCP analogs), hallucinogens (e.g., LSD, mescaline, psilocybin), opiates or opioids (e.g., codeine, fentanyl, fentanyl analogs, heroin, morphine, opium, oxycodone HCL, hydrocodone bitartrate), stimulants (e.g., amphetamine, cocaine, methylenedioxymethamphetamine, methamphetamine, methylphenidate, nicotine), inhalants (e.g., solvents), and the like.

Suitable drugs of abuse include performance enhancing agents, such as stimulants and beta-blockers, anabolic agents, oxygen carrier enhancers, masking agents, and inhalants. Suitable stimulants include caffeine and amphetamines. Suitable beta-blockers include salbutamol (used in asthma inhalers) and the like. Suitable anabolic agents include steroids (e.g., anabolic steroids), steroid analogs, and growth hormone. Suitable oxygen carrier enhancers include erythropoietin and the like.

Methods of Binding or Detecting Isomers

In an embodiment, the invention can include methods and/or devices for binding or detecting an isomer or isomers of a compound. Methods and systems for detection can include methods and systems for clinical chemistry, environmental analysis, and diagnostic assays of all types. For example, the artificial receptor can be contacted with a sample including or suspected of including at least one isomer of a compound. Then, binding of one or more of the isomers of a compound to the artificial receptor can be detected. Next, the binding results can be interpreted to provide information about the isomers. In an embodiment, the invention includes a method for detecting an isomer of a compound in a sample including contacting an artificial receptor specific to the isomer with a sample suspected of containing the isomer. The method can also include detecting or quantitating binding of the isomer to the artificial receptor.

The present method can be applied to isomers such as stereoisomers (e.g., geometric isomers or optical isomers), optical isomers (e.g., enantiomers and diastereomers), geometric isomers (e.g., cis- and trans-isomers). The present method can be employed to develop working or lead artificial receptors or working artificial complexes that can bind to one or more isomers of a compound (e.g., enantioselective receptor environments). For example, the artificial receptor or complex can bind to one stereoisomer of a compound but bind only weakly or not at all another stereoisomer of the compound. For example, the artificial receptor or complex can bind one geometric isomer of a compound but bind only weakly or not at all another geometric isomer. For example, the artificial receptor or complex can bind one optical isomer of a compound but bind only weakly or not at all another optical isomer. For example, the artificial receptor or complex can bind one enantiomer of a compound but bind only weakly or not at all another enantiomer. For example, the artificial receptor or complex can bind one diastereomer of a compound but bind only weakly or not at all another diastereomer.

FIG. 4 schematically illustrates an embodiment of a method for evaluating candidate artificial receptors for binding to a test ligand. This embodiment of the present method can be employed for detecting a test ligand such as an isomer of a compound. The method can include making an array of candidate artificial receptors. The building blocks making up the artificial receptors can be naïve to the test ligand. Working artificial receptors can be identified by contacting the array with an isomer and identifying which receptors bind the isomer. The method can include producing an array or device including the working artificial receptor or receptor complex. In an embodiment, the method can include employing the array or device for detecting or characterizing the isomer in a sample, such as a biological, laboratory, or clinical sample.

FIG. 5 schematically illustrates an embodiment of the present method employing an array of candidate artificial receptors. This embodiment of the method can employ an array including a significant number of the present artificial receptors to produce an assay or system for characterizing or detecting an isomer. The method can include evaluating an array including a significant number of candidate artificial receptors for binding to an isomer. The building blocks making up the artificial receptors can be naïve to the isomer. The isomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological, clinical, or laboratory sample, or characterizing or detecting the isomer.

In an embodiment, the method can include producing or employing the selected working artificial receptor or receptor complex on a substrate. The substrate can include working artificial receptors for a single isomer or working artificial receptors for a plurality of isomers. For example, a method can include contacting the artificial receptors with a sample. A substrate including working artificial receptors for a single isomer can be employed in a method or system for detecting that isomer. Binding to the working artificial receptors indicates that the sample includes the isomer. A substrate including working artificial receptors for a plurality of isomers can be employed in a method or system for detecting one, several, or all of the isomers. Binding to the working artificial receptors for a particular isomer or isomers indicates that the sample includes such an isomer or isomers.

The working artificial receptors or receptor complexes can be configured to provide a pattern indicative of the presence of one or more of the isomers. The method can include detecting the binding pattern of the sample and comparing it with binding patterns from known samples. FIG. 6 schematically illustrates binding patterns on an array of working artificial receptors. Such patterns and schemes can be employed for identifying a variety of test ligands including isomers.

In an embodiment, the method can employ an array including a significant number of the present artificial receptors to produce an assay or system for characterizing or detecting a stereoisomer. The method can include evaluating an array including a significant number of candidate artificial receptors for binding to the stereoisomer. The building blocks making up the artificial receptors can be naïve to the stereoisomer. The stereoisomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a lab or clinical sample or characterizing or detecting the stereoisomer.

In an embodiment, the method can employ an array including a significant number of the present artificial receptors to produce an assay or system for characterizing or detecting a geometric isomer (e.g., cis- and trans-isomers). The method can include evaluating an array including a significant number of candidate artificial receptors for binding to the geometric isomer (e.g., cis- and trans-isomers). The building blocks making up the artificial receptors can be naïve to the geometric isomer. The geometric isomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a lab or clinical sample or characterizing or detecting the geometric isomer (e.g., cis- and trans-isomers).

In an embodiment, the method can employ an array including a significant number of the present artificial receptors to produce an assay or system for characterizing or detecting an optical isomer. The method can include evaluating an array including a significant number of candidate artificial receptors for binding to the optical isomer. The building blocks making up the artificial receptors can be naïve to the optical isomer. The optical isomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a lab or clinical sample or characterizing or detecting the optical isomer.

In an embodiment, the method can employ an array including a significant number of the present artificial receptors to produce an assay or system for characterizing or detecting an enantiomer. The method can include evaluating an array including a significant number of candidate artificial receptors for binding to the enantiomer. The enantiomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a lab or clinical sample or characterizing or detecting the enantiomer.

In an embodiment, the method can employ an array including a significant number of the present artificial receptors to produce an assay or system for characterizing or detecting a diastereomer. The method can include evaluating an array including a significant number of candidate artificial receptors for binding to the diastereomer. The building blocks making up the artificial receptors can be naïve to the diastereomer. The diastereomer can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a lab or clinical sample or characterizing or detecting the diastereomer.

Methods for Binding or Detecting Peptides

In an embodiment, the invention can include methods and/or devices for binding or detecting a peptide. Methods and systems for detection can include methods and systems for clinical chemistry, environmental analysis, and diagnostic assays of all types. For example, the artificial receptor can be contacted with a sample including or suspected of including at least one peptide. Then, binding of one or more of the peptides to the artificial receptors can be detected. Next, the binding results can be interpreted to provide information about the sample. In an embodiment, the invention includes a method for detecting a peptide in a sample including contacting an artificial receptor specific to the peptide with a sample suspected of containing the peptide. The method can also include detecting or quantitating binding of the peptide to the artificial receptor.

FIG. 4 schematically illustrates an embodiment of a method for evaluating candidate artificial receptors for binding to a test ligand. This embodiment of the present method can be employed for detecting a test ligand such as a peptide. The method can include making an array of candidate artificial receptors. The building blocks making up the artificial receptors can be naïve to the test ligand. Working artificial receptors can be identified by contacting the array with a peptide and identifying which receptors bind the peptide. The method can include producing an array or device including the working artificial receptor or receptor complex. In an embodiment, the method can include employing the array or device for detecting or characterizing the peptide in a sample, such as a biological, laboratory, or clinical sample.

FIG. 5 schematically illustrates an embodiment of the present method employing an array of candidate artificial receptors. This embodiment of the method can employ an array including a significant number of the present artificial receptors to produce an assay or system for characterizing or detecting a peptide. The method can include evaluating an array including a significant number of candidate artificial receptors for binding to a peptide. The building blocks making up the artificial receptors can be naïve to the peptide. The peptide can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological or environmental sample, or characterizing or detecting the peptide.

Figure 7:
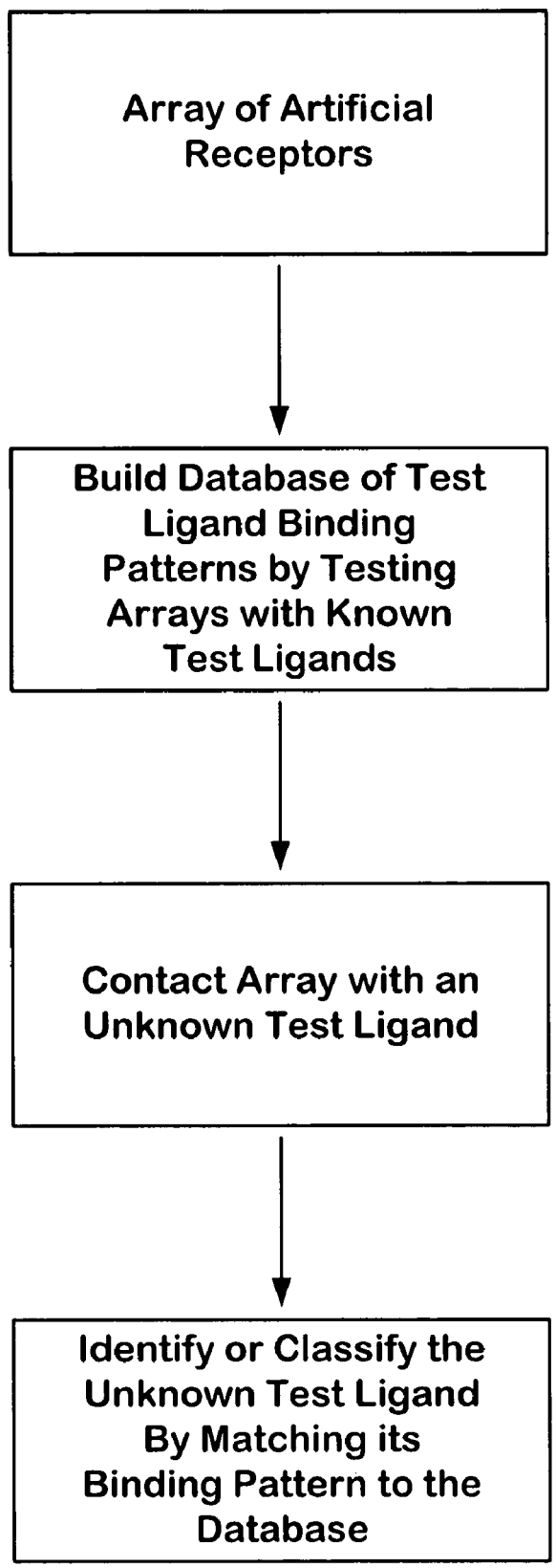
FIG. 7 schematically illustrates an embodiment of a method for developing a method and system for detecting a test ligand.
Figure 8:
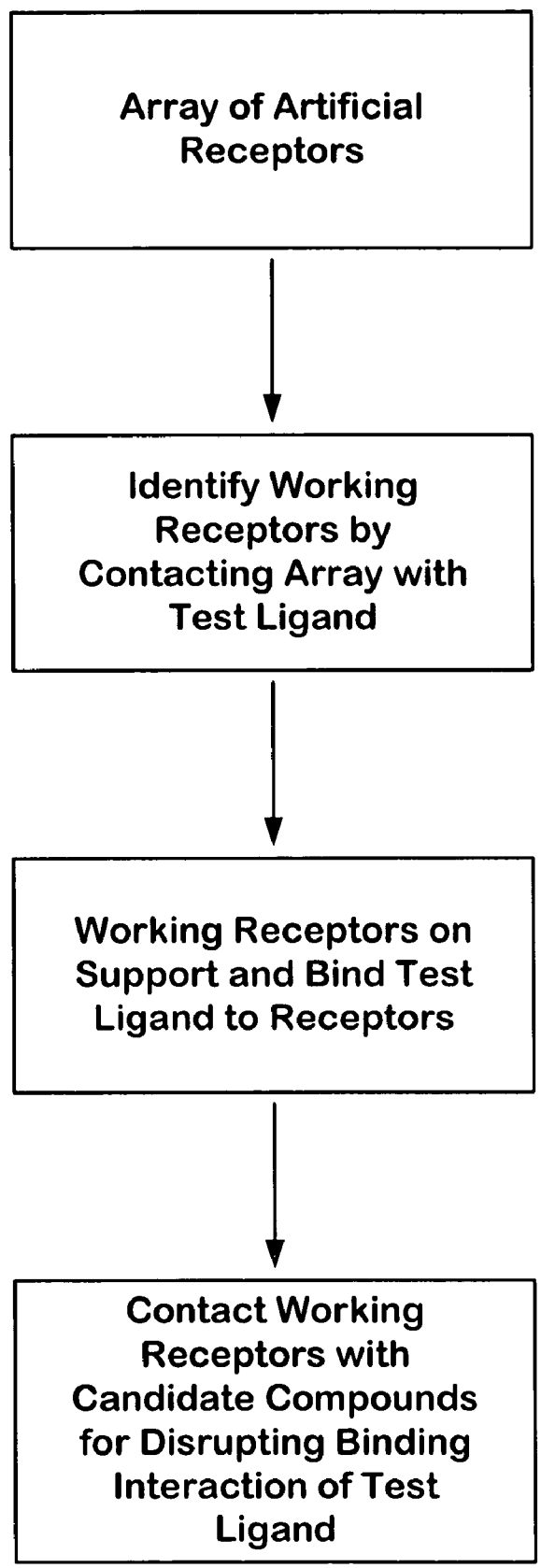
FIG. 8 schematically illustrates an embodiment of a method for detecting an agent that disrupts a binding interaction of a target molecule.

FIG. 7 schematically illustrates an embodiment of a method for developing a method and system for detecting a test ligand, such as a peptide or mixture of peptides. This embodiment of the present method includes evaluating a plurality (e.g. array) of candidate artificial receptors for binding to each of a plurality of peptides. The building blocks making up the artificial receptors can be naïve to one or more of the peptides. The plurality of peptides can include the peptides found in a cell or organism. The method can include detecting binding of individual peptides to a subset of the plurality or array of candidate artificial receptors. The method can include detecting binding of the peptides found in a cell or organism to a subset of or all of the plurality or array of candidate artificial receptors. This can be envisioned as developing a working artificial receptor or artificial receptor complex for each peptide or mixture of peptides.

Thus, each peptide or mixture of peptides can provide a pattern of bound receptors in the plurality or array. The pattern of bound receptors can be characteristic of the peptide or mixture of peptides or a sample including the peptide or mixture of peptides. The method can include storing a representation of the binding pattern as an image or a data structure. The representation of the binding pattern can be evaluated either by an operator or data processing system. The method can include such evaluating. A binding pattern from an unknown sample that matches the binding pattern for a particular peptide then characterizes the unknown sample as containing that peptide. A binding pattern from an unknown sample that matches the binding pattern for a particular mixture of peptides then characterizes the unknown sample as including or being that mixture of peptides or as including or being the organism or cell containing that mixture of peptides. A plurality of binding patterns can be stored as a database.

An embodiment of the illustrated method can include creating an array of artificial receptors. This embodiment can also include compiling a database of the binding patterns of a specific peptide or mixture of peptides, for example, by probing the array with a plurality of individual peptides or the peptides found in a cell or organism. Contacting the array with an unidentified peptide or mixture of peptides can create a test binding pattern. The method can then compare the test binding pattern with the binding patterns of known peptides or mixtures of peptides in the database in order to characterize or classify the unidentified peptide, mixture of peptides, or cell or organism. In an embodiment, the database and the array of receptors has already been constructed and the method involves probing the array with an unknown peptide or mixture of peptides to create a test binding pattern and then comparing this binding pattern with the binding patterns in the database in order to characterize or classify the unidentified peptide, mixture of peptides, or cell or organism.

An array constructed for distinguishing mixtures of peptides can be contacted with samples from an organism, cell, or tissue of interest. Peptides that bind to the array can characterize or detect the organism, cell or tissue; can indicate a disorder caused by the organism or affecting the cell or tissue; can indicate successful therapy of a disorder caused by the organism or affecting the cell or tissue; characterize disease processes; identify therapeutic leads or strategies; or the like.

In an embodiment, the method can include producing or employing the selected working artificial receptor or receptor complex on a substrate. The substrate can include working artificial receptors for a single peptide or working artificial receptors for a plurality of peptides. For example, a method can include contacting the artificial receptors with a sample. A substrate including working artificial receptors for a single peptide can be employed in a method or system for detecting that peptide. Binding to the working artificial receptors indicates that the sample includes the peptide. A substrate including working artificial receptors for a plurality of peptides can be employed in a method or system for detecting one, several, or all of the peptides. Binding to the working artificial receptors for a particular peptide or peptides indicates that the sample includes such a peptide or peptides.

The working artificial receptors or receptor complexes can be configured to provide a pattern indicative of the presence of one or more of the peptides. The method can include detecting the binding pattern of the sample and comparing it with binding patterns from known samples. FIG. 6 schematically illustrates binding patterns on an array of working artificial receptors. Such patterns and schemes can be employed for identifying a variety of test ligands including peptides.

The present method can develop or employ a plurality of working receptors specific for a particular peptide or feature on the peptide. That is, the working receptors can be specific for a particular peptide, but different receptors can interact with different distinct ligands, functional groups, or structural features of the peptide. Such a method can provide a robust test for the presence of a peptide. For example, such a robust test can reduce the chances of a false-positive or false-negative result in comparison with an assay that relies upon a single unique receptor to detect a given peptide. Further, this embodiment of the method can develop or employ working receptors that demonstrate higher binding affinity due to interaction with multiple ligands or features on the same peptide (e.g., multivalent binding).

In an embodiment, the method can employ an array including a significant number of the present artificial receptors to produce an assay or system for characterizing or detecting a peptide. The method can include evaluating an array including a significant number of candidate artificial receptors for binding to the peptide. The building blocks making up the artificial receptors can be naïve to the test ligand. The peptide can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the peptide.

The present method can include selecting artificial receptors that bind a particular peptide and/or the building blocks making up these receptors (e.g., bound to a scaffold molecule) as leads for pharmaceutical development or as active agents for modulating an activity of that peptide. The artificial receptor or building blocks making up that artificial receptor can be selected to bind to a portion of a peptide required for its interaction with an other macromolecule (e.g. carbohydrate, protein, or polynucleotide), thus disrupting this interaction.

Methods for Binding or Detecting Protein or Proteome

In an embodiment, the invention can include methods and/or devices for binding or detecting a protein, one or more of a plurality of proteins, or a proteome. Methods and systems for detection can include methods and systems for clinical chemistry, environmental analysis, diagnostic assays, and for proteome analysis. For example, the artificial receptor can be contacted with a sample including at least one protein or one proteome. The building blocks making up the artificial receptors can be naïve to the test ligand. Then, binding of one or more proteins to the artificial receptors can be detected. Next, the binding results can be interpreted to provide information about the sample, e.g., the proteome. In an embodiment, the invention includes a method for detecting a protein in a sample including contacting an artificial receptor specific to the protein with a sample suspected of containing the protein. The method can also include detecting or quantitating binding of the protein to the artificial receptor.

FIG. 4 schematically illustrates an embodiment of a method for evaluating candidate artificial receptors for binding to a test ligand. This embodiment of the present method can be employed for detecting a test ligand such as one or more proteins. The method can include making an array of candidate artificial receptors. The building blocks making up the artificial receptors can be naïve to the test ligand. Working artificial receptors can be identified by contacting the array with a protein and identifying which receptors bind the protein. The method can include producing an array or device including the working artificial receptor or receptor complex. In an embodiment, the method can include employing the array or device for detecting or characterizing the protein in a sample, such as a biological, laboratory, or environmental sample.

In an embodiment, the method can include producing or employing the selected working artificial receptor or receptor complex on a substrate. The substrate can include working artificial receptors for a single protein or working artificial receptors for a plurality of proteins. For example, a method can include contacting the artificial receptors with a sample. A substrate including working artificial receptors for a single protein can be employed in a method or system for detecting that protein. Binding to the working artificial receptors indicates that the sample includes the protein. A substrate including working artificial receptors for a plurality of proteins can be employed in a method or system for detecting one, several, or all of the proteins. Binding to the working artificial receptors for a particular protein or protein indicates that the sample includes such a protein or protein.

The working artificial receptors or receptor complexes can be configured to provide a pattern indicative of the presence of one or more of the proteins. The method can include detecting the binding pattern of the sample and comparing it with binding patterns from known samples. FIG. 6 schematically illustrates binding patterns on an array of working artificial receptors. Such patterns and schemes can be employed for identifying a variety of test ligands including proteins.

FIG. 7 schematically illustrates an embodiment of a method for developing a method and system for detecting a test ligand, such as a protein or proteome. This embodiment of the present method includes evaluating a plurality (e.g. array) of candidate artificial receptors for binding to each of a plurality of test ligands. The building blocks making up the artificial receptors can be naïve to the test ligand. The plurality of test ligands can include a plurality of proteins. The plurality of test ligands can include the proteins making up the proteome of a cell or organism. The method can include detecting binding of individual proteins to a subset of the plurality or array of candidate artificial receptors. The method can include detecting binding of proteins making up the proteome to a subset of or all of the plurality or array of candidate artificial receptors. This can be envisioned as developing a working artificial receptor or artificial receptor complex for each protein or for the proteome.

Thus, each protein or proteome can provide a pattern of bound receptors in the plurality or array. The pattern of bound receptors can be characteristic of the protein or proteome or a sample including the protein or proteome. The method can include storing a representation of the binding pattern as an image or a data structure. The representation of the binding pattern can be evaluated either by an operator or data processing system. The method can include such evaluating. A binding pattern from an unknown sample that matches the binding pattern for a particular protein then characterizes the unknown sample as containing that protein. A binding pattern from an unknown sample that matches the binding pattern for a particular proteome then characterizes the unknown sample as including or being that proteome or as including or being the organism or cell having that proteome. Similarly, a binding pattern from an unknown sample can be evaluated against the patterns of a plurality of particular proteins or proteomes and the sample can be characterized as containing one or more of the proteins or proteomes. A plurality of binding patterns can be stored as a database.

An embodiment of the illustrated method can include creating an array of artificial receptors. This embodiment can also include compiling a database of the binding patterns of specific proteins or proteomes, for example, by probing the array with a plurality of individual proteins or proteomes. Contacting the array with unidentified proteins or proteomes can create a test binding pattern. The method can then compare the test binding pattern with the binding patterns of known proteins or proteomes in the database in order to characterize or classify the unidentified protein, proteome, or cell or organism. In an embodiment, the database and the array of receptors has already been constructed and the method involves probing the array with an unknown protein or proteome to create a test binding pattern and then comparing this binding pattern with the binding patterns in the database in order to characterize or classify the unidentified protein, proteome, or cell or organism.

A proteome array can be contacted with samples from an organism, cell, or tissue of interest. Proteins that bind to the proteome array can characterize or detect the organism, cell or tissue; can indicate a disorder caused by the organism or affecting the cell or tissue; can indicate successful therapy of a disorder caused by the organism or affecting the cell or tissue; characterize disease processes; identify therapeutic leads or strategies; or the like.

The present method can develop or employ a plurality of working receptors specific for a particular protein or feature on the protein. That is, the working receptors can be specific for a particular protein, but different receptors can interact with different distinct ligands, functional groups, or structural features of the protein. Such a method can provide a robust test for the presence of a protein. For example, such a robust test can reduce the chances of a false-positive or false-negative result in comparison with an assay that relies upon a single unique receptor to detect a given protein. Further, this embodiment of the method can develop or employ working receptors that demonstrate higher binding affinity due to interaction with multiple ligands or features on the same protein (e.g., multivalent binding).

In an embodiment, the method can employ an array including a significant number of the present artificial receptors to produce an assay or system for characterizing or detecting a protein. The method can include evaluating an array including a significant number of candidate artificial receptors for binding to the protein. The building blocks making up the artificial receptors can be naïve to the test ligand. The protein can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the protein.

The present method can include selecting artificial receptors that bind a particular protein and/or the building blocks making up these receptors (e.g., bound to a scaffold molecule) as leads for pharmaceutical development or as active agents for modulating an activity of that protein. The artificial receptor or building blocks making up that artificial receptor can be selected to bind to or disrupt the activity of the active site of an enzyme or the ligand binding site of a receptor. The artificial receptor or building blocks making up that artificial receptor can be selected to bind to a portion of a protein required for its interaction with an other macromolecule (e.g. carbohydrate, protein, or polynucleotide), thus disrupting this interaction. The artificial receptor or building blocks making up that artificial receptor can be selected to bind to the binding site of a receptor and act as an agonist of that receptor.

The present method can include selecting working artificial receptors that bind a preselected protein for use in a system for proteome analysis. The working artificial receptors for the preselected protein can be provided on a substrate and the protein bound to the receptors. In an embodiment, selecting and binding employ a plurality of different working artificial receptors for the preselected protein. The plurality of artificial receptors may bind to different features on the preselected protein and leave free different features on the preselected protein. This embodiment of the method includes contacting the working receptors with bound preselected protein to at least one candidate binding partner for the preselected protein. The method can include detecting binding or absence of binding of the candidate binding partner to the preselected protein. A candidate binding partner that binds to the preselected protein can be considered a lead binding partner.

In an embodiment, the method includes contacting the working receptors with bound preselected protein with a proteome of a cell or organism serving as the source of candidate binding partners. The method can then recover from the proteome one or more lead binding partners. This can then characterize the proteome as containing or not a binding partner for the preselected protein.

In an embodiment, the present artificial receptors can be employed in studies of proteomics. In such an embodiment, an array of candidate or working artificial receptors can be contacted with a mixture of peptides, polypeptides, and/or proteins. Each mixture can produce a characteristic fingerprint of binding to the array. In addition, identification of a specific receptor environment for a target peptide, polypeptide, and/or protein can be utilized for isolation and analysis of the target. That is, in yet another embodiment, a particular receptor surface can be employed for affinity purification methods, e.g. affinity chromatography.

In an embodiment, the present candidate artificial receptors can be employed to find receptor surfaces that bind proteins in a preferred configuration or orientation. Many proteins (e.g. antibodies, enzymes, receptors) are stable and/or active in specific environments. Defined receptor surfaces can be used to produce binding environments that selectively retain or orient the protein for maximum stability and/or activity. In an embodiment, the present artificial receptors can be employed to form bioactive surfaces. For example, receptor surfaces can be used to specifically bind the active conformation of an antibody or enzyme.

In an embodiment, the present method can include labeling a protein while it remains bound to an artificial receptor. The resulting protein will be labeled on its portions accessible to the labeling reagent but not on those portions bound to the artificial receptor. The method can include releasing the labeled protein from the artificial receptor. Determining the distribution of labels on the protein indicates which portion of the protein was bound to the receptor.

In certain embodiments, the present artificial receptors can be employed to distinguish between two conformations of a single protein. Certain proteins exist in two or more stable conformations. In an embodiment, the present working artificial receptor or complex can bind a first conformation of a protein. In an embodiment, the present working artificial receptor or complex can bind a second conformation of a protein. In an embodiment, the present working artificial receptor or complex can bind a first conformation of a protein, but not a second conformation of the same protein. In an embodiment, the present working artificial receptor or complex can bind a second conformation of a protein, but not a first conformation of the same protein.

For example, in an embodiment, the present working artificial receptor or complex can bind a first or non-infectious conformation of a prion, but not its second or infectious conformation. For example, in an embodiment, the present working artificial receptor or complex can bind the second or infectious conformation of a prion, but not its first or non-infectious conformation. For example, in an embodiment, the present working artificial receptor or complex can bind a first or non-plaque-forming conformation of β-amyloid, but not its second or plaque-forming conformation. For example, in an embodiment, the present working artificial receptor or complex can bind a second or plaque-forming conformation of β-amyloid, but not its second or non-plaque-forming conformation.

In an embodiment, the method can employ an array including a significant number of the present artificial receptors to produce an assay or system for characterizing or detecting a desired conformation of a protein. The method can include evaluating an array including a significant number of candidate artificial receptors for binding to the desired conformation of the protein. The building blocks making up the artificial receptors can be naïve to the protein or its desired conformation. The desired conformation of the protein can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the desired conformation of the protein.

In an embodiment, the method can employ an array including a significant number of the present artificial receptors to produce an assay or system for characterizing or detecting a first or non-infectious conformation of a prion. The method can include evaluating an array including a significant number of candidate artificial receptors for binding to the first or non-infectious conformation of a prion. The building blocks making up the artificial receptors can be naïve to the prion. The first or non-infectious conformation of a prion can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the first or non-infectious conformation of a prion.

In an embodiment, the method can employ an array including a significant number of the present artificial receptors to produce an assay or system for characterizing or detecting a second or infectious conformation of a prion. The method can include evaluating an array including a significant number of candidate artificial receptors for binding to the second or infectious conformation of a prion. The building blocks making up the artificial receptors can be naïve to the test ligand. The second or infectious conformation of a prion can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the second or infectious conformation of a prion.

In an embodiment, the present method includes developing receptors or a receptor system that can distinguish between the first or non-infectious conformation of a prion and the second or infectious conformation of the prion. Such a method can include selecting a working artificial receptor or complex can that bind the first or non-infectious conformation of a prion, but not the second or infectious conformation of the prion. This embodiment can include selecting a working artificial receptor or complex can that bind the second or infectious conformation of a prion, but not the first or non-infectious conformation of the prion. Employed together, these two sets of working artificial receptors or systems can characterize a biological sample as containing one or both forms of the prion.

In an embodiment, the method can employ an array including a significant number of the present artificial receptors to produce an assay or system for characterizing or detecting a first or non-plaque-forming conformation of a β-amyloid. The method can include evaluating an array including a significant number of candidate artificial receptors for binding to the first or non-plaque-forming conformation of the β-amyloid. The building blocks making up the artificial receptors can be naïve to the β-amyloid. The first or non-plaque-forming conformation of the β-amyloid can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the first or non-plaque-forming conformation of the β-amyloid.

In an embodiment, the method can employ an array including a significant number of the present artificial receptors to produce an assay or system for characterizing or detecting a second or plaque-forming conformation of a β-amyloid. The method can include evaluating an array including a significant number of candidate artificial receptors for binding to the second or plaque-forming conformation of a β-amyloid. The building blocks making up the artificial receptors can be naïve to the β-amyloid. The second or plaque-forming conformation of the β-amyloid can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the second or plaque-forming conformation of the β-amyloid.

In an embodiment, the present method includes developing receptors or a receptor system that can distinguish between the first or non-plaque-forming conformation of β-amyloid and the second or plaque-forming conformation of the β-amyloid. Such a method can include selecting a working artificial receptor or complex can that bind the first or non-plaque-forming conformation of β-amyloid, but not the second or plaque-forming conformation of the β-amyloid. This embodiment can include selecting a working artificial receptor or complex can that bind the second or plaque-forming conformation of the β-amyloid, but not the first or non-plaque-forming conformation of β-amyloid. Employed together, these two sets of working artificial receptors or systems can characterize a biological sample as containing one or both forms of the β-amyloid.

In an embodiment, the method can employ an array including a significant number of the present artificial receptors to produce an assay or system for characterizing or detecting cholera toxin. The method can include evaluating an array including a significant number of candidate artificial receptors for binding to the cholera toxin. The building blocks making up the artificial receptors can be naïve to the test ligand. The cholera toxin can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting cholera toxin.

In an embodiment, the method can employ an array including a significant number of the present artificial receptors to produce an assay or system for characterizing or detecting at least one protein of a cancer cell. The method can include evaluating an array including a significant number of candidate artificial receptors for binding to the cancer cell protein. The building blocks making up the artificial receptors can be naïve to the test ligand. The cancer cell protein can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the cancer cell protein.

In an embodiment, the present method can include contacting a working artificial receptor or array with a sample from cells or tissues suspected of being cancerous or including a tumor. The sample can be serum. Binding of at least one protein to the working artificial receptor or array can indicate or characterize the presence of the particular cancer or tumor, such as by characterizing the pattern of proteins present.

Cancers that can be detected or characterized by such a method include, for example, bladder cancer, breast cancer, colon cancer, kidney cancer, liver cancer, lung cancer, including small cell lung cancer, esophageal cancer, gall-bladder cancer, ovarian cancer, pancreatic cancer, stomach cancer, cervical cancer, thyroid cancer, prostate cancer, and skin cancer, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderoma pigmentosum, keratoctanthoma, thyroid follicular cancer, Kaposi's sarcoma, and the like.

Methods of Binding or Detecting Microbes

In an embodiment, the invention can include methods and/or devices for binding or detecting a microbe, e.g., cell or virus. Methods and systems for detection can include methods and systems for clinical chemistry, environmental analysis, and diagnostic assays of all types. For example, the artificial receptor can be contacted with a sample including or suspected of including at least one microbe, e.g., cell or virus. The building blocks making up the artificial receptors can be naïve to the test ligand. Then, binding of one or more of the microbes to the artificial receptors can be detected. Next, the binding results can be interpreted to provide information about the sample. In an embodiment, the invention includes a method for detecting a microbe, e.g., cell or virus, in a sample including contacting an artificial receptor specific to the microbe, e.g., cell or virus, with a sample suspected of containing the microbe, e.g., cell or virus. The method can also include detecting or quantitating binding of the microbe, e.g., cell or virus, to the artificial receptor.

FIG. 4 schematically illustrates an embodiment of a method for evaluating candidate artificial receptors for binding to a test ligand. This embodiment of the present method can be employed for detecting a test ligand such as a microbe, e.g., cell or virus. The method can include making an array of candidate artificial receptors. The building blocks making up the artificial receptors can be naïve to the test ligand. Working artificial receptors can be identified by contacting the array with a microbe, e.g., cell or virus, and identifying which receptors bind the microbe. The method can include producing an array or device including the working artificial receptor or receptor complex. In an embodiment, the method can include employing the array or device for detecting or characterizing the microbe, e.g., cell or virus, in a sample, such as a biological, laboratory, or environmental sample.

FIG. 5 schematically illustrates an embodiment of the present method employing an array of candidate artificial receptors. This embodiment of the method can employ an array including a significant number of the present artificial receptors to produce an assay or system for characterizing or detecting a microbe, e.g., cell or virus. The method can include evaluating an array including a significant number of candidate artificial receptors for binding to a microbe, e.g., cell or virus. The building blocks making up the artificial receptors can be naïve to the test ligand. The microbe can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the microbe, e.g., cell or virus.

FIG. 7 schematically illustrates an embodiment of a method for developing a method and system for detecting a test ligand, such as a disease causing organism. This embodiment of the present method includes evaluating a plurality (e.g. array) of candidate artificial receptors for binding to each of a plurality of test ligands, such as disease causing organisms. The building blocks making up the artificial receptors can be naïve to the test ligands. The method can include detecting binding of each test ligand (e.g., disease causing organism) to a subset of the plurality or array of candidate artificial receptors. This can be envisioned as developing a working artificial receptor or artificial receptor complex for each of the plurality of test ligands.

Thus, each test ligand (e.g., disease causing organism) can provide a pattern of bound receptors in the plurality or array. The pattern of bound receptors can be characteristic of the test ligand or a sample including the test ligand. The method can include storing a representation of the binding pattern as an image or a data structure. The representation of the binding pattern can be evaluated either by an operator or data processing system. The method can include such evaluating. A binding pattern from an unknown sample that matches the binding pattern for a particular test ligand (e.g., disease causing organism) then characterizes the unknown sample as containing that test ligand. Similarly, a binding pattern from an unknown sample can be evaluated against the patterns of a plurality of particular test ligands and the sample can be characterized as containing one or more of the test ligands. A plurality of binding patterns can be stored as a database.

An embodiment of the illustrated method can include creating an array of artificial receptors. This embodiment can also include compiling a database of the binding patterns of specific disease causing organisms, for example, by probing the array with a plurality of individual organisms. Contacting the array with an unidentified organism can create a test binding pattern. The method can then compare the test binding pattern with the binding patterns of known organisms in the database in order to characterize or classify the unidentified organism. In an embodiment, the database and the array of receptors has already been constructed and the method involves probing the array with an unknown organism to create a test binding pattern and then comparing this binding pattern with the binding patterns in the database in order to characterize or classify the unidentified organism.

In an embodiment, the method can include producing or employing the selected working artificial receptor or receptor complex on a substrate. The substrate can include working artificial receptors for a single microbe, e.g., cell or virus, or working artificial receptors for a plurality of microbes, e.g., cells or viruses. For example, a method can include contacting the artificial receptors with a sample. A substrate including working artificial receptors for a single microbe, e.g., cell or virus, can be employed in a method or system for detecting that microbe. Binding to the working artificial receptors indicates that the sample includes the microbe. A substrate including working artificial receptors for a plurality of microbes, e.g., cells or viruses can be employed in a method or system for detecting one, several, or all of the microbes. Binding to the working artificial receptors for a particular microbe or microbes indicates that the sample includes such a microbe or microbes.

The working artificial receptors or receptor complexes can be configured to provide a pattern indicative of the presence of one or more of the microbes, e.g., cells or viruses. The method can include detecting the binding pattern of the sample and comparing it with binding patterns from known samples. FIG. 6 schematically illustrates binding patterns on an array of working artificial receptors. Such patterns and schemes can be employed for identifying a variety of test ligands including microbes.

The present method can develop or employ a plurality of working receptors specific for a particular microbe or feature on the microbe. That is, the working receptors can be specific for a particular microbe, but different receptors can interact with different distinct antigens (e.g., proteins or carbohydrates), ligands, or features of the microbe. Such a method can provide a robust test for the presence of a microbe. For example, such a robust test can reduce the chances of a false-positive or false-negative result in comparison with an assay that relies upon a single unique receptor to detect a given microbe. Further, this embodiment of the method can develop or employ working receptors that demonstrate higher binding affinity due to interaction with multiple antigens or ligands on the same microbe (e.g., multivalent binding).

In an embodiment, the method can employ an array including a significant number of the present artificial receptors to produce an assay or system for characterizing or detecting a bacterium. The method can include evaluating an array including a significant number of candidate artificial receptors for binding to the bacterium. The building blocks making up the artificial receptors can be naïve to the test ligand. The bacterium can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or characterizing or detecting the bacterium.

In an embodiment, the method can employ an array including a significant number of the present artificial receptors to produce an assay or system for characterizing or detecting a virus particle. The method can include evaluating an array including a significant number of candidate artificial receptors for binding to the virus particle. The building blocks making up the artificial receptors can be naïve to the test ligand. The virus particle can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample or for characterizing or detecting the virus particle.

In an embodiment, the method can employ an array including a significant number of the present artificial receptors to produce an assay or system for characterizing or detecting a biohazard. The method can include evaluating an array including a significant number of candidate artificial receptors for binding to the biohazard. The building blocks making up the artificial receptors can be naïve to the test ligand. The biohazard can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the biohazard.

In an embodiment, the method can employ an array including a significant number of the present artificial receptors to produce an assay or system for characterizing or detecting the *Vibrio cholerae*. The method can include evaluating an array including a significant number of candidate artificial receptors for binding to *V. cholerae*. The building blocks making up the artificial receptors can be naïve to the *V. cholerae*. The *V. cholerae* can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting *V. cholerae*.

In an embodiment, the method can employ an array including a significant number of the present artificial receptors to produce an assay or system for characterizing or detecting a microbe. The method can include evaluating an array including a significant number of candidate artificial receptors for binding to the microbe. The building blocks making up the artificial receptors can be naïve to the test ligand. One or more artificial receptors that bind the microbe under appropriate conditions can be selected for use on an affinity support that can bind that microbe. One or more artificial receptors that bind the microbe or cell sufficiently tightly under appropriate conditions can be selected and its building blocks incorporated onto a scaffold molecule. An embodiment of the method can employ a support with the one or more artificial receptors or scaffold-receptors on its surface for binding or immobilizing the microbe. A support with a plurality of artificial receptors, each binding to a different portion of the microbe, on its surface can be employed for multivalent capture or immobilization of the microbe.

The present method can include selecting artificial receptors that bind a particular microbe and/or the building blocks making up these receptors (e.g., bound to a scaffold molecule) as leads for pharmaceutical development or as active agents for modulating an activity of the microbe or as an antibiotic against that microbe.

In an embodiment, the method can employ an array including a significant number of the present artificial receptors to produce an assay or system for characterizing or detecting a microbe of clinical or environmental interest. The method can include evaluating an array including a significant number of candidate artificial receptors for binding to the microbe of clinical or environmental interest. The building blocks making up the artificial receptors can be naïve to the test ligand. The microbe of clinical or environmental interest can exhibit characteristic binding to one or several of the candidate artificial receptors from that array. The one or several artificial receptors can be selected as an artificial receptor (e.g., a working artificial receptor or a working artificial receptor complex) that can be employed in methods for characterizing a biological sample, or characterizing or detecting the microbe of clinical or environmental interest.

Suitable microbes of clinical or environmental interest include bacteria, mycoplasma, fungus, *rickettsia*, or virus. Suitable bacteria or mycoplasma of clinical or environmental interest include *Escherichia coli* (e.g., *E. coli* H157:O7), *Vibrio cholerae, Acinetobacter caicoaceticus, Haemophilus influenzae, Actinobacillus actinoides, Haemophilus parahaemolyticus, Actinobacillus lignieresii, Haemophilus parainfluenzae, Actinobacillus suis, Legionella pneumophila, Actinomyces bovis, Leptospira interrogans, Actinomyces israelli, Mima polymorpha, Aeromonas hydrophila, Moraxella lacunata, Arachnia propionica, Burkholderia mallei, Burkholderia pseudomallei, Moraxella osioensis, Arizona hinshawii, Mycobacterium osioensis, Bacillus cereus, Mycobacterium leprae, Bacteroides spp, Mycobacterium spp, Bartonella bacilliformis, Plesiomonas shigelloides, Bordetella bronchiseptica, Proteus spp, Clostridium difficile, Pseudomonas aeruginosa, Clostridium sordellii, Salmonella cholerasuis, Clostridium tetani, Salmonella enteritidis, Corynebacterium diphtheriae, Salmonella typhi, Edwardsiella tarda, Serratia marcescens, Enterobacter aerogenes, Shigella spp, Staphylococcus epidermidis, Francisella novicida, Vibrio parahaemolyticus, Haemophilus ducreyi, Haemophilus gallinarum, Haemophilus haemolyticus, Bacillus anthracis, Mycobacterium bovis, Bordetella pertussis, Mycobacterium tuberculosis, Borrella burgdorfii, Mycoplasma pneumoniae, Borrella spp, Neisseria gonorrhoeae, Campylobacter, Neisseria meningitides, Chlamydia psittaci, Nocardia asteroids, Chlamydia trachomatis, Nocardia brasillensis, Clostridium botulinum, Pasteurella haemolytica, Clostridium chauvoei, Pasteurelia multocida, Clostridium haemolyticus, Pasteurella pneumotropica, Clostridium histolyticum, Pseudomonas pseudomallei, Clostridium novyl, Staphylococcus aureus, Clostridium perfringens, Streptobacillus moniliformis, Clostridium septicum, Cyclospora cayatanensis, Streptococcus agalacetiae, Erysipelothrix insidiosa, Streptococcus pneumoniae, Klebsiella pneumoniae, Streptococcus pyogenes, Listeria manocytogenes, Yersinia pestis, Yersinia pseudotuberculosis, Yersinia enterocolitica, Brucella abortus, Brucella canis, Brucella melitensis, Brucella suis, and Francisella tularensis.*

Suitable fungus include *Absidia, Piedraia hortae, Aspergillus, Prototheca, Candida, Paecilomyces, Cryptococcus neoformans, Cryptosporidium parvum, Phialaphora, Dermatophilus congolensis, Rhizopus, Epidermophyton, Scopulariopsis, Exophiala, Sporothrix schenkii, Fusarium, Trichophyton, Madurella mycetomi, Toxoplasma, Trichos-*

*poron, Microsporum, Microsporidia, Wangiella dermatitidis, Mucor, Blastomyces dermatitidis, Giardia lamblia, Entamoeba histolytica, Coccidioides immitis*, and *Histoplasma capsulatum*.

Suitable *rickettsia* or viruses of clinical or environmental interest include Coronaviruses, Hepatitis viruses, Hepatitis A virus, Myxo-Paramyxoviruses (Influenza viruses, Measles virus, Mumps virus, Newcastle disease virus), Picornavirus (Coxsackie viruses, Echoviruses, Poliomyelitis virus), *Rickettsia akari, Rochalimaea Quintana, Rochalimaea vinsonii*, Norwalk Agent, Adenoviruses, Arenaviruses (Lymphocytic choriomenigitis, Viscerotrophic strains), Herpesvirus Group (*Herpesvirus hominis*, Cytomegalovirus, Epstein-Barr virus, Caliciviruses, Pseudo-rabies virus, Varicella virus), Human Immunodeficiency Virus, Parainfluenza viruses (Respiratory syncytial virus, Subsclerosing panencephalitis virus), Picornaviruses (Poliomyelitis virus), Poxviruses Variola, Cowpox virus (*Molluscum contagiosum* virus, Monkeypox virus, Orf virus, Paravaccinia virus, Tanapox virus, Vaccinia virus, Yabapox virus), Papoviruses (SV 40 virus, B-K-virus), Spongiform Encephalopathy Viruses (Creutzfeld-Jacob agent, Kuru agent, BSE), Rhabdoviruses (Rabies virus), Tobaviruses (Rubella virus), *Coxiella burnetii, Rickettsia canada, Rickettsia prowazekii, Rickettsia rickettsii, Rickettsia Tsutsugamushi, Rickettsia typhi* (*R. mooseri*), Spotted Fever Group Agents, Vesicular Stomatis Virus (VSV), and Toga, Arena (e.g., LCM, Junin, Lassa, Marchupo, Guanarito, etc.), Bunya (e.g., hantavirus, Rift Valley Fever, etc.), Flaviruses (Dengue), and Filoviruses (e.g., Ebola, Marburg, etc.) of all types, Nipah virus, viral encephalitis agents, LaCrosse, Kyasanur Forest virus, Yellow fever, and West Nile virus.

Suitable microbes of clinical or environmental interest include Variola Viruses, Congo-Crimean hemorrhagic fever, Tick-borne encephalitis virus complex (Absettarov, Hanzalova, Hypr, Kumlinge, Kyasanur Forest disease, Omsk hemorrhagic fever, and Russian Spring-Summer Encephalitis), Marburg, Ebola, Junin, Lassa, Machupo, Herpesvirus simiae, Bluetongue, Louping III, Rift Valley fever (Zinga), Wesselsbron, Foot and Mouth Disease, Newcastle Disease, African Swine Fever, Vesicular exanthema, Swine vesicular disease, Rinderpest, African horse sickness, Avian influenza, and Sheep pox. Other components of interest include *Ricinus communis*.

Methods for Disrupting Binding Interactions

In an embodiment, the present invention can include methods and/or devices for detecting agents that disrupt binding of molecules, for example, macromolecules or a macromolecule and a small molecule. Methods and systems for detecting such agents can include methods and systems useful in developing therapeutic agents, in clinical chemistry, in environmental analysis, and in diagnostic assays of all types. In an embodiment, such a method includes decreasing binding of a test ligand to one or more working artificial receptors with one or more candidate disruptors. In an embodiment, such a method includes decreasing binding of a binding partner to a test ligand with one or more candidate disruptors, the test ligand being bound to one or more working artificial receptors.

In an embodiment, the present method includes selecting a working artificial receptor or receptor complex that binds a target molecule. This embodiment of the method includes binding the target molecule to the working receptor(s). The method then includes contacting the receptor with bound target molecule with one or more disruptor candidates. Contacting can occur in a high throughput screening format. The method includes selecting one or more disruptor candidates that decreases binding of the target molecule to the working receptor(s) as a lead disruptor(s).

Any of the general types of test ligands described herein can be a target molecule. In an embodiment, the target molecule can be one known to participate in a binding interaction with another molecule. The target molecule can be on a microbe, and the entire microbe can be employed as a target molecule. The target molecule can be a complex of two or more macromolecules, for example, a complex of two proteins. The target molecule can be a protein. The target molecule can be a polynucleotide. The target molecule be on a cell, and the entire cell can be employed as a target molecule. The target molecule can be a receptor.

The lead disruptor can be subjected to further evaluation for example, as a candidate therapeutic agent, candidate vaccine, or candidate antigen. A lead disruptor that disrupts binding of a microbe to an artificial receptor of the present invention can be selected for further evaluation as an antibiotic against that microbe, as a candidate immunogen against that microbe, or as a candidate vaccine against that microbe. A lead disruptor that disrupts binding of a macromolecule to an artificial receptor of the present invention can be selected for further evaluation as a therapeutic agent, as a candidate immunogen against that macromolecule or an organism including that macromolecule, or as a candidate vaccine against that macromolecule or an organism including that macromolecule.

FIG. 8 schematically illustrates an embodiment of a method for detecting an agent that disrupts a binding interaction of a target molecule. This embodiment of the present method can be employed for detecting an agent that disrupts a binding interaction of a target molecule, such as a macromolecule or a microbe. The method can include making an array of candidate artificial receptors. The building blocks making up the artificial receptors can be naïve to the test ligand. Working artificial receptors can be identified by contacting the array with target molecule and identifying which receptors bind the target molecule. The method can include producing an array or device including the working artificial receptor or receptor complex. This method can include producing or employing the selected working artificial receptor or receptor complex on a substrate, such as a slide. The substrate can include working artificial receptors for a single target molecule or working artificial receptors for a plurality of target molecules. The method includes binding the target molecule(s) to the artificial receptors.

This illustrated embodiment includes contacting the artificial receptors with bound target molecule with one or more candidate disruptors. Release of the target molecule from the working artificial receptors or decrease in binding of the target molecule to the artificial receptors indicates that the candidate disruptor is a working or lead disruptor, and can be selected as such. A substrate including working artificial receptors for a single target molecule can be employed in a method or system for detecting disruptors of binding interactions of that target molecule. A substrate including working artificial receptors for a plurality of target molecules can be employed in a method or system for detecting disruptors of binding interactions for one, several, or all of the target molecules. The method can include washing unbound or released target molecule from the support.

In an embodiment, the present method includes selecting a working artificial receptor or receptor complex that binds a protein. This embodiment of the method includes binding the protein to the working receptor(s). The method then includes contacting the receptor with bound protein with one or more disruptor candidates. Contacting can occur in a high throughput screening format. The method includes selecting one or more disruptor candidates that decreases binding of the protein to the working receptor(s) as a lead disruptor(s).

Such a method can be employed for detecting an agent that disrupts a binding interaction of a protein. The method can include making an array of candidate artificial receptors. The building blocks making up the artificial receptors can be naïve to the test ligand. Working artificial receptors can be identified by contacting the array with protein and identifying which receptors bind the protein. The method can include producing an array or device including the working artificial receptor or receptor complex. This method can include producing or employing the selected working artificial receptor or receptor complex on a substrate, such as a slide. The substrate can include working artificial receptors for a single protein or working artificial receptors for a plurality of proteins. The method includes binding the protein(s) to the artificial receptors. This embodiment of the method includes contacting the artificial receptors with bound protein with one or more candidate disruptors. Release of the protein from the working artificial receptors or decrease in binding of the protein to the artificial receptors indicates that the candidate disruptor is a working or lead disrupter, and can be selected as such.

In an embodiment, the disruptor disrupts a binding interaction of a protein. Such a disruptor can be envisioned as a mimic of one or more structural features to which this protein binds, for example on a microbe, tissue, or cell. The disruptor can be evaluated for such mimicry. The mimic disruptor can then be used as an antigen against the structural feature on the microbe, tissue, or cell. The mimic disruptor can be used as an idiotype or anti-idiotype against the structural feature on the microbe, tissue, or cell.

In an embodiment, the present method includes selecting a working artificial receptor or receptor complex that binds a microbe. This embodiment of the method includes binding the microbe to the working receptor(s). The method then includes contacting the receptor with bound microbe with one or more disruptor candidates. Contacting can occur in a high throughput screening format. The method includes selecting one or more disrupter candidates that decreases binding of the microbe to the working receptor(s) as a lead disruptor(s).

Such a method can be employed for detecting an agent that disrupts a binding interaction of a microbe. The method can include making an array of candidate artificial receptors. The building blocks making up the artificial receptors can be naïve to the test ligand. Working artificial receptors can be identified by contacting the array with microbe and identifying which receptors bind the microbe. The method can include producing an array or device including the working artificial receptor or receptor complex. This method can include producing or employing the selected working artificial receptor or receptor complex on a substrate, such as a slide. The substrate can include working artificial receptors for a single microbe or working artificial receptors for a plurality of microbes. The method includes binding the microbe(s) to the artificial receptors. This embodiment of the method includes contacting the artificial receptors with bound microbe with one or more candidate disruptors. Release of the microbe from the working artificial receptors or decrease in binding of the microbe to the artificial receptors indicates that the candidate disruptor is a working or lead disrupter, and can be selected as such.

In an embodiment, the disruptor disrupts a binding interaction of a microbe. Such a disrupter can be envisioned as a mimic of one or more structural features to which this microbe binds, for example on a protein, another microbe, a tissue, or a cell. The disrupter can be evaluated for such mimicry. The mimic disruptor can then be used as an antigen against the structural feature on the protein, other microbe, tissue, or cell. The mimic disruptor can be used as an idiotype or anti-idiotype against the structural feature on the protein, other microbe, tissue, or cell.

In an embodiment, the present method includes selecting a working artificial receptor or receptor complex that binds a cell. This embodiment of the method includes binding the cell to the working receptor(s). The method then includes contacting the receptor with bound cell with one or more disruptor candidates. Contacting can occur in a high throughput screening format. The method includes selecting one or more disruptor candidates that decreases binding of the cell to the working receptor(s) as a lead disruptor(s).

Such a method can be employed for detecting an agent that disrupts a binding interaction of a cell. The method can include making an array of candidate artificial receptors. The building blocks making up the artificial receptors can be naïve to the test ligand. Working artificial receptors can be identified by contacting the array with cell and identifying which receptors bind the cell. The method can include producing an array or device including the working artificial receptor or receptor complex. This method can include producing or employing the selected working artificial receptor or receptor complex on a substrate, such as a slide. The substrate can include working artificial receptors for a single cell or working artificial receptors for a plurality of cells. The method includes binding the cell(s) to the artificial receptors. This embodiment of the method includes contacting the artificial receptors with bound cell with one or more candidate disruptors. Release of the cell from the working artificial receptors or decrease in binding of the cell to the artificial receptors indicates that the candidate disruptor is a working or lead disruptor, and can be selected as such.

In an embodiment, the disruptor disrupts a binding interaction of a cell. Such a disruptor can be envisioned as a mimic of one or more structural features to which this cell binds, for example on a protein, another cell, a tissue, or a microbe. The disrupter can be evaluated for such mimicry. The mimic disruptor can then be used as an antigen against the structural feature on the protein, microbe, tissue, or other cell. The mimic disruptor can be used as an idiotype or anti-idiotype against the structural feature on the protein, microbe, tissue, or other cell.

Any of a variety of compounds can be employed as a candidate disruptor. For example, candidate disruptors can include at least one small molecule. For example, candidate disruptors can include a library of small molecules. For example, candidate disruptors can include at least one peptide. For example, candidate disruptors can include a library of peptides.

Disrupting a Complex

In an embodiment, the present method includes a method for detecting a disruptor of binding of a binding partner to a test ligand (e.g., target molecule), the test ligand being bound to one or more working artificial receptors. In an embodiment, the present method includes selecting a working artificial receptor or receptor complex that binds a complex including a target molecule. Such selecting can include evaluating artificial receptors for binding to the target molecule. The building blocks making up the artificial receptors can be naïve to the test ligand. From among those artificial receptors that bind the target molecule, the method selects those artificial receptors that can bind the complex. The complex including the target molecule can also include one or more binding partners for the target molecule. This embodiment of the method includes binding the complex to the selected working receptor(s). The method then includes contacting the receptor with bound complex with one or more disruptor candidates. Contacting can occur in a high throughput screening format. The method includes selecting one or more disruptor candidates that decrease binding of at least one binding partner to the complex as a lead disruptor(s).

Figure 9:
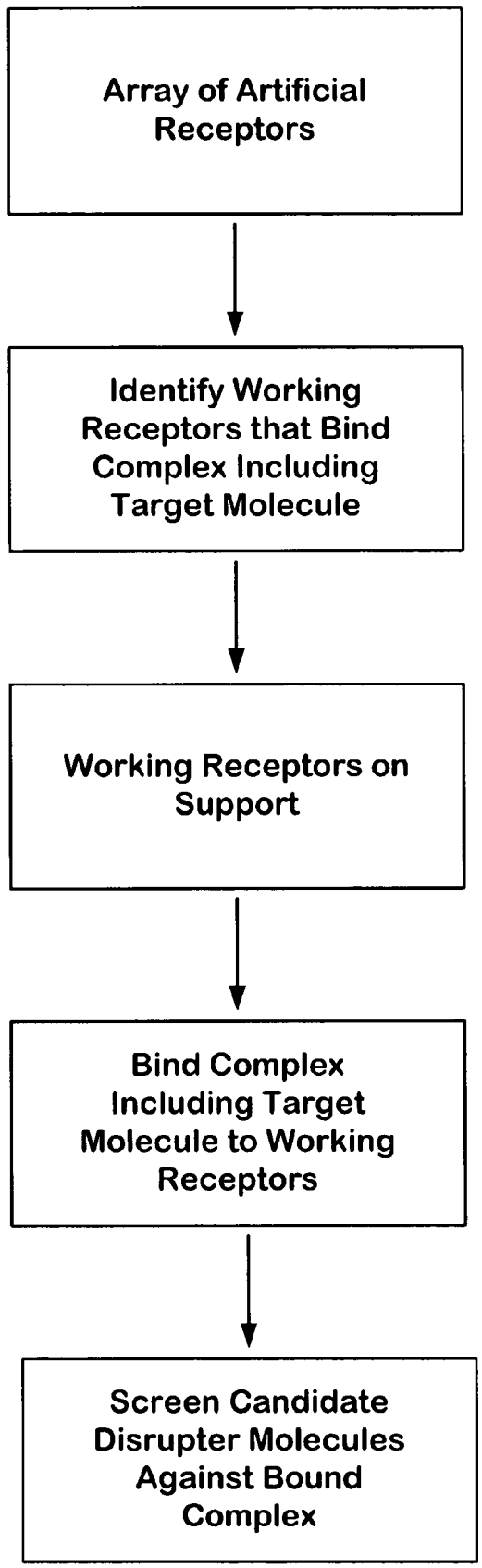
FIG. 9 schematically illustrates an embodiment of a method for detecting an agent that disrupts a binding interaction of a complex including a target molecule.

FIG. 9 schematically illustrates an embodiment of a method for detecting an agent that disrupts a binding interaction of a complex including a target molecule. This embodiment of the present method can be employed for detecting an agent that disrupts a binding interaction of a complex, such as a protein:small molecule complex, a protein:protein complex, a protein:polynucleotide complex, a protein:polysaccharide complex, a protein:microbe complex, or a protein:cell complex. The method can include making an array of candidate artificial receptors. The building blocks making up the artificial receptors can be naïve to the test ligand. Working artificial receptors can be identified by contacting the array with target molecule and identifying which receptors bind the target molecule. The identified working artificial receptors can be contacted with the complex including the target molecule and the receptors that bind the complex can be selected. The method can include producing an array or device including the selected working artificial receptor or receptor complex. This method can include producing or employing the selected working artificial receptor or receptor complex on a substrate, such as a slide. The method includes binding the complex to the artificial receptors.

This illustrated embodiment includes contacting the artificial receptors with bound complex with one or more candidate disruptors. Release of the binding partner portion of the complex from the working artificial receptors but retaining the target molecule on the receptors indicates that the candidate disruptor is a working or lead complex disrupter, and can be selected as such. Decrease in binding of the binding partner portion of the complex to the artificial receptors but retaining the target molecule on the receptors indicates that the candidate disruptor is a working or lead complex disruptor, and can be selected as such. The working or lead complex disruptor can, in an embodiment, be selected as a lead for developing a therapeutic agent for a disorder mediated by the complex. The method can include washing unbound or released binding partner from the support.

Figure 10:
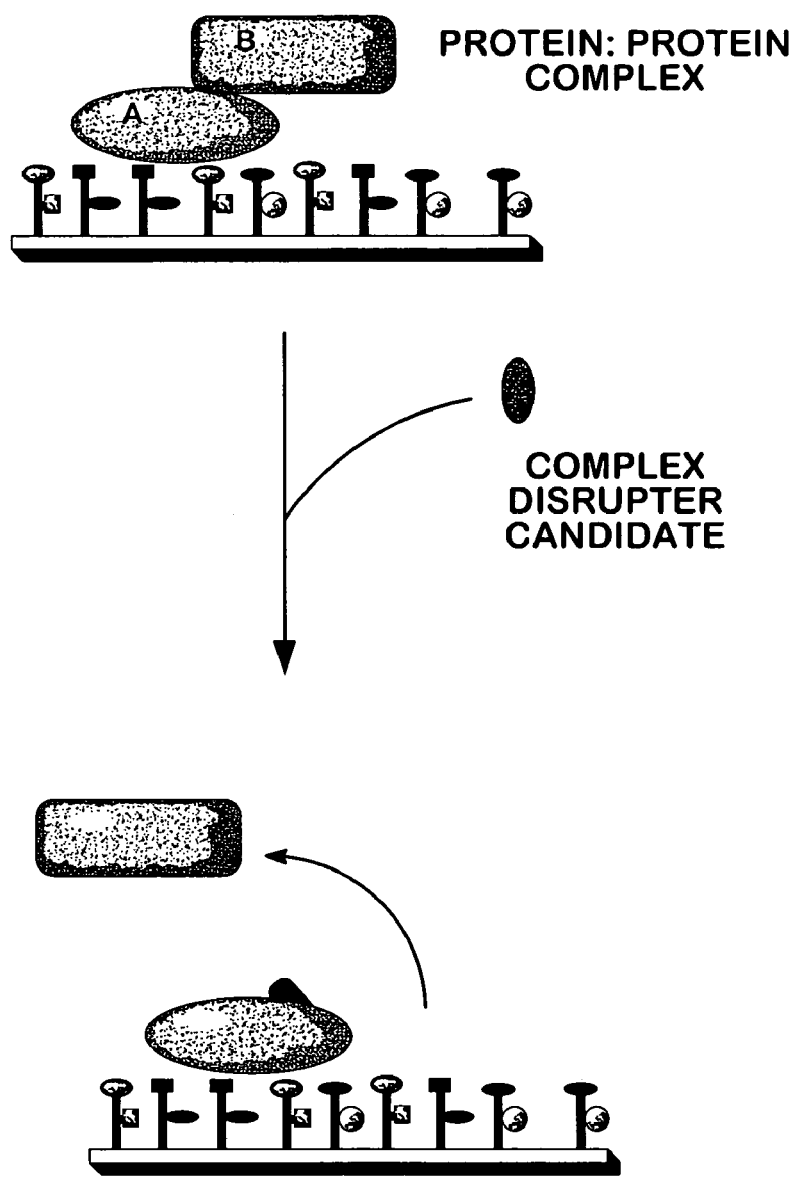
FIG. 10 schematically illustrates a candidate disruptor disrupting a protein:protein complex.

In an embodiment, the complex disruptor disrupts a complex including at least two proteins, a first protein and a second protein. FIG. 10 schematically illustrates a candidate disruptor disrupting a protein:protein complex. In this embodiment, one protein component remains bound to the receptor and the other dissociates and leaves the receptor. An embodiment of such a disrupter can be envisioned as a mimic of one or more structural features of the binding portion of one of the proteins included in the complex. The disruptor can be evaluated for such mimicry. For example, the disruptor can mimic a structural feature of the first protein that interacts with the second protein. The mimic disruptor can then be used as an antigen against that feature of the first protein. The mimic disruptor can be used as an idiotype or anti-idiotype against the structural feature on the first protein.

In an embodiment, the present method includes contacting at least one candidate artificial receptor with a complex, for example, a protein:protein complex, a protein:polynucleotide complex, or the like. This embodiment of the method can include detecting those artificial receptors that bound only one member of the complex or bound less than the complete complex. Such artificial receptors can be selected as lead complex disruptors.

Methods for Making and Using Affinity Supports

Figure 11:
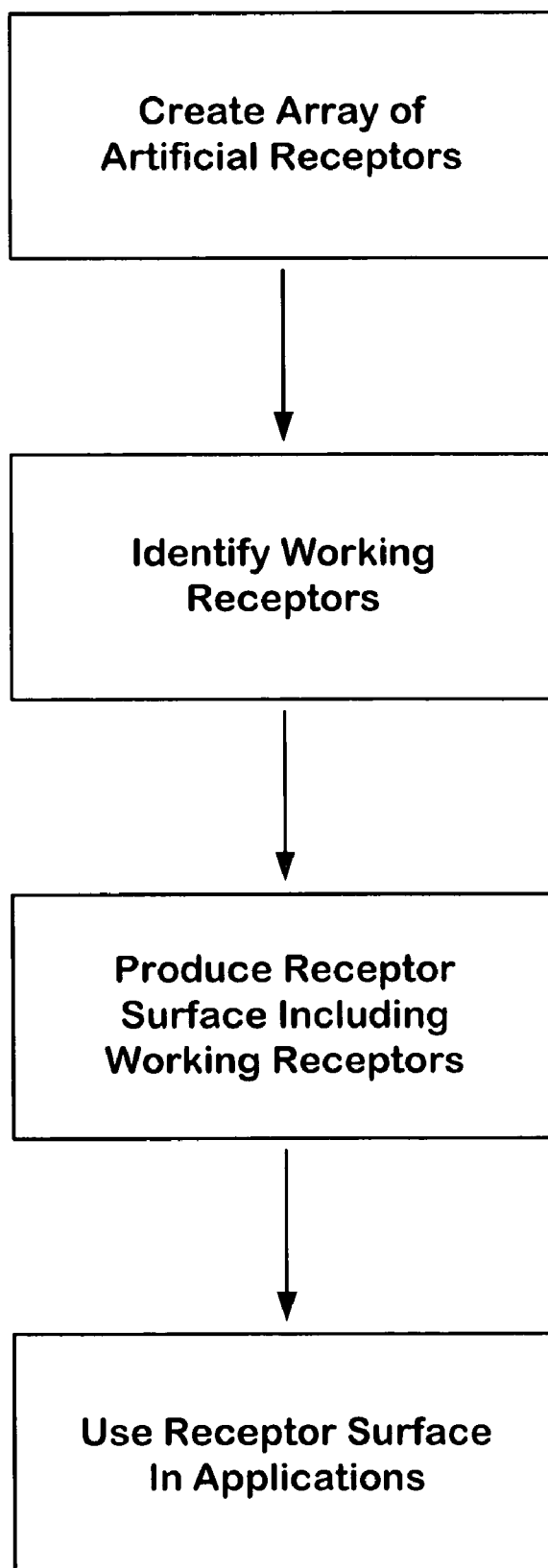
FIG. 11 schematically illustrates an embodiment of a method of employing the present artificial receptors to produce or as an affinity support.

In an embodiment, a working artificial receptor or receptor complex can be employed to produce or as an affinity support for any of the test ligands described herein. For example, the present method can include a method for producing an affinity support for a test ligand. This method can include selecting a working artificial receptor or receptor complex that binds to the test ligand. This method can also include coupling the working artificial receptor or receptor complex to a support. FIG. 11 schematically illustrates an embodiment of such a method. The support can be suitable for use as an affinity support for, for example, chromatography, membrane filtration, electrophoresis (e.g., 1 or 2 dimensional electrophoresis), or the like.

The present method can include selecting artificial receptors that bind a particular test ligand and/or the building blocks making up these receptors (e.g., bound to a scaffold molecule) for isolation or analysis of a particular test ligand. The building blocks making up the artificial receptors can be naïve to the test ligand. For example, the artificial receptor can be employed as a receptor surface that can bind the test ligand and remove (e.g., purify) it from a mixture or biological sample.

Such a method can include contacting one or more candidate artificial receptors with a test ligand of interest. The building blocks making up the artificial receptors can be naïve to the test ligand. The method can include selecting one or more of the candidate artificial receptors that bind the test ligand as working artificial receptor(s). The method can then include employing the working artificial receptor(s) to make a receptor surface. Making a receptor surface can include coupling the building blocks making up the working artificial receptor(s) to a support. The support can have sufficient area to bind a significant quantity of the test ligand of interest. The support can be a chromatography support or medium. The support can be a plate, tube, or membrane. In an embodiment, binding of the test ligand of interest to the support can be followed by eluting the test ligand of interest from the support. Eluting can employ a wash with a pH, buffer, solvent, salt concentration, or ligand concentration effective to elute the test ligand of interest from the support.

Figure 12A:
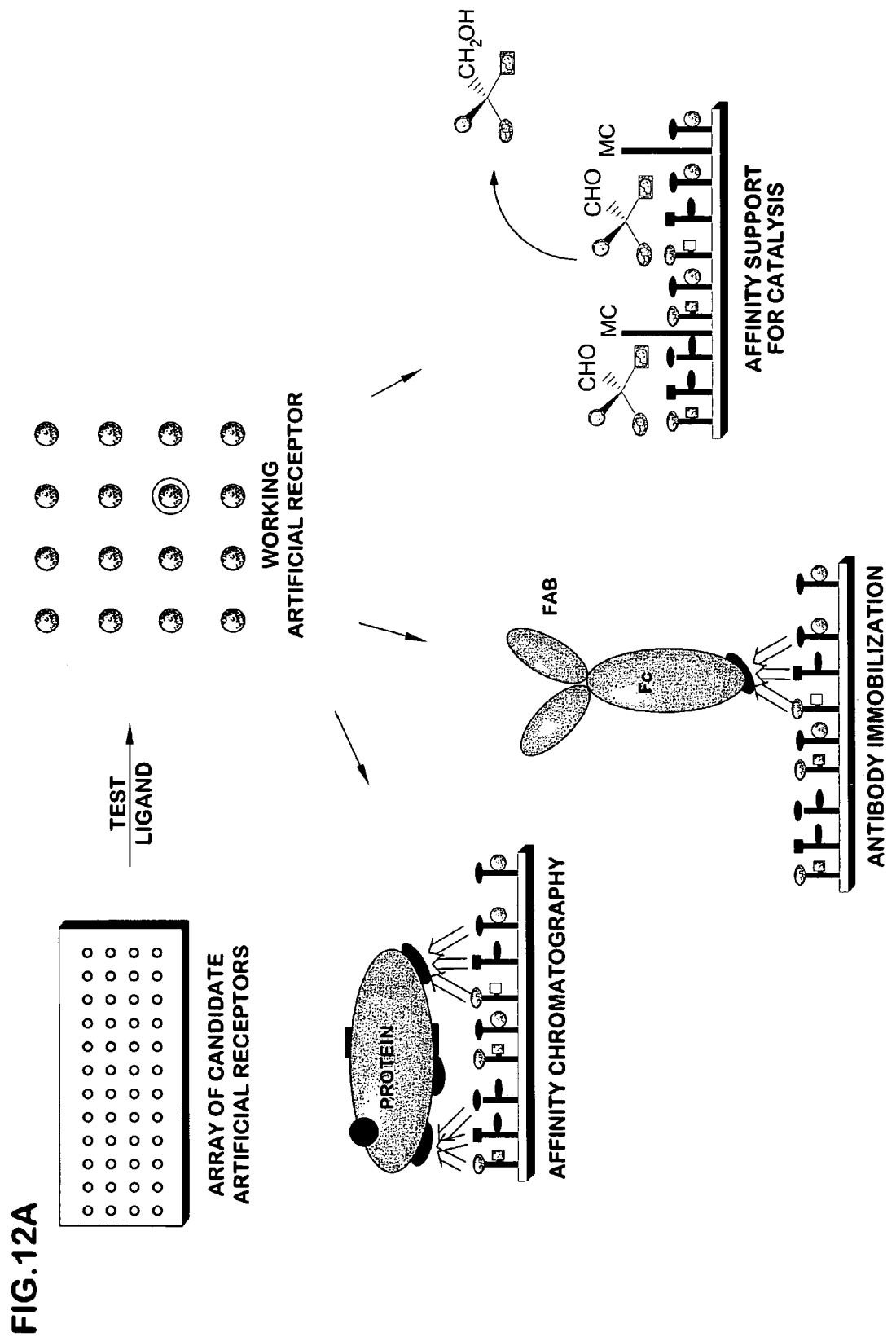
FIG. 12 schematically illustrates evaluating an array of candidate artificial receptors for binding of a test ligand and selecting one or more working artificial receptors for binding or operating on a test ligand.
Figure 12B:
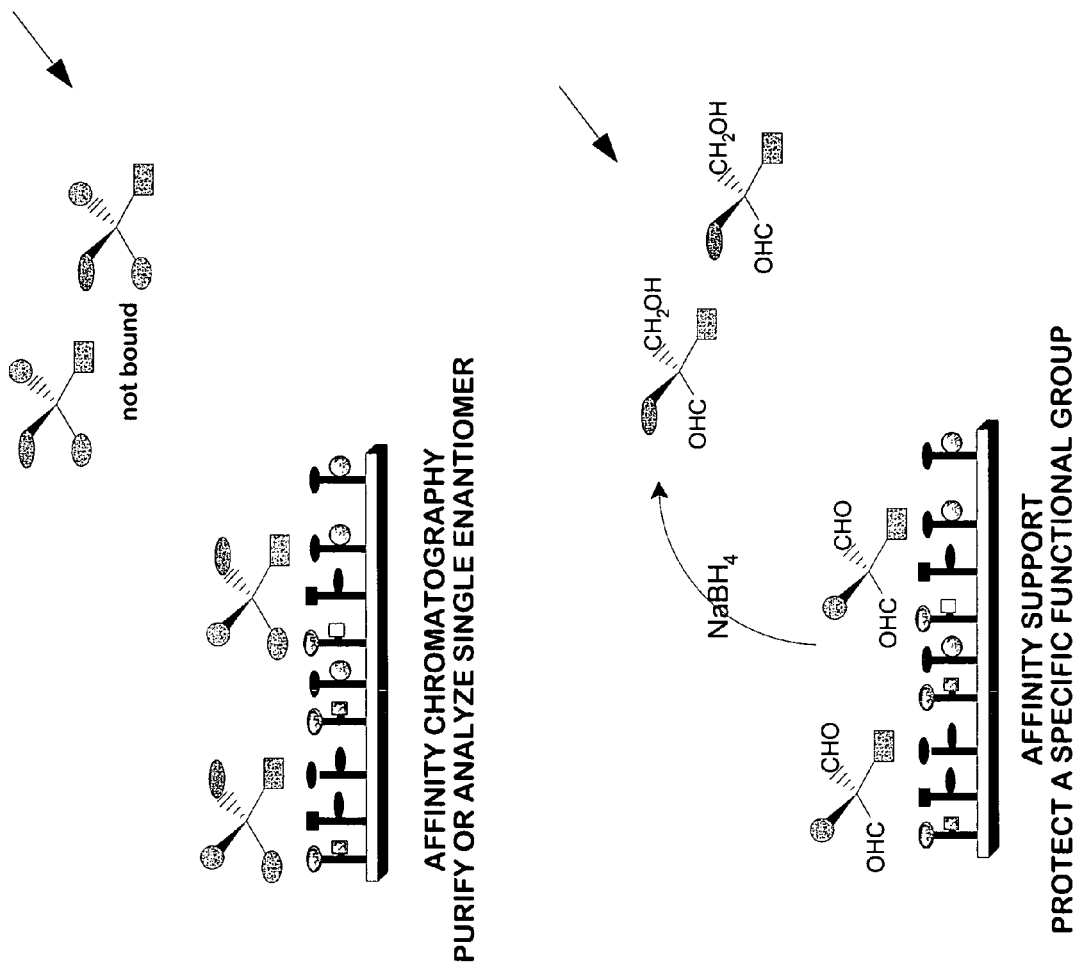

FIG. 12 schematically illustrates evaluating an array of candidate artificial receptors for binding of a test ligand and selecting one or more working artificial receptors. The building blocks making up the artificial receptors can be naïve to the test ligand. FIG. 12 illustrates that a receptor surface employing such a working artificial receptor can be employed for binding a protein, immobilizing an antibody, binding a single enantiomer, or protecting a structural feature (e.g., a functional group) on a compound. In an embodiment, the receptor surface can bind more than one structural feature on the protein. In an embodiment, the working artificial receptor can be selected to bind the constant portion, rather than the variable portions, of an antibody. In an embodiment, the receptor surface can include a catalytic moiety that can catalyze a reaction of a functional group of the bound test ligand. Such a catalytic moiety can be a building block, for example, an organometallic building block.

The present method can include selecting artificial receptors that bind a particular isomer of a compound and/or the building blocks making up these receptors (e.g., bound to a scaffold molecule) for isolation or analysis of a particular isomer. For example, the artificial receptor can be employed as a receptor surface that can bind the isomer and remove (e.g., purify) it from a mixture or biological sample.

Such a method can include contacting one or more candidate artificial receptors with an isomer of interest. The building blocks making up the artificial receptors can be naïve to the test ligand. The method can include selecting one or more of the candidate artificial receptors that bind the isomer as working artificial receptor(s). The method can then include employing the working artificial receptor(s) to make a receptor surface. Making a receptor surface can include coupling the building blocks making up the working artificial receptor(s) to a support. The support can have sufficient area to bind a significant quantity of the isomer of interest. The support can be a chromatography support or medium. The support can be a plate, tube, or membrane. In an embodiment, binding of the isomer of interest to the support can be followed by eluting the isomer of interest from the support. Eluting can employ a wash with a pH, buffer, solvent, salt concentration, or ligand concentration effective to elute the isomer of interest from the support.

The present method can include selecting artificial receptors that bind or protect a particular structural feature of a compound and/or the building blocks making up these receptors (e.g., bound to a scaffold molecule) for isolation or analysis of the compound including the structural feature. For example, the artificial receptor can be employed as a receptor surface that can bind or protect the structural feature of the compound. Binding of the structural feature can be determined by lack of binding of an analogous compound the lacking the structural feature. Protection of the structural feature can be evaluated by that structural feature being unavailable to a, for example, solution phase reactive species when the compound is bound to the receptor surface.

Such a method can include contacting one or more candidate artificial receptors with a compound of interest. The building blocks making up the artificial receptors can be naïve to the test ligand. The method can include selecting one or more of the candidate artificial receptors that bind the structural feature of the compound as lead artificial receptor(s). The lead artificial receptor can be evaluated for protecting the structural feature. The method can then include employing the working artificial receptor(s) to make a receptor surface. Making a receptor surface can include coupling the building blocks making up the working artificial receptor(s) to a support. The support can have sufficient area to bind a significant quantity of the compound of interest. In an embodiment, binding of the compound of interest to the support can be followed by reacting a portion of the compound that is not the bound or protected structure feature.

The present method can include selecting artificial receptors that bind a particular peptide or protein and/or the building blocks making up these receptors (e.g., bound to a scaffold molecule) for isolation or analysis of a particular peptide or protein. For example, the artificial receptor can be employed as a receptor surface that can bind the peptide or protein and remove (e.g., purify) it from a mixture or biological sample.

Such a method can include contacting one or more candidate artificial receptors with a peptide or protein of interest. The building blocks making up the artificial receptors can be naïve to the test ligand. The method can include selecting one or more of the candidate artificial receptors that bind the peptide or protein as working artificial receptor(s). The method can then include employing the working artificial receptor(s) to make a receptor surface. Making a receptor surface can include coupling the building blocks making up the working artificial receptor(s) to a support. The support can have sufficient area to bind a significant quantity of the peptide or protein of interest. The support can be a chromatography support or medium. The support can be a plate, tube, or membrane. In an embodiment, binding of the peptide or protein of interest to the support can be followed by eluting the peptide or protein of interest from the support. Eluting can employ a wash with a pH, buffer, salt concentration, or ligand concentration effective to elute the peptide or protein of interest from the support.

In an embodiment, the present artificial receptors can be employed to form selective membranes. Such a selective membrane can be based on a molecular gate including an artificial receptor surface. For example, an artificial receptor surface can line the walls of pores in the membrane and either allow or block a target molecule from passing through the pores. For example, an artificial receptor surface can line the walls of pores in the membrane and act as "gatekeepers" on e.g. micro cantilevers/molecular cantilevers to allow gate opening or closing on binding of the target. The artificial receptors to be used in the selective membranes can be identified by exposing the target molecule to a plurality of distinct artificial receptors and then determining which ones it binds to. For example, the binding can be detected through any of the techniques described herein, including fluorescence.

In certain embodiments, the method can include producing one or more receptor surfaces, each receptor surface including building blocks from a working receptor for a particular test ligand. Such a method can include employing the receptor surface for chromatography of the test ligand. Chromatographing the test ligand against a plurality of such receptor surfaces can rank the affinity of the surfaces for the test ligand. Under a given set of conditions, the receptor surface that retains the chromatographed test ligand the longest exhibits the greatest affinity for the test ligand. The method can include selecting the receptor surface with suitable (e.g., the greatest) affinity for use as an affinity support for the test ligand.

Any of a variety of supports can be employed as the affinity support. In certain embodiments, the affinity support can be a dish, a tube, a well, a bead, a chromatography support, a microchannel, or the like. The artificial receptor affinity support can be used in various applications, such as chromatography, microchannel devices, as an immunoassay support, or the like. A microchannel with the artificial receptor on its surface can be employed as an analytical device. In an embodiment, the present artificial receptors can be employed to form bioactive surfaces. For example, receptor surfaces can be used to specifically bind antibodies or enzymes.

Methods for Making and Using Reaction Supports

In an embodiment, a working artificial receptor or receptor complex can be employed to produce or as a reaction support for any of the test ligands described herein. For example, the present method can include a method for producing a reaction support for at least one test ligand. This method can include selecting a working artificial receptor or receptor complex that binds to the test ligand under conditions suitable for a desired reaction with that test ligand. This method can also include coupling the working artificial receptor or receptor complex to a support. FIG. 11 schematically illustrates an embodiment of such a method. The support can be suitable for use as a reaction support for, for example, oxidation, reduction, substitution, or displacement reactions.

The present method can include selecting artificial receptors that bind a particular test ligand and/or the building blocks making up these receptors (e.g., bound to a scaffold molecule) for reaction of a particular test ligand. For example, the artificial receptor can be employed as a receptor surface that can bind the test ligand and position it for reaction at a particular prochiral group, functional group, or orientation.

Such a method can include contacting one or more candidate artificial receptors with a test ligand of interest. The building blocks making up the artificial receptors can be naïve to the test ligand. The method can include selecting one or more of the candidate artificial receptors that bind the test ligand as working artificial receptor(s). The method can then include employing the working artificial receptor(s) to make a receptor surface. Making a receptor surface can include coupling the building blocks making up the working artificial receptor(s) to a support. The support can have sufficient area to bind a desired quantity of the test ligand of interest. The support can be a chromatography support or medium. The support can be a plate, bead, tube, or membrane.

The method also includes contacting the support including bound test ligand with a reactant for the desired reaction. Suitable reactants include reducing agent, oxidizing agent, nucleophile, electrophile, solvent (e.g., aqueous or organic solvent), or the like. The method can include contacting with one or more reactants and selecting reactant or reactants suitable for participating in the desired reaction. This embodiment of the method includes reacting the test ligand with the reactant. In an embodiment, reacting can be followed by washing the reactant or side products from the support. In an embodiment, reacting can be followed by eluting the product (e.g., reacted test ligand) from the support. Eluting can employ a wash with a pH, buffer, solvent, salt concentration, or ligand concentration effective to elute the product from the support.

FIG. 12 schematically illustrates evaluating an array of candidate artificial receptors for binding of a test ligand and selecting one or more working artificial receptors. The building blocks making up the artificial receptors can be naïve to the test ligand. FIG. 12 illustrates that a receptor surface employing such a working artificial receptor can be employed for binding a test ligand. The test ligand can be bound in an orientation that leaves a reactive moiety available for reaction with a reactant placed into contact with the receptor surface. In an embodiment, the test ligand can be bound in an orientation that occludes or protects a second reactive moiety from reacting with the reactant. This embodiment includes reacting the test ligand and release of the reacted test ligand from the receptor surface. Specifically, the illustration shows the reduction of an aldehyde with sodium borohydride to produce an alcohol. In an embodiment, the receptor surface can include a catalytic moiety that can catalyze a reaction of a functional group of the bound to test ligand the catalytic reaction can also employ the reactant. Such a catalytic moiety can be a building block, for example, an organometallic building block.

The present method can include selecting artificial receptors that bind or protect a particular structural feature of a compound and/or the building blocks making up these receptors (e.g., bound to a scaffold molecule) for reacting the compound including the structural feature. For example, the artificial receptor can be employed as a receptor surface that can bind and protect the structural feature of the compound while another feature of the compound reacts with a reactant. Protection of the structural feature can be evaluated by that structural feature not reacting with the reactant. For example, a substrate (e.g. a steroid) can be stereospecifically bound to the artificial receptor and present a particular moiety/substructure/"face" for reaction with a reagent in solution.

In an embodiment, a first side of a molecule (or a functional group) is bound to a receptor surface while a second side is left exposed. Then a reagent is added that could react with either side (or group) but is hindered from reacting with the first side of the molecule since it is bound to the receptor surface, accordingly the reagent reacts with the second side of the molecule only.

Such a method can include contacting one or more candidate artificial receptors with a compound of interest. The method can include selecting one or more of the candidate artificial receptors that bind the structural feature of the compound as lead artificial receptor(s). The lead artificial receptor can be evaluated for protecting the structural feature. The method can then include employing the working artificial receptor(s) to make a receptor surface. Making a receptor surface can include coupling the building blocks making up the working artificial receptor(s) to a support. The support can have sufficient area to bind a desired quantity of the compound of interest. In an embodiment, binding of the compound of interest to the support can be followed by reacting a portion of the compound that is not the bound or protected structure feature.

Conventional synthesis of a chiral compound generally requires complicated procedures. In an embodiment, the present candidate artificial receptors can be employed to find receptor surfaces that provide a spatially oriented binding surface for a stereospecific reaction. For example, an artificial receptor surface can bind a small molecule so that particular functional groups are exposed to the environment, and others are obscured by the receptor. In this manner, the stereospecificity of the reaction can be controlled. Therefore, an artificial receptor surface can be employed in synthesis including chiral induction. Similarly, regiospecificity can also be controlled using receptors of the present invention.

The present method can include selecting artificial receptors that bind a first reaction ligand and a second reaction ligand or the building blocks making up these receptors (e.g., bound to a scaffold molecule) for a reaction including the first and second reaction ligands. For example, the artificial receptor can be employed as a receptor surface that can bind the first reaction ligand and the second reaction ligand at a distance or orientation at which these ligands can react with one another. The reaction can optionally include one or more reactants not bound to the receptor surface.

Such a method can include contacting one or more candidate artificial receptors with a first reaction ligand and a second reaction ligand. The building blocks making up the artificial receptors can be naïve to the ligands. The method can include selecting one or more of the candidate artificial receptors that bind both of the reaction ligands as working artificial receptor(s). The method can then include employing the working artificial receptor(s) to make a receptor surface. Making a receptor surface can include coupling the building blocks making up the working artificial receptor(s) to a support. The support can have sufficient area to bind a desired quantity of the first and second reaction ligands. The support can be a chromatography support or medium. The support can be a plate, bead, tube, or membrane. The first and second reaction ligands can be bound to the support at one or several molar ratios, the reaction evaluated, and a molar ratio selected for conducting the reaction.

The method can also include contacting the support including bound reaction ligands with a reactant for the desired reaction. Suitable reactants include reducing agent, oxidizing agent, nucleophile, electrophile, or the like. This embodiment of the method includes reacting the test ligand with the reactant. In an embodiment, reacting can be followed by washing the reactant or side products from the support. In an embodiment, the first and second reaction ligands react without the reactant. In an embodiment, reacting can be followed by eluting the product (e.g., reacted test ligand) from the support. Eluting can employ a wash with a pH, buffer, solvent, salt concentration, or ligand concentration effective to elute the product from the support.

In an embodiment, the present candidate artificial receptors can be employed to find receptor surfaces that provide a spatially oriented binding surface for a stereospecific reaction. For example, an artificial receptor surface can bind a small molecule with particular functional groups exposed to the environment, and others obscured by the receptor. Such an artificial receptor surface can be employed in synthesis including chiral induction. For example, a substrate (e.g. a steroid) can be stereospecifically bound to the artificial receptor and present a particular moiety/sub-structure/"face" for reaction with a reagent in solution. Similarly, the artificial receptor surface can act as a protecting group where a reactive moiety of a molecule is "protected" by binding to the receptor surface so that a different moiety with similar reactivity can be transformed.

In an embodiment, the one or more working artificial receptors that bind a plurality (e.g., 2) of the reactants can be produced on a substrate and the reactants bound. Each receptor with a plurality of bound reactants can then be screened against one or more reagents or conditions (e.g., various molar ratios of the reactants or various solvents). The artificial receptor allowing or promoting reaction between the two or more reactants can be identified. The artificial receptor can then be produced on a substrate to provide a reactor for the reaction of interest.

Any of a variety of supports can be employed as the reaction support. In certain embodiments, the reaction support can be a dish, a tube, a well, a bead, a chromatography support, a microchannel, or the like. The artificial receptor reaction support can be used in various applications, such as a microchannel device. A microchannel with the artificial receptor on its surface can be employed as a reactor.

Methods for Making and Using Supported Catalysts

In an embodiment, a working artificial receptor or receptor complex can be employed to produce or as a supported catalyst for any of the test ligands described herein. For example, the present method can include a method for producing a supported catalyst for at least one test ligand. This method can include selecting a working artificial receptor or receptor complex that binds to the test ligand under conditions suitable for catalyzing a reaction with that test ligand. This method can also include coupling the working artificial receptor or receptor complex to a support. FIG. 11 schematically illustrates an embodiment of such a method. The support can be suitable for use as a supported catalyst for any of a variety of catalytic moieties or building blocks, such as an organometallic moiety, a coenzyme, a redox active moiety, a nucleophilic moiety, an acid moiety, a base moiety, or the like.

The present method can include selecting artificial receptors that bind and catalyze a reaction of a particular test ligand and/or the building blocks making up these receptors (e.g., bound to a scaffold molecule) for catalyzing a reaction of a particular test ligand. For example, the artificial receptor can be employed as a receptor surface that can bind the test ligand and position it for reaction with the catalytic moiety at a particular prochiral group, functional group, or orientation.

Such a method can include contacting one or more candidate artificial receptors with a test ligand of interest. The building blocks making up the artificial receptors can be naïve to the test ligand. The method can include selecting one or more of the candidate artificial receptors that bind and catalyze a desired reaction of the test ligand as working artificial receptor(s). The method can then include employing the working artificial receptor(s) to make a receptor surface. Making a receptor surface can include coupling the building blocks making up the working artificial receptor(s) to a support. The support can have sufficient area to bind a desired quantity of the test ligand of interest. The support can be a chromatography support or medium. The support can be a plate, bead, tube, or membrane.

The method also includes contacting the support including bound test ligand with a reactant or cofactor for the desired reaction. Suitable reactants include reducing agent, oxidizing agent, nucleophile, electrophile, solvent (e.g., aqueous or organic solvent), or the like. The method can include contacting with one or more selecting reactants and selecting reactant or reactants suitable for participating in the desired reaction. This embodiment of the method includes reacting the test ligand with the reactant. In an embodiment, reacting can be followed by washing the reactant or side products from the support. In an embodiment, reacting can be followed by eluting the product (e.g., reacted test ligand) from the support. Eluting can employ a wash with a pH, buffer, solvent, salt concentration, or ligand concentration effective to elute the product from the support.

FIG. 12 schematically illustrates evaluating an array of candidate artificial receptors for binding and catalysis of a reaction of a test ligand and selecting one or more working artificial receptors. The building blocks making up the artificial receptors can be naïve to the test ligand. FIG. 12 illustrates that a receptor surface employing such a working artificial receptor can be employed for binding and catalysis of a reaction of a test ligand. The test ligand can be bound in an orientation that leaves a reactive moiety available for reaction with a the catalytic moiety of the receptor. In an embodiment, the test ligand can be bound in an orientation that occludes or protects a second reactive moiety from reacting with the catalytic moiety. This embodiment includes reacting the test ligand and release of the reacted test ligand from the receptor surface. Specifically, the illustration shows the reduction of an aldehyde with a catalytic moiety (MC) on the catalytic support to produce an alcohol. In an embodiment, the receptor surface can include a catalytic moiety that can catalyze a reaction of a functional group of the bound to test ligand the catalytic reaction can also employ the reactant. Such a catalytic moiety can be a building block, for example, an organometallic building block.

In an embodiment, the invention includes a method for identifying a catalyst including binding a first reaction ligand to an artificial receptor array, contacting the array with a reactant, and identifying those artificial receptors that have promoted the reaction. The array can be screened for those artificial receptors that produce (e.g., catalyze conversion of the reactant to) a desired product.

Any of a variety of supports can be employed as the catalytic support. In certain embodiments, the catalytic support can be a dish, a tube, a well, a bead, a chromatography support, a microchannel, or the like. The artificial receptor reaction support can be used in various applications, such as a microchannel device. A microchannel with the artificial receptor on its surface can be employed as a reactor.

Methods for Making or Detecting Non-Binding Surfaces or Substances

In an embodiment, the invention can include methods and/or devices for not binding a test ligand. Methods and systems for not binding a test ligand can be employed in systems useful in clinical chemistry, environmental analysis, and diagnostic assays of all types. In an embodiment, the invention includes a method for making a substrate that does not bind a test ligand. The method can include contacting at least one candidate artificial receptor with the test ligand, detecting binding or lack of binding of the test ligand to one or more of the artificial receptors, and selecting an artificial receptor that does not bind the test ligand as a working non-binding surface. The artificial receptor or receptors that do not bind a first test ligand can be tested against one or more additional test ligands. In such a manner, the non-binding artificial receptors can be screened for those artificial receptors that do not bind any of a plurality of test ligands. A surface covered with the building blocks making up such non-binding artificial receptors can then be employed as a working non-binding surface.

In an embodiment, the present method can employ an array of candidate artificial receptors. This embodiment of the method can employ an array including a significant number of the present artificial receptors to produce one or more working artificial receptors or non-binding surfaces for one or more test ligands. The method can include evaluating an array including a significant number of candidate artificial receptors for not binding to at least one test ligand. Those candidate artificial receptors that do not bind to any of one or more test ligands can be selected as a non-binding surface for those one or more test ligands.

In an embodiment, the present method can evaluate an array of candidate artificial receptors to develop a surface that does not bind one or more proteins (e.g., plasma proteins). This embodiment of the method can employ an array including a significant number of the present artificial receptors to produce one or more working artificial receptors or non-binding surfaces for one or more proteins (e.g., plasma proteins). The method can include evaluating an array including a significant number of candidate artificial receptors for not binding to at least one protein (e.g., plasma protein). Those candidate artificial receptors that do not bind to any of one or more proteins (e.g., plasma proteins) can be selected as a non-binding surface for those proteins. Such a surface can be employed on an implantable medical device.

In an embodiment, the present method can evaluate an array of candidate artificial receptors to develop a surface that does not bind one or more cells. This embodiment of the method can employ an array including a significant number of the present artificial receptors to produce one or more working artificial receptors or non-binding surfaces for one or more cells. The method can include evaluating an array including a significant number of candidate artificial receptors for not binding to at least one cell. Those candidate artificial receptors that do not bind to any of one or more cells can be selected as a non-binding surface for those cells. Such a surface can be employed on an implantable medical device.

In an embodiment, the present method can evaluate an array of candidate artificial receptors to develop a surface that does not bind one or more microbes. This embodiment of the method can employ an array including a significant number of the present artificial receptors to produce one or more working artificial receptors or non-binding surfaces for one or more microbes. The method can include evaluating an array including a significant number of candidate artificial receptors for not binding to at least one microbe. Those candidate artificial receptors that do not bind to any of one or more microbes can be selected as a non-binding surface for those microbes. Such a surface can be employed on an implantable medical device. Such a surface can be employed in a system otherwise subject to biofouling, such as water piping, reservoirs or flumes in a food processing plant, cooling towers, ship bottoms.

Methods for Detecting

Contacting an array including a plurality of artificial receptors with a test ligand can identify one or more lead or working artificial receptors. Binding of the test ligand to the lead or working artificial receptor or complex can produce a detectable signal. The detectable signal can be produced, for example, through mechanisms and properties such as scattering, absorbing or emitting light, producing or quenching fluorescence or luminescence, producing or quenching an electrical signal, and the like. Spectroscopic detection methods include use of labels or enzymes to produce light for detection by optical sensors or optical sensor arrays. The light can be ultraviolet, visible, or infrared light, which can be produced and/or detected through fluorescence, fluorescence polarization, chemiluminescence, bioluminescence, or chemibioluminescence.

Systems and methods for detecting electrical conduction, and changes in electrical conduction, include ellipsometry, surface plasmon resonance, capacitance, conductometry, surface acoustic wave, quartz crystal microbalance, Love-wave, infrared evanescent wave, enzyme labels with electrochemical detection, nanowire field effect transistors, MOSFETS—metal oxide semiconductor field effect transistors, CHEMFETS—organic membrane metal oxide semiconductor field effect transistors, ICP—intrinsically conducting polymers, FRET—fluorescence resonance energy transfer.

In an embodiment, the working artificial receptor or complex can be configured on the surface of an optical fiber, for example, as a series of discrete areas, spots, zones, or the like. The working artificial receptor or complex can be contacted with the test ligand or sample suspected of containing the test ligand. The test ligand sample can be in the form of a stream of air, an aerosol, or liquid (e.g., a solution or suspension). A detectable calorimetric, fluorometric, or like signal can be produced by a label incorporated into the optic fiber surface. The colorimetric or fluorogenic signal can be intrinsic to the ligand or can be produced upon binding of the ligand to the working artificial receptors.

Apparatus that can detect such binding to or signal from a working artificial receptor or complex includes UV, visible, or infrared spectrometer, fluorescence or luminescence spectrometer, surface plasmon resonance, surface acoustic wave or quartz crystal microbalance detectors, pH, voltammetry or amperometry meters, radioisotope detector, or the like.

In such an apparatus, a working artificial receptor or complex can be positioned on an optic fiber to provide a detectable signal, such as an increase or decrease in transmitted light, reflected light, fluorescence, luminescence, or the like. The detectable signal can originate from, for example, a signaling moiety incorporated into the working artificial receptor or complex or a signaling moiety added to the working artificial receptor. The signal can also be intrinsic to the working artificial receptor or to the test ligand. The signal can come from, for example, the interaction of the test ligand with the working artificial receptor, the interaction of the test ligand with a signaling moiety that has been incorporated into the working artificial receptor, into the optic fiber or onto the optic fiber. In an embodiment, the present method can include selecting an artificial receptor for which binding induces a change in the signal from the signaling moiety, e.g., a fluorescent moiety. Such a change can signal binding to the artificial receptor.

In an embodiment, the working artificial receptor can be on a support such as a surface of a test tube, microwell, capillary, microchannel, or the like. The test ligand or a sample suspected of containing the test ligand can be contacted with the working artificial receptor or complex by addition of a solution containing the test ligand or a sample suspected of containing the test ligand. A detectable signal can be produced by a labeled compound or conjugate of the test ligand. This labeled moiety can be reacted with the working artificial receptor or complex in competition with the solution containing the test ligand or the sample suspected of containing the test ligand.

In an embodiment of the system, the working artificial receptor is on a support such as the surface of a surface acoustic wave or quartz crystal microbalance or surface plasmon resonance detector. The test ligand or a sample suspected of containing the test ligand can be brought into contact with the working artificial receptor or complex by exposure to a stream of air, to an aerosol, or to a solution containing the test ligand or a sample suspected of containing the test ligand. A detectable electrical signal can be produced by the interaction of the test ligand with the working artificial receptor or complex on the active surface of the surface acoustic wave or quartz crystal microbalance or surface plasmon resonance detector.

In an embodiment of the system, more than one working artificial receptor, arranged as regions or spots in an array, on a support, such as a glass or plastic surface can be incorporated onto the signaling surfaces of one or more surface plasmon resonance detectors. The ligands of interest or a sample suspected of containing the ligands of interest (e.g., a sample containing a mixture of DNA segments or fragments, proteins or protein fragments, carbohydrates or carbohydrate fragments, or the like) is brought into contact with the working artificial receptors or array. Contacting can be accomplished by addition of a solution of the ligands of interest or a sample suspected of containing the ligands of interest. Detectable electrical signals can be produced by binding of the ligands of interest to the working artificial receptors array on the surface of the surface plasmon resonance detectors. Such detectors produce a signal for each working artificial receptor in the array, which produces a pattern of signal response, which is characteristic of the composition of the sample of interest.

The present artificial receptors can be part of products used in: analyzing a genome and/or proteome; pharmaceutical development; detectors for any of the test ligands; drug of abuse diagnostics or therapy; hazardous waste analysis or remediation; chemical warfare alert or intervention; disease diagnostics or therapy; cancer diagnostics or therapy; biowarfare alert or intervention; food chain contamination analysis or remediation; and the like.

More specifically, the present artificial receptors can be used in products for identification of sequence specific small molecule leads; protein isolation and identification; identification of protein to protein interactions; detecting contaminants in food or food products; clinical analysis of food contaminants; clinical analysis of prostate specific antigen; clinical and field or clinical analysis of cocaine; clinical and field or clinical analysis of other drugs of abuse; other clinical analysis systems, home test systems, or field analysis systems; monitors or alert systems for bioterrorism or chemical warfare agents; and the like.

Embodiments of the Methods

The present invention includes methods for making an artificial receptor for binding a test ligand. In an embodiment, the method of the present invention can include contacting at least one candidate artificial receptor with a test ligand, detecting binding of the test ligand to at least one candidate artificial receptor, and selecting at least one candidate artificial receptor for which test ligand binding was detected as a working artificial receptor for the test ligand. The candidate artificial receptor can include a plurality of building blocks coupled to a region of a support.

In an embodiment, contacting at least one artificial receptor with the test ligand can include contacting an array of candidate artificial receptors with the test ligand. In an embodiment, the array can include at least about 100 candidate artificial receptors. In an embodiment, the array can include at least about 10,000 candidate artificial receptors. In an embodiment, the array can include at least about 1,000,000 candidate artificial receptors.

In an embodiment, the test ligand can include at least one of drug of abuse, peptide, polypeptide, oligonucleotide, polynucleotide, and microbe. In an embodiment, the test ligand comprises at least one of isomer, conformation of protein, and proteome.

In an embodiment, a method of the invention can include contacting at least one candidate artificial receptor with a first protein to produce at least one protein treated candidate artificial receptor; contacting the protein treated candidate artificial receptor with a proteome including proteome proteins; detecting binding of at least one proteome protein to the at least one protein treated candidate artificial receptor; and selecting those candidate artificial receptors that bind both the first protein and at least one proteome protein as working artificial receptors, or selecting the at least one proteome protein for which binding was detected and the first protein for analysis.

In an embodiment, a method of the invention can include contacting at least one candidate artificial receptor with a mixture comprising the test ligand and a candidate disruptor; detecting binding of the test ligand to at least one candidate artificial receptor in the presence of the candidate disruptor; and selecting at least one candidate artificial receptor for which test ligand binding occurred in the absence of candidate disruptor but for which test ligand binding was disrupted by the candidate disruptor as a working artificial receptor for the test ligand.

The present invention includes methods for detecting a test ligand. In an embodiment, a method of the invention can include contacting at least one working artificial receptor with a sample suspected of containing the test ligand and monitoring for binding to the at least one working artificial receptor, wherein binding to the at least one working artificial receptor indicates the presence of the test ligand in the sample. The working artificial receptor can include a plurality of building blocks coupled to a region of a support. In an embodiment, the at least one working artificial receptor is known to bind the test ligand. In an embodiment, the at least one working artificial receptor can include a plurality of artificial receptors.

In an embodiment, the binding of the test ligand produces a detectable pattern among the plurality of artificial receptors. In an embodiment, test ligand can include at least one of drug of abuse, peptide, polypeptide, oligonucleotide, polynucleotide, and microbe. In an embodiment, the test ligand can include at least one of isomer, conformation of protein, and proteome.

In an embodiment, a method of the present invention can include contacting a plurality of candidate artificial receptors with a first test ligand; detecting binding of the first test ligand to at least one candidate artificial receptor; and cataloging location or composition of the at least one artificial receptor that bound the first test ligand. Each candidate artificial receptor independently can include a plurality of building blocks coupled to a region of a support.

The methods of the invention can detect more than one test ligand. In an embodiment, the method can include contacting one or more of the plurality of candidate artificial receptors with a second test ligand; detecting binding of the second test ligand to at least one candidate artificial receptor; and cataloging location or composition of the at least one artificial receptor that bound the second test ligand.

In an embodiment, the method can include comparing the location or composition of the at least one artificial receptor that bound the first test ligand to location or composition of the at least one artificial receptor that bound the second test ligand; and cataloging the comparison of the location or composition. In an embodiment, the method can include distinguishing the first test ligand from the second test ligand based on the comparison.

The present invention includes methods for detecting a compound that disrupts an interaction of a test ligand. This method can include contacting at least one working artificial receptor with a test ligand and a candidate disruptor. Contacting can be simultaneous, contacting with test ligand can come before contacting with candidate disruptor, or contacting with candidate disrupter ligand can come before contacting with test ligand. In an embodiment, the method can include contacting at least one working artificial receptor with a mixture comprising the test ligand and a candidate disrupter. The method can also include monitoring for those candidate disruptors that decrease binding of the test ligand to the at least one working artificial receptor, wherein decreased binding indicates that the candidate disrupter is a lead disruptor. The working artificial receptor can include a plurality of building blocks coupled to a region of a support. In an embodiment, the at least one working artificial receptor is known to bind the test ligand.

In an embodiment, the test ligand can include at least one of drug of abuse, peptide, polypeptide, oligonucleotide, polynucleotide, and microbe. In an embodiment, the test ligand can include at least one of isomer, conformation of protein, and proteome.

In an embodiment, the candidate disruptor can include a compound with molecular weight less than 500. In an embodiment, the candidate disruptor can include a polypeptide.

The present invention includes methods for making an affinity support for a test ligand. In an embodiment, a method of the invention can include contacting at least one candidate artificial receptor with the test ligand; detecting binding of the test ligand to at least one candidate artificial receptor; selecting at least one candidate artificial receptor for which test ligand binding was detected as a working artificial receptor for the test ligand; and coupling the working artificial receptor to a second support to form an affinity support. The candidate artificial receptor can include a plurality of building blocks coupled to a region of a first support.

In an embodiment, the test ligand can include at least one of drug of abuse, peptide, polypeptide, oligonucleotide, polynucleotide, and microbe. In an embodiment, the test ligand can include at least one of isomer, conformation of protein, and proteome.

The present invention includes methods for isolating a test ligand. In an embodiment, a method of the invention can include contacting a sample containing the test ligand with a working artificial receptor. The working artificial receptor can include a plurality of building blocks coupled to a region of a support. In an embodiment, the working artificial receptor is known to bind the test ligand.

The present invention includes methods for making a reaction support for a reactant. In an embodiment, a method of the invention can include contacting at least one candidate artificial receptor with the reactant; detecting binding of the test ligand to at least one candidate artificial receptor; selecting at least one candidate artificial receptor for which test ligand binding was detected as a working artificial receptor for the test ligand; contacting at least one working artificial receptor with the reactant and monitoring for a reaction of the reactant; selecting a working artificial receptor for which the reaction was observed as a reaction artificial receptor; and coupling the reaction artificial receptor to a second support to form a reaction support. The candidate artificial receptor can include a plurality of building blocks coupled to a region of a first support. In an embodiment, the method can include contacting at least one working artificial receptor with a second reactant.

In an embodiment, the reactant can include at least one of molecule with molecular weight less than 500, protein, polynucleotide, organic polymer, or mixture thereof. In an embodiment, the reactant can include an isomer of a molecule with molecular weight less than 500.

The present invention includes methods for reacting a reactant. In an embodiment, a method of the invention can include contacting a sample containing the reactant with a working artificial receptor. The working artificial receptor can include a plurality of building blocks coupled to a region of a support. In an embodiment, the working artificial receptor is known to bind the test ligand. In an embodiment, the method can include contacting the working artificial receptor with a second reactant.

The present invention includes methods of making a catalytic support for a reactant. In an embodiment, a method of the present invention can include contacting at least one candidate artificial receptor with the reactant; detecting catalysis of a reaction of the reactant in the presence of the at least one candidate artificial receptor; selecting at least one candidate artificial receptor for which catalysis was detected as a working artificial receptor for the test ligand; and coupling the working receptor to a second support to form a catalytic support. The candidate artificial receptor can include a plurality of building blocks coupled to a region of a first support. In an embodiment, the method can include contacting at least one working artificial receptor with a second reactant.

In an embodiment, the reactant can include at least one of drug of abuse, peptide, polypeptide, oligonucleotide, polynucleotide, and microbe. In an embodiment, the reactant can include at least one of isomer, conformation of protein, and proteome.

The present invention includes methods of catalyzing a reaction. In an embodiment, a method of the invention can include contacting a sample containing a reactant with a working artificial receptor. The working artificial receptor can include a plurality of building blocks coupled to a region of a support. In an embodiment, the working artificial receptor is known to bind the test ligand and catalyze the reaction.

The present invention includes methods of making a surface that does not bind a test ligand. In an embodiment, a method of the invention can include contacting at least one candidate artificial receptor with the test ligand; detecting lack of binding of the test ligand to at least one candidate artificial receptor; and selecting at least one candidate artificial receptor for which test lack of ligand binding was detected as a nonbinding surface for the test ligand. The candidate artificial receptor can include a plurality of building blocks coupled to a region of a support. In an embodiment, the test ligand comprises a plurality of test ligands.

The present invention includes methods for detecting a compound that disrupts an interaction of a test ligand with a second ligand. In an embodiment, a method of the invention can include binding the test ligand to at least one working artificial receptor.

This method can include contacting at least one working artificial receptor with a second ligand and a candidate disrupter. Contacting can be simultaneous, contacting with second ligand can come before contacting with candidate disrupter, or contacting with candidate disruptor ligand can come before contacting with second ligand. In an embodiment, the method can include monitoring for those candidate disruptors that decrease binding of the second ligand to the test ligand wherein decreased binding indicates that the candidate disrupter is a lead disruptor. The working artificial receptor can include a plurality of building blocks coupled to a region of a support. In an embodiment, the at least one working artificial receptor is known to bind the test ligand.

In an embodiment, the test ligand can include at least one of peptide, polypeptide, oligonucleotide, polynucleotide, and microbe. In an embodiment, the test ligand can include a first protein and the second ligand comprises a second protein; the first protein and the second protein forming a complex. In an embodiment, the test ligand can include a protein and the second ligand comprises a polynucleotide; the protein and the polynucleotide forming a complex.

In an embodiment, the candidate disruptor can include a compound with molecular weight less than 500. In an embodiment, the candidate disruptor can include a polypeptide.

In an embodiment, in this method contacting with the first ligand comprises contacting with the complex; and contacting the at least one working artificial receptor with bound test ligand with the second ligand and with a candidate disruptor comprises contacting with the candidate disrupter.

Test Ligands

The test ligand can be any ligand for which binding to an array or surface can be detected. The test ligand can be a pure compound, a mixture, or a "dirty" mixture containing a natural product or pollutant. Such dirty mixtures can be tissue homogenate, biological fluid, soil sample, water sample, or the like.

Test ligands include prostate specific antigen, other cancer markers, insulin, warfarin, other anti-coagulants, cocaine, other drugs-of-abuse, markers for *E. coli*, markers for *Salmonella* sp., markers for other food-borne toxins, food-borne toxins, markers for Smallpox virus, markers for anthrax, markers for other possible toxic biological agents, pharmaceuticals and medicines, pollutants and chemicals in hazardous waste, toxic chemical agents, markers of disease, pharmaceuticals, pollutants, biologically important cations (e.g., potassium or calcium ion), peptides, carbohydrates, enzymes, bacteria, viruses, mixtures thereof, and the like. In certain embodiments, the test ligand can be at least one of small organic molecules, inorganic/organic complexes, metal ion, mixture of proteins, protein, nucleic acid, mixture of nucleic acids, mixtures thereof, and the like.

Suitable test ligands include any compound or category of compounds described elsewhere in this document as being a test ligand, including, for example, the microbes, proteins, cancer cells, drugs of abuse, and the like described above.

Methods of Making an Artificial Receptor

The present invention relates to a method of making an artificial receptor or a candidate artificial receptor. In an embodiment, this method includes preparing a spot or region on a support, the spot or region including a plurality of building blocks immobilized on the support. The method can include forming a plurality of spots on a solid support, each spot including a plurality of building blocks, and immobilizing (e.g., reversibly) a plurality of building blocks on the solid support in each spot. In an embodiment, an array of such spots is referred to as a heterogeneous building block array.

The method can include mixing a plurality of building blocks and employing the mixture in forming the spot(s). Alternatively, the method can include spotting individual building blocks on the support. Coupling building blocks to the support can employ covalent bonding or noncovalent interactions. Suitable noncovalent interactions include interactions between ions, hydrogen bonding, van der Waals interactions, and the like. In an embodiment, the support can be functionalized with moieties that can engage in covalent bonding or noncovalent interactions. Forming spots can yield a microarray of spots of heterogeneous combinations of building blocks, each of which can be a candidate artificial receptor. The method can apply or spot building blocks onto a support in combinations of 2, 3, 4, or more building blocks.

In an embodiment, the present method can be employed to produce a solid support having on its surface a plurality of regions or spots, each region or spot including a plurality of building blocks. For example, the method can include spotting a glass slide with a plurality of spots, each spot including a plurality of building blocks. Such a spot can be referred to as including heterogeneous building blocks. A plurality of spots of building blocks can be referred to as an array of spots.

In an embodiment, the present method includes making a receptor surface. Making a receptor surface can include forming a region on a solid support, the region including a plurality of building blocks, and immobilizing (e.g., reversibly) the plurality of building blocks to the solid support in the region. The method can include mixing a plurality of building blocks and employing the mixture in forming the region or regions. Alternatively, the method can include applying individual building blocks in a region on the support. Forming a region on a support can be accomplished, for example, by soaking a portion of the support with the building block solution. The resulting coating including building blocks can be referred to as including heterogeneous building blocks.

A region including a plurality of building blocks can be independent and distinct from other regions including a plurality of building blocks. In an embodiment, one or more regions including a plurality of building blocks can overlap to produce a region including the combined pluralities of building blocks. In an embodiment, two or more regions including a single building block can overlap to form one or more regions each including a plurality of building blocks. The overlapping regions can be envisioned, for example, as portions of overlap in a Ven diagram, or as portions of overlap in a pattern like a plaid or tweed.

In an embodiment, the method produces a spot or surface with a density of building blocks sufficient to provide interactions of more than one building block with a ligand. That is, the building blocks can be in proximity to one another. Proximity of different building blocks can be detected by determining different (e.g., greater) binding of a test ligand to a spot or surface including a plurality of building blocks compared to a spot or surface including only one of the building blocks.

In an embodiment, the method includes forming an array of heterogeneous spots made from combinations of a subset of the total building blocks and/or smaller groups of the building blocks in each spot. That is, the method forms spots including only, for example, 2 or 3 building blocks, rather than 4 or 5. For example, the method can form spots from combinations of a full set of building blocks (e.g. 81 of a set of 81) in groups of 2 and/or 3. For example, the method can form spots from combinations of a subset of the building blocks (e.g., 25 of the set of 81) in groups of 4 or 5. For example, the method can form spots from combinations of a subset of the building blocks (e.g., 25 of a set of 81) in groups of 2 or 3. The method can include forming additional arrays incorporating building blocks, lead artificial receptors, or structurally similar building blocks.

In an embodiment, the method includes forming an array including one or more spots that function as controls for validating or evaluating binding to artificial receptors of the present invention. In an embodiment, the method includes forming one or more regions, tubes, or wells that function as controls for validating or evaluating binding to artificial receptors of the present invention. Such a control spot, region, tube, or well can include no building block, only a single building block, only functionalized lawn, or combinations thereof.

The method can immobilize (e.g., reversibly) building blocks on supports using known methods for immobilizing compounds of the types employed as building blocks. Coupling building blocks to the support can employ covalent bonding or noncovalent interactions. Suitable noncovalent interactions include interactions between ions, hydrogen bonding, van der Waals interactions, and the like. In an embodiment, the support can be functionalized with moieties that can engage in reversible covalent bonding, moieties that can engage in noncovalent interactions, a mixture of these moieties, or the like.

In an embodiment, the support can be functionalized with moieties that can engage in covalent bonding, e.g., reversible covalent bonding. The present invention can employ any of a variety of the numerous known functional groups, reagents, and reactions for forming reversible covalent bonds. Suitable reagents for forming reversible covalent bonds include those described in Green, TW; Wuts, PGM (1999), *Protective Groups in Organic Synthesis Third Edition*, Wiley-Interscience, New York, 779 pp. For example, the support can include functional groups such as a carbonyl group, a carboxyl group, a silane group, boric acid or ester, an amine group (e.g., a primary, secondary, or tertiary amine, a hydroxylamine, a hydrazine, or the like), a thiol group, an alcohol group (e.g., primary, secondary, or tertiary alcohol), a diol group (e.g., a 1,2 diol or a 1,3 diol), a phenol group, a catechol group, or the like. These functional groups can form groups with reversible covalent bonds, such as ether (e.g., alkyl ether, silyl ether, thioether, or the like), ester (e.g., alkyl ester, phenol ester, cyclic ester, thioester, or the like), acetal (e.g., cyclic acetal), ketal (e.g., cyclic ketal), silyl derivative (e.g., silyl ether), boronate (e.g., cyclic boronate), amide, hydrazide, imine, carbamate, or the like. Such a functional group can be referred to as a covalent bonding moiety, e.g., a first covalent bonding moiety.

A carbonyl group on the support and an amine group on a building block can form an imine or Schiff's base. The same is true of an amine group on the support and a carbonyl group on a building block. A carbonyl group on the support and an alcohol group on a building block can form an acetal or ketal. The same is true of an alcohol group on the support and a carbonyl group on a building block. A thiol (e.g., a first thiol) on the support and a thiol (e.g., a second thiol) on the building block can form a disulfide.

A carboxyl group on the support and an alcohol group on a building block can form an ester. The same is true of an alcohol group on the support and a carboxyl group on a building block. Any of a variety of alcohols and carboxylic acids can form esters that provide covalent bonding that can be reversed in the context of the present invention. For example, reversible ester linkages can be formed from alcohols such as phenols with electron withdrawing groups on the aryl ring, other alcohols with electron withdrawing groups acting on the hydroxyl-bearing carbon, other alcohols, or the like; and/or carboxyl groups such as those with electron withdrawing groups acting on the acyl carbon (e.g., nitrobenzylic acid, R—$CF_2$—COOH, R—$CCl_2$—COOH, and the like), other carboxylic acids, or the like.

In an embodiment, the support, matrix, or lawn can be functionalized with moieties that can engage in noncovalent interactions. For example, the support can include functional groups such as an ionic group, a group that can hydrogen bond, or a group that can engage in van der Waals or other hydrophobic interactions. Such functional groups can include cationic groups, anionic groups, lipophilic groups, amphiphilic groups, and the like.

In an embodiment, the support, matrix, or lawn includes a charged moiety (e.g., a first charged moiety). Suitable charged moieties include positively charged moieties and negatively charged moieties. Suitable positively charged moieties (e.g., at neutral pH in aqueous compositions) include amines, quaternary ammonium moieties, ferrocene, or the like. Suitable negatively charged moieties (e.g., at neutral pH in aqueous compositions) include carboxylates, phenols substituted with strongly electron withdrawing groups (e.g., tetrachlorophenols), phosphates, phosphonates, phosphinates, sulphates, sulphonates, thiocarboxylates, hydroxamic acids, or the like.

In an embodiment, the support, matrix, or lawn includes groups that can hydrogen bond (e.g., a first hydrogen bonding group), either as donors or acceptors. The support, matrix, or lawn can include a surface or region with groups that can hydrogen bond. For example, the support, matrix, or lawn can include a surface or region including one or more carboxyl groups, amine groups, hydroxyl groups, carbonyl groups, or the like. Ionic groups can also participate in hydrogen bonding.

In an embodiment, the support, matrix, or lawn includes a lipophilic moiety (e.g., a first lipophilic moiety). Suitable lipophilic moieties include branched or straight chain $C_{6-36}$ alkyl, $C_{8-24}$ alkyl, $C_{12-24}$ alkyl, $C_{12-18}$ alkyl, or the like; $C_{6-36}$ alkenyl, $C_{8-24}$ alkenyl, $C_{12-24}$ alkenyl, $C_{12-18}$ alkenyl, or the like, with, for example, 1 to 4 double bonds; $C_{6-36}$ alkynyl, $C_{8-24}$ alkynyl, $C_{12-24}$ alkynyl, $C_{12-18}$ alkynyl, or the like, with, for example, 1 to 4 triple bonds; chains with 1-4 double or triple bonds; chains including aryl or substituted aryl moieties (e.g., phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. A lipophilic moiety like a quaternary ammonium lipophilic moiety can also include a positive charge.

Artificial Receptors

A candidate artificial receptor, a lead artificial receptor, or a working artificial receptor includes combination of building blocks immobilized (e.g., reversibly) on, for example, a support. An individual artificial receptor can be a heterogeneous building block spot on a slide or a plurality of building blocks coated on a slide, tube, or well. The building blocks can be immobilized through any of a variety of interactions, such as covalent, electrostatic, or hydrophobic interactions. For example, the building block and support or lawn can each include one or more functional groups or moieties that can form covalent, electrostatic, hydrogen bonding, van der Waals, or like interactions.

An array of candidate artificial receptors can be a commercial product sold to parties interested in using the candidate artificial receptors as implements in developing receptors for test ligands of interest. In an embodiment, a useful array of candidate artificial receptors includes at least one glass slide, the at least one glass slide including spots of a predetermined number of combinations of members of a set of building blocks, each combination including a predetermined number of building blocks.

One or more lead artificial receptors can be developed from a plurality of candidate artificial receptors. In an embodiment, a lead artificial receptor includes a combination of building blocks and binds detectable quantities of test ligand upon exposure to, for example, several picomoles of test ligand at a concentration of 1, 0.1, or 0.01 µg/ml, or at 1, 0.1, or 0.01 ng/ml test ligand; at a concentration of 0.01 µg/ml, or at 1, 0.1, or 0.01 ng/ml test ligand; or a concentration of 1, 0.1, or 0.01 ng/ml test ligand.

Artificial receptors, particularly candidate or lead artificial receptors, can be in the form of an array of artificial receptors. Such an array can include, for example, 1.66 million spots, each spot including one combination of 4 building blocks from a set of 81 building blocks. Such an array can include, for example, 28,000 spots, each spot including one combination of 2, 3, or 4 building blocks from a set of 29 building blocks. Each spot is a candidate artificial receptor and a combination of building blocks. The array can also be constructed to include lead artificial receptors. For example, the array of artificial receptors can include combinations of fewer building blocks and/or a subset of the building blocks.

In an embodiment, an array of candidate artificial receptors includes building blocks of general Formula 2 (shown hereinbelow), with $RE_1$ being B1, B2, B3, B3a, B4, B5, B6, B7, B8, or B9 (shown hereinbelow) and with $RE_2$ being A1, A2, A3, A3a, A4, A5, A6, A7, A8, or A9 (shown hereinbelow). In an embodiment, the framework is tyrosine.

One or more working artificial receptors can be developed from one or more lead artificial receptors. In an embodiment, a working artificial receptor includes a combination of building blocks and binds categorizing or identifying quantities of test ligand upon exposure to, for example, several picomoles of test ligand at a concentration of 100, 10, 1, 0.1, 0.01, or 0.001 ng/ml test ligand; at a concentration of 10, 1, 0.1, 0.01, or 0.001 ng/ml test ligand; or a concentration of 1, 0.1, 0.01, or 0.001 ng/ml test ligand.

In an embodiment, the artificial receptor of the invention includes a plurality of building blocks coupled to a support. In an embodiment, the plurality of building blocks can include or be building blocks of Formula 2 (shown below). An abbreviation for the building block including a linker, a tyrosine framework, and recognition elements AxBy is TyrAxBy. In an embodiment, a candidate artificial receptor can include combinations of building blocks of formula TyrA1B1, TyrA2B2, TyrA2B4, TyrA2B6, TyrA2B8, TyrA3B3, TyrA4B2, TyrA4B4, TyrA4B6, TyrA4B8, TyrA5B5, TyrA6B2, TyrA6B4, TyrA6B6, TyrA6B8, TyrA7B7, TyrA8B2, TyrA8B4, TyrA8B6, or TyrA8B8.

The present artificial receptors can employ any of a variety of supports to which building blocks or other array materials can be coupled. For example, the support can be glass or plastic; a slide, a tube, or a well; an optical fiber; a nanotube or a buckyball, a nanodevice; a dendrimer, or a scaffold; or the like.

Building Blocks

The present invention relates to building blocks for making or forming candidate artificial receptors. Building blocks can be designed, made, and selected to provide a variety of structural characteristics among a small number of compounds. A building block can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A building block can be bulky or it can be small.

A building block can be visualized as including several components, such as one or more frameworks, one or more linkers, and/or one or more recognition elements. The framework can be covalently coupled to each of the other building block components. The linker can be covalently coupled to the framework. The linker can be coupled to a support through one or more of covalent, electrostatic, hydrogen bonding, van der Waals, or like interactions. The recognition element can be covalently coupled to the framework. In an embodiment, a building block includes a framework, a linker, and a recognition element. In an embodiment, a building block includes a framework, a linker, and two recognition elements.

A description of general and specific features and functions of a variety of building blocks and their synthesis can be found in copending U.S. patent application Ser. No. 10/244,727, filed Sep. 16, 2002, Ser. No. 10/813,568, filed Mar. 29, 2004, and Application No. PCT/US03/05328, filed Feb. 19, 2003, each entitled "ARTIFICIAL RECEPTORS, BUILDING BLOCKS, AND METHODS"; U.S. patent application Ser. Nos. 10/812,850 and 10/813,612, and application No. PCT/U.S. 2004/009649, each filed Mar. 29, 2004 and each entitled "ARTIFICIAL RECEPTORS INCLUDING REVERSIBLY IMMOBILIZED BUILDING BLOCKS, THE BUILDING BLOCKS, AND METHODS"; and U.S. Provisional Patent Application No. 60/499,965, filed Sep. 3, 2003, and 60/526,699, filed Dec. 2, 2003, each entitled BUILDING BLOCKS FOR ARTIFICIAL RECEPTORS; the disclosures of which are incorporated herein by reference. These patent documents include, in particular, a detailed written description of: function, structure, and configuration of building blocks, framework moieties, recognition elements, synthesis of building blocks, specific embodiments of building blocks, specific embodiments of recognition elements, and sets of building blocks.

Framework

The framework can be selected for functional groups that provide for coupling to the recognition moiety and for coupling to or being the linking moiety. The framework can interact with the ligand as part of the artificial receptor. In an embodiment, the framework includes multiple reaction sites with orthogonal and reliable functional groups and with controlled stereochemistry. Suitable functional groups with orthogonal and reliable chemistries include, for example, carboxyl, amine, hydroxyl, phenol, carbonyl, and thiol groups, which can be individually protected, deprotected, and derivatized. In an embodiment, the framework has two, three, or four functional groups with orthogonal and reliable chemistries. In an embodiment, the framework has three functional groups. In such an embodiment, the three functional groups can be independently selected, for example, from carboxyl, amine, hydroxyl, phenol, carbonyl, or thiol group. The framework can include alkyl, substituted alkyl, cycloalkyl, heterocyclic, substituted heterocyclic, aryl alkyl, aryl, heteroaryl, heteroaryl alkyl, and like moieties.

A general structure for a framework with three functional groups can be represented by Formula 1a:

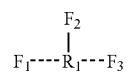

A general structure for a framework with four functional groups can be represented by Formula 1b:

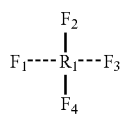

In these general structures: $R_1$ can be a 1-12, a 1-6, or a 1-4 carbon alkyl, substituted alkyl, cycloalkyl, heterocyclic, substituted heterocyclic, aryl alkyl, aryl, heteroaryl, heteroaryl alkyl, or like group; and $F_1$, $F_2$, $F_3$, or $F_4$ can independently be a carboxyl, amine, hydroxyl, phenol, carbonyl, or thiol group. $F_1$, $F_2$, $F_3$, or $F_4$ can independently be a 1-12, a 1-6, a 1-4 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group. $F_3$ and/or $F_4$ can be absent.

A variety of compounds fit the formulas and text describing the framework including amino acids, and naturally occurring or synthetic compounds including, for example, oxygen and sulfur functional groups. The compounds can be racemic, optically active, or achiral. For example, the compounds can be natural or synthetic amino acids, α-hydroxy acids, thioic acids, and the like.

Suitable molecules for use as a framework include a natural or synthetic amino acid, particularly an amino acid with a functional group (e.g., third functional group) on its side chain. Amino acids include carboxyl and amine functional groups. The side chain functional group can include, for natural amino acids, an amine (e.g., alkyl amine, heteroaryl amine), hydroxyl, phenol, carboxyl, thiol, thioether, or amidino group. Natural amino acids suitable for use as frameworks include, for example, serine, threonine, tyrosine, aspartic acid, glutamic acid, asparagine, glutamine, cysteine, lysine, arginine, histidine. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups. Suitable synthetic amino acids include β-amino acids and homo or β analogs of natural amino acids. In an embodiment, the framework amino acid can be serine, threonine, or tyrosine, e.g., serine or tyrosine, e.g., tyrosine.

Although not limiting to the present invention, a framework amino acid, such as serine, threonine, or tyrosine, with a linker and two recognition elements can be visualized with one of the recognition elements in a pendant orientation and the other in an equatorial orientation, relative to the extended carbon chain of the framework.

All of the naturally occurring and many synthetic amino acids are commercially available. Further, forms of these amino acids derivatized or protected to be suitable for reactions for coupling to recognition element(s) and/or linkers can be purchased or made by known methods (see, e.g., Green, TW; Wuts, PGM (1999), *Protective Groups in Organic Synthesis Third Edition*, Wiley-Interscience, New York, 779 pp.; Bodanszky, M.; Bodanszky, A. (1994), The Practice of Peptide Synthesis Second Edition, Springer-Verlag, New York, 217 pp.).

Recognition Element

The recognition element can be selected to provide one or more structural characteristics to the building block. The recognition element can interact with the ligand as part of the artificial receptor. For example, the recognition element can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A recognition element can be a small group or it can be bulky.

In an embodiment the recognition element can be a 1-12, a 1-6, or a 1-4 carbon alkyl, substituted alkyl, cycloalkyl, heterocyclic, substituted heterocyclic, aryl alkyl, aryl, heteroaryl, heteroaryl alkyl, or like group. The recognition element can be substituted with a group that includes or imparts positive charge, negative charge, acid, base, electron acceptor, electron donor, hydrogen bond donor, hydrogen bond acceptor, free electron pair, π electrons, charge polarization, hydrophilicity, hydrophobicity, and the like.

Recognition elements with a positive charge (e.g., at neutral pH in aqueous compositions) include amines, quaternary ammonium moieties, sulfonium, phosphonium, ferrocene, and the like. Suitable amines include alkyl amines, alkyl diamines, heteroalkyl amines, aryl amines, heteroaryl amines, aryl alkyl amines, pyridines, heterocyclic amines (saturated or unsaturated, the nitrogen in the ring or not), amidines, hydrazines, and the like. Alkyl amines generally have 1 to 12 carbons, e.g., 1-8, and rings can have 3-12 carbons, e.g., 3-8. Suitable alkyl amines include that of formula B9. Suitable heterocyclic or alkyl heterocyclic amines include that of formula A9. Suitable pyridines include those of formulas A5 and B5. Any of the amines can be employed as a quaternary ammonium compound. Additional suitable quaternary ammonium moieties include trimethyl alkyl quaternary ammonium moieties, dimethyl ethyl alkyl quaternary ammonium moieties, dimethyl alkyl quaternary ammonium moieties, aryl alkyl quaternary ammonium moieties, pyridinium quaternary ammonium moieties, and the like.

Recognition elements with a negative charge (e.g., at neutral pH in aqueous compositions) include carboxylates, phenols substituted with strongly electron withdrawing groups (e.g., substituted tetrachlorophenols), phosphates, phosphonates, phosphinates, sulphates, sulphonates, thiocarboxylates, and hydroxamic acids. Suitable carboxylates include alkyl carboxylates, aryl carboxylates, and aryl alkyl carboxylates. Suitable phosphates include phosphate mono-, di-, and tri-esters, and phosphate mono-, di-, and tri-amides. Suitable phosphonates include phosphonate mono- and di-esters, and phosphonate mono- and di-amides (e.g., phosphonamides). Suitable phosphinates include phosphinate esters and amides.

Recognition elements with a negative charge and a positive charge (at neutral pH in aqueous compositions) include sulfoxides, betaines, and amine oxides.

Acidic recognition elements can include carboxylates, phosphates, sulphates, and phenols. Suitable acidic carboxylates include thiocarboxylates. Suitable acidic phosphates include the phosphates listed hereinabove.

Basic recognition elements include amines. Suitable basic amines include alkyl amines, aryl amines, aryl alkyl amines, pyridines, heterocyclic amines (saturated or unsaturated, the nitrogen in the ring or not), amidines, and any additional amines listed hereinabove. Suitable alkyl amines include that of formula B9. Suitable heterocyclic or alkyl heterocyclic amines include that of formula A9. Suitable pyridines include those of formulas A5 and B5.

Recognition elements including a hydrogen bond donor include amines, amides, carboxyls, protonated phosphates, protonated phosphonates, protonated phosphinates, protonated sulphates, protonated sulphinates, alcohols, and thiols. Suitable amines include alkyl amines, aryl amines, aryl alkyl amines, pyridines, heterocyclic amines (saturated or unsaturated, the nitrogen in the ring or not), amidines, ureas, and any other amines listed hereinabove. Suitable alkyl amines include that of formula B9. Suitable heterocyclic or alkyl heterocyclic amines include that of formula A9. Suitable pyridines include those of formulas A5 and B5. Suitable protonated carboxylates, protonated phosphates include those listed hereinabove. Suitable amides include those of formulas A8 and B8. Suitable alcohols include primary alcohols, secondary alcohols, tertiary alcohols, and aromatic alcohols (e.g., phenols). Suitable alcohols include those of formulas A7 (a primary alcohol) and B7 (a secondary alcohol).

Recognition elements including a hydrogen bond acceptor or one or more free electron pairs include amines, amides, carboxylates, carboxyl groups, phosphates, phosphonates, phosphinates, sulphates, sulphonates, alcohols, ethers, thiols, and thioethers. Suitable amines include alkyl amines, aryl amines, aryl alkyl amines, pyridines, heterocyclic amines (saturated or unsaturated, the nitrogen in the ring or not), amidines, ureas, and amines as listed hereinabove. Suitable alkyl amines include that of formula B9. Suitable heterocyclic or alkyl heterocyclic amines include that of formula A9. Suitable pyridines include those of formulas A5 and B5. Suitable carboxylates include those listed hereinabove. Suitable amides include those of formulas A8 and B8. Suitable phosphates, phosphonates and phosphinates include those listed hereinabove. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include alkyl ethers, aryl alkyl ethers. Suitable alkyl ethers include that of formula A6. Suitable aryl alkyl ethers include that of formula A4. Suitable thioethers include that of formula B6.

Recognition elements including uncharged polar or hydrophilic groups include amides, alcohols, ethers, thiols, thioethers, esters, thio esters, boranes, borates, and metal complexes. Suitable amides include those of formulas A8 and B8. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include those listed hereinabove. Suitable ethers include that of formula A6. Suitable aryl alkyl ethers include that of formula A4.

Recognition elements including uncharged hydrophobic groups include alkyl (substituted and unsubstituted), alkene (conjugated and unconjugated), alkyne (conjugated and unconjugated), aromatic. Suitable alkyl groups include lower alkyl, substituted alkyl, cycloalkyl, aryl alkyl, and heteroaryl alkyl. Suitable lower alkyl groups include those of formulas A1, A3, A3a, and B1. Suitable aryl alkyl groups include those of formulas A3, A3a, A4, B3, B3a, and B4. Suitable alkyl cycloalkyl groups include that of formula B2. Suitable alkene groups include lower alkene and aryl alkene. Suitable aryl alkene groups include that of formula B4. Suitable aromatic groups include unsubstituted aryl, heteroaryl, substituted aryl, aryl alkyl, heteroaryl alkyl, alkyl substituted aryl, and polyaromatic hydrocarbons. Suitable aryl alkyl groups include those of formulas A3, A3a and B4. Suitable alkyl heteroaryl groups include those of formulas A5 and B5.

Spacer (e.g., small) recognition elements include hydrogen, methyl, ethyl, and the like. Bulky recognition elements include 7 or more carbon or hetero atoms.

Formulas A1-A9 and B1-B9 are:

A1

A2

A3
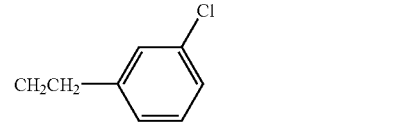

A3a
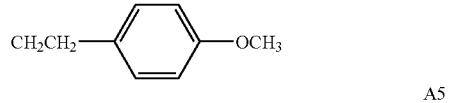

A4
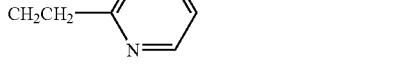

A5

A6

A7

A8
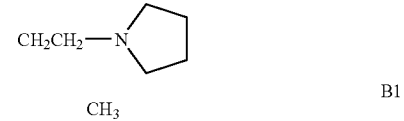

A9

B1

B2
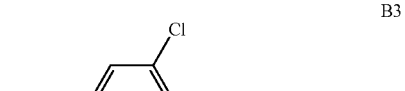

B3
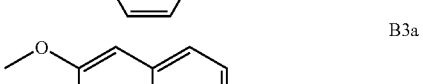

B3a
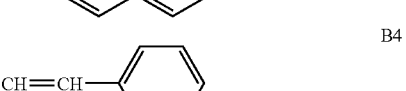

B4
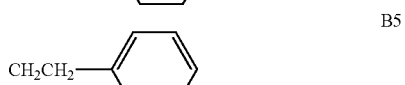

B5
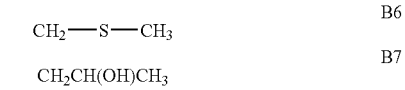

B6

B7

B8
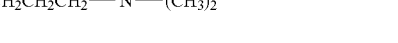

B9
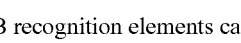

These A and B recognition elements can be called derivatives of, according to a standard reference: A1, ethylamine; A2, isobutylamine; A3, phenethylamine; A4, 4-methoxyphenethylamine; A5,2-(2-aminoethyl)pyridine; A6,2-methoxyethylamine; A7, ethanolamine; A8, N-acetylethylenediamine; A9,1-(2-aminoethyl)pyrrolidine; B1, acetic acid, B2, cyclopentylpropionic acid; B3,3-chlorophenylacetic acid; B4, cinnamic acid; B5, 3-pyridinepropionic acid; B6, (methylthio)acetic acid; B7,3-hydroxybutyric acid; B8, succinamic acid; and B9,4-(dimethylamino)butyric acid.

In an embodiment, the recognition elements include one or more of the structures represented by formulas A1, A2, A3, A3a, A4, A5, A6, A7, A8, and/or A9 (the A recognition elements) and/or B1, B2, B3, B3a, B4, B5, B6, B7, B8, and/or B9 (the B recognition elements). In an embodiment, each building block includes an A recognition element and a B recognition element. In an embodiment, a group of 81 such building blocks includes each of the 81 unique combinations of an A recognition element and a B recognition element. In an embodiment, the A recognition elements are linked to a framework at a pendant position. In an embodiment, the B recognition elements are linked to a framework at an equatorial position. In an embodiment, the A recognition elements are linked to a framework at a pendant position and the B recognition elements are linked to the framework at an equatorial position.

Although not limiting to the present invention, it is believed that the A and B recognition elements represent the assortment of functional groups and geometric configurations employed by polypeptide receptors. Although not limiting to the present invention, it is believed that the A recognition elements represent six advantageous functional groups or configurations and that the addition of functional groups to several of the aryl groups increases the range of possible binding interactions. Although not limiting to the present invention, it is believed that the B recognition elements represent six advantageous functional groups, but in different configurations than employed for the A recognition elements. Although not limiting to the present invention, it is further believed that this increases the range of binding interactions and further extends the range of functional groups and configurations that is explored by molecular configurations of the building blocks.

In an embodiment, the building blocks including the A and B recognition elements can be visualized as occupying a binding space defined by lipophilicity/hydrophilicity and volume. A volume can be calculated (using known methods) for each building block including the various A and B recognition elements. A measure of lipophilicity/hydrophilicity (logP) can be calculated (using known methods) for each building block including the various A and B recognition elements. Negative values of logP show affinity for water over nonpolar organic solvent and indicate a hydrophilic nature. A plot of volume versus logP can then show the distribution of the building blocks through a binding space defined by size and lipophilicity/hydrophilicity.

Reagents that form many of the recognition elements are commercially available. For example, reagents for forming recognition elements A1, A2, A3, A3a, A4, A5, A6, A7, A8, A9 B1, B2, B3, B3a, B4, B5, B6, B7, B8, and B9 are commercially available.

Linkers

The linker is selected to provide a suitable coupling of the building block to a support. The framework can interact with the ligand as part of the artificial receptor. The linker can also provide bulk, distance from the support, hydrophobicity, hydrophilicity, and like structural characteristics to the building block. Coupling building blocks to the support can employ covalent bonding or noncovalent interactions. Suitable noncovalent interactions include interactions between ions, hydrogen bonding, van der Waals interactions, and the like. In an embodiment, the linker includes moieties that can engage in covalent bonding or noncovalent interactions. In an embodiment, the linker includes moieties that can engage in covalent bonding. Suitable groups for forming covalent and reversible covalent bonds are described hereinabove.

Linkers for Reversibly Immobilizable Building Blocks

The linker can be selected to provide suitable reversible immobilization of the building block on a support or lawn. In an embodiment, the linker forms a covalent bond with a functional group on the framework. In an embodiment, the linker also includes a functional group that can reversibly interact with the support or lawn, e.g., through reversible covalent bonding or noncovalent interactions.

In an embodiment, the linker includes one or more moieties that can engage in reversible covalent bonding. Suitable groups for reversible covalent bonding include those described hereinabove. An artificial receptor can include building blocks reversibly immobilized on the lawn or support through, for example, imine, acetal, ketal, disulfide, ester, or like linkages. Such functional groups can engage in reversible covalent bonding. Such a functional group can be referred to as a covalent bonding moiety, e.g., a second covalent bonding moiety.

In an embodiment, the linker can be functionalized with moieties that can engage in noncovalent interactions. For example, the linker can include functional groups such as an ionic group, a group that can hydrogen bond, or a group that can engage in van der Waals or other hydrophobic interactions. Such functional groups can include cationic groups, anionic groups, lipophilic groups, amphiphilic groups, and the like.

In an embodiment, the present methods and compositions can employ a linker including a charged moiety (e.g., a second charged moiety). Suitable charged moieties include positively charged moieties and negatively charged moieties. Suitable positively charged moieties include amines, quaternary ammonium moieties, sulfonium, phosphonium, ferrocene, and the like. Suitable negatively charged moieties (e.g., at neutral pH in aqueous compositions) include carboxylates, phenols substituted with strongly electron withdrawing groups (e.g., tetrachlorophenols), phosphates, phosphonates, phosphinates, sulphates, sulphonates, thiocarboxylates, and hydroxamic acids.

In an embodiment, the present methods and compositions can employ a linker including a group that can hydrogen bond, either as donor or acceptor (e.g., a second hydrogen bonding group). For example, the linker can include one or more carboxyl groups, amine groups, hydroxyl groups, carbonyl groups, or the like. Ionic groups can also participate in hydrogen bonding.

In an embodiment, the present methods and compositions can employ a linker including a lipophilic moiety (e.g., a second lipophilic moiety). Suitable lipophilic moieties include one or more branched or straight chain $C_{6-36}$ alkyl, $C_{8-24}$ alkyl, $C_{12-24}$ alkyl, $C_{12-18}$ alkyl, or the like; $C_{6-36}$ alkenyl, $C_{8-24}$ alkenyl, $C_{12-24}$ alkenyl, $C_{12-18}$ alkenyl, or the like, with, for example, 1 to 4 double bonds; $C_{6-36}$ alkynyl, $C_{8-24}$ alkynyl, $C_{12-24}$ alkynyl, $C_{12-18}$ alkynyl, or the like, with, for example, 1 to 4 triple bonds; chains with 1-4 double or triple bonds; chains including aryl or substituted aryl moieties (e.g., phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. In an embodiment the linker includes or is a lipid, such as a phospholipid. In an embodiment, the lipophilic moiety includes or is a 12-carbon aliphatic moiety.

In an embodiment, the linker includes a lipophilic moiety (e.g., a second lipophilic moiety) and a covalent bonding moiety (e.g., a second covalent bonding moiety). In an embodiment, the linker includes a lipophilic moiety (e.g., a second lipophilic moiety) and a charged moiety (e.g., a second charged moiety).

In an embodiment, the linker forms or can be visualized as forming a covalent bond with an alcohol, phenol, thiol, amine, carbonyl, or like group on the framework. Between the bond to the framework and the group participating in or formed by the reversible interaction with the support or lawn, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

For example, suitable linkers can include: the functional group participating in or formed by the bond to the framework, the functional group or groups participating in or formed by the reversible interaction with the support or lawn, and a linker backbone moiety. The linker backbone moiety can include about 4 to about 48 carbon or heteroatoms, about 8 to about 14 carbon or heteroatoms, about 12 to about 24 carbon or heteroatoms, about 16 to about 18 carbon or heteroatoms, about 4 to about 12 carbon or heteroatoms, about 4 to about 8 carbon or heteroatoms, or the like. The linker backbone can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, mixtures thereof, or like moiety.

In an embodiment, the linker includes a lipophilic moiety, the functional group participating in or formed by the bond to the framework, and, optionally, one or more moieties for forming a reversible covalent bond, a hydrogen bond, or an ionic interaction. In such an embodiment, the lipophilic moiety can have about 4 to about 48 carbons, about 8 to about 14 carbons, about 12 to about 24 carbons, about 16 to about 18 carbons, or the like. In such an embodiment, the linker can include about 1 to about 8 reversible bond/interaction moieties or about 2 to about 4 reversible bond/interaction moieties. Suitable linkers have structures such as $(CH_2)_n COOH$, with n=12-24, n=17-24, or n=16-18.

Additional Embodiments of Linkers

The linker can be selected to provide a suitable covalent coupling of the building block to a support. The framework can interact with the ligand as part of the artificial receptor. The linker can also provide bulk, distance from the support, hydrophobicity, hydrophilicity, and like structural characteristics to the building block. In an embodiment, the linker forms a covalent bond with a functional group on the framework. In an embodiment, before attachment to the support the linker also includes a functional group that can be activated to react with or that will react with a functional group on the support. In an embodiment, once attached to the support, the linker forms a covalent bond with the support and with the framework.

In an embodiment, the linker forms or can be visualized as forming a covalent bond with an alcohol, phenol, thiol, amine, carbonyl, or like group on the framework. The linker can include a carboxyl, alcohol, phenol, thiol, amine, carbonyl, maleimide, or like group that can react with or be activated to react with the support. Between the bond to the framework and the group formed by the attachment to the support, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

The linker can include a good leaving group bonded to, for example, an alkyl or aryl group. The leaving group being "good" enough to be displaced by the alcohol, phenol, thiol, amine, carbonyl, or like group on the framework. Such a linker can include a moiety represented by the formula: R—X, in which X is a leaving group such as halogen (e.g., —Cl, —Br or —I), tosylate, mesylate, triflate, and R is alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

Suitable linker groups include those of formula: $(CH_2)_n COOH$, with n=1-16, n=2-8, n=2-6, or n=3. Reagents that form suitable linkers are commercially available and include any of a variety of reagents with orthogonal functionality.

Embodiments of Building Blocks

In an embodiment, building blocks can be represented by Formula 2:

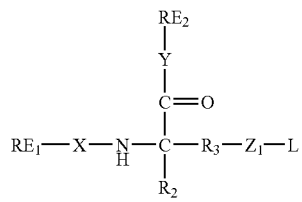

in which: $RE_1$ is recognition element 1, $RE_2$ is recognition element 2, and L is a linker. X is absent, C=O, $CH_2$, NR, $NR_2$, NH, NHCONH, SCONH, CH=N, or $OCH_2NH$. In certain embodiments, X is absent or C=O. Y is absent, NH, O, $CH_2$, or NRCO. In certain embodiments, Y is NH or O. In an embodiment, Y is NH. $Z_1$ and $Z_2$ can independently be CH2, O, NH, S, CO, NR, $NR_2$, NHCONH, SCONH, CH=N, or $OCH_2NH$. In an embodiment, $Z_1$ and/or $Z_2$ can independently be O. $Z_2$ is optional. $R_2$ is H, $CH_3$, or another group that confers chirality on the building block and has size similar to or smaller than a methyl group. $R_3$ is $CH_2$; $CH_2$-phenyl; $CHCH_3$; $(CH_2)_n$ with n=2-3; or cyclic alkyl with 3-8 carbons, e.g., 5-6 carbons, phenyl, naphthyl. In certain embodiments, $R_3$ is $CH_2$ or $CH_2$-phenyl.

$RE_1$ is B1, B2, B3, B3a, B4, B5, B6, B7, B8, B9, A1, A2, A3, A3a, A4, A5, A6, A7, A8, or A9. In certain embodiments, $RE_1$ is B1, B2, B3, B3a, B4, B5, B6, B7, B8, or B9. $RE_2$ is A1, A2, A3, A3a, A4, A5, A6, A7, A8, A9, B1, B2, B3, B3a, B4, B5, B6, B7, B8, or B9. In certain embodiments, $RE_2$ is A1, A2, A3, A3a, A4, A5, A6, A7, A8, or A9. In an embodiment, $RE_1$ can be B2, B3a, B4, B5, B6, B7, or B8. In an embodiment, $RE_2$ can be A2, A3a, A4, A5, A6, A7, or A8.

In an embodiment, L is the functional group participating in or formed by the bond to the framework (such groups are described herein), the functional group or groups participating in or formed by the reversible interaction with the support or lawn (such groups are described herein), and a linker backbone moiety. In an embodiment, the linker backbone moiety is about 4 to about 48 carbon or heteroatom alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or mixtures thereof; or about 8 to about 14 carbon or heteroatoms, about 12 to about 24 carbon or heteroatoms, about 16 to about 18 carbon or heteroatoms, about 4 to about 12 carbon or heteroatoms, about 4 to about 8 carbon or heteroatoms.

In an embodiment, the L is the functional group participating in or formed by the bond to the framework (such groups are described herein) and a lipophilic moiety (such groups are described herein) of about 4 to about 48 carbons, about 8 to about 14 carbons, about 12 to about 24 carbons, about 16 to about 18 carbons. In an embodiment, this L also includes about 1 to about 8 reversible bond/interaction moieties (such groups are described herein) or about 2 to about 4 reversible bond/interaction moieties. In an embodiment, L is $(CH_2)_n$ COOH, with n=12-24, n=17-24, or n=16-18.

In an embodiment, L is $(CH_2)_n$COOH, with n=1-16, n=2-8, n=4-6, or n=3.

Building blocks including an A and/or a B recognition element, a linker, and an amino acid framework can be made by methods illustrated in general Scheme 1.

Sets of Building Blocks

The present invention also relates to sets of building blocks. The sets of building blocks can include isolated building blocks, building blocks with an activated linker for coupling to a support, and/or building blocks coupled to a support. Sets of building blocks include a plurality of building blocks. The plurality of building blocks can be a component of a coating, of a spot or spots (e.g., forming candidate artificial receptor(s)), or of a kit. The plurality of building blocks can include a sufficient number of building blocks and recognition elements for exploring candidate artificial receptors or for defining receptors for a ligand. That is, the set of building blocks can include a majority (preferably at least 6) of the structural characteristics selected from positive charge, negative charge, acid, base, electron acceptor, electron donor, hydrogen bond donor, hydrogen bond acceptor, free electron pair, π electrons, charge polarization, hydrophilicity, hydrophobicity.

For a set of building blocks, the recognition elements are preferably selected to provide a variety of structural characteristics to the individual members of the set. A single building block can include recognition elements with more than one of the structural characteristics. A set of building blocks can include recognition elements with each of the structural characteristics. For example, a set of building blocks can include one or more building blocks including a positively charged recognition element, one or more building blocks including a negatively charged recognition element, one or more building blocks including an acidic recognition element, one or more building blocks including a basic recognition element, one or more building blocks including an electron donating recognition element, one or more building blocks including an electron accepting recognition element, one or more building blocks including a hydrogen bond donor recognition element, one or more building blocks including a hydrogen bond acceptor recognition element, one or more building blocks including a polar recognition element, one or more building blocks including a recognition element with free electron pair(s), one or more building blocks including a recognition element with π electrons, one or more building blocks including a hydrophilic recognition element, one or more building blocks including a hydrophobic recognition element, one or more building blocks including a small recognition element, and/or one or more building blocks including a bulky recognition element.

In an embodiment, the number and variety of recognition elements is selected to provide a set of building blocks with a manageable number of members. A manageable number of building blocks provides, typically, fewer than 10 million combinations, preferably about 2 million combinations, with each combination including, preferably, 3, 4, 5, or 6 building blocks. In an embodiment, the recognition elements provide a set of building blocks that incorporate the functional groups and configurations found in the components of natural receptors, preferably with the smallest number of building blocks.

Techniques for Using Artificial Receptors

Figure 13:
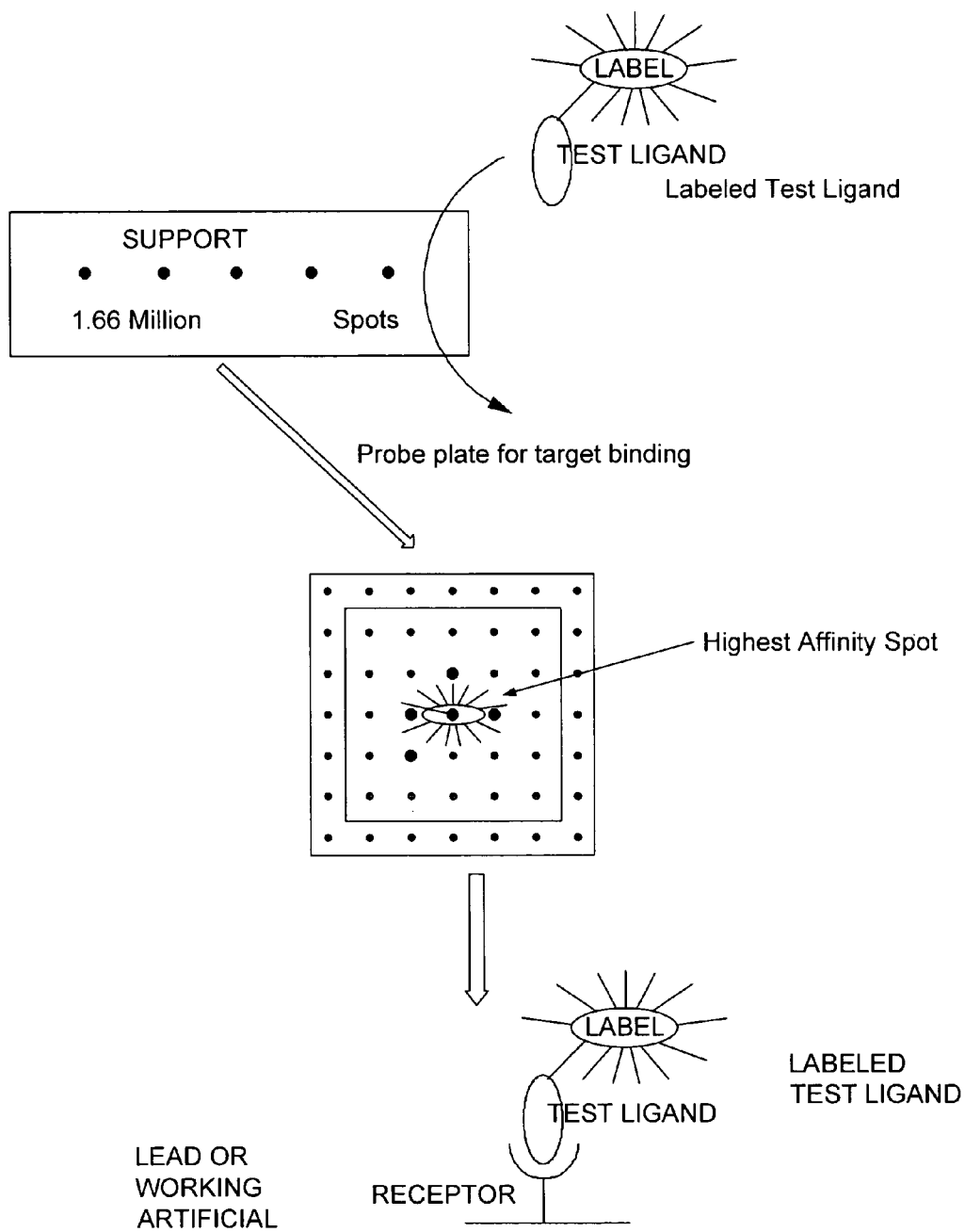
FIG. 13 schematically illustrates identification of a lead artificial receptor from among candidate artificial receptors.

The present invention includes a method of using artificial receptors. The present invention includes a method of screening candidate artificial receptors to find lead artificial receptors that bind a particular test ligand. Detecting test ligand bound to a candidate artificial receptor can be accomplished using known methods for detecting binding to arrays on a slide or to coated tubes or wells. For example, the method can employ test ligand labeled with a detectable label, such as a fluorophore or an enzyme that produces a detectable product. Alternatively, the method can employ an antibody (or other binding agent) specific for the test ligand and including a detectable label. One or more of the spots that are labeled by the test ligand or that are more or most intensely labeled with the test ligand are selected as lead artificial receptors. The degree of labeling can be evaluated by evaluating the signal strength from the label. The amount of signal can be directly proportional to the amount of label and binding. FIG. 13 provides a schematic illustration of an embodiment of this process.

According to the present method, screening candidate artificial receptors against a test ligand can yield one or more lead artificial receptors. One or more lead artificial receptors can be a working artificial receptor. That is, the one or more lead artificial receptors can be useful for detecting the ligand of interest as is. The method can then employ the one or more artificial receptors as a working artificial receptor for monitoring or detecting the test ligand. Alternatively, the one or more lead artificial receptors can be employed in the method for developing a working artificial receptor. For example, the one or more lead artificial receptors can provide structural or other information useful for designing or screening for an improved lead artificial receptor or a working artificial receptor. Such designing or screening can include making and testing additional candidate artificial receptors including combinations of a subset of building blocks, a different set of building blocks, or a different number of building blocks.

The present invention includes a method of screening candidate artificial receptors to find lead artificial receptors that bind a particular test ligand. The method can include allowing movement of the building blocks that make up the artificial receptors. Movement of building blocks can include mobilizing the building block to move along or on the support and/or to leave the support and enter a fluid (e.g., liquid) phase separate from the support or lawn.

In an embodiment, building blocks can be mobilized to move along or on the support (translate or shuffle). Such translation can be employed, for example, to allow building blocks already bound to a test ligand to rearrange into a lower energy or tighter binding configuration still bound to the test ligand. Such translation can be employed, for example, to allow the ligand access to building blocks that are on the support but not bound to the ligand. These building blocks can translate into proximity with and bind to a test ligand.

Building blocks can be induced to move along or on the support or to be reversibly immobilized on the support through any of a variety of mechanisms. For example, inducing mobility of building blocks can include altering the conditions of the support or lawn. That is, altering the conditions can reverse the immobilization of the building blocks, thus mobilizing them. Reversibly immobilizing the building blocks after they have moved can include, for example, returning to the previous conditions. Suitable alterations of conditions include changing pH, changing temperature, changing polarity or hydrophobicity, changing ionic strength, changing nucleophilicity or electrophilicity (e.g. of solvent or solute), and the like.

A building block reversibly immobilized by hydrophobic interactions can be mobilized by increasing the temperature, by exposing the surface, lawn, or building block to a more hydrophobic solvent (e.g., an organic solvent or a surfactant), or by reducing ionic strength around the building block. In an embodiment, the organic solvent includes acetonitrile, acetic acid, an alcohol, tetrahydrofuran (THF), dimethylformamide (DMF), hydrocarbons such as hexane or octane, acetone, chloroform, methylene chloride, or the like, or mixture thereof. In an embodiment, the surfactant includes a nonionic surfactant, such as a nonylphenol ethoxylate, or the like. A building block that is mobile on a support can be reversibly immobilized by hydrophobic interactions, for example, by decreasing the temperature, exposing the surface, lawn, or building block to a more hydrophilic solvent (e.g., an aqueous solvent) or increased ionic strength.

A building block reversibly immobilized by hydrogen bonding can be mobilized by increasing the ionic strength, concentration of hydrophilic solvent, or concentration of a competing hydrogen bonder in the environs of the building block. A building block that is mobile on a support can be reversibly immobilized through an electrostatic interaction by decreasing ionic strength of the hydrophilic solvent, or the like.

A building block reversibly immobilized by an electrostatic interaction can be mobilized by increasing the ionic strength in the environs of the building block. Increasing ionic strength can disrupt electrostatic interactions. A building block that is mobile on a support can be reversibly immobilized through an electrostatic interaction by decreasing ionic strength.

A building block reversibly immobilized by an imine, acetal, or ketal bond can be mobilized by decreasing the pH or increasing concentration of a nucleophilic catalyst in the environs of the building block. In an embodiment, the pH is about 1 to about 4. Imines, acetals, and ketals undergo acid catalyzed hydrolysis. A building block that is mobile on a support can be reversibly immobilized by a reversible covalent interaction, such as by forming an imine, acetal, or ketal bond, by increasing the pH.

In an embodiment, building blocks can be mobilized to leave the support and enter a fluid (e.g., liquid) phase separate from the support or lawn (exchange). For example, building blocks can be exchanged onto and/or off of the support. Exchange can be employed, for example, to allow building blocks on a support but not bound to a test ligand to be removed from the support. Exchange can be employed, for example, to add additional building blocks to the support. The added building blocks can have structures selected based on knowledge of the structures of the building blocks in artificial receptors that bind the test ligand. The added building blocks can have structures selected to provide additional structural diversity. The added building blocks can include all of the building blocks.

A building block reversibly immobilized by hydrophobic interactions can be released from the support by, for example, raising the temperature, e.g., of the support and/or artificial receptor. For example, the hydrophobic interactions (e.g., the hydrophobic group on the support or lawn and on the building block) can be selected to provide immobilized building block at about room temperature or below and release can be accomplished at a temperature above room temperature. For example, the hydrophobic interactions can be selected to provide immobilized building block at about refrigerator temperature (e.g., 4° C.) or below and release can be accomplished at a temperature of, for example, room temperature or above. By way of further example, a building block can be reversibly immobilized by hydrophobic interactions, for example, by contacting the surface or artificial receptor with a fluid containing the building block and that is at or below room temperature.

A building block reversibly immobilized by hydrophobic interactions can be released from the support by, for example, contacting the artificial receptor with a sufficiently hydrophobic fluid (e.g., an organic solvent or a surfactant). In an embodiment, the organic solvent includes acetonitrile, acetic acid, an alcohol, tetrahydrofuran (THF), dimethylformamide (DMF), hydrocarbons such as hexane or octane, acetone, chloroform, methylene chloride, or the like, or mixture thereof. In an embodiment, the surfactant includes a nonionic surfactant, such as a nonylphenol ethoxylate, or the like. Such reversible immobilization can also be effected by contacting the surface or artificial receptor with a hydrophilic solvent and allowing the somewhat lipophilic building block to partition on to the hydrophobic surface or lawn.

A building block reversibly immobilized by an imine, acetal, or ketal bond can be released from the support by, for example, contacting the artificial receptor with fluid having an acid pH or including a nucleophilic catalyst. In an embodiment, the pH is about 1 to about 4. A building block can be reversibly immobilized by a reversible covalent interaction, such as by forming an imine, acetal, or ketal bond, by contacting the surface or artificial receptor with fluid having a neutral or basic pH.

A building block reversibly immobilized by an electrostatic interaction can be released by, for example, contacting the artificial receptor with fluid having sufficiently high ionic strength to disrupt the electrostatic interaction. A building block can be reversibly immobilized through an electrostatic interaction by contacting the surface or artificial receptor with fluid having ionic strength that promotes electrostatic interaction between the building block and the support and/or lawn.

The present invention may be better understood with reference to the following examples. These examples are intended to be representative of specific embodiments of the invention, and are not intended as limiting the scope of the invention.

EXAMPLES

Example 1

Synthesis of Building Blocks

Selected building blocks representative of the alkyl-aromatic-polar span of the an embodiment of the building blocks were synthesized and demonstrated effectiveness of these building blocks for making candidate artificial receptors. These building blocks were made on a framework that can be represented by tyrosine and included numerous recognition element pairs. These recognition element pairs include enough of the range from alkyl, to aromatic, to polar to represent a significant degree of the interactions and functional groups of the full set of 81 such building blocks.

Synthesis

Building block synthesis employed a general procedure outlined in Scheme 7, which specifically illustrates synthesis of a building block on a tyrosine framework with recognition element pair A4B4. This general procedure was employed for synthesis of building blocks including TyrA1B1 [1-1] TyrA2B2, TyrA2B4, TyrA2B6, TyrA2B8, TyrA4B2, TyrA4B4, TyrA4B6, TyrA4B8, TyrA6B2, TyrA6B4, TyrA6B6, TyrA6B8, TyrA8B2, TyrA8B4, TyrA8B6, TyrA8B8, and TyrA9B9, respectively.,

Scheme 7

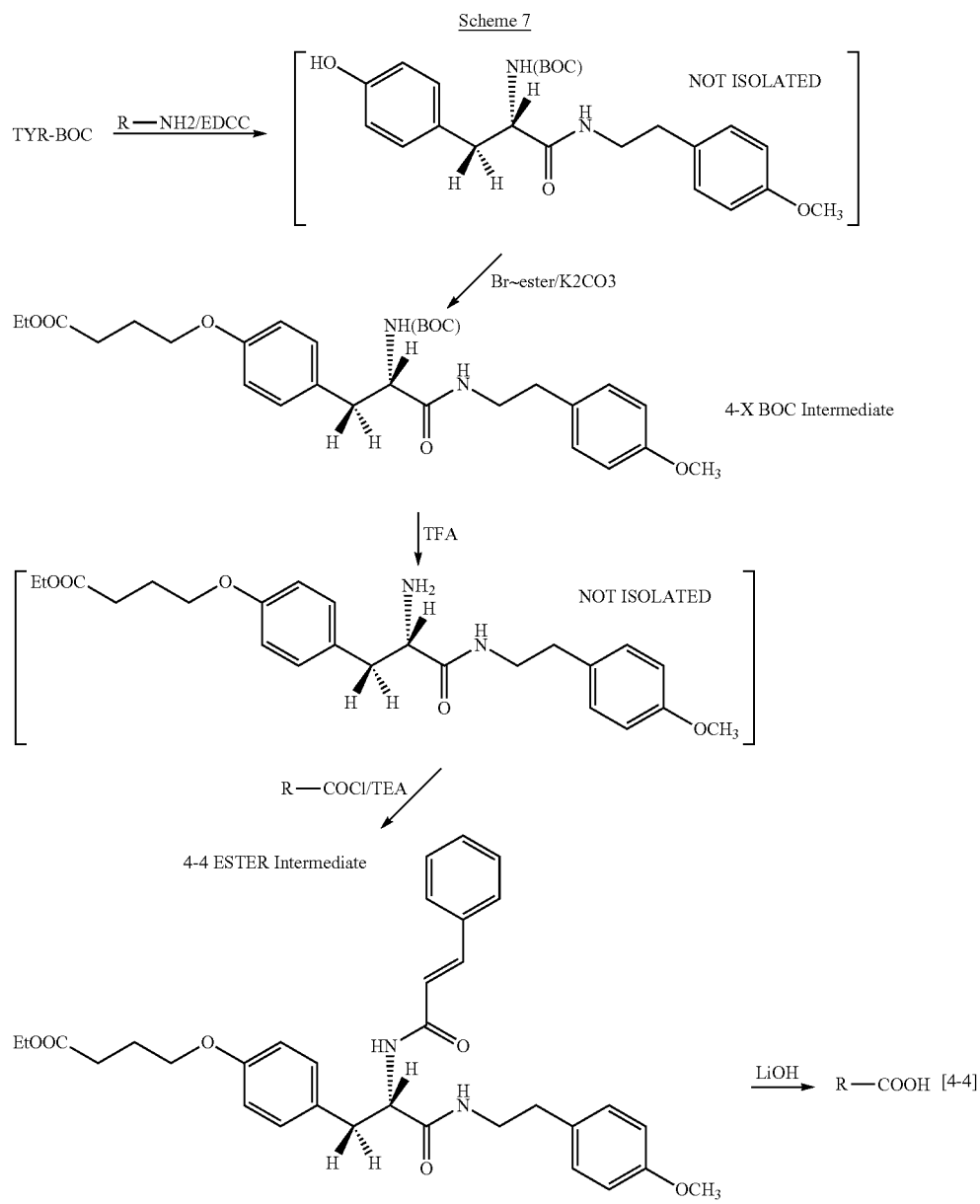

Results

Synthesis of the desired building blocks proved to be generally straightforward. These syntheses illustrate the relative simplicity of preparing the building blocks with 2 recognition elements having different structural characteristics or structures (e.g. A4B2, A6B3, etc.) once the building blocks with corresponding recognition elements (e.g. A2B2, A4B4, etc) have been prepared via their X BOC intermediate.

The conversion of one of these building blocks to a building block with a lipophilic linker can be accomplished by reacting the activated building block with, for example, dodecyl amine.

Example 2

Preparation and Evaluation of Microarrays of Candidate Artificial Receptors

Microarrays of candidate artificial receptors were made and evaluated for binding several protein ligands. The results obtained demonstrate the 1) the simplicity with which microarrays of candidate artificial receptors can be prepared, 2) binding affinity and binding pattern reproducibility, 3) significantly improved binding for building block heterogeneous receptor environments when compared to the respective homogeneous controls, and 4) ligand distinctive binding patterns (e.g., working receptor complexes).

Materials and Methods

Building blocks were synthesized and activated as described in Example 1. The building blocks employed in this example were TyrA1B1 [1-1], TyrA2B2, TyrA2B4, TyrA2B6, TyrA4B2, TyrA4B4, TyrA4B6, TyrA6B2, TyrA6B4, and TyrA6B6. The abbreviation for the building block including a linker, a tyrosine framework, and recognition elements AxBy is TyrAxBy.

Microarrays for the evaluation of the 130 n=2 and n=3, and for evaluation of the 273 n=2, n=3, and n=4, candidate receptor environments were prepared as follows by modifications of known methods. As used herein, "n" is the number of different building blocks employed in a receptor environment. Briefly: Amine modified (amine "lawn"; SuperAmine Microarray plates) microarray plates were purchased from Telechem Inc., Sunnyvale, Calif. (www.arrayit.com). These plates were manufactured specifically for microarray preparation and had a nominal amine load of 2-4 amines per square nm according to the manufacturer. The CAM microarrays were prepared using a pin microarray spotter instrument from Telechem Inc. (SpotBot™ Arrayer) typically with 200 um diameter spotting pins from Telechem Inc. (Stealth Micro Spotting Pins, SMP6) and 400-420 um spot spacing.

The 9 building blocks were activated in aqueous dimethylformamide (DMF) solution as described above. For preparing the 384-well feed plate, the activated building block solutions were diluted 10-fold with a solution of DMF/$H_2O$/PEG400 (90/10/10, v/v/v; PEG400 is polyethylene glycol nominal 400 FW, Aldrich Chemical Co., Milwaukee, Wis.). These stock solutions were aliquotted (10 µl per aliquot) into the wells of a 384-well microwell plate (Telechem Inc.). A separate series of controls were prepared by aliquotting 10 µl of building block with either 10 µl or 20 µl of the activated [1-1] solution. The plate was covered with aluminum foil and placed on the bed of a rotary shaker for 15 minutes at 1,000 RPM. This master plate was stored covered with aluminum foil at −20° C. when not in use.

For preparing the 384-well SpotBot™ plate, a well-to-well transfer (e.g. A-1 to A-1, A-2 to A-2, etc.) from the feed plate to a second 384-well plate was performed using a 4 µl transfer pipette. This plate was stored tightly covered with aluminum foil at −20° C. when not in use. The SpotBot™ was used to prepare up to 13 microarray plates per run using the 4 µl microwell plate. The SpotBot™ was programmed to spot from each microwell in quadruplicate. The wash station on the SpotBot™ used a wash solution of EtOH/$H_2O$ (20/80, v/v). This wash solution was also used to rinse the microarrays on completion of the SpotBot™ printing run. The plates were given a final rinse with deionized (DI) water, dried using a stream of compressed air, and stored at room temperature.

Certain of the microarrays were further modified by reacting the remaining amines with succinic anhydride to form a carboxylate lawn in place of the amine lawn.

The following test ligands and labels were used in these experiments:

1) r-Phycoerythrin, a commercially available and intrinsically fluorescent protein with a FW of 2,000,000.

2) Ovalbumin labeled with the Alexa™ fluorophore (Molecular Probes Inc., Eugene, Oreg.).

3) BSA, bovine serum albumin, labeled with activated Rhodamine (Pierce Chemical, Rockford, Ill.) using the known activated carboxyl protocol. BSA has a FW of 68,000; the material used for this study had ca. 1.0 rhodamine per BSA.

4) Horseradish peroxidase (HRP) modified with extra amines and labeled as the acetamide derivative or with a 2,3,7,8-tetrachlorodibenzodixoin derivative were available through known methods. Fluorescence detection of these HRP conjugates was based on the Alexa 647-tyramide kit available from Molecular Probes, Eugene, Oreg.

5) Cholera toxin labeled with the Alexa™ fluorophore (Molecular Probes Inc., Eugene, Oreg.).

Microarray incubation and analysis was conducted as follows: For test ligand incubation with the microarrays, solutions (e.g. 500 µl) of the target proteins in PBS-T (PBS with 20 µl/L of Tween-20) at typical concentrations of 10, 1.0 and 0.1 µg/ml were placed onto the surface of a microarray and allowed to react for, e.g., 30 minutes. The microarray was rinsed with PBS-T and DI water and dried using a stream of compressed air.

The incubated microarray was scanned using an Axon Model 4200A Fluorescence Microarray Scanner (Axon Instruments, Union City, Calif.). The Axon scanner and its associated software produce a false color 16-bit image of the fluorescence intensity of the plate. This 16-bit data is integrated using the Axon software to give a Fluorescence Units value (range 0-65,536) for each spot on the microarray. This data is then exported into an Excel file (Microsoft) for further analysis including mean, standard deviation and coefficient of variation calculations.

Results

The CARA™: Combinatorial Artificial Receptor Array™ concept has been demonstrated using a microarray format. A CARA microarray based on N=9 building blocks was prepared and evaluated for binding to several protein and substituted protein ligands. This microarray included 144 candidate receptors (18 n=1 controls plus 6 blanks; 36 n=2 candidate receptors; 84 n=3 candidate receptors). This microarray demonstrated: 1) the simplicity of CARA microarray preparation, 2) binding affinity and binding pattern reproducibility, 3) significantly improved binding for building block heterogeneous receptor environments when compared to the respective homogeneous controls, and 4) ligand distinctive binding patterns.

Reading the Arrays

Figure 14:
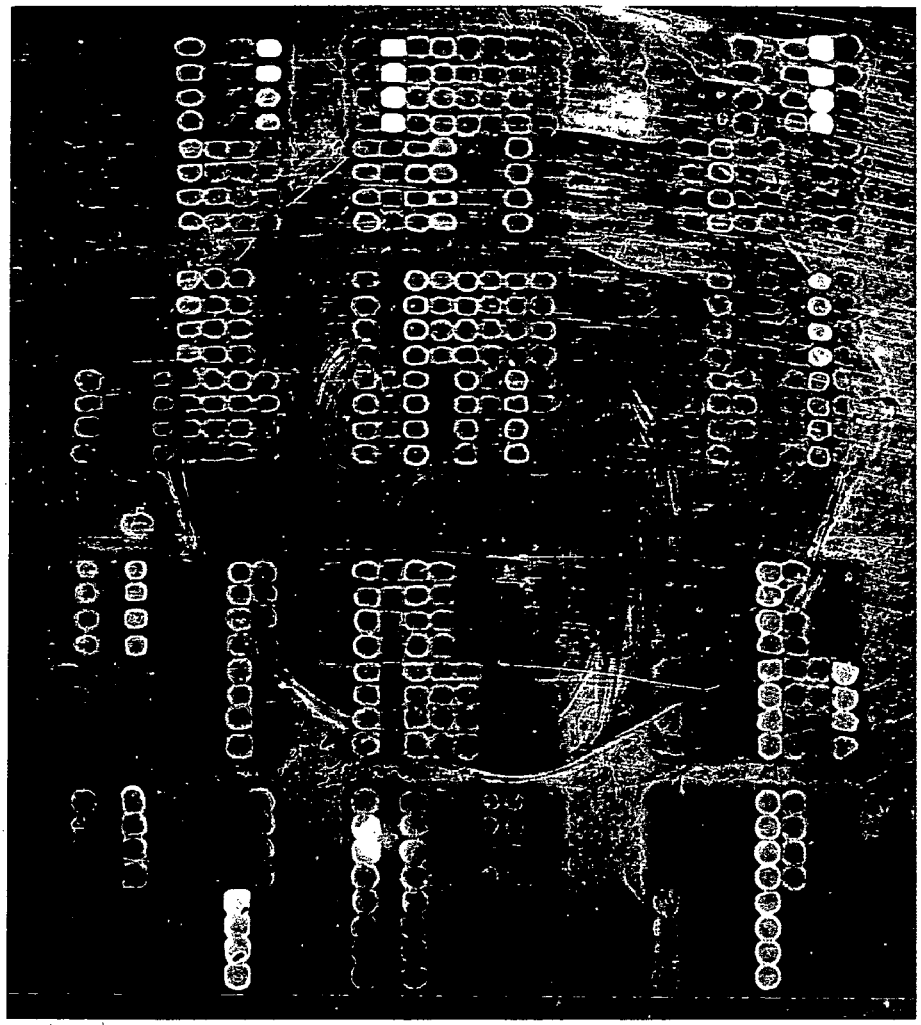
FIG. 14 schematically illustrates a false color fluorescence image of a labeled microarray according to an embodiment of the present invention.

A typical false color/gray scale image of a microarray that was incubated with 2.0 µg/ml r-phycoerythrin is shown in FIG. 14. This image illustrates that the processes of both preparing the microarray and probing it with a protein test ligand produced the expected range of binding as seen in the visual range of relative fluorescence from dark to bright spots.

The starting point in analysis of the data was to take the integrated fluorescence units data for the array of spots and normalize to the observed value for the [1-1] building block control. Subsequent analysis included mean, standard deviation and coefficient of variation calculations. Additionally, control values for homogeneous building blocks were obtained from the building block plus [1-1] data.

First Set of Experiments

The following protein ligands were evaluated for binding to the candidate artificial receptors in the microarray. The resulting Fluorescence Units versus candidate receptor environment data is presented in both a 2D format where the candidate receptors are placed along the X-axis and the Fluorescence Units are shown on the Y-axis and a 3D format where the Candidate Receptors are placed in an X-Y format and the Fluorescence Units are shown on the Z-axis. A key for the composition of each spot was developed (not shown). A key for the building blocks in each of the 2D and 3D representations of the results was also developed (not shown). The data presented are for 1-2 µg/ml protein concentrations.

Figure 15:
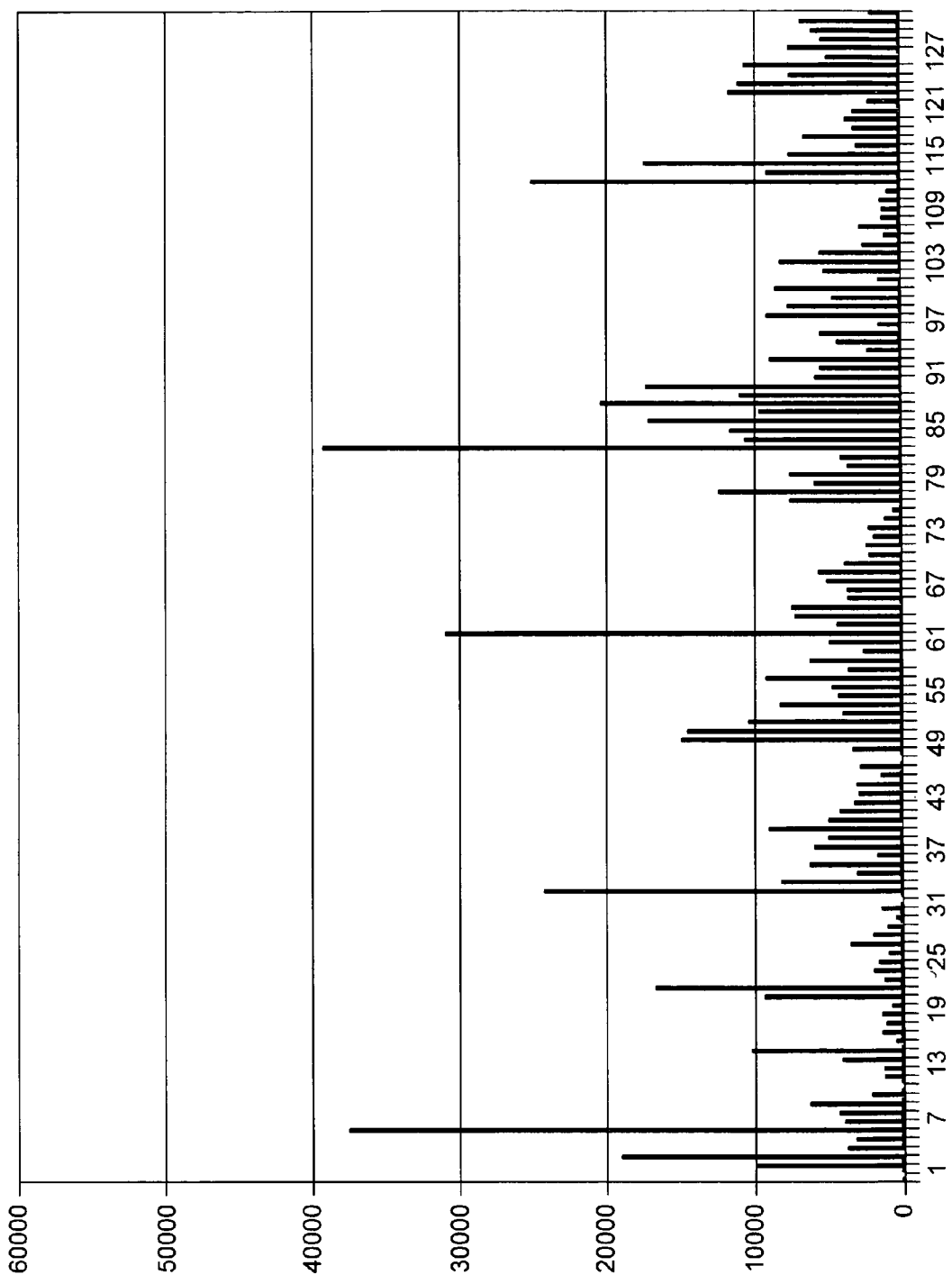
FIG. 15 schematically illustrates a two dimensional plot of data obtained for candidate artificial receptors contacted with and/or binding phycoerythrin.
Figure 16:
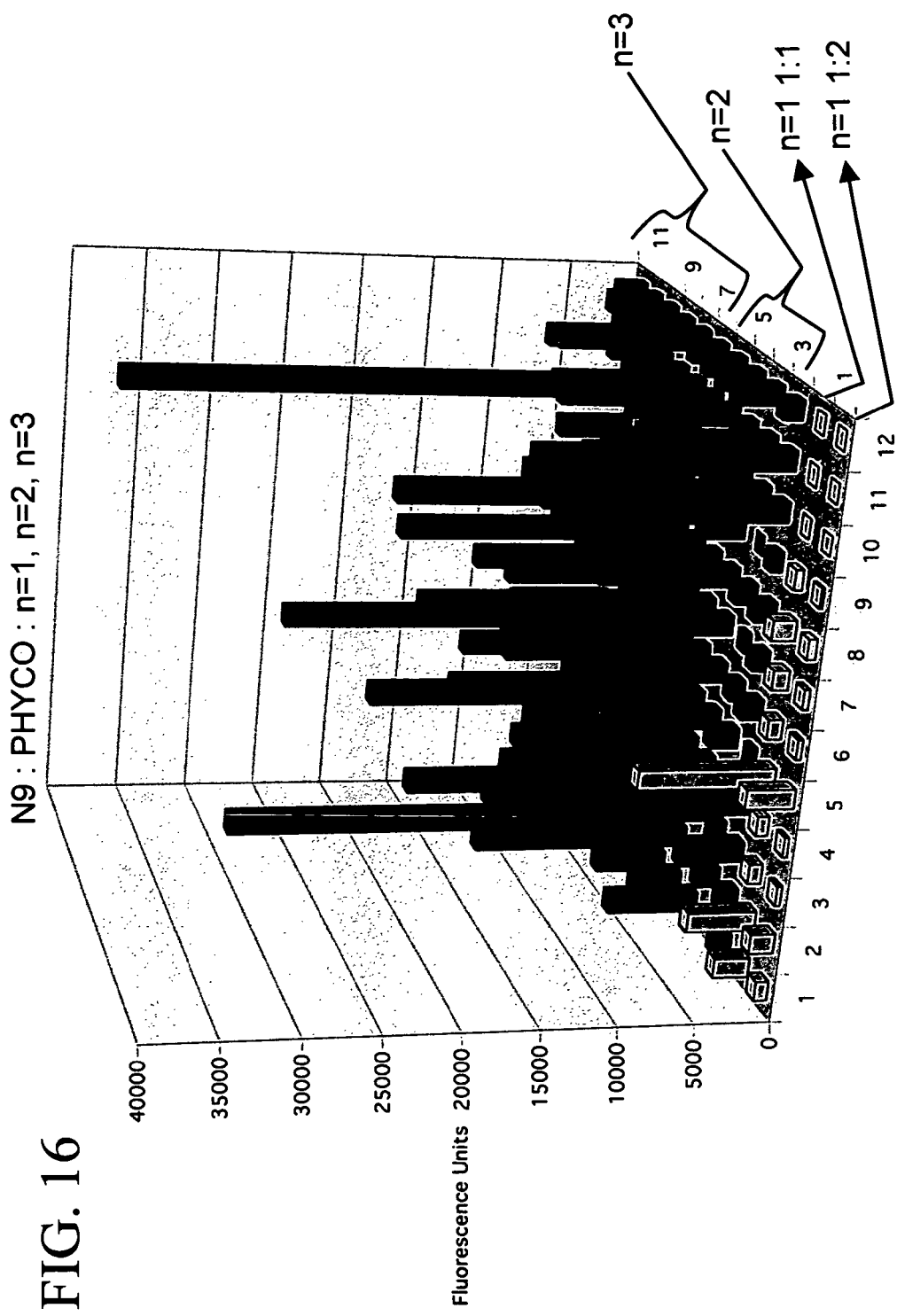
FIG. 16 schematically illustrates a three dimensional plot of data obtained for candidate artificial receptors contacted with and/or binding phycoerythrin.
Figure 17:
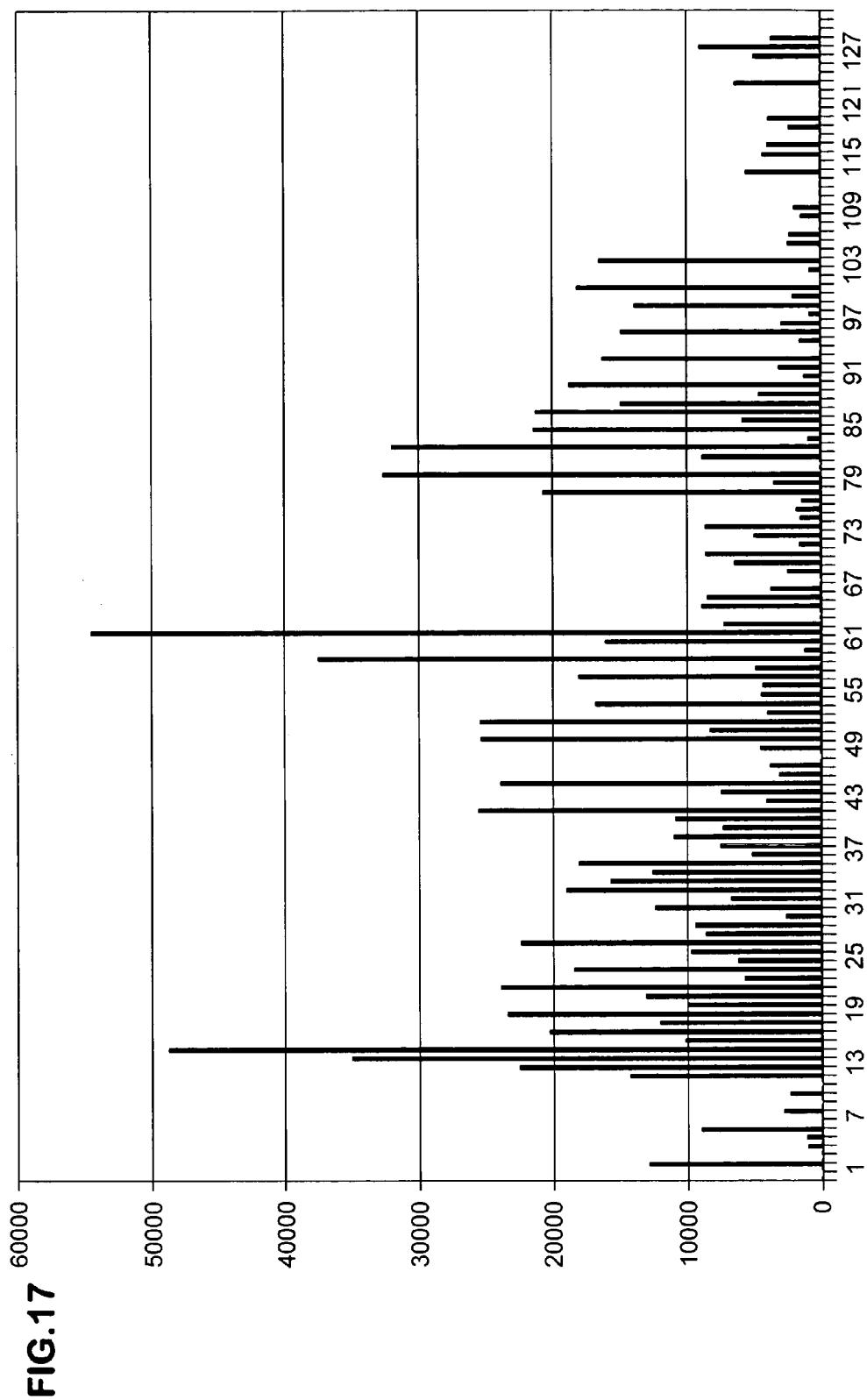
FIG. 17 schematically illustrates a two dimensional plot of data obtained for candidate artificial receptors contacted with and/or binding a fluorescent derivative of ovalbumin.
Figure 18:
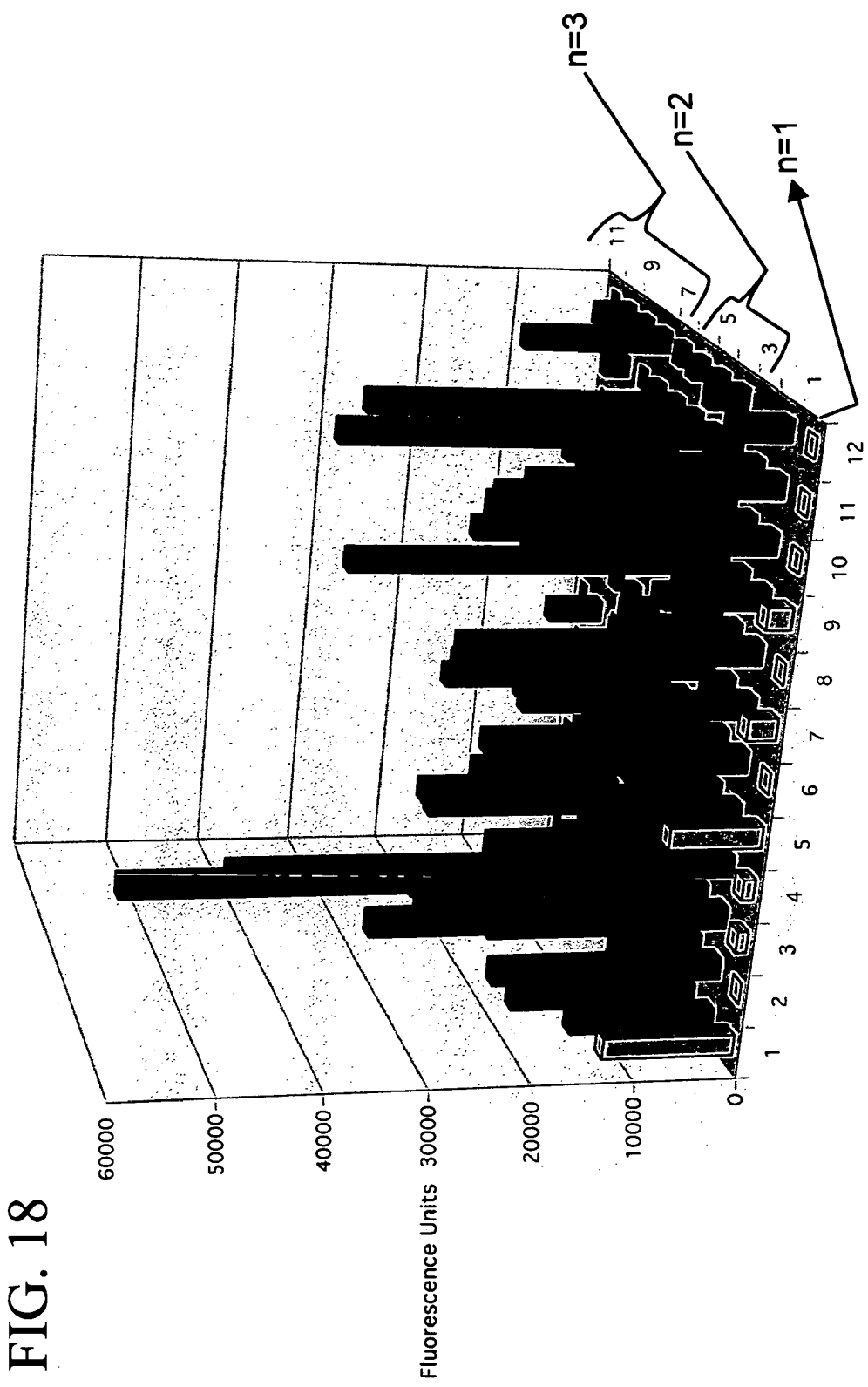
FIG. 18 schematically illustrates a three dimensional plot of data obtained for candidate artificial receptors contacted with and/or binding a fluorescent derivative of ovalbumin.
Figure 19:
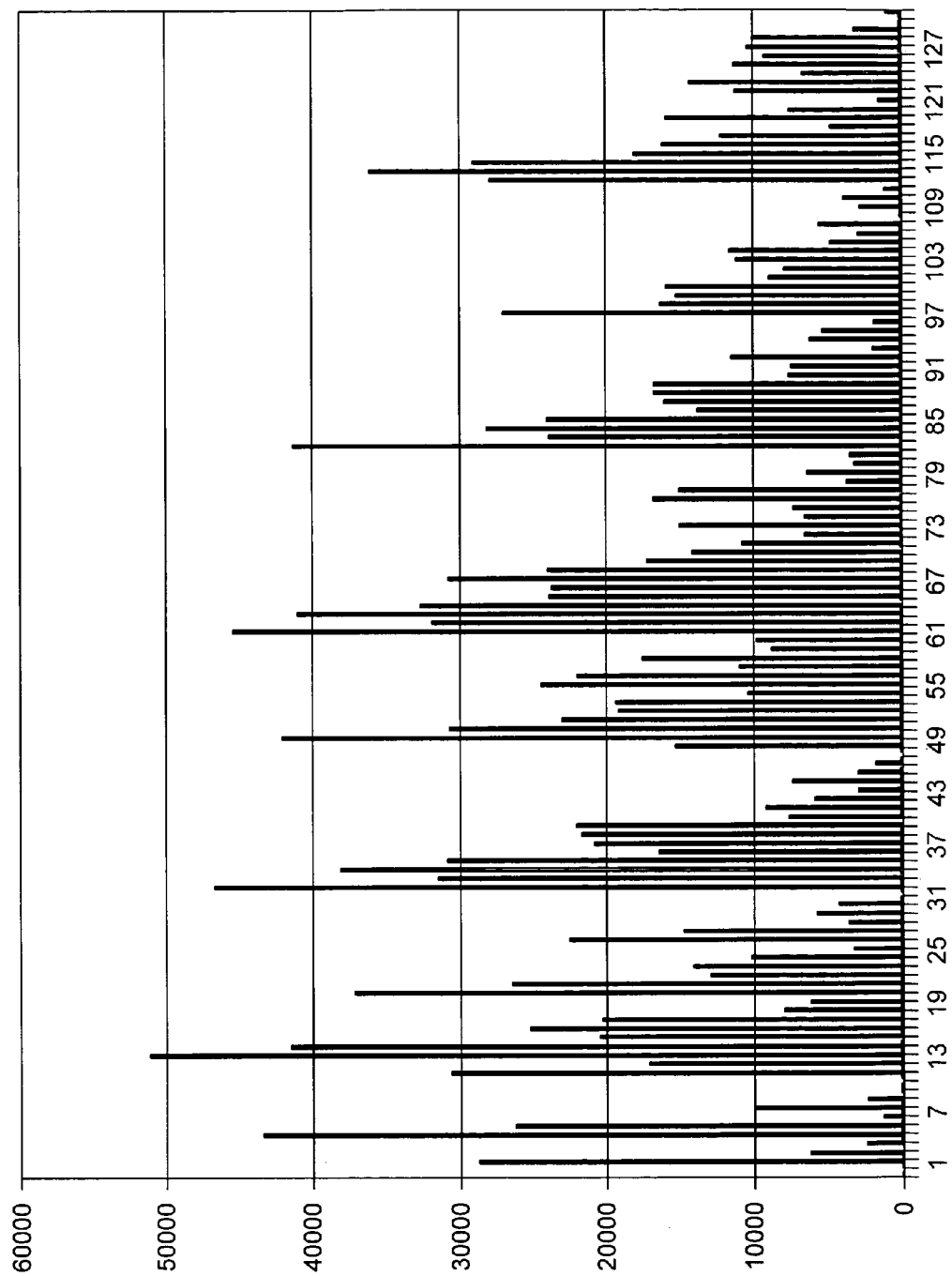
FIG. 19 schematically illustrates a two dimensional plot of data obtained for candidate artificial receptors contacted with and/or binding a fluorescent derivative of bovine serum albumin.
Figure 20:
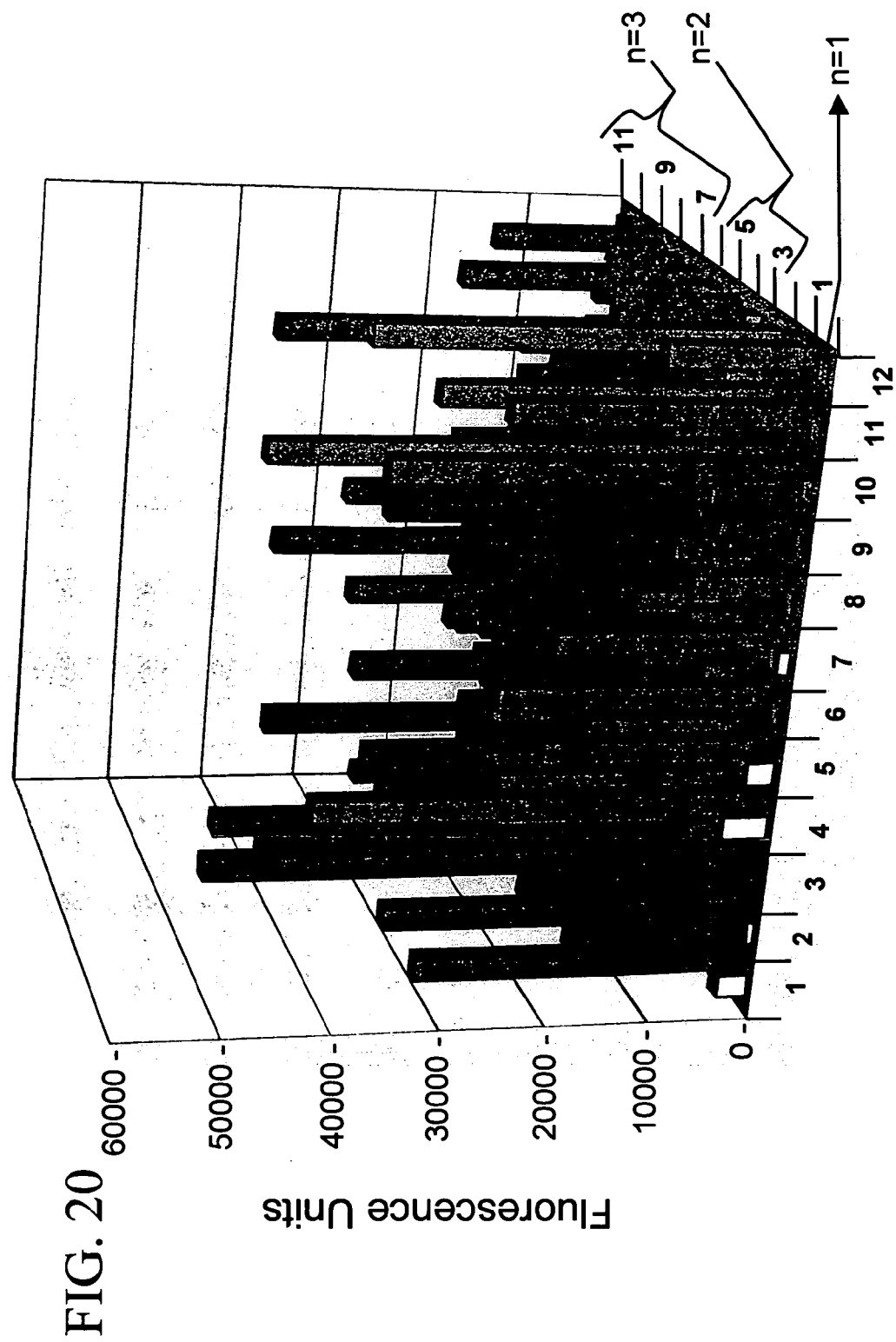
FIG. 20 schematically illustrates a three dimensional plot of data obtained for candidate artificial receptors contacted with and/or binding a fluorescent derivative of bovine serum albumin.
Figure 21:
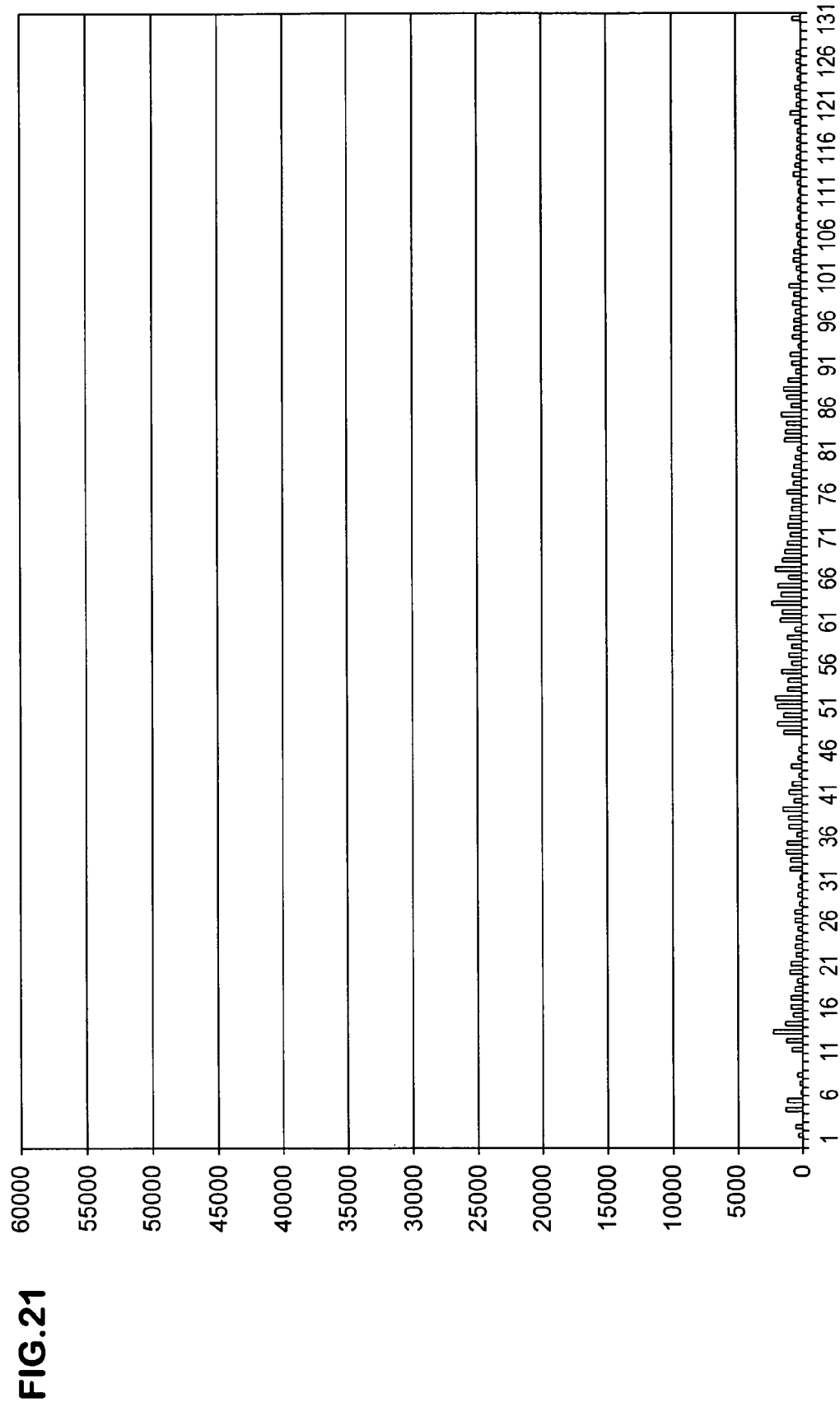
FIG. 21 schematically illustrates a two dimensional plot of data obtained for candidate artificial receptors contacted with and/or binding an acetylated horseradish peroxidase.
Figure 22:
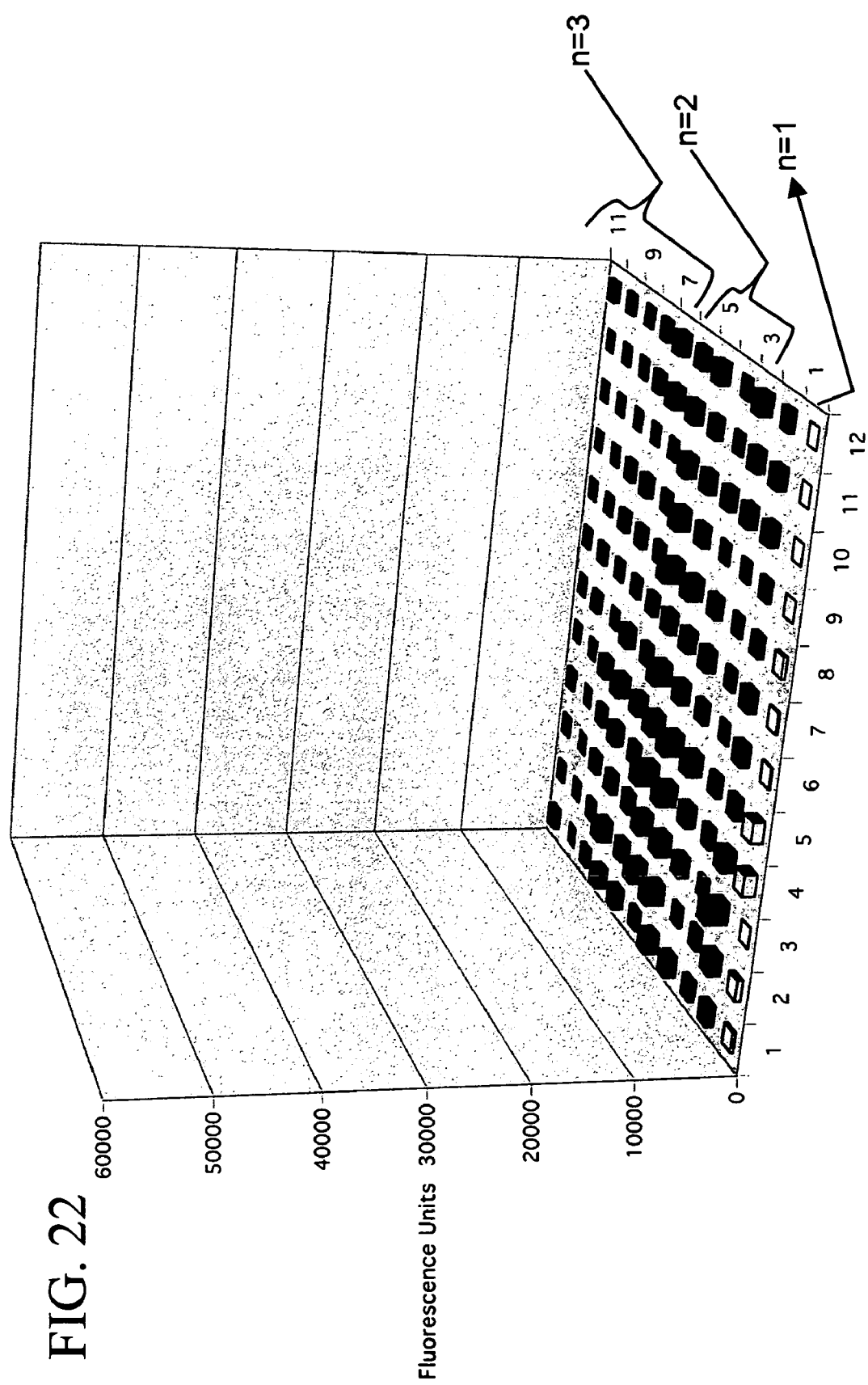
FIG. 22 schematically illustrates a three dimensional plot of data obtained for candidate artificial receptors contacted with and/or binding an acetylated horseradish peroxidase.
Figure 23:
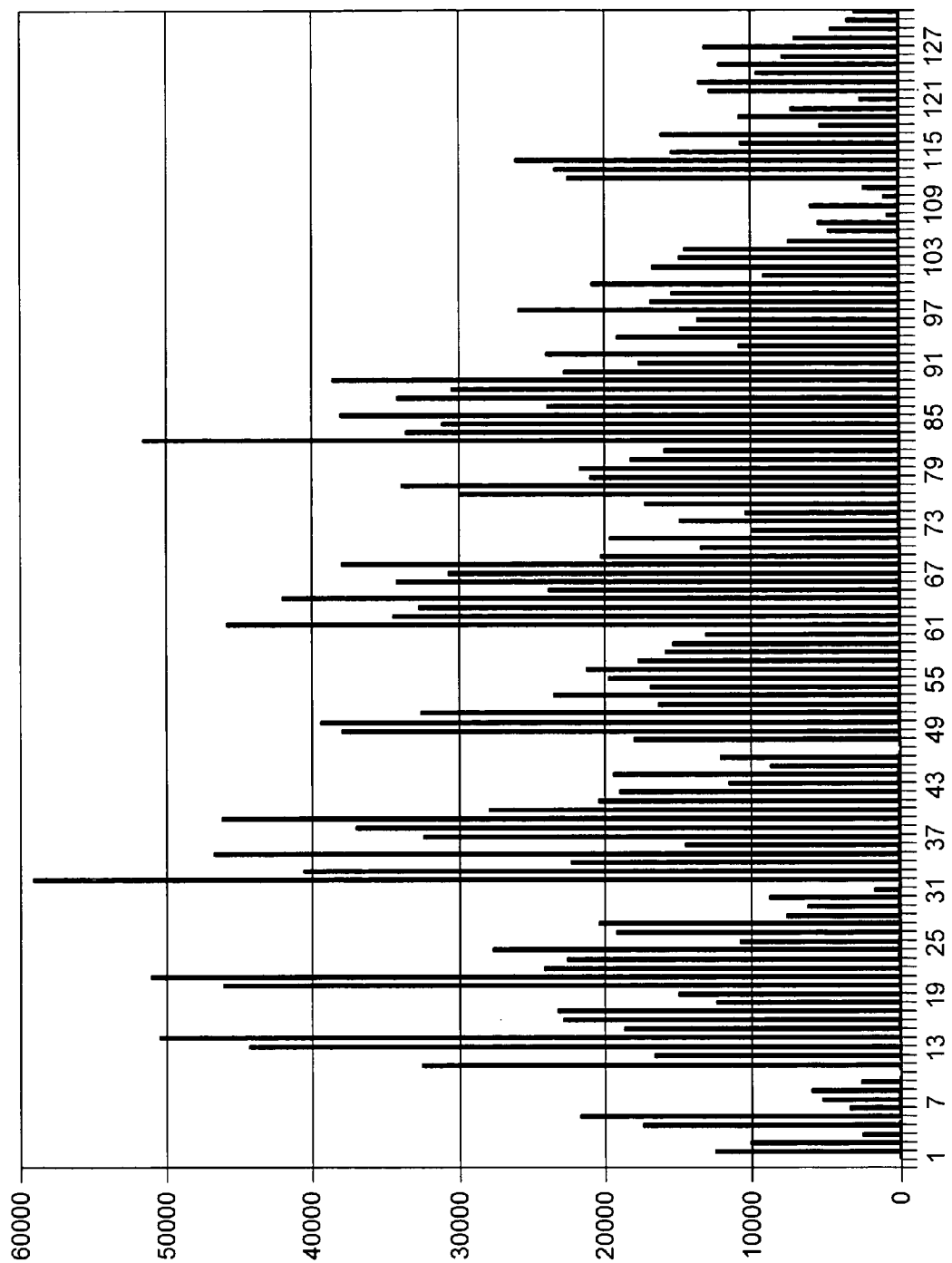
FIG. 23 schematically illustrates a two dimensional plot of data obtained for candidate artificial receptors contacted with and/or binding a TCDD derivative of horseradish peroxidase.
Figure 24:
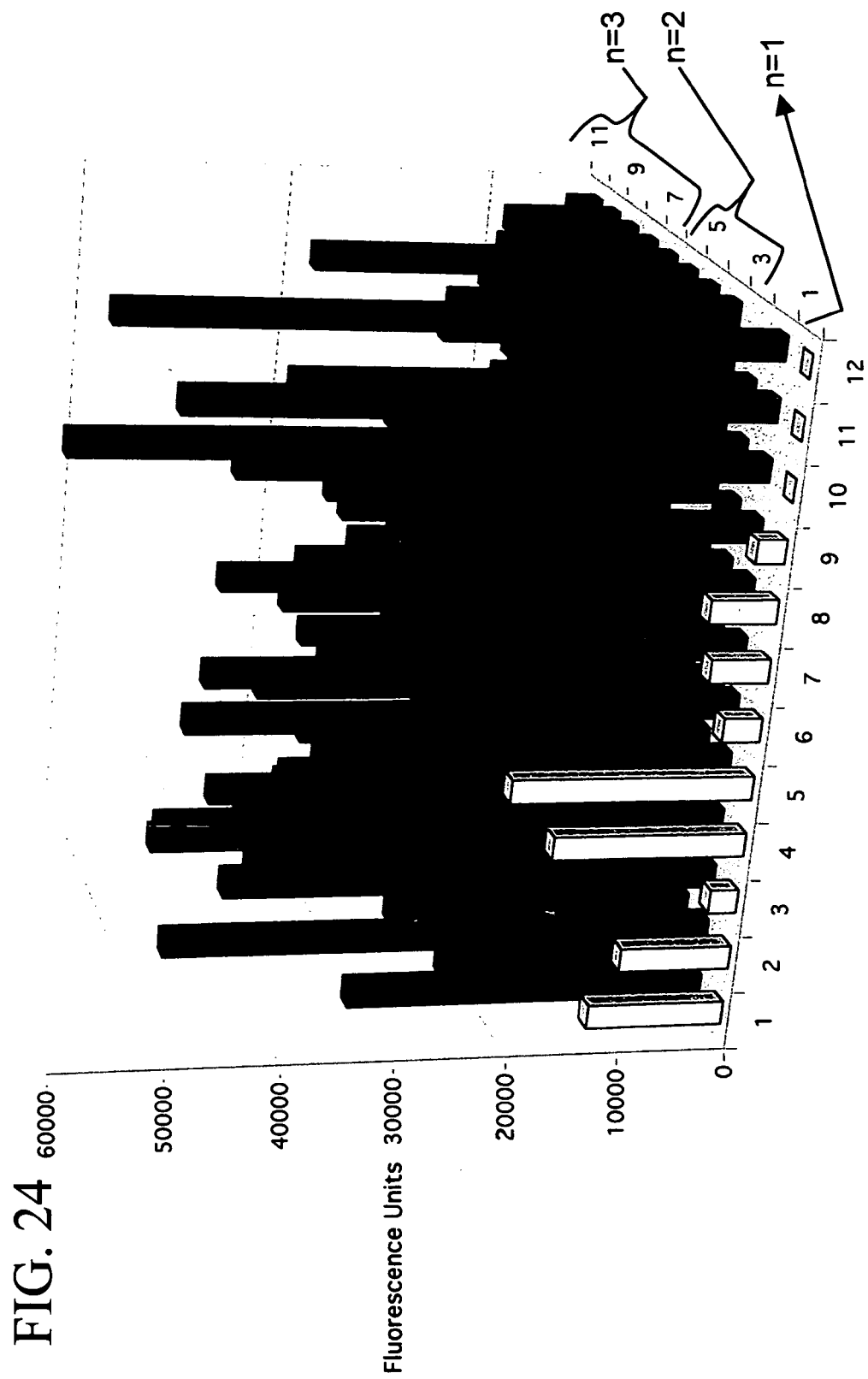
FIG. 24 schematically illustrates a three dimensional plot of data obtained for candidate artificial receptors contacted with and/or binding a TCDD derivative of horseradish peroxidase.

FIGS. 15 and 16 illustrate binding data for r-phycoerythrin (intrinsic fluorescence). FIGS. 17 and 18 illustrate binding data for ovalbumin (commercially available with fluorescence label). FIGS. 19 and 20 illustrate binding data for bovine serum albumin (labeled with rhodamine). FIGS. 21 and 22 illustrate binding data for HRP—NH—Ac (fluorescent tyramide read-out). FIGS. 23 and 24 illustrate binding data for HRP—NH-TCDD (fluorescent tyramide read-out).

These results demonstrate not only the application of the CARA microarray to candidate artificial receptor evaluation but also a few of the many read-out methods (e.g. intrinsic fluorescence, fluorescently labeled, in situ fluorescence labeling) which can be utilized for high throughput candidate receptor evaluation.

The evaluation of candidate receptors benefits from reproducibility. The following results demonstrate that the present microarrays provided reproducible ligand binding.

Figure 25:
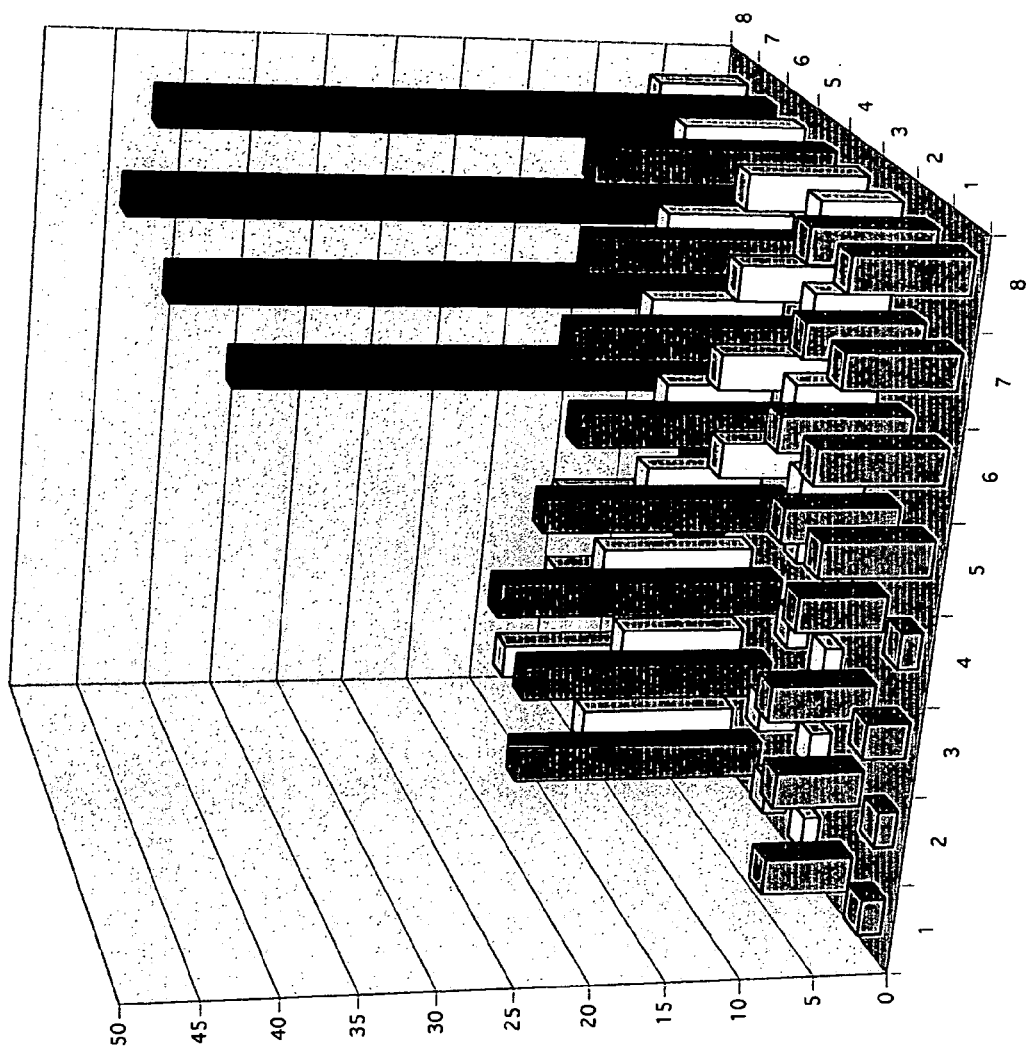
FIG. 25 schematically illustrates a subset of the data illustrated in FIG. 16.

The microarrays were printed with each combination of building blocks spotted in quadruplicate. Visual inspection of a direct plot (FIG. 25) of the raw fluorescence data (from the run illustrated in FIG. 14) for one block of binding data obtained for r-phycoerythrin demonstrates that the candidate receptor environment "spots" showed reproducible binding to the test ligand. Further analysis of the r-phycoerythrin data (FIG. 14) led to only 9 out of 768 spots (1.2%) being deleted as outliers. Analysis of the r-phycoerythrin quadruplicate data for the entire array gives a mean standard deviation for each experimental quadruplicate set of 938 fluorescence units, with a mean coefficient of variation of 19.8%.

Although these values are acceptable, a more realistic comparison employed the standard deviation and coefficient of variation of the more strongly bound, more fluorescent receptors. The overall mean standard deviation unrealistically inflates the coefficient of variation for the weakly bound, less fluorescent receptors. The coefficient of variation for the 19 receptors with greater than 10,000 Fluorescent Units of bound target is 11.1%, which is well within the range required to produce meaningful binding data.

One goal of the CARA approach is the facile preparation of a significant number of candidate receptors through combinations of structurally simple building blocks. The following results establish that both the individual building blocks and combinations of building blocks have a significant, positive effect on test ligand binding.

The binding data illustrated in FIGS. 23-24 demonstrate that heterogeneous combinations of building blocks (n=2, n=3) are dramatically superior candidate receptors made from a single building block (n=1). For example, FIG. 16 illustrates both the diversity of binding observed for n=2, n=3 candidate receptors with fluorescent units ranging from 0 to ca. 40,000. These data also illustrate and the ca. 10-fold improvement in binding affinity obtained upon going from the homogeneous (n=1) to heterogeneous (n=2, n=3) receptor environments.

Figure 26:
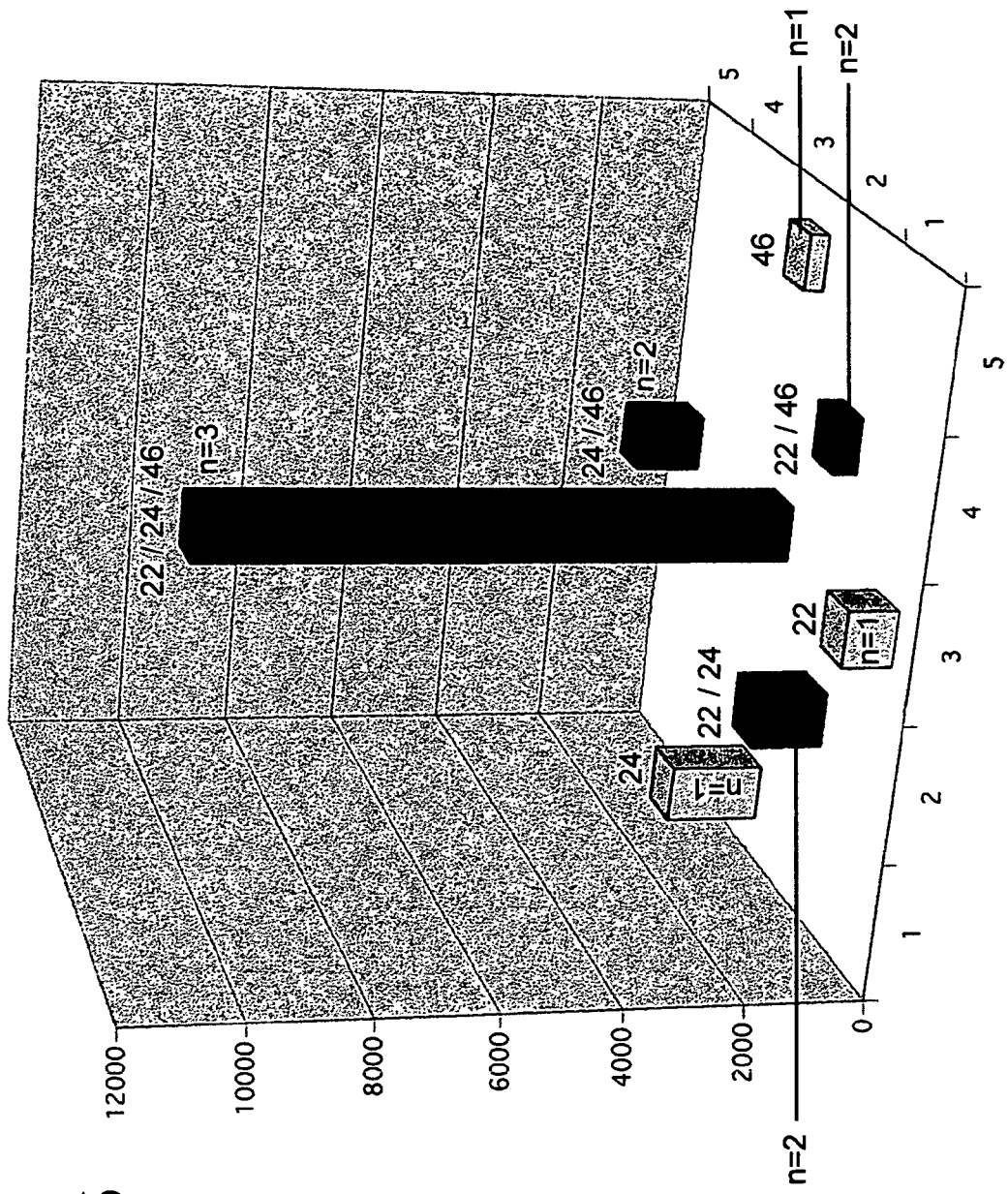
FIG. 26 schematically illustrates a subset of the data illustrated in FIG. 16.
Figure 27:
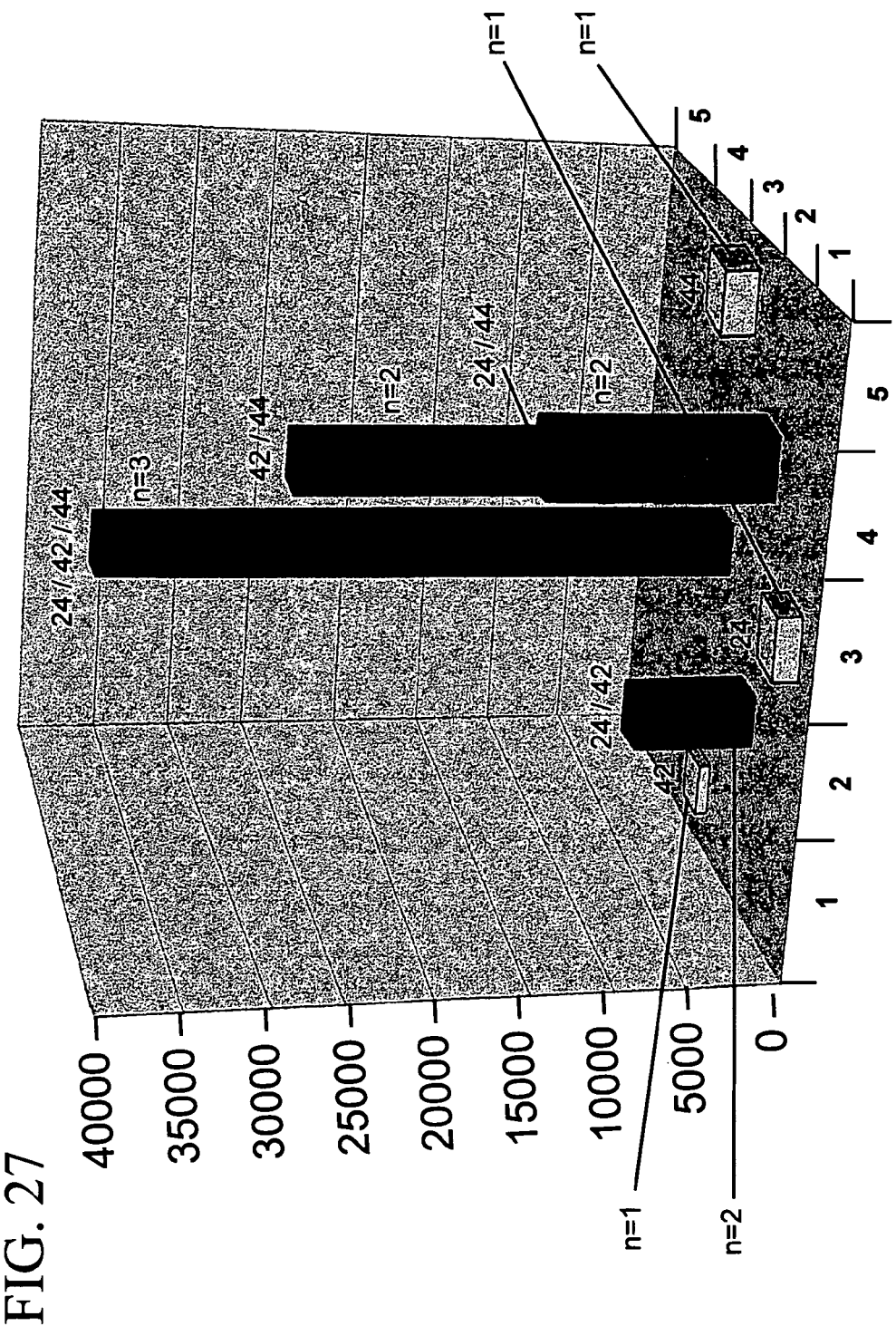
FIG. 27 schematically illustrates a subset of the data illustrated in FIG. 16.

The effect of heterogeneous building blocks is most easily observed by comparing selected n=3 receptor environments candidate receptors including 1 or 2 of those building blocks (their n=2 and n=1 subsets). FIGS. 26 and 27 illustrate this comparison for two different n=3 receptor environments using the r-phycoerythrin data. In these examples, it is clear that progression from the homogeneous system (n=1) to the heterogeneous systems (n=2, n=3) produces significantly enhanced binding.

Although van der Waals interactions are an important part of molecular recognition, it is important to establish that the observed binding is not a simple case of hydrophobic/hydrophilic partitioning. That is, that the observed binding was the result of specific interactions between the individual building blocks and the target The simplest way to evaluate the effects of hydrophobicity and hydrophilicity is to compare building block logP value with observed binding. LogP is a known and accepted measure of lipophilicity, which can be measured or calculated by known methods for each of the building blocks.

Figure 28:
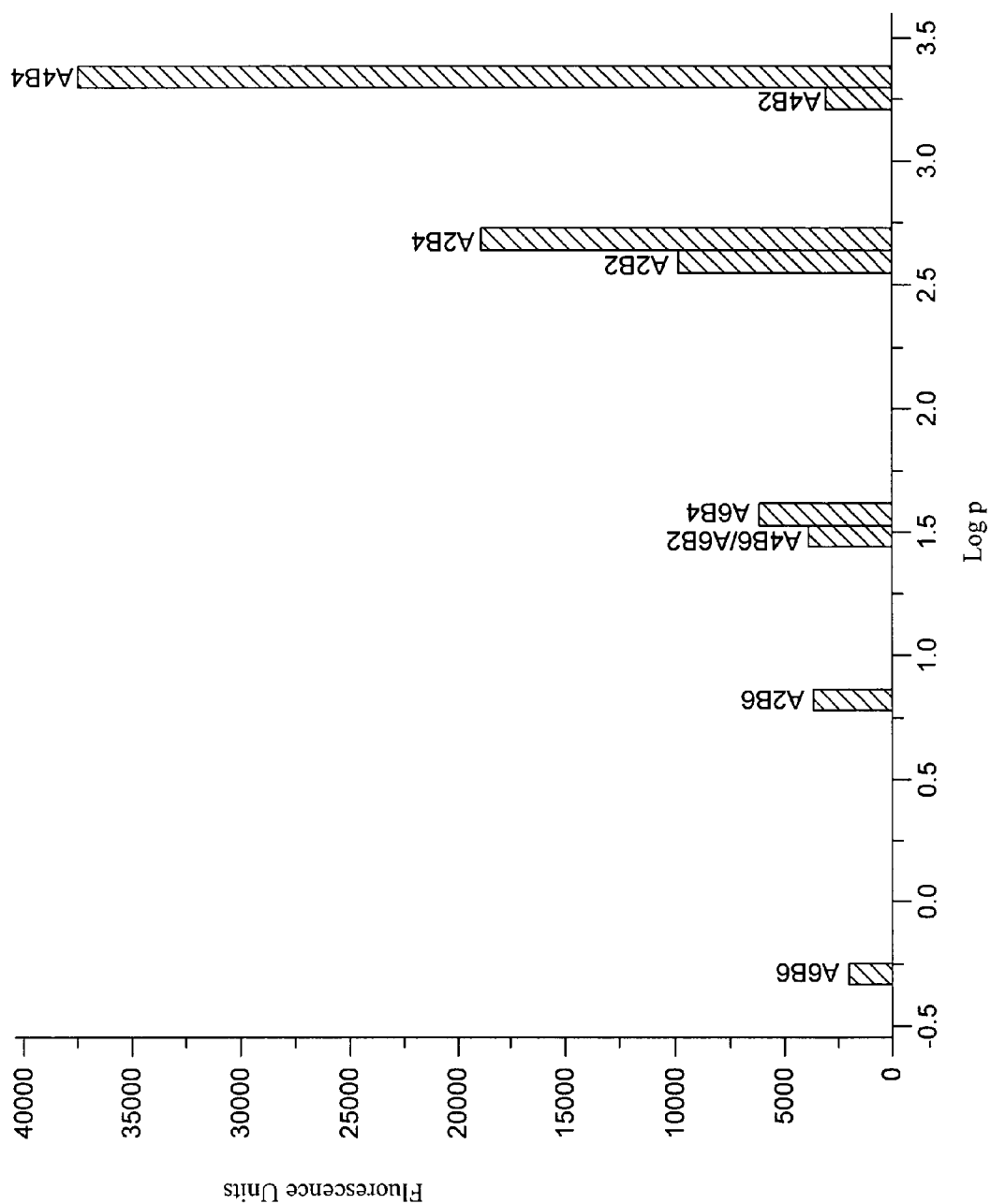
FIG. 28 schematically illustrates a correlation of binding data for phycoerythrin against logP for the building blocks making up the artificial receptor.
Figure 29:
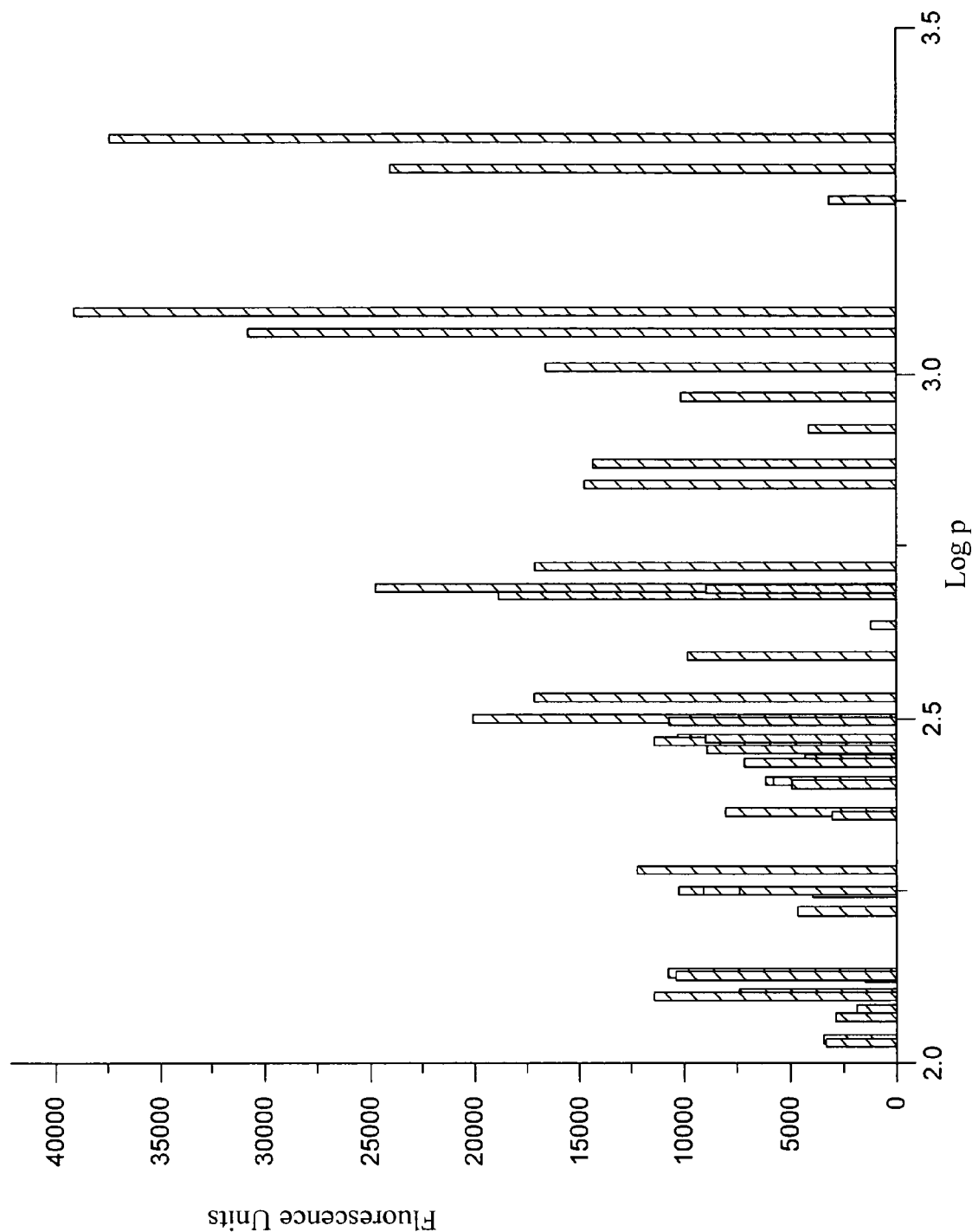
FIG. 29 schematically illustrates a correlation of binding data for phycoerythrin against logP for the building blocks making up the artificial receptor.

FIGS. 28 and 29 establish that the observed target binding, as measured by fluorescence units, is not directly proportional to building block logP. The plots in FIGS. 28 and 29 illustrate a non-linear relationship between binding (fluorescence units) and building block logP.

One advantage of the present methods and arrays is that the ability to screen large numbers of candidate receptor environments will lead to a combination of useful target affinities and to significant target binding diversity. High target affinity is useful for specific target binding, isolation, etc. while binding diversity can provide multiplexed target detection systems. This example employed a relatively small number of building blocks to produce ca. 120 binding environments. The following analysis of the present data clearly demonstrates that even a relatively small number of binding environments can produce diverse and useful artificial receptors.

The target binding experiments performed for this study used protein concentrations including 0.1 to 10 μg/ml. Considering the BSA data as representative, it is clear that some of the receptor environments readily bound 1.0 ug/ml BSA concentrations near the saturation values for fluorescence units (see, e.g., FIG. 20). Based on these data and the formula weight of 68,000 for BSA, several of the receptor environments readily bind BSA at ca. 15 picomole/ml or 15 nanomolar concentrations. Additional experiments using lower concentrations of protein (data not shown) indicate that, even with a small selection of candidate receptor environments, femptomole/ml or picomolar detection limits have been attained.

Figure 30:
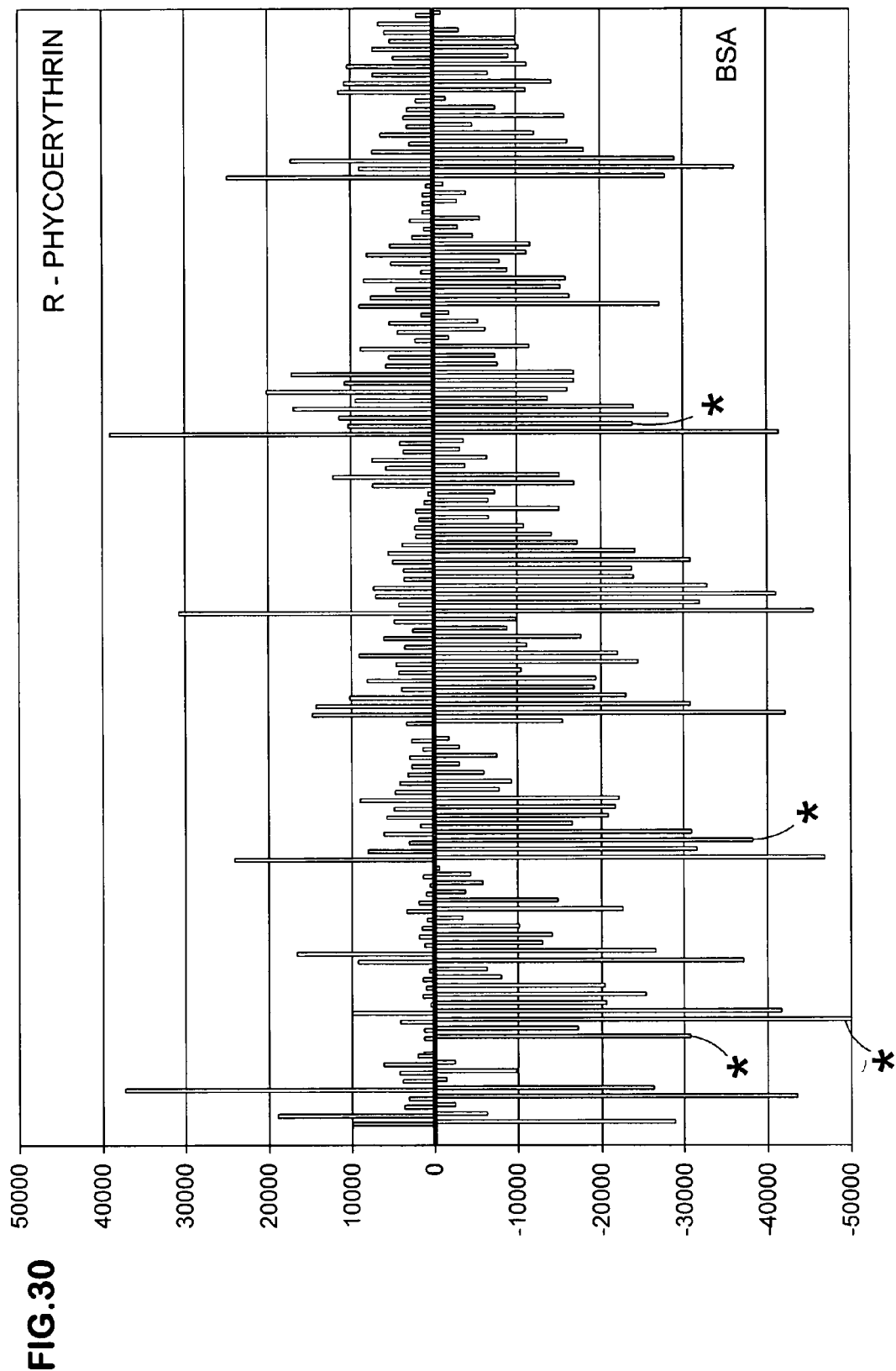
FIG. 30 schematically illustrates a two dimensional plot comparing data obtained for candidate artificial receptors contacted with and/or binding phycoerythrin to data obtained for candidate artificial receptors contacted with and/or binding a fluorescent derivative of bovine serum albumin.

One goal of artificial receptor development is the specific recognition of a particular target. FIG. 30 compares the observed binding for r-phycoerythrin and BSA. Comparison of the overall binding pattern indicates some general similarities. However, comparison of specific features of binding for each receptor environment demonstrates that the two targets have distinctive recognition features as indicated by the (*) in FIG. 30.

Figure 31:
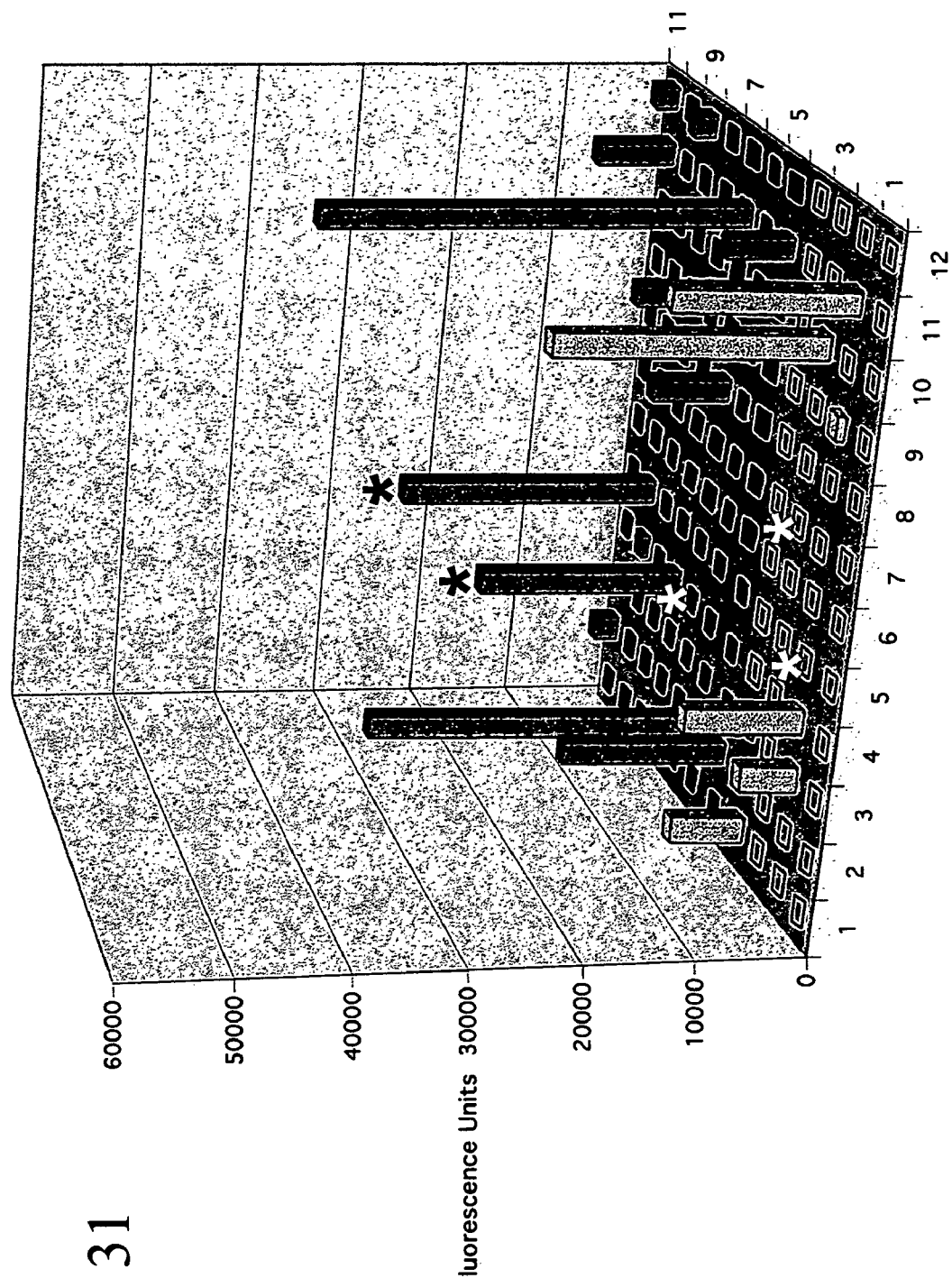
FIGS. 31, 32, and 33 schematically illustrate subsets of data from FIGS. 16, 20, and 18, respectively, and demonstrate that the array of artificial receptors according to the present invention yields receptors distinguished between three analytes, phycoerythrin, bovine serum albumin, and ovalbumin.
Figure 32:
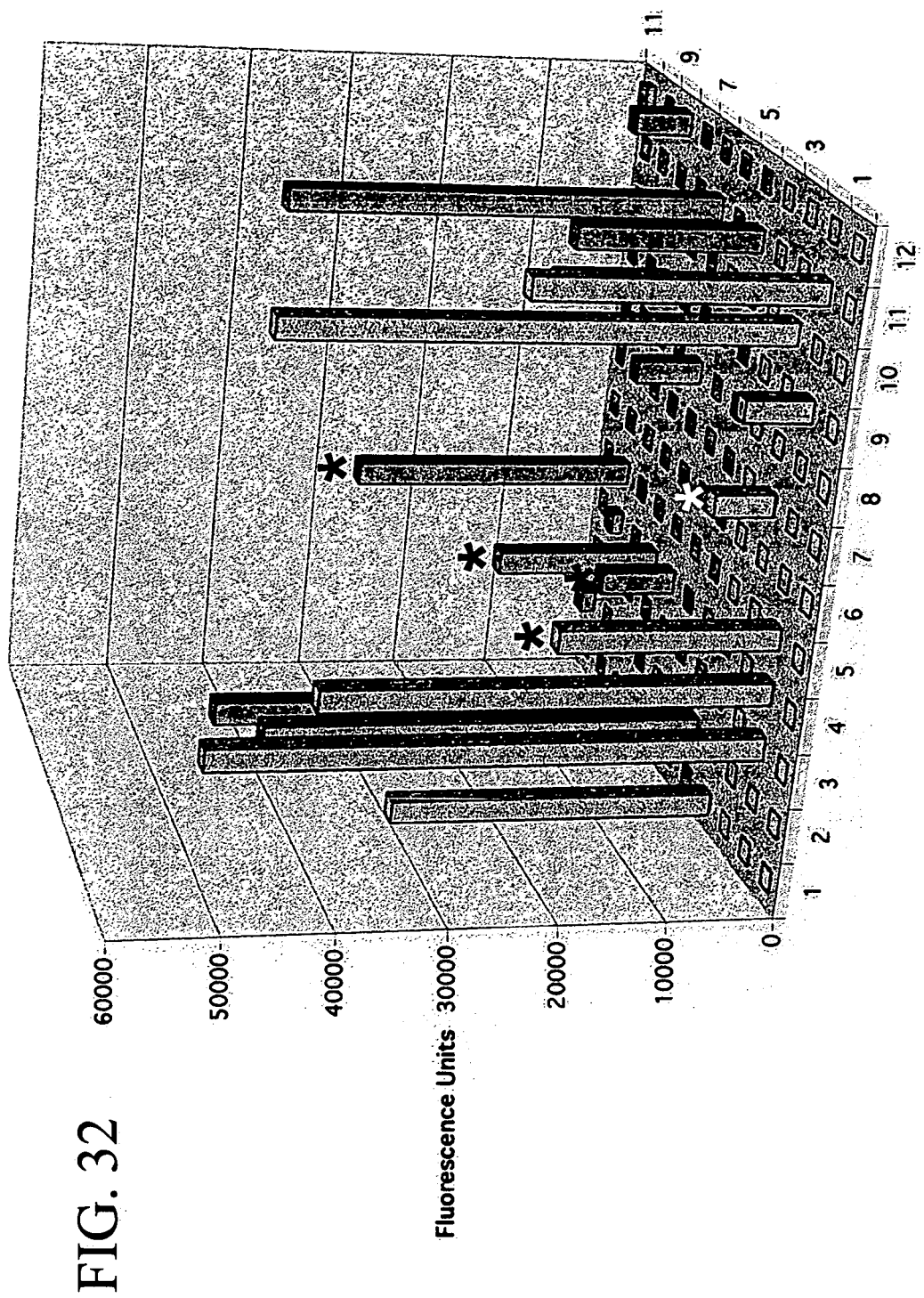
Figure 33:
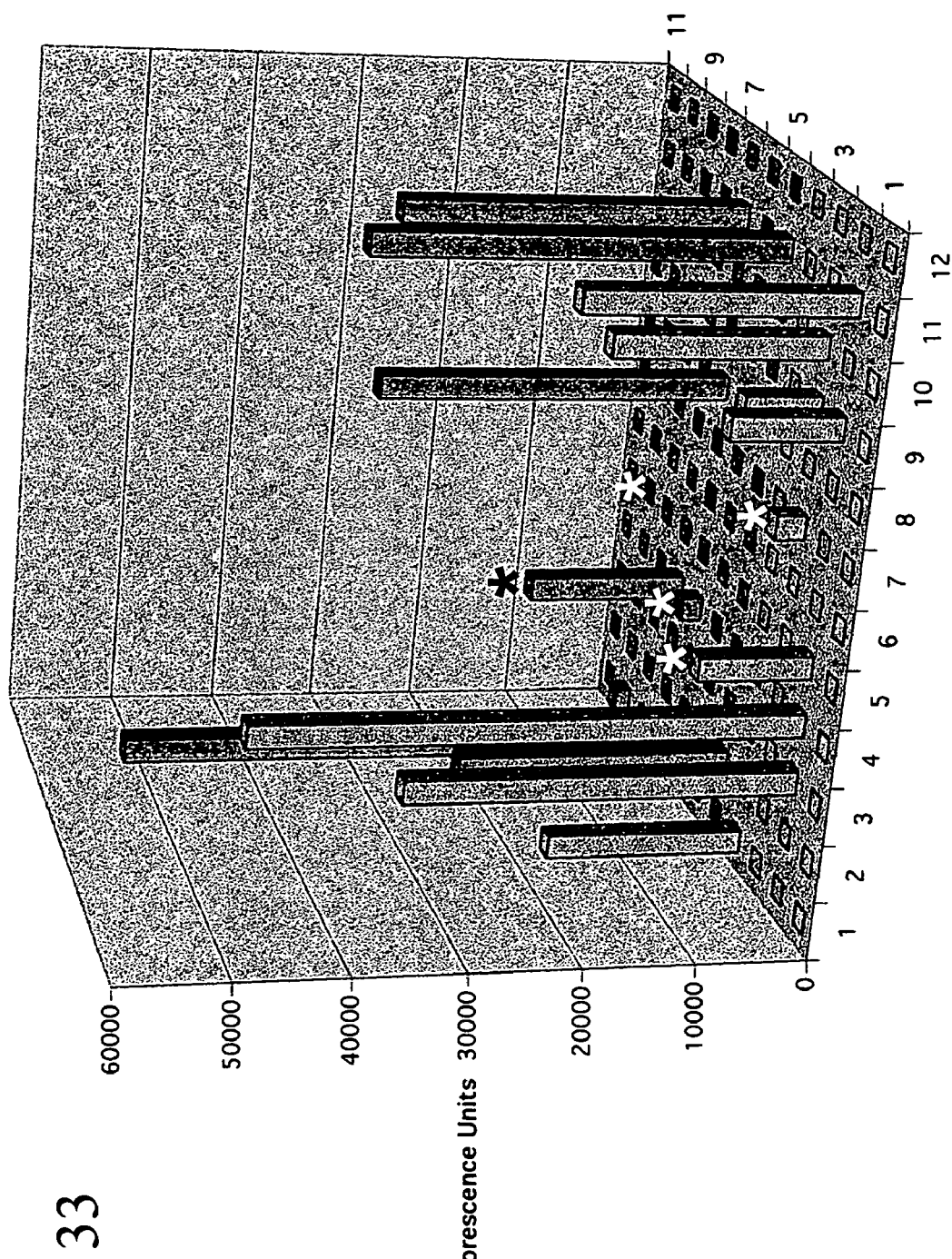

One goal of artificial receptor development is to develop receptors which can be used for the multiplexed detection of specific targets. Comparison of the r-phycoerythrin, BSA and ovalbumin data from this study (FIGS. 16, 18, and 20) were used to select representative artificial receptors for each target. FIGS. 31, 32 and 33 employ data obtained in the present example to illustrate identification of each of these three targets by their distinctive binding patterns.

Conclusions

The optimum receptor for a particular target requires molecular recognition which is greater than the expected sum of the individual hydrophilic, hydrophobic, ionic, etc. interactions. Thus, the identification of an optimum (specific, sensitive) artificial receptor from the limited pool of candidate receptors explored in this prototype study, was not expected and not likely. Rather, the goal was to demonstrate that all of the key components of the CARA: Combinatorial Artificial Receptor Array concept could be assembled to form a functional receptor microarray. This goal has been successfully demonstrated.

This study has conclusively established that CARA microarrays can be readily prepared and that target binding to the candidate receptor environments can be used to identify artificial receptors and test ligands. In addition, these results demonstrate that there is significant binding enhancement for the building block heterogeneous (n=2, n=3, or n=4) candidate receptors when compared to their homogeneous (n=1) counterparts. When combined with the binding pattern recognition results and the demonstrated importance of both the heterogeneous receptor elements and heterogeneous building blocks, these results clearly demonstrate the significance of the CARA Candidate Artificial Receptor->Lead Artificial Receptor->Working Artificial Receptor strategy.

Example 3

Preparation and Evaluation of Microarrays of Candidate Artificial Receptors Including Reversibly Immobilized Building Blocks Microarrays of candidate artificial receptors including building blocks immobilized through van der Waals interactions were made and evaluated for binding of a protein ligand. The evaluation was conducted at several temperatures, above and below a phase transition temperature for the lawn (vide infra).

Materials and Methods

Building blocks 2-2,2-4, 2-6,4-2, 4-4,4-6, 6-2,6-4, 6-6 where prepared as described in Example 1. The C12 amide was prepared using the previously described carbodiimide activation of the carboxyl followed by addition of dodecylamine. This produced a building block with a 12 carbon alkyl chain linker for reversible immobilization in the C18 lawn.

Amino lawn microarray plates (Telechem) were modified to produce the C18 lawn by reaction of stearoyl chloride (Aldrich Chemical Co.) in A) dimethylformamide/PEG 400 solution (90:10, v/v, PEG 400 is polyethylene glycol average MW 400 (Aldrich Chemical Co.) or B) methylene chloride/TEA solution (100 ml methylene chloride, 200 µl triethylamine) using the lawn modification procedures generally described in Example 2.

The C18 lawn plates where printed using the SpotBot standard procedure as described in Example 2. The building blocks were in printing solutions prepared by solution of ca. 10 mg of each building block in 300 µl of methylene chloride and 100 µl methanol. To this stock was added 900 µl of dimethylformamide and 100 µl of PEG 400. The 36 combinations of the 9 building blocks taken two at a time (N9:n2, 36 combinations) where prepared in a 384-well microwell plate which was then used in the SpotBot to print the microarray in quadruplicate. A random selection of the print positions contained only print solution.

The selected microarray was incubated with a 1.0 µg/ml solution of the test ligand, cholera toxin subunit B labeled with the Alexa™ fluorophore (Molecular Probes Inc., Eugene, Oreg.), using the following variables: 1) the microarray was washed with methylene chloride, ethanol and water to create a control plate; and 2) the microarray was incubated at 4° C., 23° C., or 44° C. After incubation, the plate(s) were rinsed with water, dried and scanned (AXON 4100A). Data analysis was as described in Example 2.

Results

Figure 34:
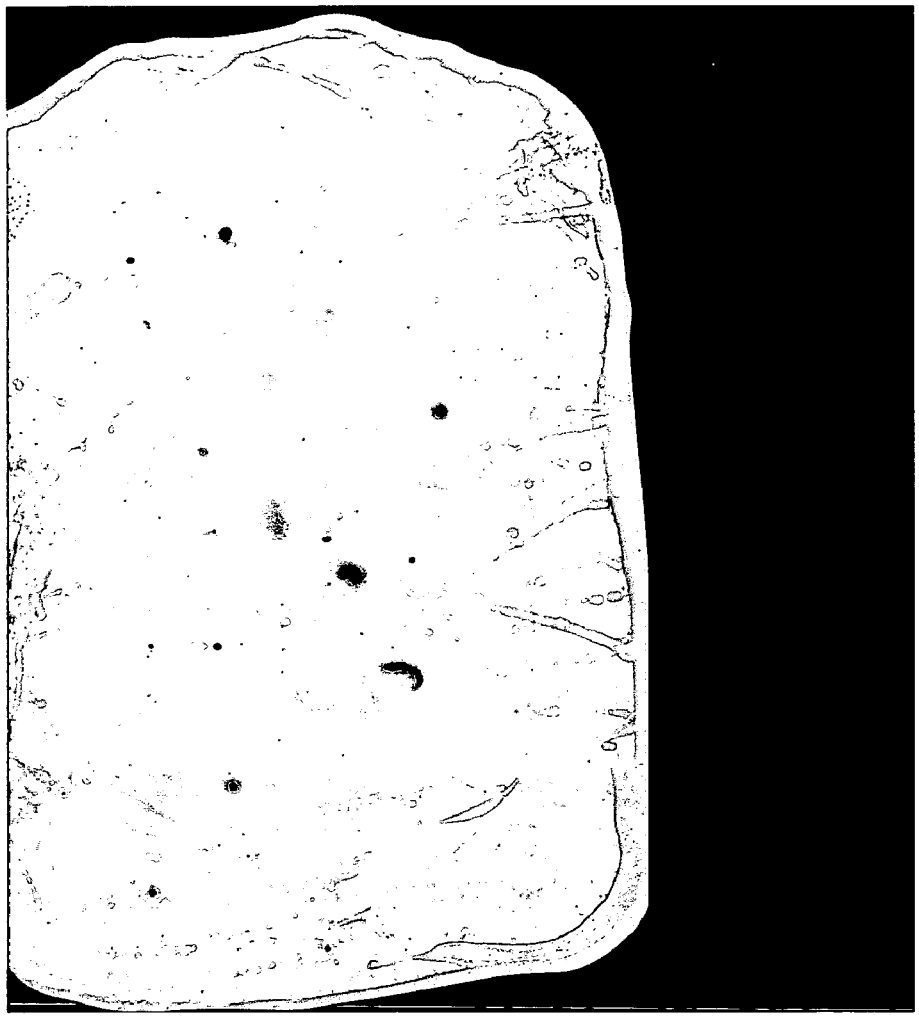
FIG. 34 schematically illustrates a gray scale image of the fluorescence signal from a scan of a control plate which was prepared by washing off the building blocks with organic solvent before incubation with the test ligand.
Figure 35:
FIG. 35 schematically illustrates a gray scale image of the fluorescence signal from a scan of an experimental plate which was incubated with 1.0 µg/ml Cholera Toxin B at 23° C.
Figure 36:
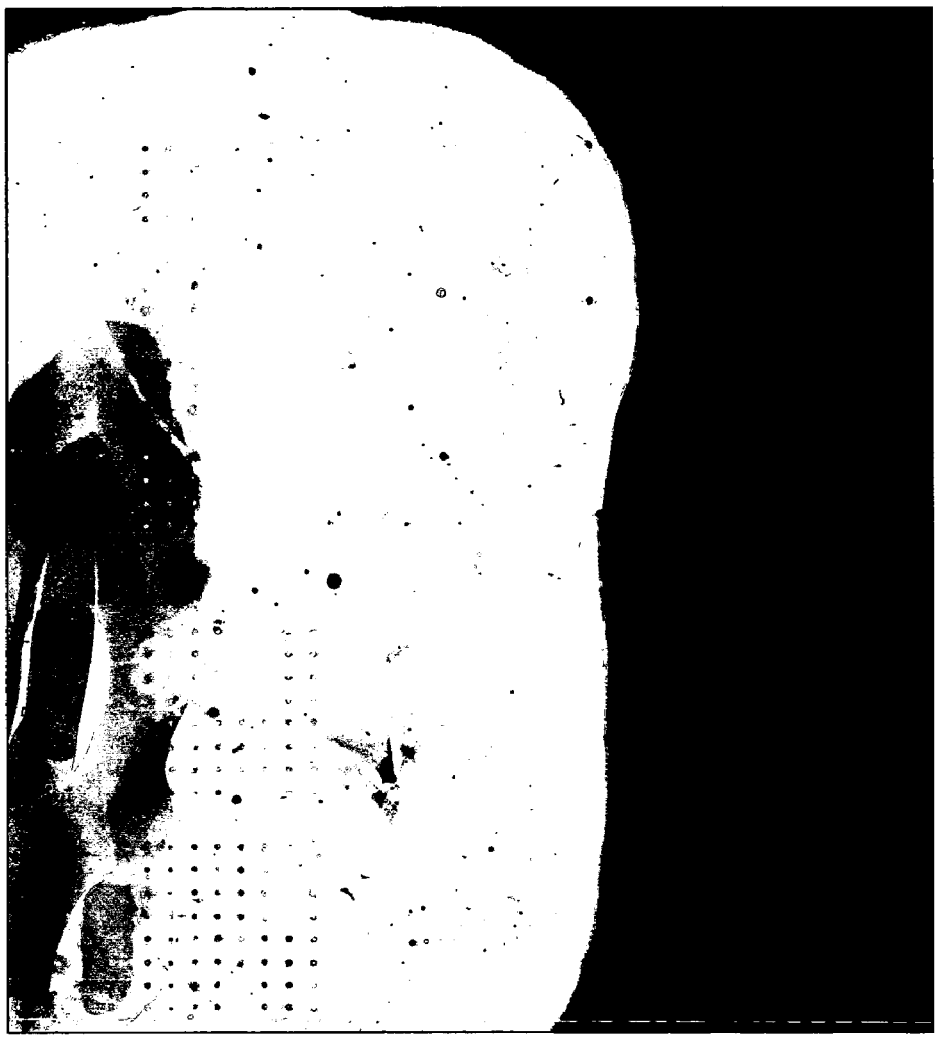
FIG. 36 schematically illustrates a gray scale image of the fluorescence signal from a scan of an experimental plate which was incubated with 1.0 µg/ml Cholera Toxin B at 3° C.
Figure 37:
FIG. 37 schematically illustrates a gray scale image of the fluorescence signal from a scan of an experimental plate which was incubated with 1.0 µg/ml Cholera Toxin B at 43° C.
Figure 38:
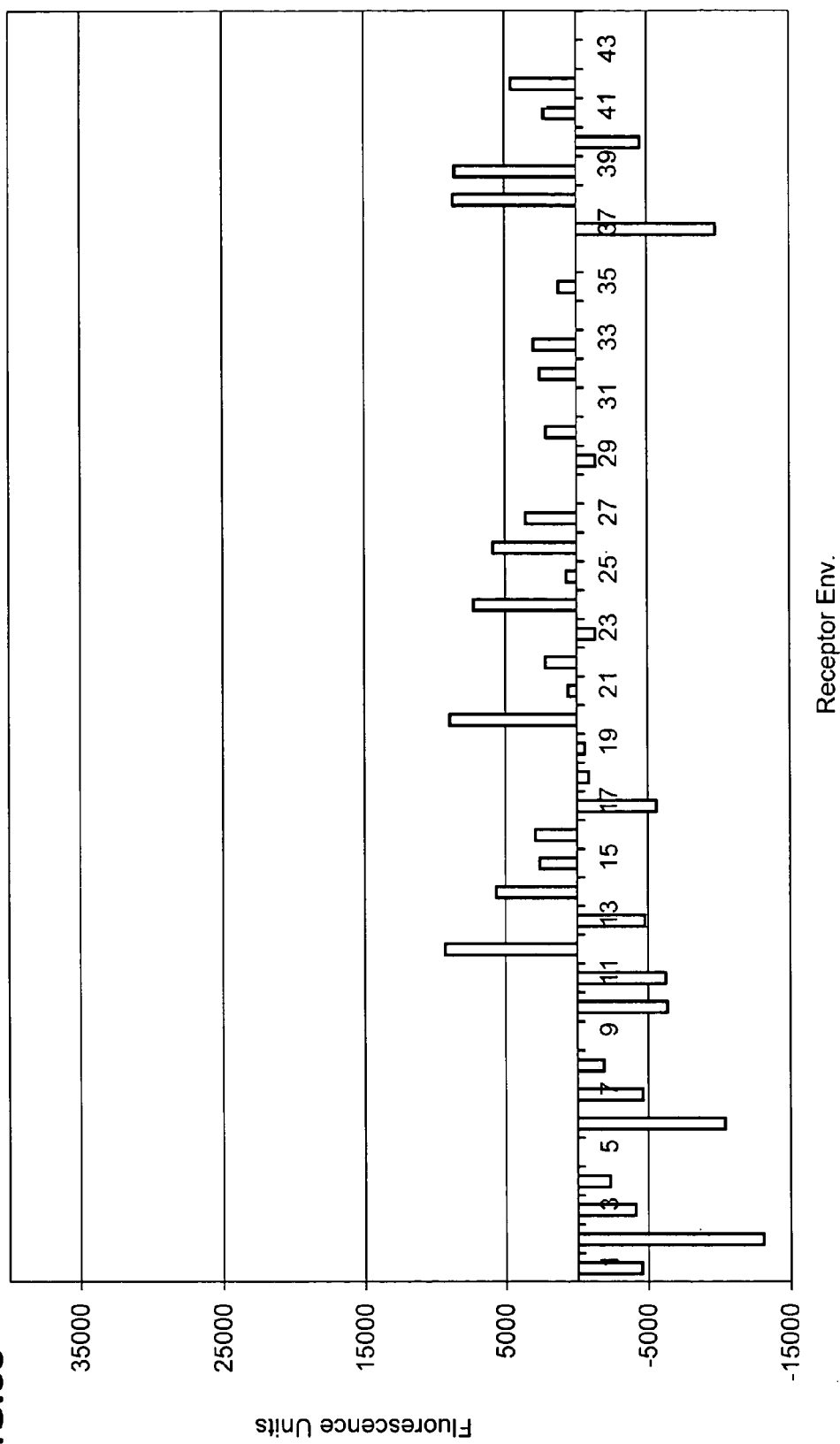
FIGS. 38-40 schematically illustrate plots of the fluorescence signals obtained from the candidate artificial receptors illustrated in FIGS. 35-37.
Figure 39:
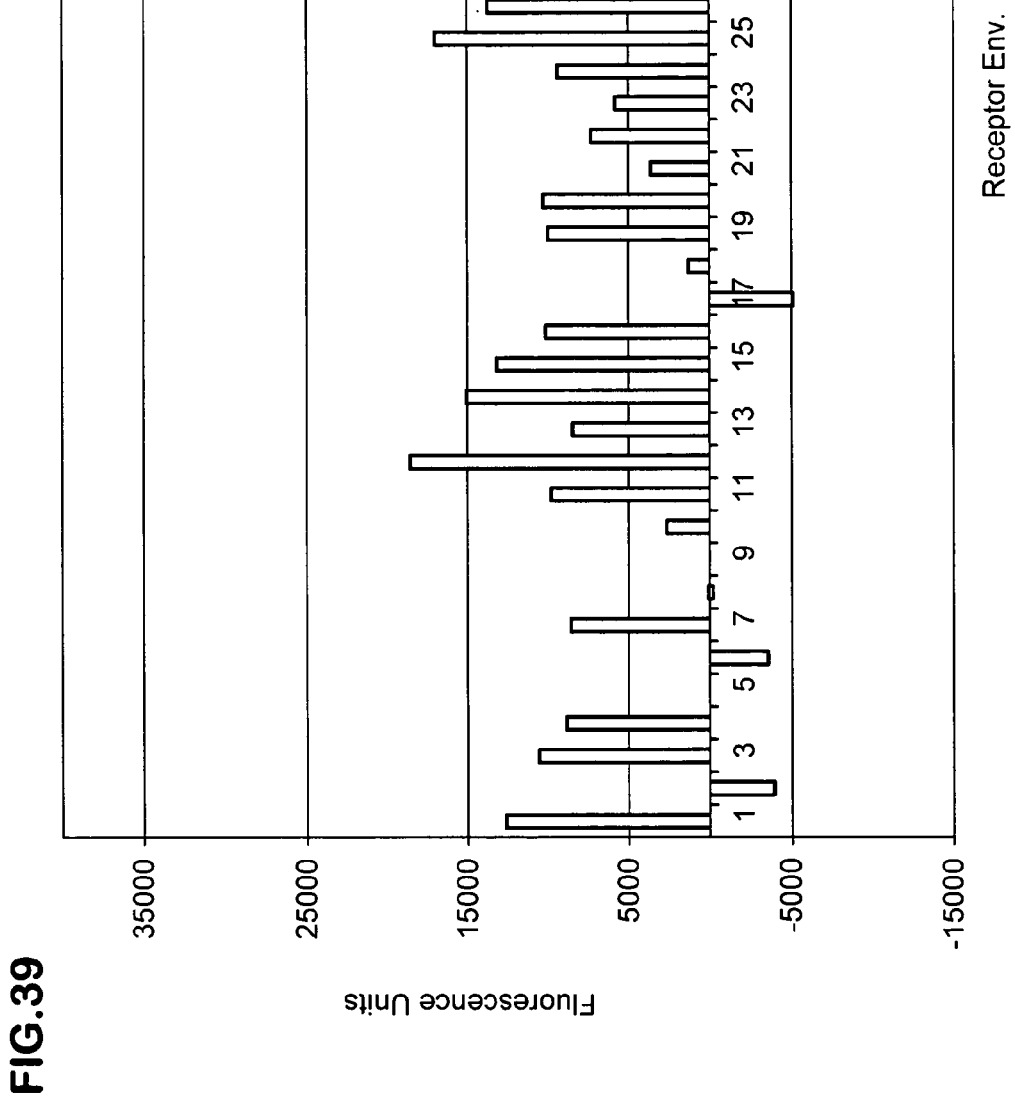
Figure 40:
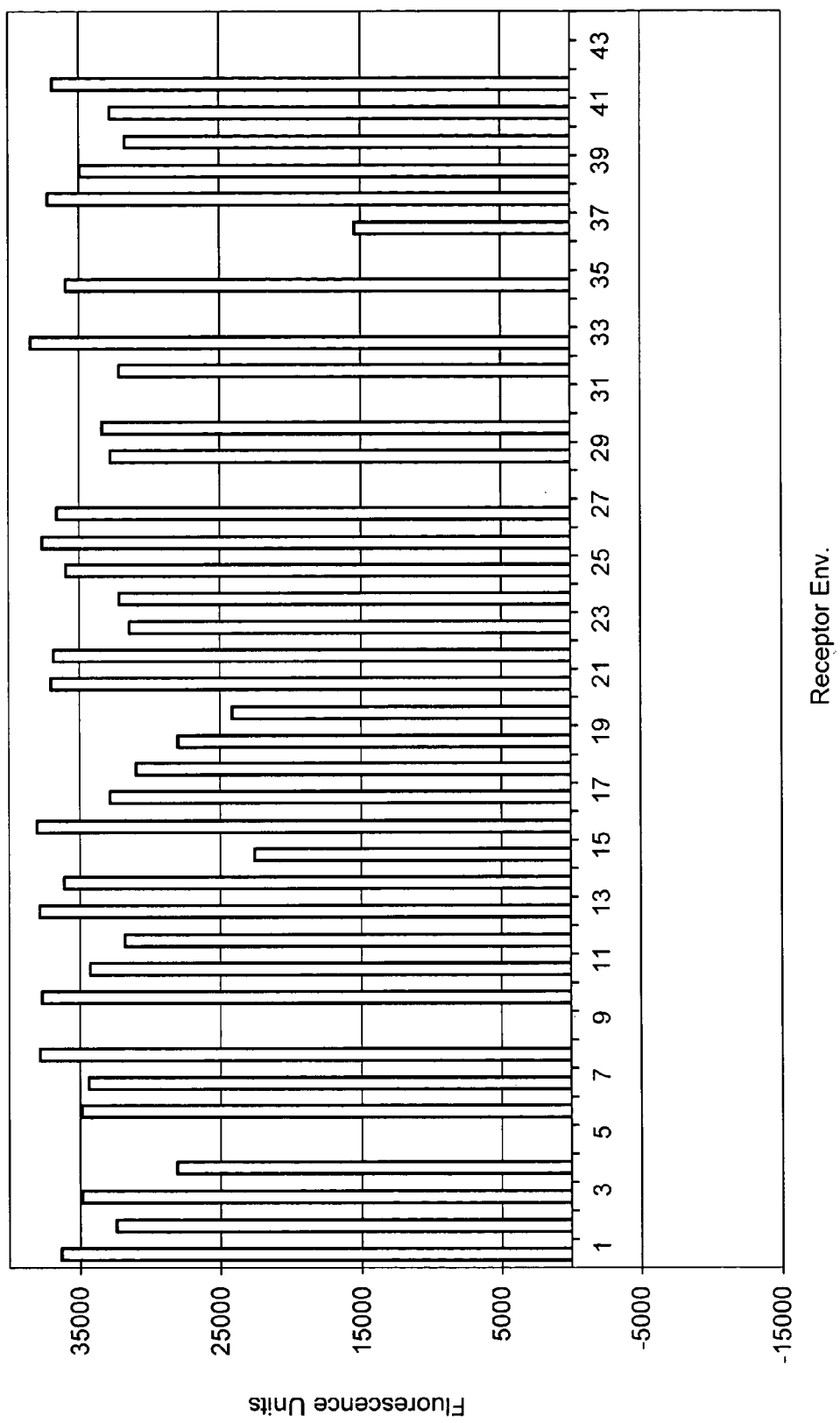

A control array from which the building blocks had been removed by washing with organic solvent did not bind cholera toxin (FIG. 34). FIGS. 35-37 illustrate fluorescence signals from arrays printed identically, but incubated with cholera toxin at 4° C., 23° C., or 44° C., respectively. Spots of fluorescence can be seen in each array, with very pronounced spots produced by incubation at 44° C. The fluorescence values for the spots in each of these three arrays are shown in FIGS. 38-40. Fluorescence signal generally increases with temperature, with many nearly equally large signals observed after incubation at 44° C. Linear increases with temperature can reflect expected improvements in binding with temperature. Nonlinear increases reflect rearrangement of the building blocks on the surface to achieve improved binding, which occurred above the phase transition for the lipid surface (vide infra).

Figure 41:
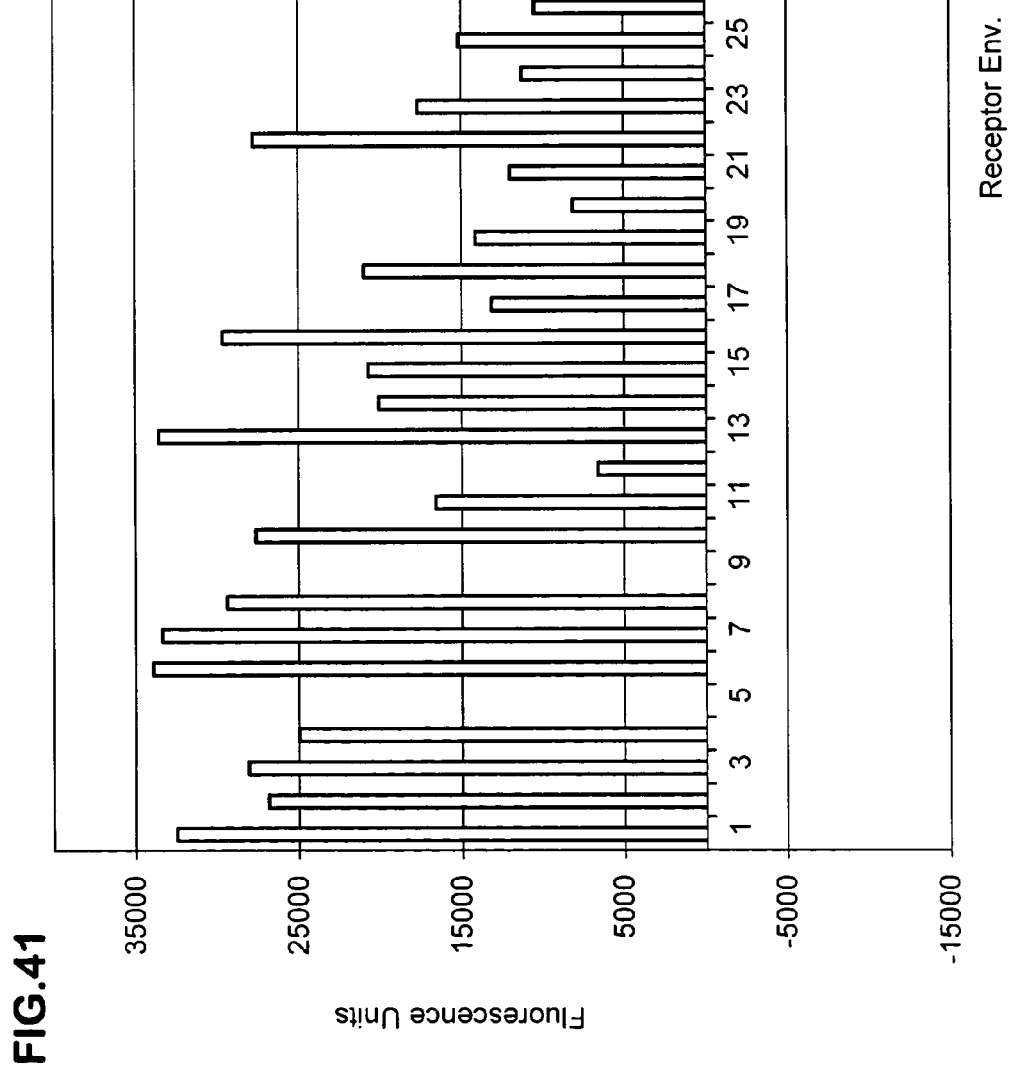
FIG. 41 schematically illustrate plots of the fluorescence signals obtained from the combinations of building blocks employed in the present studies, when those building blocks are covalently linked to the support. Binding was conducted at 23° C.

FIG. 41 can be compared to FIG. 39. The fluorescence signals plotted in FIG. 39 resulted from binding to reversibly immobilized building blocks on a support at 23° C. The fluorescence signals plotted in FIG. 41 resulted from binding to covalently immobilized building blocks on a support at 23° C. These figures compare the same combinations of building blocks in the same relative positions, but immobilized in two different ways.

Figure 42:
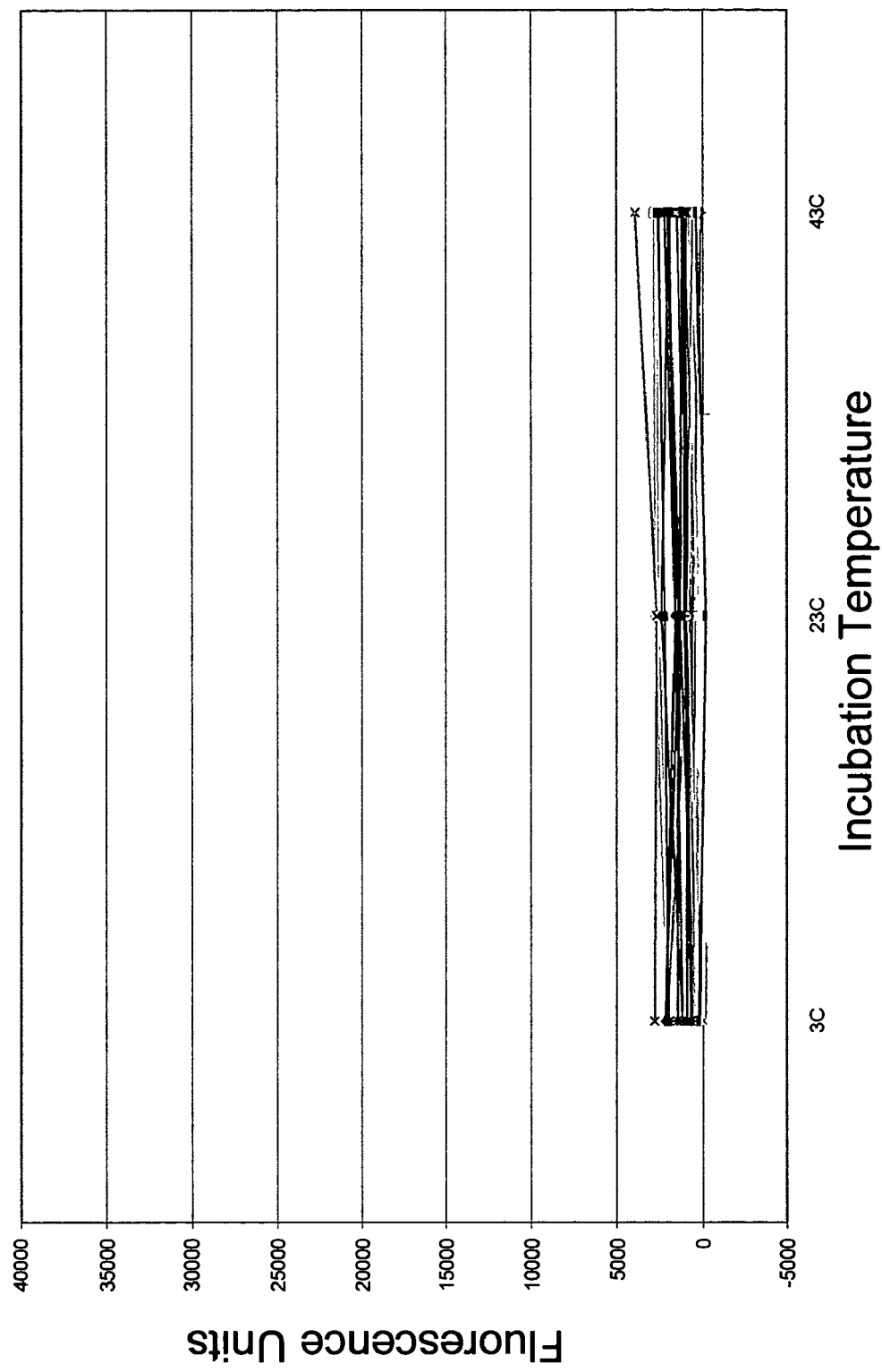
FIG. 42 schematically illustrates the changes in fluorescence signal from individual combinations of covalently immobilized building blocks at 4° C., 23° C., or 44° C.

The binding to covalently immobilized building blocks was also evaluated at 4° C., 23° C., or 44° C. FIG. 42 illustrates the changes in fluorescence signal from individual combinations of covalently immobilized building blocks at 4° C., 23° C., or 44° C. Binding increased modestly with temperature. The mean increase in binding was 1.3-fold. A plot of the fluorescence signal for each of the covalently immobilized artificial receptors at 23° C. against its signal at 44° C. (not shown) yields a linear correlation with a correlation coefficient of 0.75. This linear correlation indicates that the mean 1.3-fold increase in binding is a thermodynamic effect and not optimization of binding.

Figure 43:
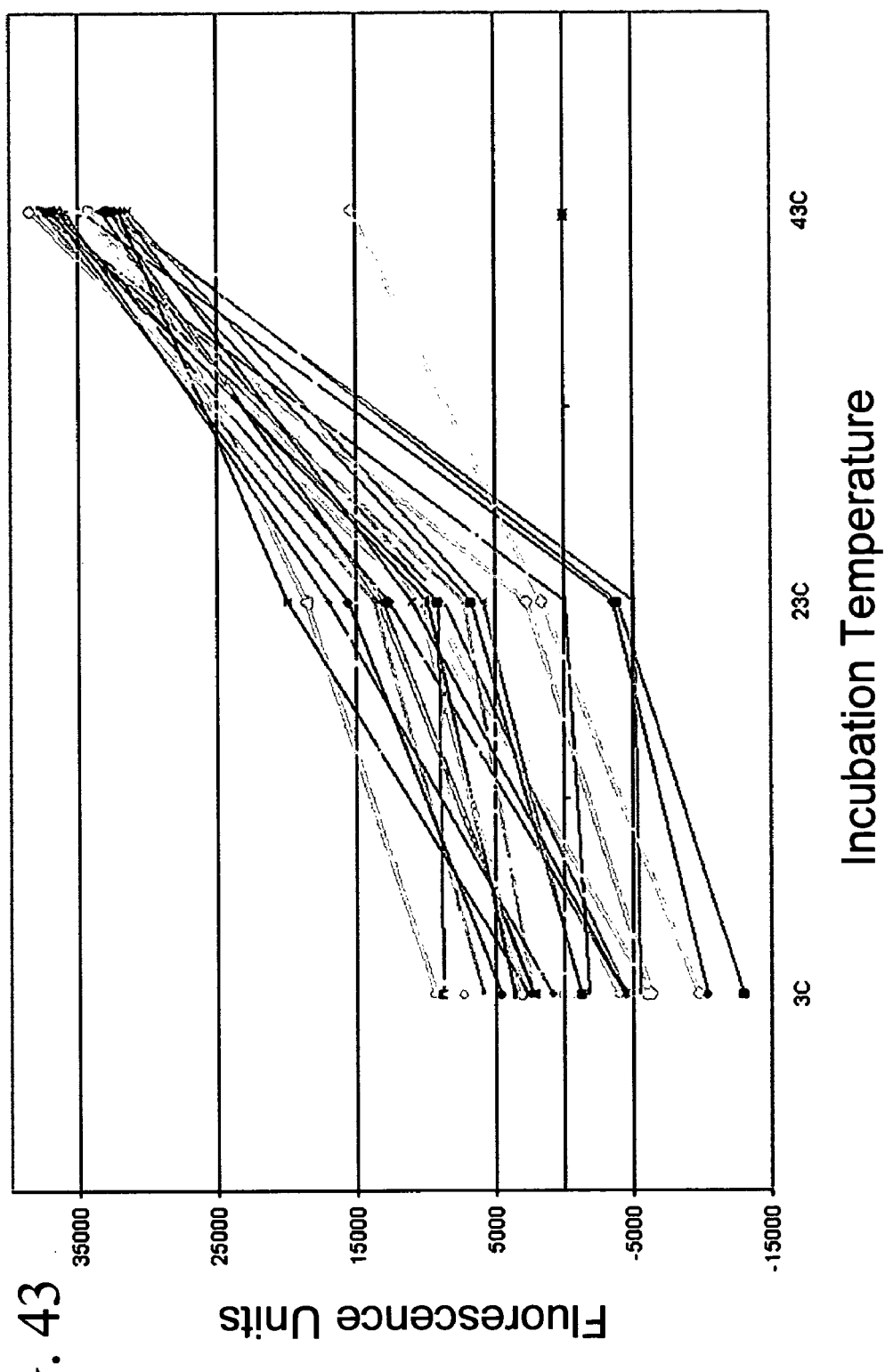
FIG. 43 schematically illustrates a graph of the changes in fluorescence signal from individual combinations of building blocks at 4° C., 23° C., or 44° C.

FIG. 43 illustrates the changes in fluorescence signal from individual combinations of reversibly immobilized building blocks at 4° C., 23° C., or 44° C. This graph illustrates that at least one combination of building blocks (candidate artificial receptor) exhibited a signal that remained constant as temperature increased. At least one candidate artificial receptor exhibited an approximately linear increase in signal as temperature increased. Such a linear increase indicates normal temperature effects on binding. The candidate artificial receptor with the lowest binding signal at 4° C. became one of the best binders at 44° C. This indicates that rearrangement of the building blocks of this receptor above the phase transition for the lawn, which increases the building blocks' mobility, produced increased binding. Other receptors characterized by greater changes in binding between 23° C. and 44° C. (compared to between 4° C. and 23° C.) also underwent dynamic affinity optimization.

Figure 44:
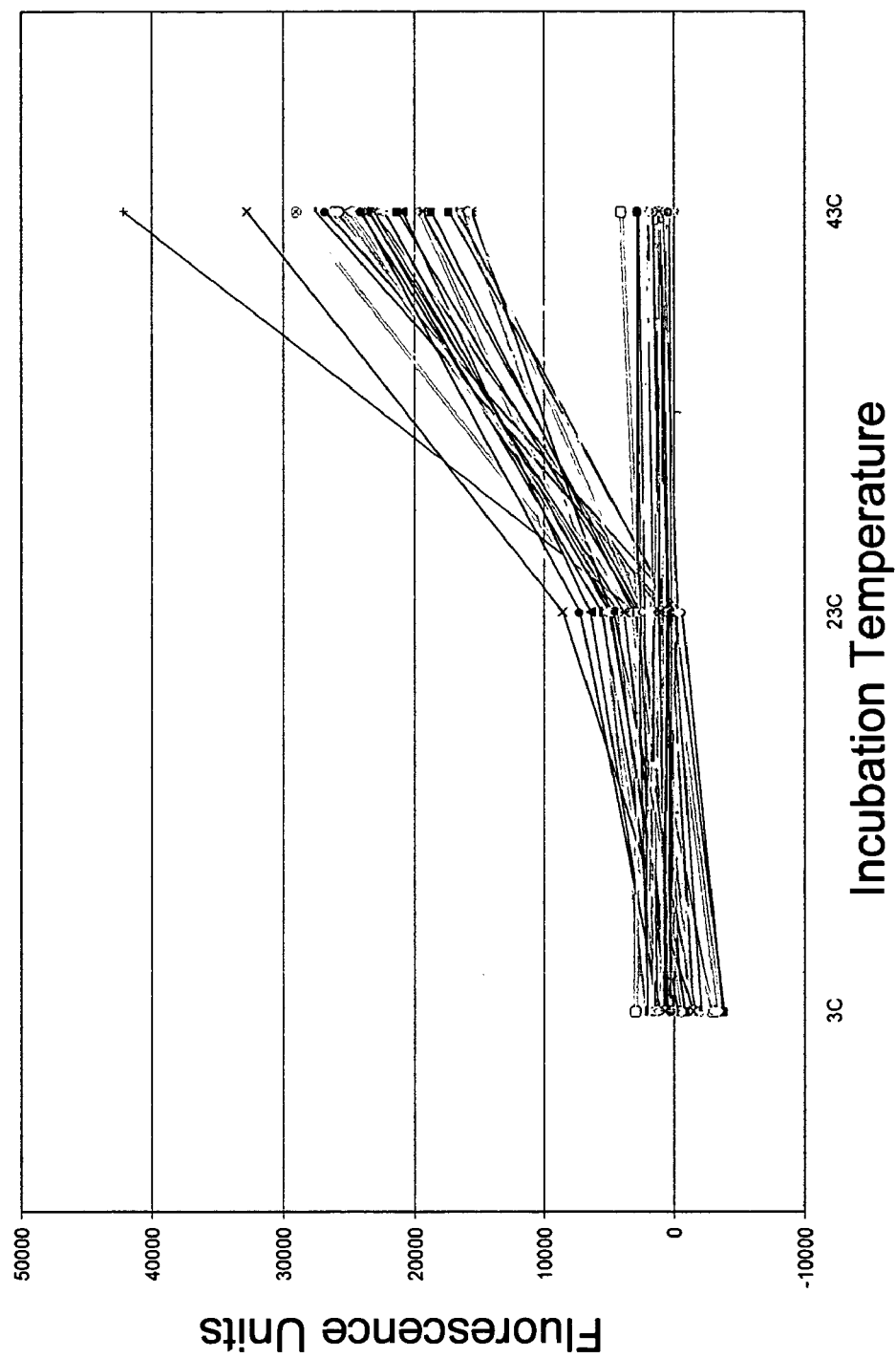
FIG. 44 schematically illustrates the data presented in FIG. 42 (lines marked A) and the data presented in FIG. 43 (lines marked B).

FIG. 44 illustrates the data presented in FIG. 42 (lines marked A) and the data presented in FIG. 43 (lines marked B). The increases in binding observed with the reversibly immobilized building blocks are significantly greater than the increases observed with covalently bound building blocks. Binding to reversibly immobilized building blocks increased from 23° C. and 44° C. by a median value of 6.1-fold and a mean value of 24-fold. This confirms that movement of the reversibly immobilized building blocks within the receptors increased binding (i.e., the receptor underwent dynamic affinity optimization).

A plot of the fluorescence signal for each of the reversibly immobilized artificial receptors at 23° C. against its signal at 44° C. (not shown) yields no correlation (correlation coefficient of 0.004). A plot of the fluorescence signal for each of the reversibly immobilized artificial receptors at 44° C. against the signal for the corresponding covalently immobilized receptor (not shown) also yields no correlation (correlation coefficient 0.004). This lack of correlation provides further evidence that movement of the reversibly immobilized building blocks within the receptors increased binding.

Figure 45:
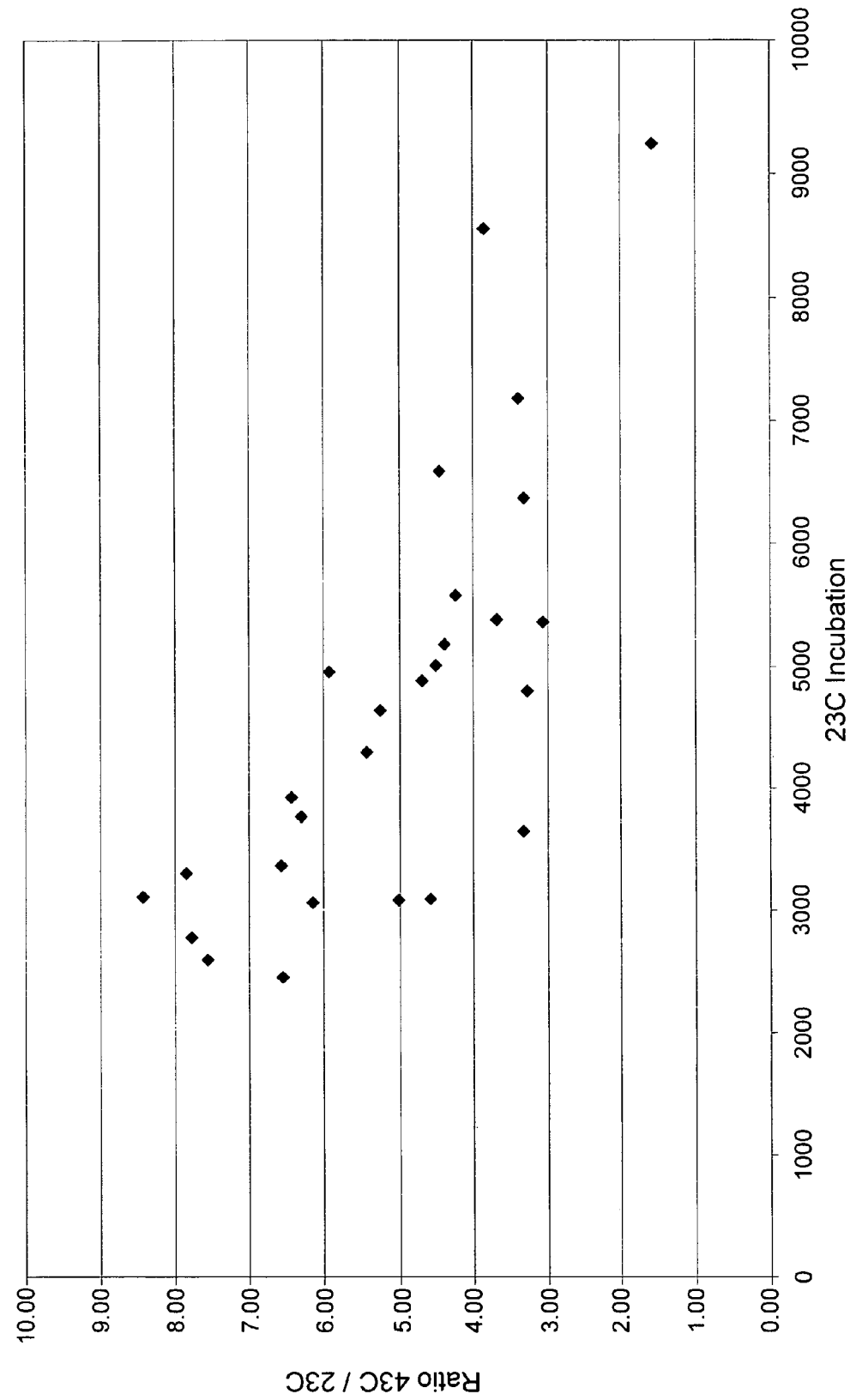
FIG. 45 schematically illustrates a graph of the fluorescence signal at 44° C. divided by the signal at 23° C. against the fluorescence signal obtained from binding at 23° C. for the artificial receptors with reversibly immobilized receptors.

FIG. 45 illustrates a graph of the fluorescence signal at 44° C. divided by the signal at 23° C. against the fluorescence signal obtained from binding at 23° C. for the artificial receptors with reversibly immobilized receptors. This comparison indicates that the binding enhancement is independent of the initial affinity of the receptor for the test ligand.

Table 1 identifies the reversibly immobilized building blocks making up each of the artificial receptors, lists the fluorescence signal (binding strength) at 44° C. and 23° C., and the ratios of the observed binding at these two temperatures. These data illustrate that each artificial receptor reflects a unique attribute for each combination of building blocks relative to the role of each individual building block.

TABLE 1

| Building Blocks Making Up Receptor | Signal at 44° C. | Signal at 23° C. | Ratio of Signals, 44° C./23° C. |
|---|---|---|---|
| 22 24 | 24136 | 4611 | 5.23 |
| 22 26 | 16660 | 43 | 387.44 |
| 22 42 | 17287 | −167 | −103.51 |
| 22 44 | 16726 | 275 | 60.82 |
| 22 46 | 25016 | 3903 | 6.41 |
| 22 62 | 13990 | 3068 | 4.56 |
| 22 64 | 15294 | 3062 | 4.99 |
| 22 66 | 11980 | 3627 | 3.30 |
| 24 26 | 22688 | 1291 | 17.57 |
| 24 42 | 26808 | −662 | −40.50 |
| 24 44 | 23154 | 904 | 25.61 |
| 24 46 | 42197 | 2814 | 15.00 |
| 24 62 | 19374 | 2567 | 7.55 |
| 24 64 | 27599 | 262 | 105.34 |
| 24 66 | 16238 | 5334 | 3.04 |
| 26 42 | 22282 | 4974 | 4.48 |
| 26 44 | 26240 | 530 | 49.51 |
| 26 46 | 23144 | 4273 | 5.42 |
| 26 62 | 29022 | 4920 | 5.90 |
| 26 64 | 23416 | 5551 | 4.22 |
| 26 66 | 19553 | 5353 | 3.65 |
| 42 44 | 29093 | 6555 | 4.44 |
| 42 46 | 18637 | 3039 | 6.13 |
| 42 62 | 22643 | 4853 | 4.67 |
| 42 64 | 20836 | 6343 | 3.28 |
| 42 66 | 14391 | 9220 | 1.56 |
| 44 46 | 25600 | 3266 | 7.84 |
| 44 62 | 15544 | 4771 | 3.26 |
| 44 64 | 25842 | 3073 | 8.41 |
| 44 66 | 22471 | 5142 | 4.37 |
| 46 62 | 32764 | 8522 | 3.84 |
| 46 64 | 21901 | 3343 | 6.55 |
| 46 66 | 23516 | 3742 | 6.28 |
| 62 64 | 24069 | 7149 | 3.37 |
| 62 66 | 15831 | 2424 | 6.53 |
| 64 66 | 21310 | 2746 | 7.76 |

Conclusions

This experiment demonstrated that an array including reversibly immobilized building blocks binds a protein substrate, like an array with covalently immobilized building blocks. The binding increased nonlinearly as temperature increased, indicating that movement of the building blocks increased binding. Many of the candidate artificial receptors demonstrated improved binding upon mobilization of the building blocks.

Example 4

The Oligosaccharide Portion of GM1 Competes With Artificial Receptors for Binding to Cholera Toxin Microarrays of candidate artificial receptors were made and evaluated for binding of cholera toxin. The arrays were also evaluated for disrupting that binding. Disrupting of binding employed a compound that binds to cholera toxin, the oligosaccharide moiety from GM1 (GM1 OS). The results obtained demonstrate that a ligand of a protein specifically disrupted binding of the protein to the microarray.

Materials and Methods

Building blocks were synthesized and activated as described in Example 1. The building blocks employed in this example were TyrA1B1 [1-1], TyrA2B2, TyrA2B4, TyrA2B6, TyrA2B8, TyrA3B3, TyrA3B5, TyrA3B7, TyrA4B2, TyrA4B4, TyrA4B6, TyrA4B8, TyrA5B3, TyrA5B5, TyrA5B7, TyrA6B2, TyrA6B4, TyrA6B6, TyrA6B8, TyrA7B3, TyrA7B5, TyrA7B7, TyrA8B2, TyrA8B4, TyrA8B6, and TyrA8B8. The abbreviation for the building block including a linker, a tyrosine framework, and recognition elements AxBy is TyrAxBy.

Microarrays for the evaluation of the 171 n=2 candidate receptor environments were prepared as follows by modifications of known methods. An "n=2" receptor environment includes two different building blocks. Briefly: Amine modified (amine "lawn"; SuperAmine Microarray plates) microarray plates were purchased from Telechem Inc., Sunnyvale, Calif. These plates were manufactured specifically for microarray preparation and had a nominal amine load of 2-4 amines per square nm according to the manufacturer. The microarrays were prepared using a pin microarray spotter instrument from Telechem Inc. (SpotBot™ Arrayer) typically with 200 μm diameter spotting pins from Telechem Inc. (Stealth Micro Spotting Pins, SMP6) and 400-420 lm spot spacing.

The 19 building blocks were activated in aqueous dimethylformamide (DMF) solution as described above. For preparing the 384-well feed plate, the activated building block solutions were diluted 10-fold with a solution of DMF/H$_2$O/PEG400 (90/10/10, v/v/v; PEG400 is polyethylene glycol nominal 400 FW, Aldrich Chemical Co., Milwaukee, Wis.). These stock solutions were aliquotted (10 μl per aliquot) into the wells of a 384-well microwell plate (Telechem Inc.). Control spots included the building block [1-1]. The plate was covered with aluminum foil and placed on the bed of a rotary shaker for 15 minutes at 1,000 RPM. This master plate was stored covered with aluminum foil at −20° C. when not in use.

For preparing the 384-well SpotBot™ plate, a well-to-well transfer (e.g. A-1 to A-1, A-2 to A-2, etc.) from the feed plate to a second 384-well plate was performed using a 4 μl transfer pipette. This plate was stored tightly covered with aluminum foil at −20° C. when not in use. The SpotBot™ was used to prepare up to 13 microarray plates per run using the 4 μl microwell plate. The SpotBot™ was programmed to spot from each microwell in quadruplicate. The wash station on the SpotBot™ used a wash solution of EtOH/H$_2$O (20/80, v/v). This wash solution was adjusted to pH 4 with 1 M HCl and used to rinse the microarrays on completion of the SpotBot™ printing run. The plates were given a final rinse with deionized (DI) water, dried using a stream of compressed air, and stored at room temperature. The microarrays were further modified by reacting the remaining amines with acetic anhydride to form an acetamide lawn in place of the amine lawn.

The test ligand employed in these experiments was cholera toxin labeled with the Alexa™ fluorophore (Molecular Probes Inc., Eugene, Oreg.). The candidate disruptor employed in these experiments was GM1 OS (GM1 oligosaccharide), a known ligand for cholera toxin.

Microarray incubation and analysis was conducted as follows: For control incubations with the microarrays, solutions (e.g. 500 μl) of the cholera toxin in PBS-T (PBS with 20 μl/L of Tween-20) at a concentrations of 1.7 pmol/ml (0.1 μg/ml) was placed onto the surface of a microarray and allowed to react for 30 minutes. For disruptor incubations with the microarrays, solutions (e.g. 500 μl) of the cholera toxin (1.7 pmol/ml, 0.1 μg/ml) and the desired concentration of GM1 OS in PBS-T (PBS with 20 μl/L of Tween-20) was placed onto the surface of a microarray and allowed to react for 30 minutes. GM1 OS was added at 0.34 and at 5.1 μM in separate experiments. After either of these incubations, the microarray was rinsed with PBS-T and DI water and dried using a stream of compressed air.

The incubated microarray was scanned using an Axon Model 4200A Fluorescence Microarray Scanner (Axon Instruments, Union City, Calif.). The Axon scanner and its associated software produce a false color 16-bit image of the fluorescence intensity of the plate. This 16-bit data is integrated using the Axon software to give a Fluorescence Units value (range 0-65,536) for each spot on the microarray. This data is then exported into an Excel file (Microsoft) for further analysis including mean, standard deviation and coefficient of variation calculations.

Table 2 identifies the building blocks in each of the first 150 receptor environments.

TABLE 2

|  | Building Blocks |
|---|---|
| 1 | 22 24 |
| 2 | 22 28 |
| 3 | 22 42 |
| 4 | 22 46 |
| 5 | 22 55 |
| 6 | 22 64 |
| 7 | 22 68 |
| 8 | 22 82 |
| 9 | 22 86 |
| 10 | 24 26 |
| 11 | 24 33 |
| 12 | 24 44 |
| 13 | 26 77 |
| 14 | 26 84 |
| 15 | 26 88 |
| 16 | 28 42 |
| 17 | 22 26 |
| 18 | 22 33 |
| 19 | 22 44 |
| 20 | 22 48 |
| 21 | 22 62 |
| 22 | 22 66 |
| 23 | 22 77 |
| 24 | 22 84 |
| 25 | 22 88 |
| 26 | 24 28 |
| 27 | 24 42 |
| 28 | 26 82 |
| 29 | 26 85 |
| 30 | 28 33 |
| 31 | 28 44 |
| 32 | 28 46 |
| 33 | 28 55 |
| 34 | 28 64 |
| 35 | 28 68 |
| 36 | 28 82 |
| 37 | 28 86 |
| 38 | 33 42 |
| 39 | 33 46 |
| 40 | 42 88 |
| 41 | 44 48 |
| 42 | 44 62 |
| 43 | 44 66 |
| 44 | 44 77 |
| 45 | 44 84 |
| 46 | 44 88 |
| 47 | 46 55 |
| 48 | 28 48 |
| 49 | 28 62 |
| 50 | 28 66 |
| 51 | 28 77 |
| 52 | 28 84 |
| 53 | 28 88 |
| 54 | 33 44 |
| 55 | 44 46 |

TABLE 2-continued

|  | Building Blocks |
|---|---|
| 56 | 44 55 |
| 57 | 44 64 |
| 58 | 44 68 |
| 59 | 44 82 |
| 60 | 44 86 |
| 61 | 46 48 |
| 62 | 46 62 |
| 63 | 24 46 |
| 64 | 24 55 |
| 65 | 24 64 |
| 66 | 24 68 |
| 67 | 24 82 |
| 68 | 24 86 |
| 69 | 26 28 |
| 70 | 26 42 |
| 71 | 26 46 |
| 72 | 26 55 |
| 73 | 26 64 |
| 74 | 26 68 |
| 75 | 33 48 |
| 76 | 33 63 |
| 77 | 33 66 |
| 78 | 33 77 |
| 79 | 24 48 |
| 80 | 24 62 |
| 81 | 24 66 |
| 82 | 24 77 |
| 83 | 24 84 |
| 84 | 24 88 |
| 85 | 26 33 |
| 86 | 26 44 |
| 87 | 26 48 |
| 88 | 26 62 |
| 89 | 26 66 |
| 90 | 33 55 |
| 91 | 33 64 |
| 92 | 33 68 |
| 93 | 33 82 |
| 94 | 33 84 |
| 95 | 33 88 |
| 96 | 42 46 |
| 97 | 42 55 |
| 98 | 42 64 |
| 99 | 42 68 |
| 100 | 42 82 |
| 101 | 42 86 |
| 102 | 46 88 |
| 103 | 48 62 |
| 104 | 48 66 |
| 105 | 46 77 |
| 106 | 48 84 |
| 107 | 48 88 |
| 108 | 55 64 |
| 109 | 55 68 |
| 110 | 33 86 |
| 111 | 42 44 |
| 112 | 42 48 |
| 113 | 42 62 |
| 114 | 42 66 |
| 115 | 42 77 |
| 116 | 42 84 |
| 117 | 48 55 |
| 118 | 48 64 |
| 119 | 48 68 |
| 120 | 48 82 |
| 121 | 48 86 |
| 122 | 55 62 |
| 123 | 55 66 |
| 124 | 55 77 |
| 125 | 46 64 |
| 126 | 46 68 |
| 127 | 46 82 |
| 128 | 46 86 |
| 129 | 62 77 |
| 130 | 62 84 |
| 131 | 62 88 |
| 132 | 64 68 |
| 133 | 64 82 |

TABLE 2-continued

| | Building Blocks |
|---|---|
| 134 | 64 86 |
| 135 | 66 68 |
| 136 | 66 82 |
| 137 | 66 86 |
| 138 | 68 77 |
| 139 | 68 84 |
| 140 | 68 88 |
| 141 | 46 66 |
| 142 | 46 77 |
| 143 | 46 84 |
| 144 | 62 82 |
| 145 | 62 86 |
| 146 | 64 66 |
| 147 | 64 77 |
| 148 | 64 84 |
| 149 | 64 88 |
| 150 | 66 77 |

Results
Low Concentration of GM1 OS

Figure 46:
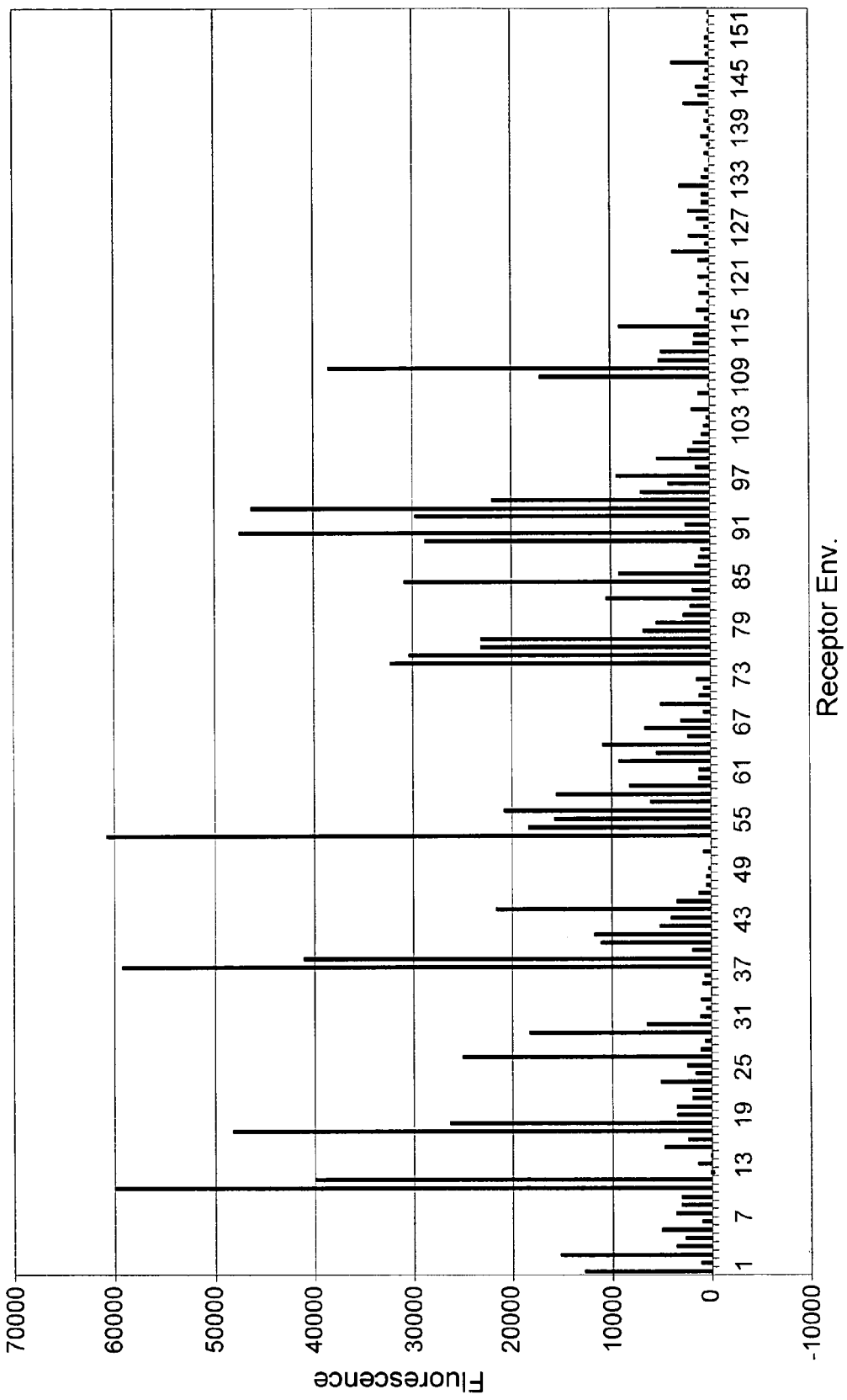
FIG. 46 illustrates fluorescence signals produced by binding of cholera toxin to a microarray of the present candidate artificial receptors followed by washing with buffer in an experiment reported in Example 4.

FIG. 46 illustrates binding of cholera toxin to the microarray of candidate artificial receptor followed by washing with buffer produced fluorescence signals. These fluorescence signals demonstrate that the cholera toxin bound strongly to certain receptor environments, weakly to others, and undetectably to some. Comparison to experiments including those reported in Example 2 indicates that cholera toxin binding was reproducible from array to array and from month to month.

Figure 47:
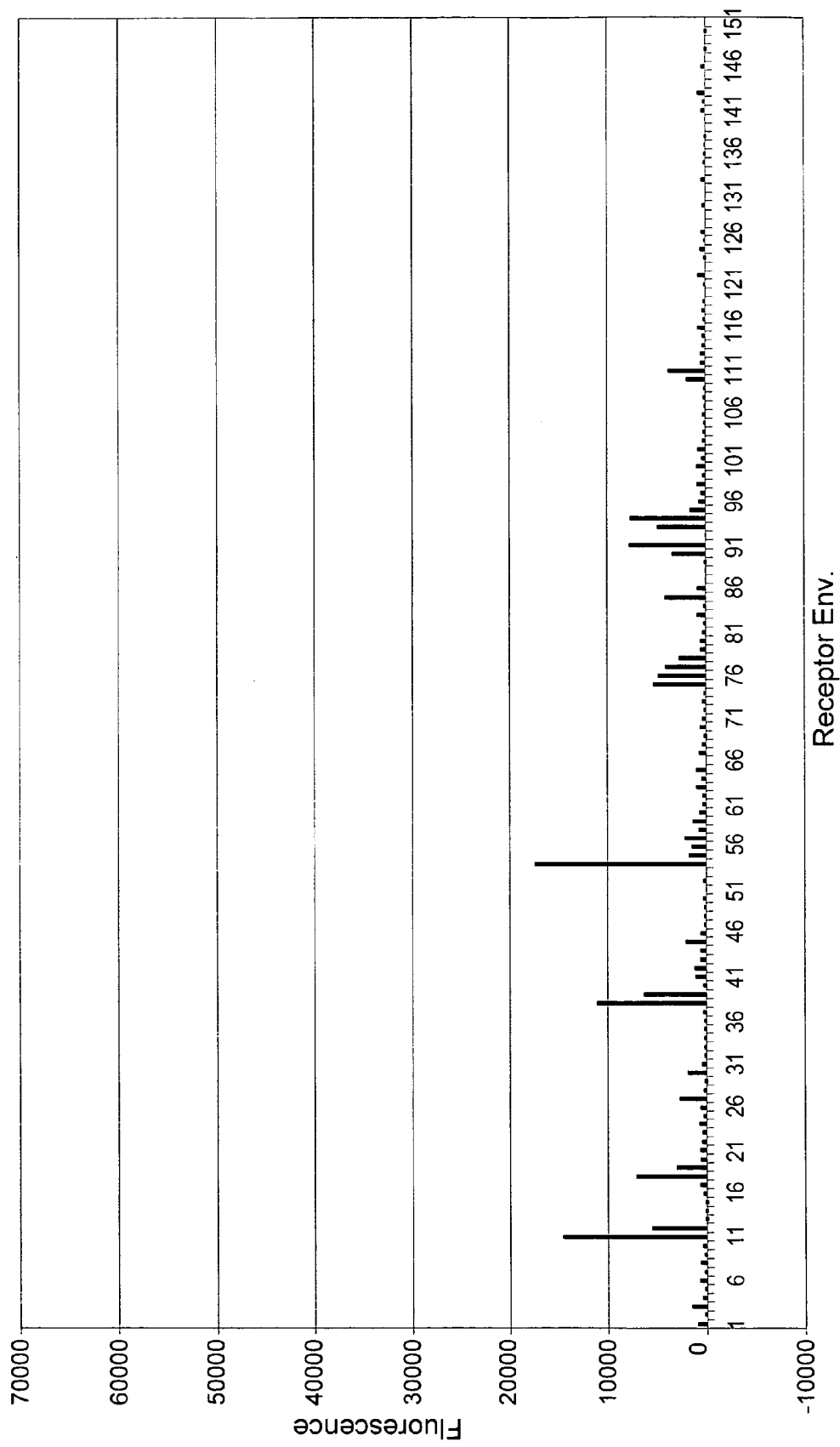
FIG. 47 illustrates the fluorescence signals due to cholera toxin binding that were detected upon competition with GM1 OS (0.34 µM) in an experiment reported in Example 4.

Binding of cholera toxin was also conducted with competition from GM1 OS (0.34 µM). FIG. 47 illustrates the fluorescence signals due to cholera toxin binding that were detected after this competition. Notably, many of the signals illustrated in FIG. 47 are significantly smaller than the corresponding signals recorded in FIG. 46. The small signals observed in FIG. 47 represent less cholera toxin bound to the array. GM1 OS significantly disrupted binding of cholera toxin to many of the receptor environments.

Figure 48:
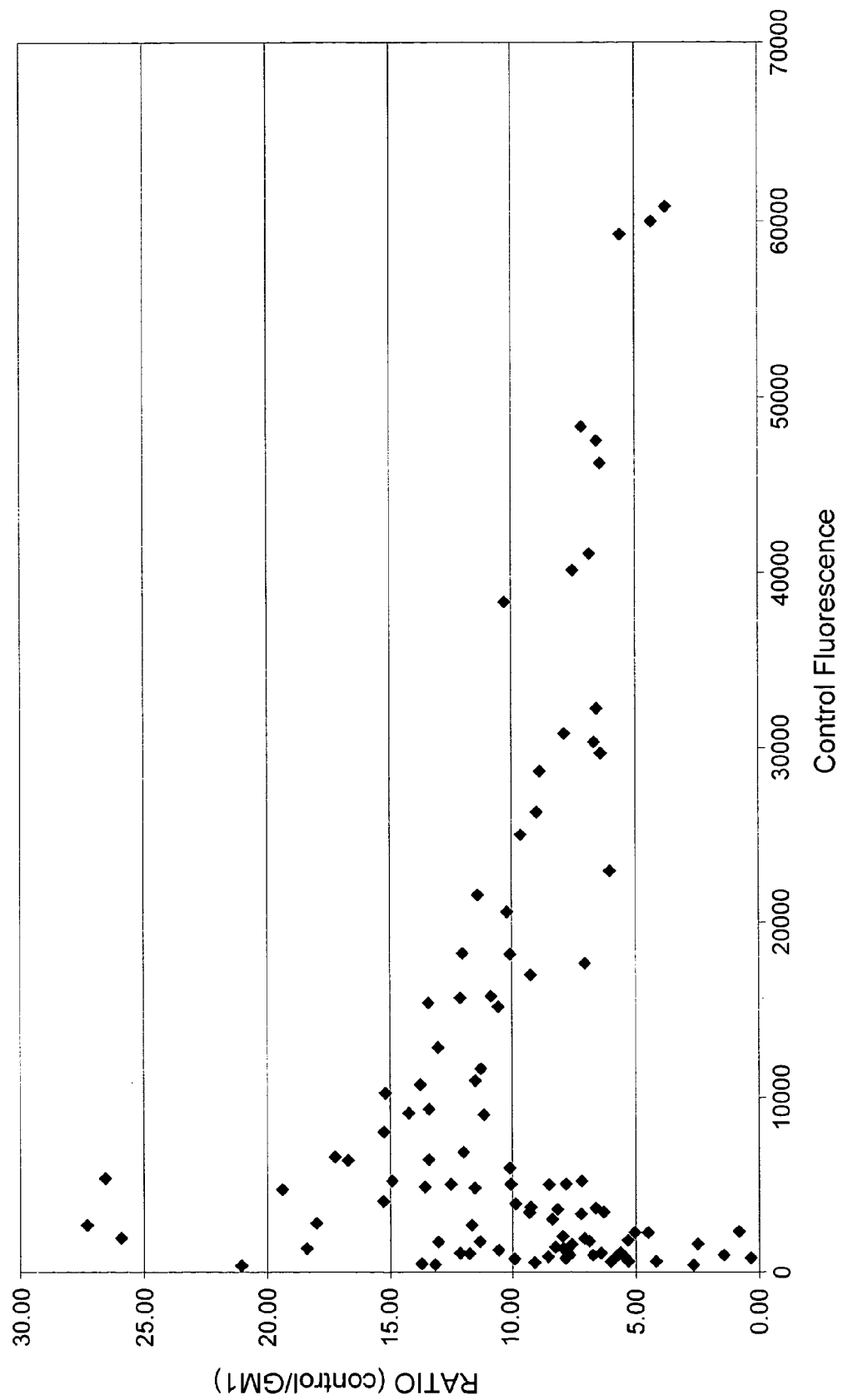
FIG. 48 illustrates the ratio of the amount bound in the absence of GM1 OS to the amount bound in competition with GM1 OS (0.34 µM) in an experiment reported in Example 4.

The disruption in cholera toxin binding caused by GM1 OS can be visualized as the ratio of the amount bound in the absence of GM1 OS to the amount bound in competition with GM1 OS. This ratio is illustrated in FIG. 48. The larger the ratio, the less cholera toxin remained bound to the artificial receptor after competition with GM1 OS. The ratio can be as large as about 30. The ratios are independent of the quantity bound in the control.

High Concentration of GM1 OS

Figure 49:
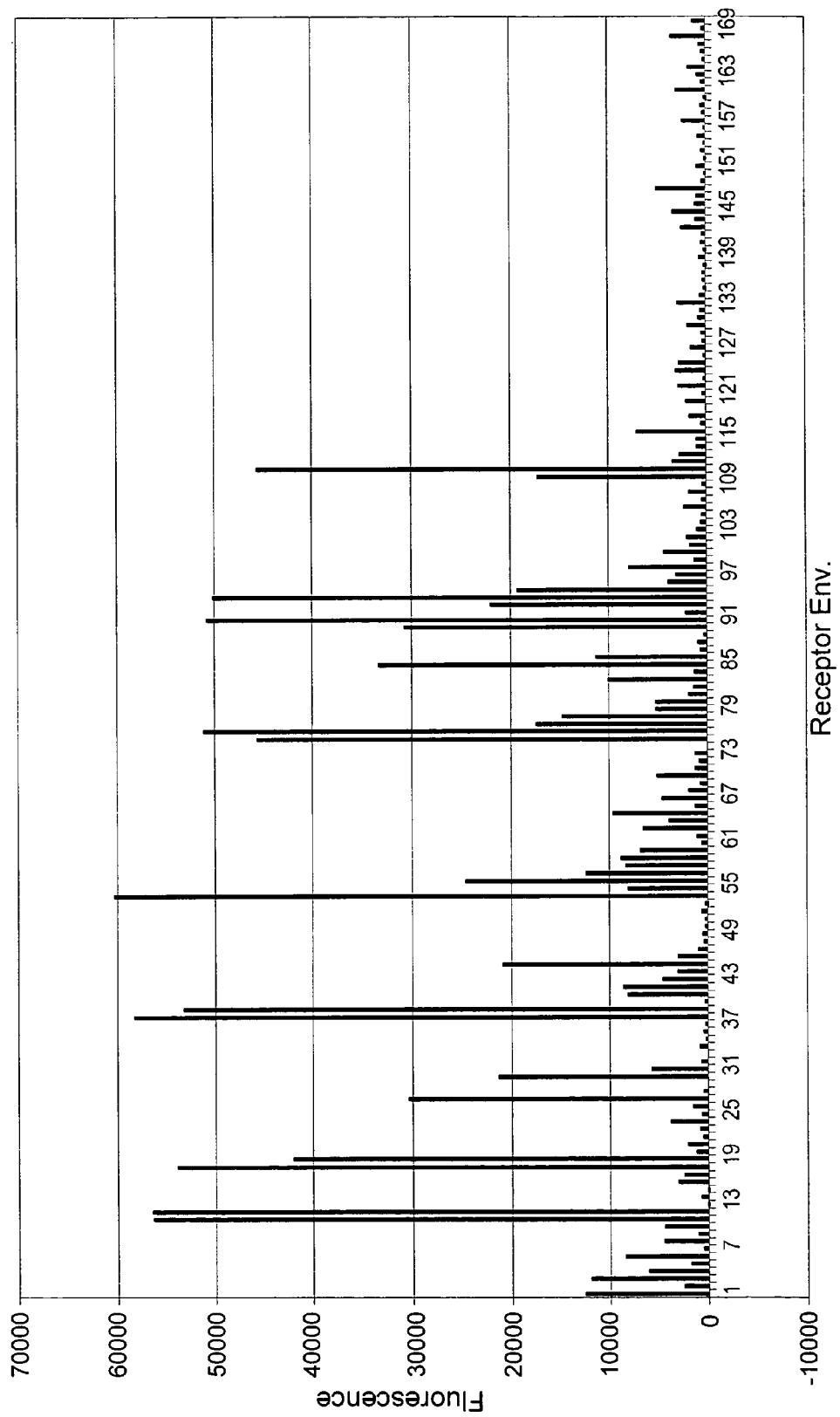
FIG. 49 illustrates fluorescence signals produced by binding of cholera toxin to a microarray of the present candidate artificial receptors followed by washing with buffer in an experiment reported in Example 4 and for comparison with competition experiments using 5.1 µM GM1 OS.
Figure 50:
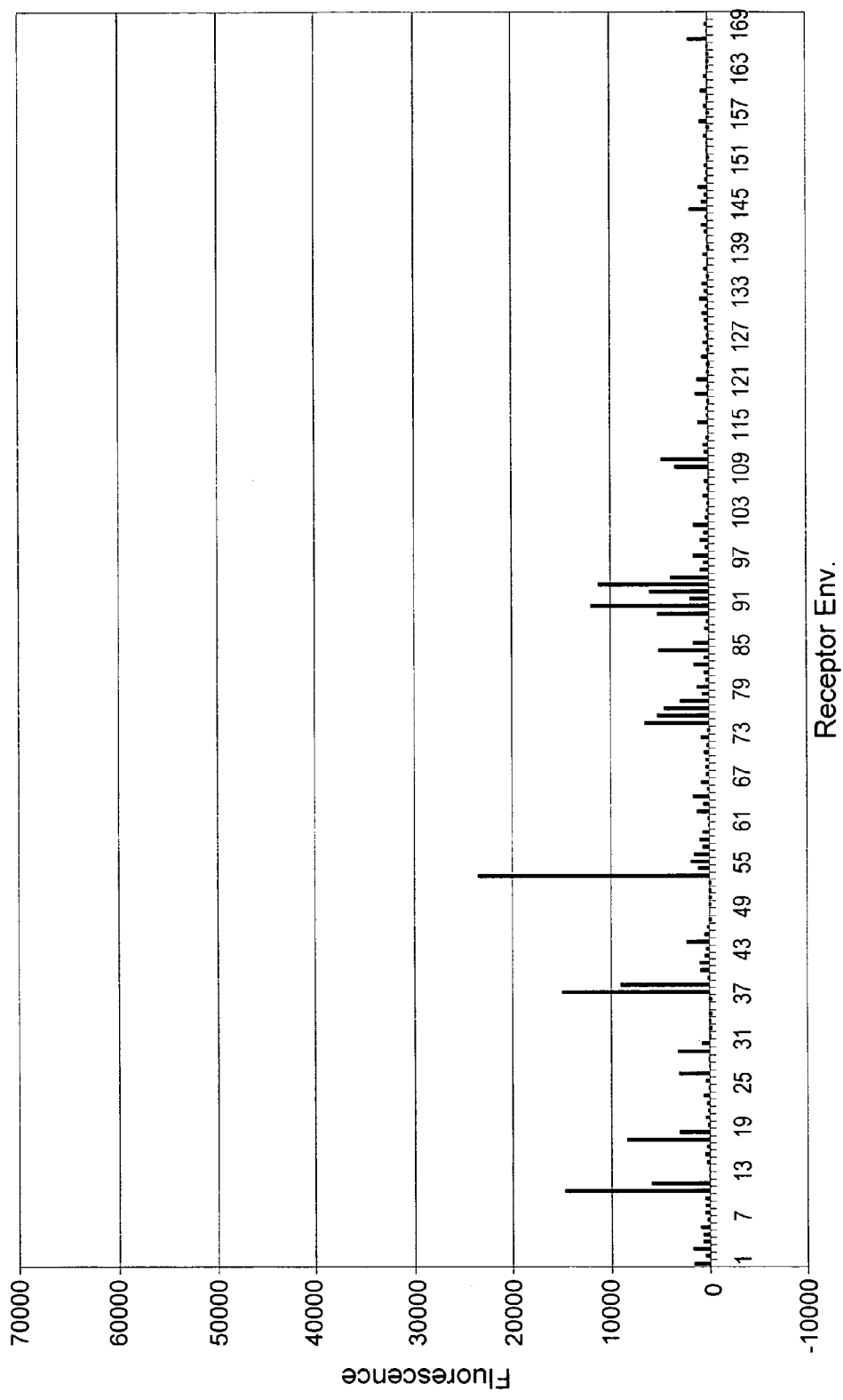
FIG. 50 illustrates the fluorescence signals due to cholera toxin binding that were detected upon competition with GM1 OS (5.1 µM) in an experiment reported in Example 4.

Binding of cholera toxin to the microarray of candidate artificial receptors followed by washing with buffer produced fluorescence signals illustrated in FIG. 49. As before, cholera toxin was reproducible and it bound strongly to certain receptor environments, weakly to others, and undetectably to some. FIG. 50 illustrates the fluorescence signals detected due to cholera toxin binding that were detected upon competition with GM1 OS at 5.1 µM. Again, GM1 OS significantly disrupted binding of cholera toxin to many of the receptor environments.

Figure 51:
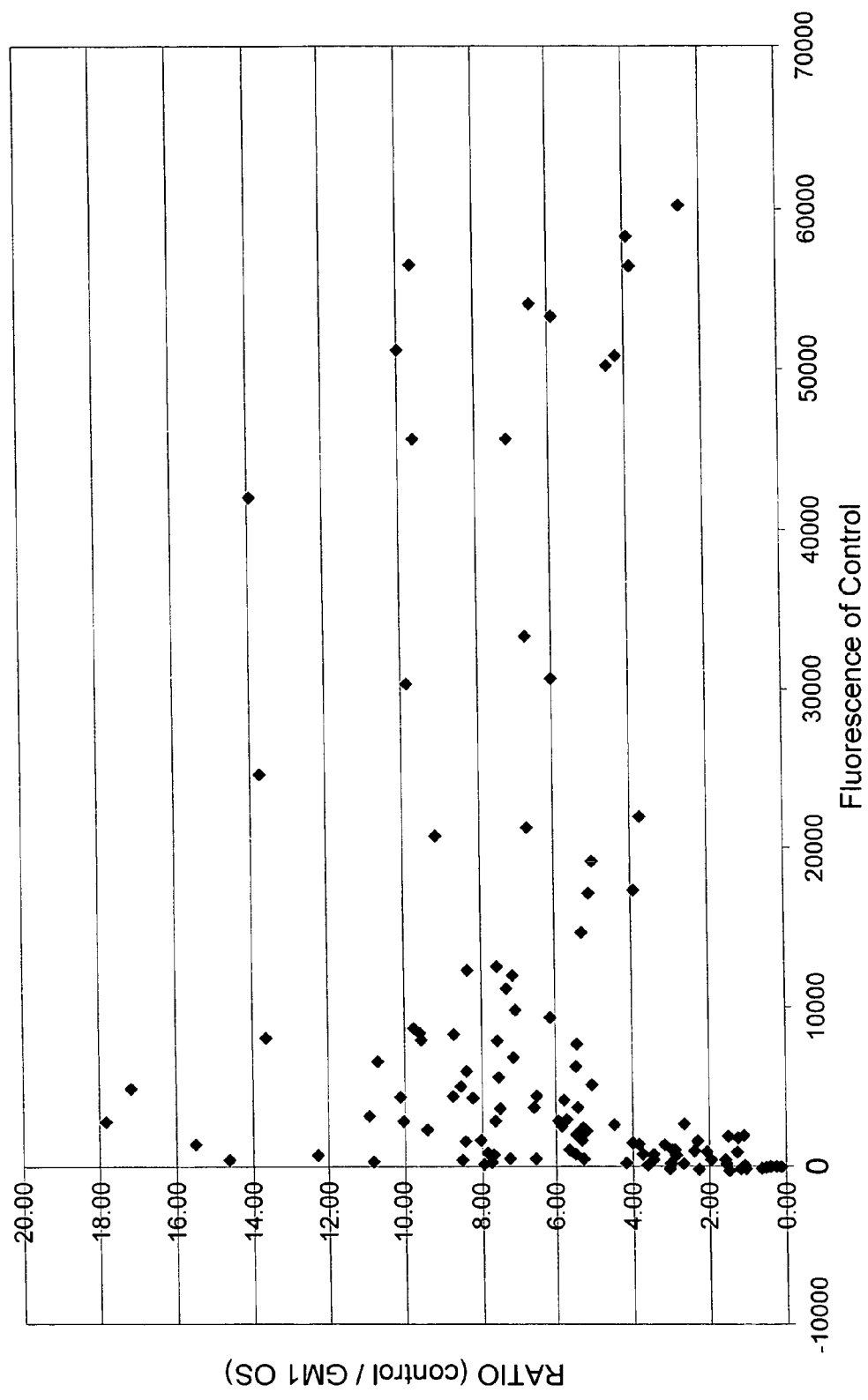
FIG. 51 illustrates the ratio of the amount bound in the absence of GM1 OS to the amount bound in competition with GM1 OS (5.1 µM) in an experiment reported in Example 4.

This disruption is presented as the ratio of the amount bound in the absence of GM 1 OS to the amount bound after contacting with GM1 OS in FIG. 51. The ratios range up to about 18 and are independent of the quantity bound in the control.

Conclusions

This experiment demonstrated that binding of a test ligand to an artificial receptor of the present invention can be diminished (e.g., competed) by a candidate disruptor molecule. In this case the test ligand was the protein cholera toxin and the candidate disruptor was a compound known to bind to cholera toxin, GM1 OS. The degree to which binding of the test ligand was disrupted was independent of the degree to which the test ligand bound to the artificial receptor.

Example 5

GM1 Competes With Artificial Receptors for Binding to Cholera Toxin

Microarrays of candidate artificial receptors were made and evaluated for binding of cholera toxin. The arrays were also evaluated for disrupting that binding. Disrupting of binding employed a compound that binds to cholera toxin, the liposaccharide GM1. The results obtained demonstrate that a ligand of a protein specifically disrupts binding of the protein to the microarray.

Materials and Methods

Building blocks were synthesized and activated as described in Example 1. The building blocks employed in this example were TyrA1B1 [1-1], TyrA2B2, TyrA2B4, TyrA2B6, TyrA4B2, TyrA4B4, TyrA4B6, TyrA6B2, TyrA6B4, and TyrA6B6 in groups of 4 building blocks per artificial receptor. The abbreviation for the building block including a linker, a tyrosine framework, and recognition elements AxBy is TyrAxBy.

Microarrays for the evaluation of the 126 n=4 candidate receptor environments were prepared as described above for Example 4. The test ligand employed in these experiments was cholera toxin labeled with the Alexa™ fluorophore (Molecular Probes Inc., Eugene, Oreg.). Cholera toxin was employed at 5.3 nM in both the control and the competition experiments. The candidate disruptor employed in these experiments was GM1, a known ligand for cholera toxin, which competed at concentrations of 0.042, 0.42, and 8.4 µM. Microarray incubation and analysis was conducted as described for Example 4.

Table 3 identifies the building blocks in each receptor environment.

TABLE 3

| | Building Blocks |
|---|---|
| 1 | 22 24 26 42 |
| 2 | 22 24 26 44 |
| 3 | 22 24 26 46 |
| 4 | 22 24 26 61 |
| 5 | 22 24 26 64 |
| 6 | 22 24 26 66 |
| 7 | 22 24 42 44 |
| 8 | 22 24 42 46 |
| 9 | 22 24 42 62 |
| 10 | 22 24 42 46 |
| 11 | 22 24 42 66 |
| 12 | 22 24 44 46 |
| 13 | 22 24 44 62 |
| 14 | 22 24 44 64 |
| 15 | 22 24 44 66 |
| 16 | 22 24 46 62 |
| 17 | 22 24 46 64 |
| 18 | 22 24 46 66 |
| 19 | 22 24 62 64 |
| 20 | 22 24 62 66 |
| 21 | 22 24 64 66 |
| 22 | 22 26 42 44 |
| 23 | 22 26 42 46 |
| 24 | 22 26 42 62 |
| 25 | 22 26 42 64 |
| 26 | 22 26 42 66 |
| 27 | 22 26 44 46 |

TABLE 3-continued

| | Building Blocks |
|---|---|
| 28 | 22 26 44 62 |
| 29 | 22 26 44 64 |
| 30 | 22 26 44 66 |
| 31 | 22 26 46 62 |
| 32 | 22 26 46 64 |
| 33 | 22 26 46 66 |
| 34 | 22 26 62 64 |
| 35 | 22 26 62 66 |
| 36 | 22 26 64 66 |
| 37 | 22 42 44 46 |
| 38 | 22 42 44 62 |
| 39 | 22 42 44 64 |
| 40 | 22 42 44 66 |
| 41 | 22 42 46 62 |
| 42 | 22 42 46 64 |
| 43 | 22 42 46 66 |
| 44 | 22 42 62 64 |
| 45 | 22 42 62 66 |
| 46 | 22 42 64 66 |
| 47 | 22 44 46 62 |
| 48 | 22 44 46 64 |
| 49 | 22 44 46 66 |
| 50 | 22 44 62 64 |
| 51 | 22 44 62 66 |
| 52 | 22 44 64 66 |
| 53 | 22 46 62 64 |
| 54 | 22 46 62 66 |
| 55 | 22 46 64 66 |
| 56 | 22 62 64 66 |
| 57 | 24 26 42 44 |
| 58 | 24 26 42 46 |
| 59 | 24 26 42 62 |
| 60 | 24 26 42 64 |
| 61 | 24 26 42 66 |
| 62 | 24 26 44 46 |
| 63 | 24 26 44 62 |
| 64 | 24 26 44 64 |
| 65 | 24 26 44 66 |
| 66 | 24 26 46 62 |
| 67 | 24 26 46 64 |
| 68 | 24 26 46 66 |
| 69 | 24 26 62 64 |
| 70 | 24 26 62 66 |
| 71 | 24 26 64 66 |
| 72 | 24 42 44 46 |
| 73 | 24 42 44 62 |
| 74 | 24 42 44 64 |
| 75 | 24 42 44 66 |
| 76 | 24 42 46 62 |
| 77 | 24 42 46 64 |
| 78 | 24 42 46 66 |
| 79 | 24 42 62 64 |
| 80 | 24 42 62 66 |
| 81 | 24 42 64 66 |
| 82 | 24 44 46 62 |
| 83 | 24 44 46 64 |
| 84 | 24 44 46 66 |
| 85 | 24 44 62 64 |
| 86 | 24 44 62 66 |
| 87 | 24 44 64 66 |
| 88 | 24 46 62 64 |
| 89 | 24 46 62 66 |
| 90 | 24 46 64 66 |
| 91 | 24 62 64 66 |
| 92 | 26 42 44 46 |
| 93 | 26 42 44 62 |
| 94 | 26 42 44 64 |
| 95 | 26 42 44 66 |
| 96 | 26 42 46 62 |
| 97 | 26 42 46 64 |
| 98 | 26 42 46 66 |
| 99 | 26 42 62 64 |
| 100 | 26 42 62 66 |
| 101 | 26 42 64 66 |
| 102 | 26 44 46 62 |
| 103 | 26 44 46 64 |
| 104 | 26 44 46 66 |
| 105 | 26 44 62 64 |
| 106 | 26 44 62 66 |
| 107 | 26 44 64 66 |
| 108 | 26 46 62 64 |
| 109 | 26 46 62 66 |
| 110 | 26 46 64 66 |
| 111 | 26 62 64 66 |
| 112 | 42 44 46 62 |
| 113 | 42 44 46 64 |
| 114 | 42 44 46 66 |
| 115 | 42 44 62 64 |
| 116 | 42 44 62 66 |
| 117 | 42 44 64 66 |
| 118 | 42 46 62 64 |
| 119 | 42 46 62 66 |
| 120 | 42 46 64 66 |
| 121 | 42 62 64 66 |
| 122 | 44 46 62 64 |
| 123 | 44 46 62 66 |
| 124 | 44 46 64 66 |
| 125 | 44 62 64 66 |
| 126 | 46 62 64 66 |

Results

Figure 52:
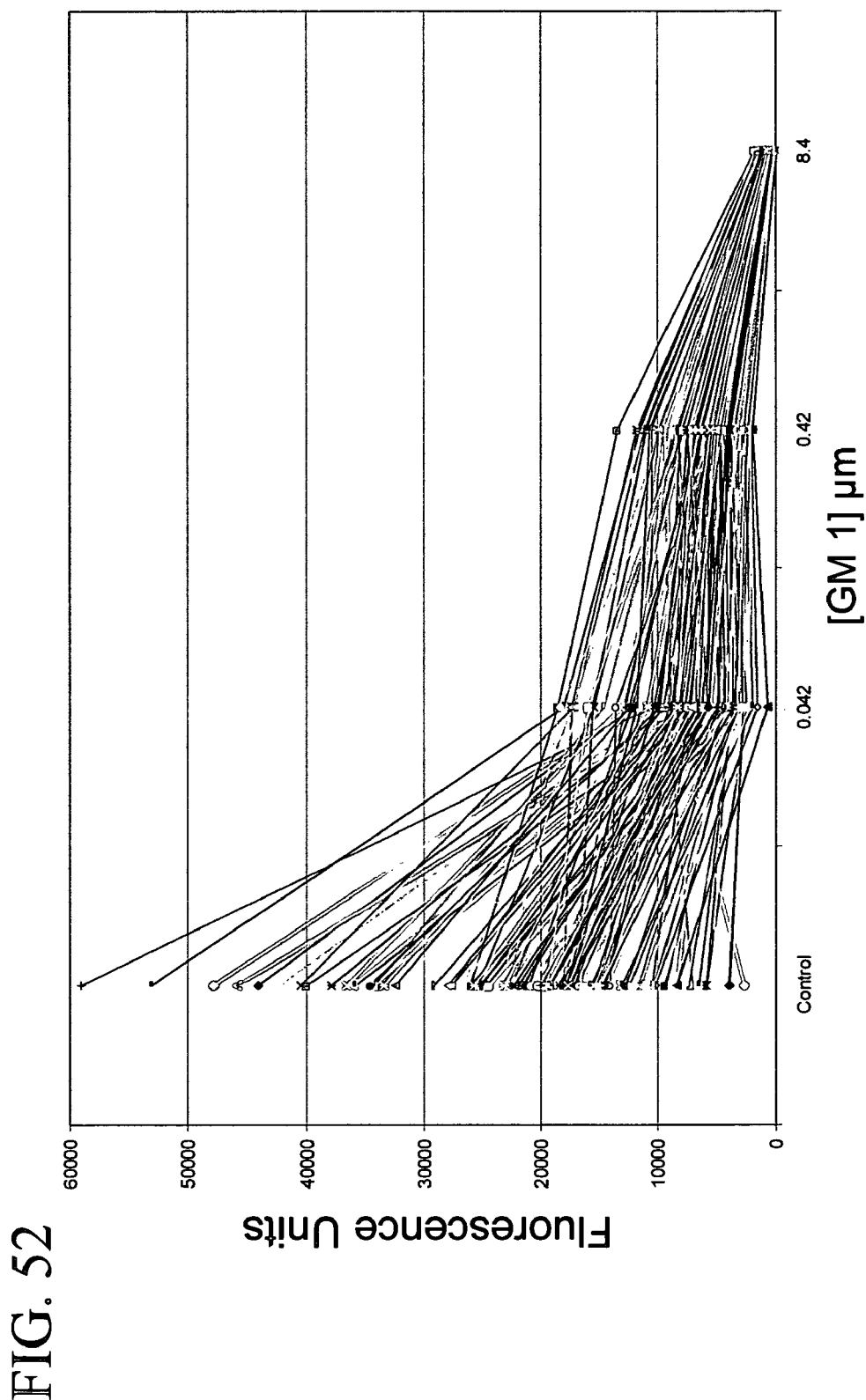
FIG. 52 illustrates the fluorescence signals produced by binding of cholera toxin to the microarray of candidate artificial receptors alone and in competition with each of the three concentrations of GM1 in the experiment reported in Example 5.

FIG. 52 illustrates the fluorescence signals produced by binding of cholera toxin to the microarray of candidate artificial receptors alone and in competition with each of the three concentrations of GM1. The magnitude of the fluorescence signal decreases steadily with increasing concentration of GM1. The amount of decrease is not quantitatively identical for all of the receptor, but each receptor experienced decreased binding of cholera toxin. These decreases indicate that GM1 competed with the artificial receptor for binding to the cholera toxin.

The decreases show a pattern of relative competition for the binding site on cholera toxin. This can be demonstrated through graphs of fluorescence signal obtained at a particular concentration of GM1 against fluorescence signal in the absence of GM1 (not shown). Certain of the receptors appear at similar relative positions on these plots as concentration of GM1 increases.

Figure 53:
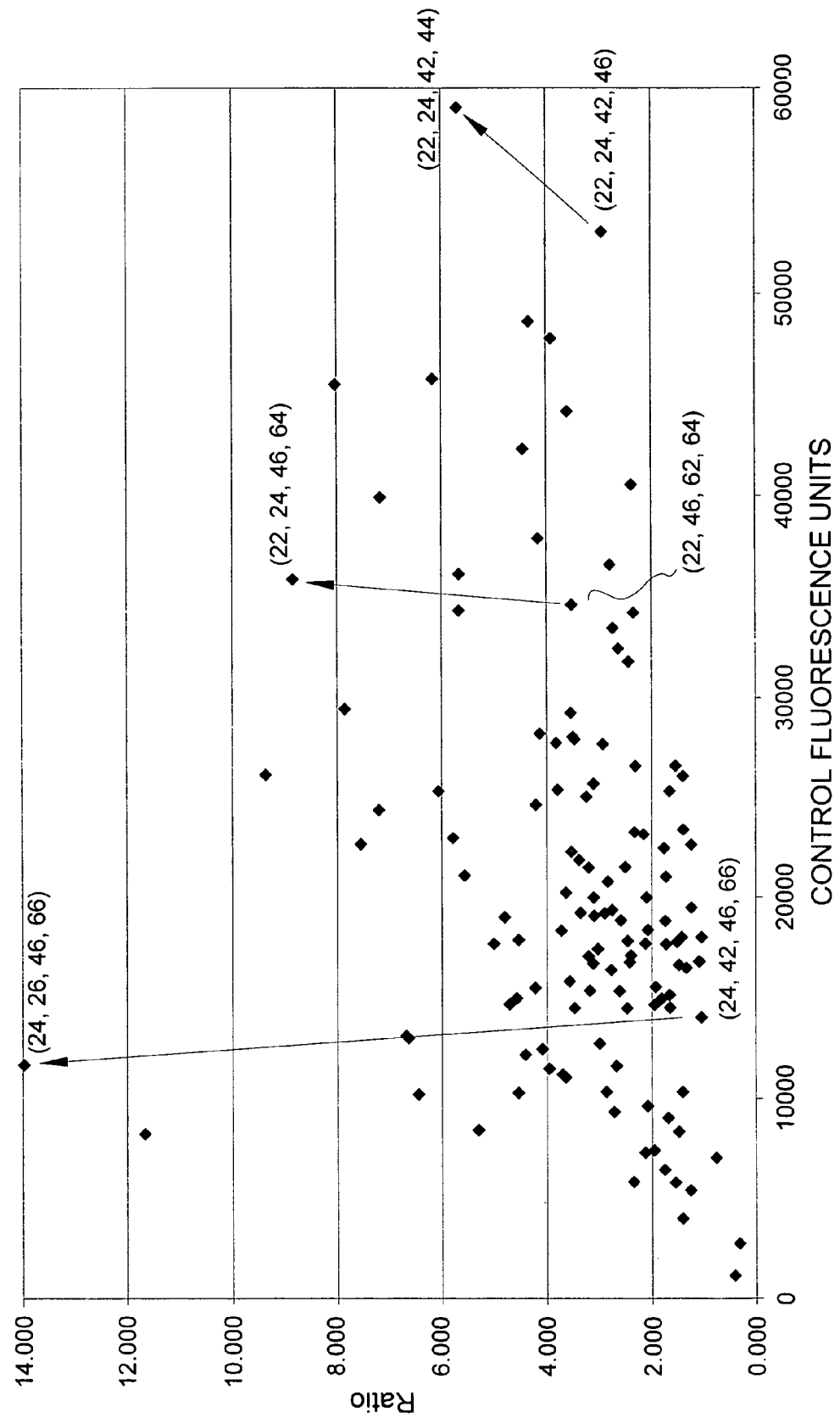
FIG. 53 illustrates the ratio of the amount bound in the absence of GM1 OS to the amount bound upon competition with GM1 for the low concentration of GM1 employed in Example 5.

The disruption in cholera toxin binding caused by GM1 can be visualized as the ratio of the amount bound in the absence of GM1 OS to the amount bound upon competition with GM1. This ratio is illustrated in FIG. 53. The larger the ratio, the more cholera toxin remained bound to the artificial receptor upon competition with GM1. The ratio can be as large as about 14. The ratios are independent of the quantity bound in the control.

Interestingly, in several instances minor changes in structure to the artificial receptor caused significant changes in the ratio. For example, the artificial receptor including building blocks 24, 26, 46, and 66 differs from that including 24, 42, 46, and 66 by only substitution of a single building block. (xy indicates building block TyrAxBy.) The substitution of building block 42 for 26 increased binding in the presence of GM1 by about 14-fold.

By way of further example, the artificial receptor including building blocks 22, 24, 46, and 64 differs from that including 22, 46, 62, and 64 by only substitution of a single building block. The substitution of building block 24 for 62 increased binding in the presence of GM1 by about 3-fold.

Even substitution of a single recognition element affected binding. The artificial receptor including building blocks 22, 24, 42, and 44 differs from that including 22, 24, 42, and 46 by only substitution of a single recognition element. The substitution of building block 44 for 46 (a change of recognition element B6 to B4) increased binding in the presence of GM1 by about 3-fold.

Conclusions

This experiment demonstrated that binding of a test ligand to an artificial receptor of the present invention can be diminished (e.g., competed) by a candidate disrupter molecule. In this case the test ligand was the protein cholera toxin and the candidate disruptor was a compound known to bind to cholera toxin, GM1. Minor changes in structure of the building blocks making up the artificial receptor caused significant changes in the competition.

Example 6

GM1 Employed as a Building Block Alters Binding of Cholera Toxin to the Present Artificial Receptors Microarrays of candidate artificial receptors were made, GM1 was bound to the arrays, and they were evaluated for binding of cholera toxin. The results obtained demonstrate that adding GM1 as a building block in an array of artificial receptors can increase binding to certain of the receptors.

Materials and Methods

Building blocks were synthesized and activated as described in Example 1. The building blocks employed in this example were those described in Example 4. Microarrays for the evaluation of the 171 n=2 candidate receptor environments were prepared as described above for Example 4. The test ligand employed in these experiments was cholera toxin labeled with the Alexa™ fluorophore (Molecular Probes Inc., Eugene, Oreg.). Cholera toxin was employed at 0.01 ug/ml (0.17 pM) or 0.1 ug/ml (1.7 pM) in both the control and the competition experiments. GM1 was employed as a test ligand for the artificial receptors and became a building block for receptors used to bind cholera toxin. The arrays were contacted with GM1 at either 100 µg/ml, 10 µg/ml, or 1 µg/ml as described above for cholera toxin and then rinsed with deionized water. The arrays were then contacted with cholera toxin under the conditions described above. Microarray analysis was conducted as described for Example 4. Table 2 identifies the building blocks in each receptor environment.

Results

Figure 54:
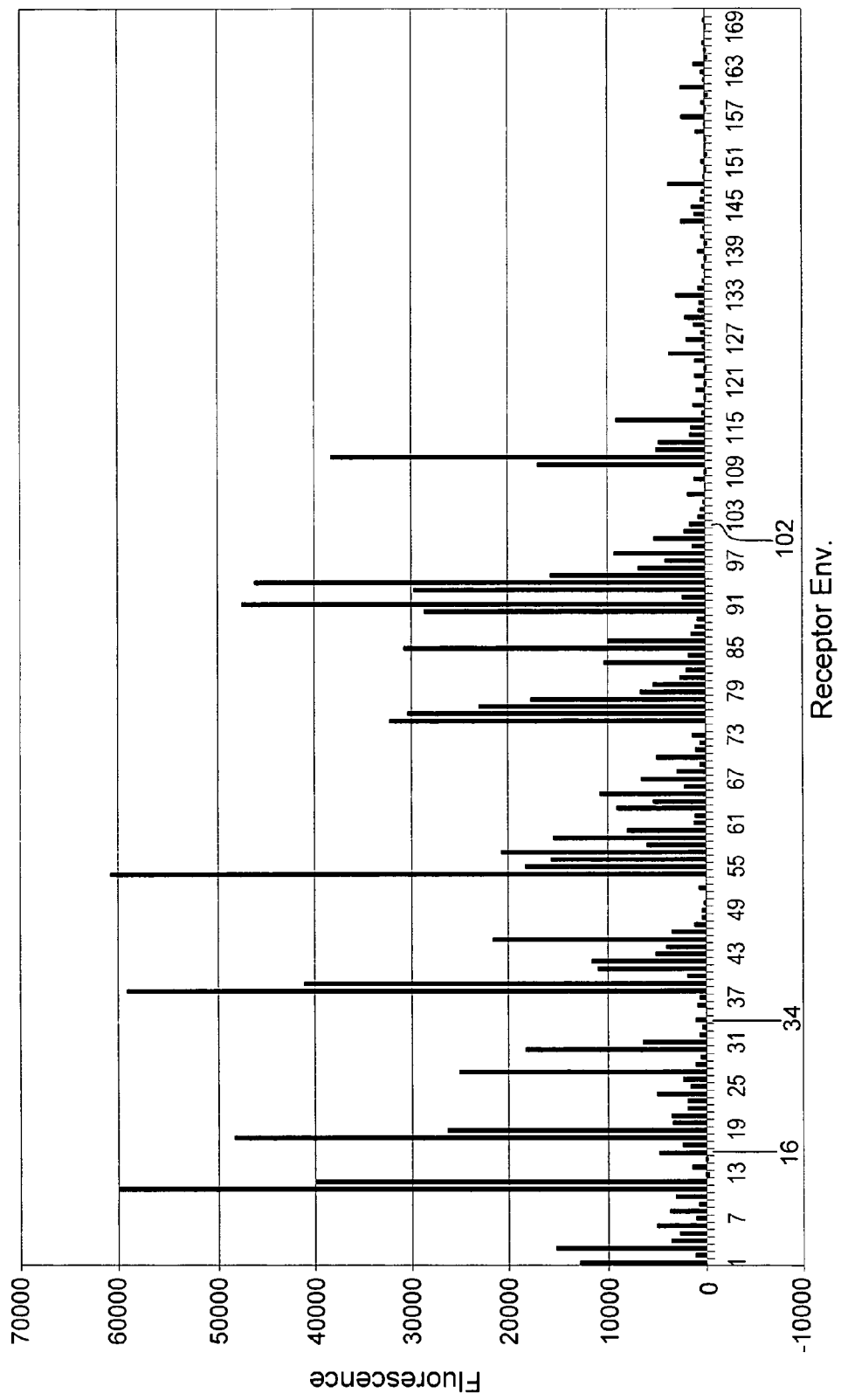
FIG. 54 illustrates the fluorescence signals produced by binding of cholera toxin to the microarray of candidate artificial receptors without pretreatment with GM1 in the experiment reported in Example 6.
Figure 55:
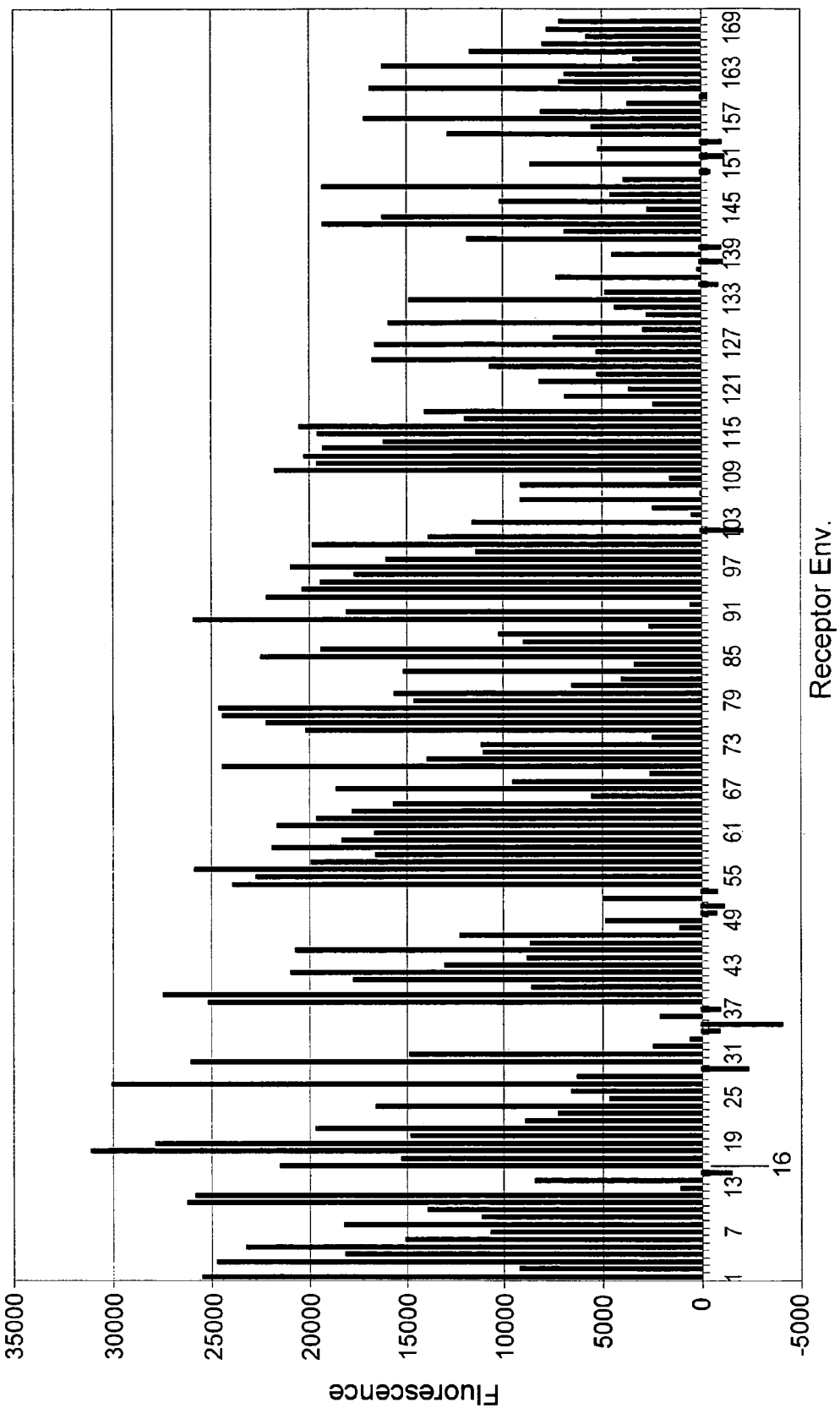
FIGS. 55-57 illustrate the fluorescence signals produced by binding of cholera toxin to the microarray of candidate artificial receptors with pretreatment with GM1 (100 µg/ml, 10 µg/ml, and 1 µg/ml GM1, respectively) in the experiment reported in Example 6.
Figure 56:
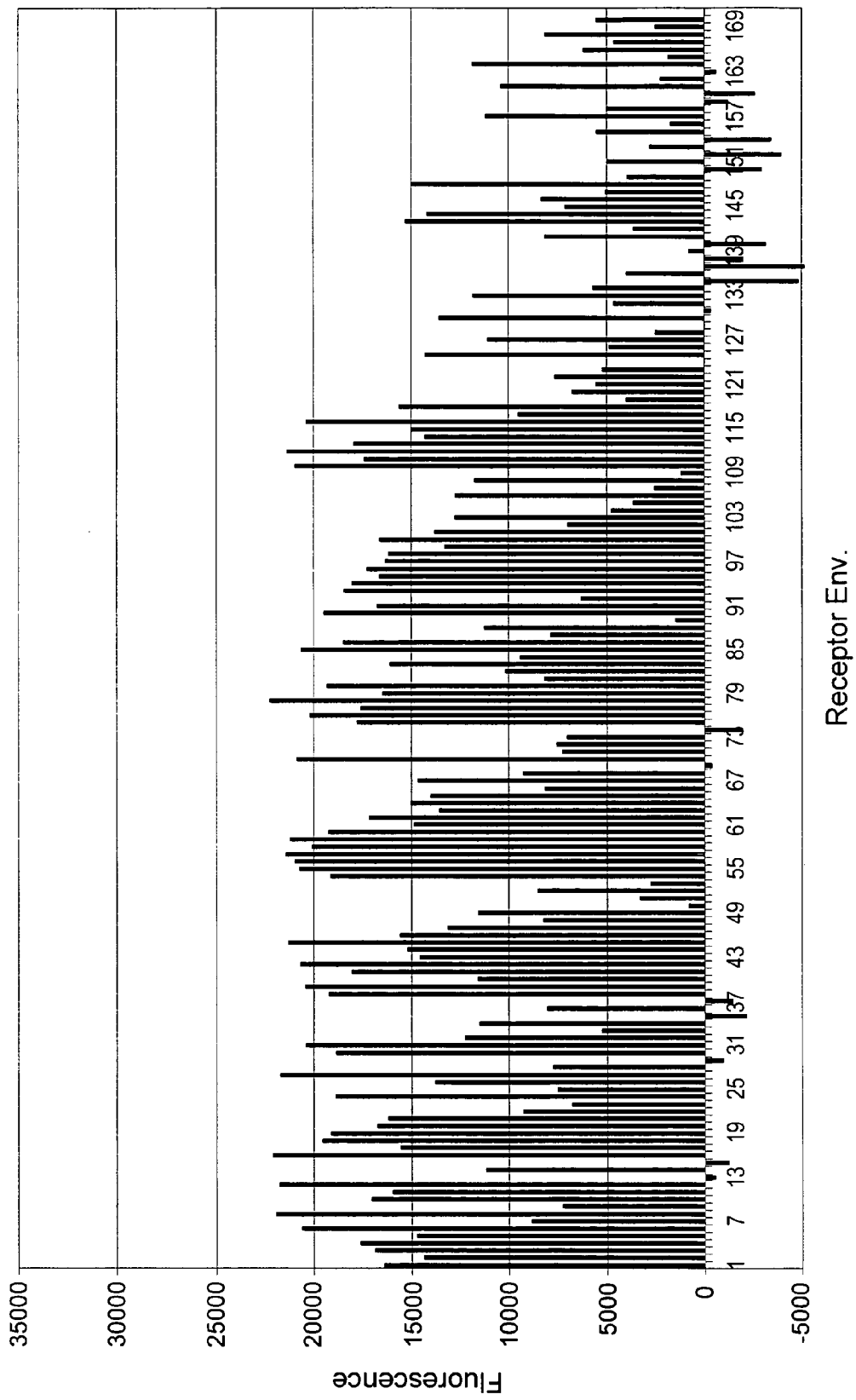
Figure 57:
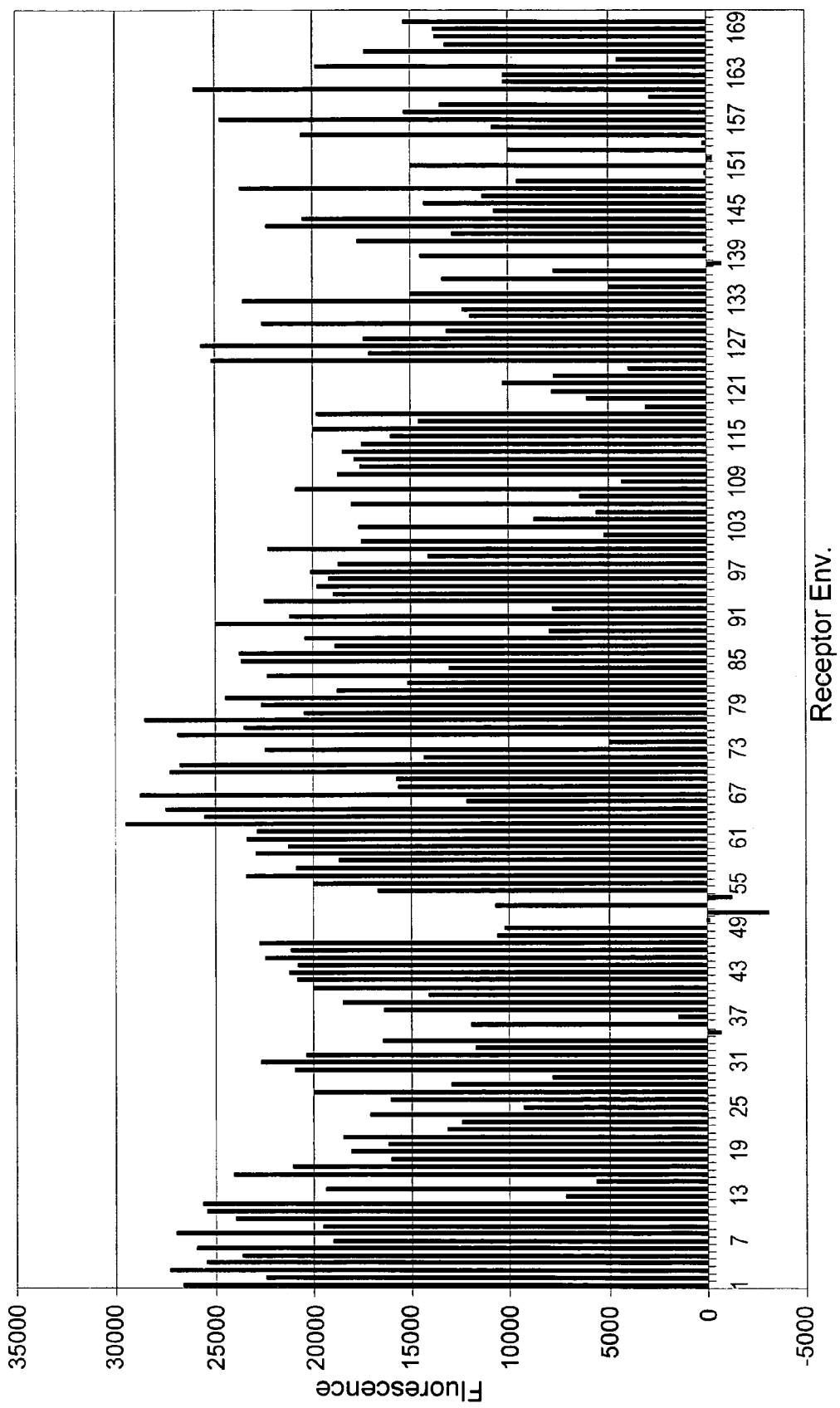

FIG. 54 illustrates the fluorescence signals produced by binding of cholera toxin to the microarray of candidate artificial receptors without pretreatment with GM1. Binding of GM1 to the microarray of candidate artificial receptors followed by binding of cholera toxin produced fluorescence signals illustrated in FIGS. 55, 56, and 57 (100 µg/ml, 10 µg/ml, and 1 µg/ml GM1, respectively).

Figure 58:
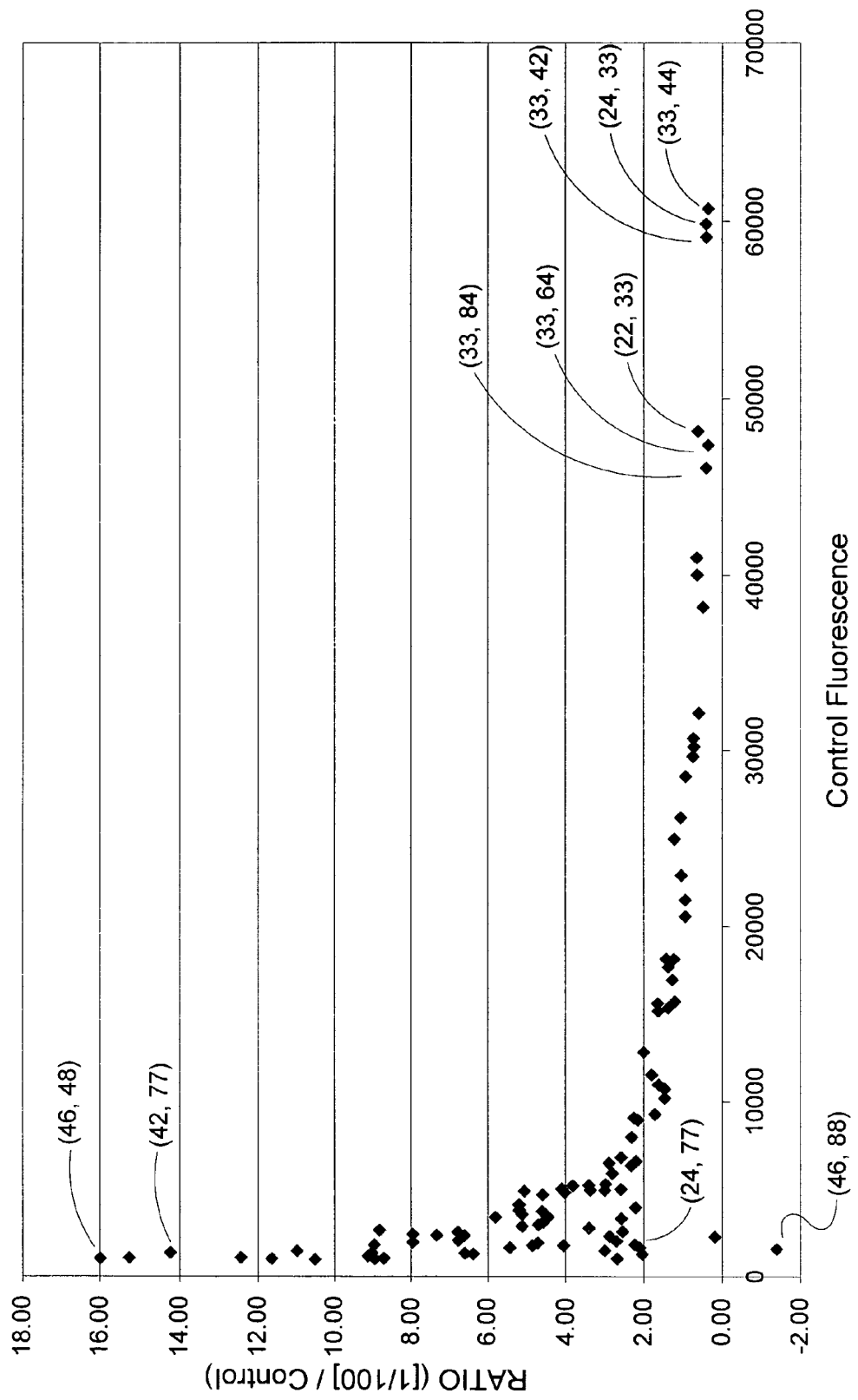
FIG. 58 illustrates the ratio of the amount bound in the presence of 1 µg/ml GM1 to the amount bound in the absence of GM1 in the experiment reported in Example 6.

The enhancement of cholera toxin binding caused by pretreatment with GM1 can be visualized as the ratio of the amount bound in the presence of GM1 to the amount bound in the absence of GM1. This ratio is illustrated in FIG. 58 for 1 µg/ml GM1. The larger the ratio, the more cholera toxin bound to the artificial receptor after pretreatment with GM 1. The ratio can be as large as about 16.

In several instances minor changes in structure to the artificial receptor caused significant changes in the ratio. For example, the artificial receptor including building blocks 46 and 48 differs from that including 46 and 88 by only substitution of a single recognition element on a single building block. (xy indicates building block TyrAxBy.) The substitution of building block 48 for 88 (a change of recognition element A8 to A4) increased the ratio representing increased binding the presence of GM1 building block from about 0.5 to about 16. Similarly, the artificial receptor including building blocks 42 and 77 differs from that including 24 and 77 by only substitution of a single building block. The substitution of building block 42 for 24 increased the ratio representing increased binding the presence of GM1 building block from about 2 to about 14.

Interestingly, several building blocks that exhibited high levels of binding of cholera toxin (signals of 45,000 to 65,000 fluorescence units) and that include the building block 33 were not strongly affected by the presence of GM1 as a building block.

Conclusions

This experiment demonstrated that binding of GM 1 to an artificial receptor of the present invention can significantly increase binding by cholera toxin. Minor changes in structure of the building blocks making up the artificial receptor caused significant changes in the degree to which GM1 enhanced binding of cholera toxin.

Discussion of Examples 4-6

We have previously demonstrated that an array of working artificial receptors bind to a protein target in a manner which is complementary to the specific environment presented by each region of the proteins surface topology. Thus the pattern of binding of a protein target to an array of working artificial receptors describes the proteins surface topology; including surface structures which participate in e.g., protein~small molecule, protein~peptide, protein-protein, protein~carbohydrate, protein~DNA, etc. interactions. It is thus possible to use the binding of a selected protein to a working artificial receptor array to characterize these protein~small molecule, protein~peptide, protein-protein, protein~carbohydrate, protein~DNA, etc. interactions. Moreover, it is possible to utilize the protein to array interactions to define "leads" for the disruption of these interactions.

Cholera Toxin B sub-unit binds to GM1 on the cell surface. Studies to identify competitors to this binding event have shown that competitors to the cholera toxin: GM1 interaction (binding site) can utilize both a sugar and an alkyl/aromatic functionality (Pickens, et al., *Chemistry and Biology*, vol. 9, pp 215-224 (2002)). We have previously demonstrated that fluorescently labeled Cholera Toxin B sub-unit binds to arrays of the present artificial receptors to give a defined binding pattern which reflects cholera toxin B's surface topology. For this study, we sought to demonstrate that the binding of the cholera toxin to at least some members of the array could be disrupted using cholera toxin's natural ligand, GM1.

The results presented in the figures clearly demonstrate that these goals have been achieved. Specifically, competition between the GM1 OS pentasaccharide or GM1 and an artificial receptor array for cholera binding clearly gave a binding pattern which was distinct from the cholera binding pattern control. Moreover, these results demonstrated the complementarity between several of the working artificial receptors which contained a naphthyl moiety when compared to working artificial receptors which only contained phenyl functionality. These results are in keeping with the active site competition studies in Pickens, et al. and indicate that the naphthyl and phenyl derivatives represent good mimics/probes for the cholera to GM1 interaction. The specificity of these interactions was demonstrated by the observation that the change of a single building block out of 4 in a combination of 4 building blocks system changed a non-competitive to a significantly competitive environment. These results also indicated that selected working artificial receptors can be used to develop a high-throughput screen for the further evaluation of the cholera:GM1 interaction.

Additionally, we sought to demonstrate that an affinity support/membrane mimic could be prepared by pre-incubating an array of artificial receptors with GM1 which would then bind/capture cholera toxin in a binding pattern which could be used to select a working significantly increased their cholera binding, presumably through an affinity interaction between the cholera toxin and both the immobilized GM1 pentasaccharide moiety and the working artificial receptor building block environment.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

What is claimed is:

1. A method of producing an affinity support, the method comprising:
    providing a plurality of candidate artificial receptors; the plurality of candidate artificial receptors independently comprising:
        at least 6 structural characteristics selected from the group consisting of positive charge, negative charge, acid, base, electron acceptor, electron donor, hydrogen bond donor, hydrogen bond acceptor, free electron pair, π electrons, charge polarization, hydrophilicity, and hydrophobicity;
        a region on a solid support comprising 2, 3, 4, 5, or 6 different building block molecules; each of the building block molecules being independently covalently coupled to the region; a plurality of adjacent building block molecules forming a binding site;
        the region being a contiguous portion of the surface of the solid support with the different building block molecules distributed randomly throughout the contiguous region;
    contacting one or more candidate artificial receptors with a test ligand;
    identifying one or more artificial receptors that bind the test ligand as one or more working artificial receptors;
    selecting one or more of the working artificial receptors;
    producing an affinity support comprising the one or more selected working artificial receptors;
    wherein:
        each of the building block molecules comprises a framework and n recognition elements and is independently of the formula:

framework-(recognition element)$_n$ in which:
    n=1, 2, or 3; each recognition element is independently covalently coupled to the framework; and the framework comprises a functional group effective for covalent coupling to a support or a linker;
    the framework is alkyl, substituted alkyl, cycloalkyl, heterocyclic, substituted heterocyclic, aryl alkyl, aryl, heteroaryl, or heteroaryl alkyl; substituted with 1 to 4 functional groups;
        the functional groups independently being carboxyl, amine, hydroxyl, phenol, carbonyl, or thiol;
    each recognition element is independently a 1-12 carbon alkyl, substituted alkyl, cycloalkyl, heterocyclic, substituted heterocyclic, aryl alkyl, aryl, heteroaryl, or heteroaryl alkyl moiety; optionally, substituted with a group with a property of positive charge, negative charge, acid, base, electron acceptor, electron donor, hydrogen bond donor, hydrogen bond acceptor, free electron pair, π electrons, charge polarization, hydrophilicity, or hydrophobicity; and
    when the building block molecule comprises an amino acid derivative, wherein amino acid derivatives are defined as a core feature having the chemical structure —NH—C—C(O)—, the building block molecule comprises a single derivatized amino acid and the framework is the amino acid derivative.

2. The method of claim 1, comprising contacting an array of candidate artificial receptors with the test ligand.

3. The method of claim 2, wherein the array comprises at least about 100 candidate artificial receptors.

4. The method of claim 1, wherein the artificial receptor is made up of building blocks that are naïve to the test ligand.

5. The method of claim 1, wherein the affinity support comprises a chromatography support, a filtration membrane, or an electrophoresis medium.

6. The method of claim 5, wherein the affinity support comprises a chromatography support.

7. The method of claim 1, wherein the test ligand is a protein and the protein is a component of a mixture of individual proteins or a proteome.

8. The method of claim 1, wherein the test ligand is a protein and the protein is a component of an antibody or a component of a mixture of antibodies.

9. The method of claim 1, wherein each recognition element is independently unsubstituted or substituted with a moiety selected from the group consisting of amine, quaternary ammonium, carboxylate, phenol, phosphate, phosphonate, phosphinate, sulphate, sulphonate, thiocarboxylate, hydroxamic acid, sulfoxide, betaine, amine oxide, amide, carboxyl, alcohol, ether, thiol, thioether, ester, thio ester, borane, borate, metal complex, alkyl, alkene, alkyne, aromatic moiety, and plurality thereof.

10. The method of claim 1, wherein the recognition element is substituted with or to form:
    protonated phosphate, protonated phosphonate, protonated phosphinate, protonated sulphate, or protonated sulphinate;
    alkyl amine, alkyl diamine, heteroalkyl amine, aryl amine, heteroaryl amine, aryl alkyl amine, heterocyclic amine, amidine, hydrazine, urea, trimethyl alkyl quaternary ammonium, dimethyl ethyl alkyl quaternary ammonium, dimethyl alkyl quaternary ammonium, aryl alkyl quaternary ammonium, or pyridinium quaternary ammonium;

alkyl carboxylate, aryl carboxylate, aryl alkyl carboxylate, or thiocarboxylate;

phosphonate or phosphinate;

primary alcohol, secondary alcohol, tertiary alcohol, or aromatic alcohol;

lower alkyl, substituted alkyl, cycloalkyl, aryl alkyl, heteroaryl alkyl, lower alkene, aryl alkene, unsubstituted aryl, heteroaryl, substituted aryl, aryl alkyl, heteroaryl alkyl, alkyl substituted aryl, or polyaromatic hydrocarbon; or a plurality thereof.

11. The method of claim 1, wherein the framework has the formula:

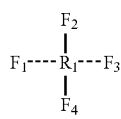

in which:

$R_1$ is 1-12 carbon alkyl, substituted alkyl, cycloalkyl, heterocyclic, substituted heterocyclic, aryl alkyl, aryl, heteroaryl, or heteroaryl alkyl;

$F_1$ and $F_2$ are independently carboxyl, amine, hydroxyl, phenol, carbonyl, or thiol group; or are independently 1-12 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group;

$F_3$ and $F_4$ are independently absent, carboxyl, amine, hydroxyl, phenol, carbonyl, or thiol group; or are independently absent, or 1-12 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group.

12. The method of claim 11, wherein:

$R_1$ is 1-6 carbon alkyl, substituted alkyl, cycloalkyl, heterocyclic, substituted heterocyclic, aryl alkyl, aryl, heteroaryl, or heteroaryl alkyl;

$F_1$, $F_2$, $F_3$, or $F_4$ are independently 1-6 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group.

$F_3$ is absent; or $F_3$ and $F_4$ are absent.

13. The method of claim 1, wherein the framework is:

a natural or synthetic amino acid, an α-hydroxy acid, or a thioic acid; or a β-amino acid or homo or β analog of a natural amino acid.

14. The method of claim 1, wherein the framework is an amino acid with an amine, hydroxyl, phenol, carboxyl, thiol, thioether, or amidino group on its side chain.

15. The method of claim 14, wherein the framework is a serine, threonine, tyrosine, aspartic acid, glutamic acid, asparagine, glutamine, cysteine, lysine, arginine, or histidine moiety.

16. The method of claim 1, wherein one or more of the building block molecules further comprises a linker and independently has the formula:

linker-framework-(first recognition element) (second recognition element)

in which the linker, first recognition element, and second recognition element are independently covalently coupled to the framework.

17. The method of claim 16, wherein the framework is of the formula of an amino acid.

18. The method of claim 17, wherein the amino acid is serine, threonine, or tyrosine.

19. The method of claim 18, wherein the amino acid is tyrosine.

20. The method of claim 16, wherein the linker is of the formula $(CH_2)_nC(O)—$, with n=1-16.

21. The method of claim 1, wherein one or more of the building block molecules further comprises a linker and independently is of formula:

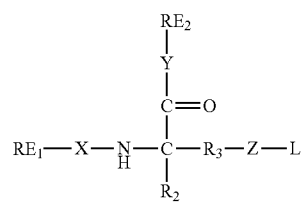

in which:

X is absent or C=O;

Y is absent, NH, or O; Z is O;

$R_2$ is H or $CH_3$;

$R_3$ is $CH_2$ or $CH_2$-phenyl;

$RE_1$ is B1, B2, B3, B4, B5, B69, B7, B8, B9, A1, A2, A3, A4, A5, A69, A7, A8, or A9;

$RE_2$ is A1, A2, A3, A4, A5, A69, A7, A8, A9, B1, B2, B3, B4, B5, B69, B7, B8, or B9;

L is $(CH_2)_n$COOH, with n=1-16;

A1 is
$CH_2CH_3$;

A2 is
$CH_2CH(CH_3)_2$;

A3 is

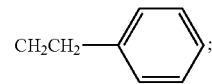

A4 is

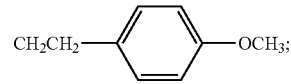

A5 is

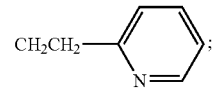

A6 is
$CH_2CH_2—O—CH_3$;

A7 is
$CH_2CH_2—OH$,

A8 is
    CH$_2$CH$_2$—NH—C(O)CH$_3$;
A9 is

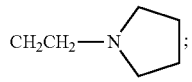

B1 is
    CH$_3$;
B2 is

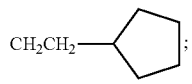

B3 is

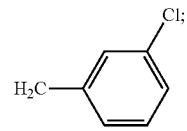

B4 is

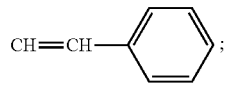

B5 is

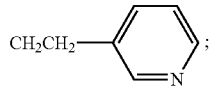

B6 is
    CH$_2$—S—CH$_3$;
B7 is
    CH$_2$CH(OH)CH$_3$;
B8 is
    CH$_2$CH$_2$C(O)—NH$_2$; and
B9 is
    CH$_2$CH$_2$CH$_2$—N—(CH$_3$)$_2$.

22. The method of claim 1, wherein the building block molecule further comprises a linker, and
    the linker is a alkyl, substituted alkyl, cycloalkyl, heterocyclic, substituted heterocyclic, aryl alkyl, aryl, heteroaryl, heteroaryl alkyl, ethoxy or propoxy oligomer, or glycoside moiety;
        substituted with a carboxyl, alcohol, phenol, thiol, amine, carbonyl, or maleimide group.

23. The method of claim 1, wherein the building block molecules coupled to the support are in proximity to one another.

24. The method of claim 1, wherein the test ligand comprises an antibody or mixture of antibodies.

25. The method of claim 1, wherein the test ligand comprises a protein or a mixture of proteins.

26. The method of claim 25, wherein the protein or mixture of proteins comprises a prion.

27. The method of claim 25, wherein the protein or mixture of proteins comprises a β-amyloid.

28. The method of claim 25, wherein the protein or mixture of proteins comprises a cholera toxin.

29. The method of claim 25, wherein the protein or mixture of proteins comprises at least one protein of a cancer cell.

30. The method of claim 29, wherein the cancer comprises bladder cancer, breast cancer, colon cancer, kidney cancer, liver cancer, lung cancer, esophageal cancer, gall-bladder cancer, ovarian cancer, pancreatic cancer, stomach cancer, cervical cancer, thyroid cancer, prostate cancer, skin cancer, a hematopoietic tumor of lymphoid lineage, a hematopoietic tumor of myeloid lineage, a tumor of mesenchymal origin, a tumor of the central nervous system, a tumor of the peripheral nervous system, melanoma, seminoma, teratocarcinoma, osteosarcoma, xeroderma pigmentosum, keratoctanthoma, thyroid follicular cancer, or Kaposi's sarcoma.

31. The method of claim 30, wherein the cancer comprises small cell lung cancer, squamous cell carcinoma, leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute myelogenous leukemia, chronic myelogenous leukemia, myelodysplastic syndrome, promyelocytic leukemia, fibrosarcoma, rhabdomyosarcoma, astrocytoma, neuroblastoma, glioma, or schwannoma.

32. The method of claim 25, wherein a sample from cells or tissues suspected of being cancerous or including a tumor comprises the protein or mixture of proteins.

33. The method of claim 25, wherein serum comprises the protein or mixture of proteins.

34. The method of claim 1, wherein the test ligand comprises a microbe.

35. The method of claim 34, wherein the microbe comprises *Vibrio cholerae*.

36. The method of claim 34, wherein the microbe comprises a bacterium, a mycoplasma, a fungus, a rickettsia, or a virus.

37. The method of claim 36, wherein the bacteria or mycoplasma comprises *Escherichia coli, Vibrio cholerae, Acinetobacter caicoaceticus, Haemophilus influenzae, Actinobacillus actinoides, Haemophilus parahaemolyticus, Actinobacillus lignieresii, Haemophilus parainfluenzae, Actinobacillus suis, Legionella pneumophila, Actinomyces bovis, Leptospira interrogans, Actinomyces israelli, Mima polymorphs, Aeromonas hydrophile, Moraxella lacunata, Arachnia propionica, Burkholderia mallei, Burkholderia pseudomallei, Moraxella osioensis, Arizona hinshawii, Mycobacterium osioensis, Bacillus cereus, Mycobacterium leprae, Bacteroides spp, Mycobacterium spp, Bartonella bacilliformis, Plesiomonas shigelloides, Bordetella bronchiseptica, Proteus spp, Clostridium difficile, Pseudomonas aeruginosa, Clostridium sordellii, Salmonella cholerasuis, Clostridium tetani, Salmonella enteritidis, Corynebacterium diphtheriae, Salmonella typhi, Edwardsiella tarda, Serratia marcescens, Enterobacter aerogenes, Shigella spp, Staphylococcus epidermidis, Francisella novicida, Vibrio parahaemolyticus, Haemophilus ducreyi, Haemophilus gallinarum, Haemophilus haemolyticus, Bacillus anthracis, Mycobacterium bovis, Bordetella pertussis, Mycobacterium tuberculosis, Borrella burgdorfii, Mycoplasma pneumoniae, Borrella spp, Neisseria gonorrhoeae, Campylobacter, Neisseria meningitides, Chlamydia psittaci, Nocardia asteroids, Chlamydia trachomatis, Nocardia brasiliensis, Clostridium botulinum, Pasteurella haemolytica, Clostridium chauvoei,*

*Pasteurelia multocida, Clostridium haemolyticus, Pasteurella pneumotropica, Clostridium histolyticum, Pseudomonas pseudomallei, Clostridium novyl, Staphylococcus aureus, Clostridium perfringens, Streptobacillus moniliformis, Clostridium septicum, Cyclospora cayatanensis, Streptococcus agalacetiae, Erysipelothrix insidiosa, Streptococcus pneumoniae, Klebsiella pneumoniae, Streptococcus pyogenes, Listeria manocytogenes, Yersinia pestis, Yersinia pseudotuberculosis, Yersinia enterocolitica, Brucella abortus, Brucella canis, Brucella melitensis, Brucella suis,* or *Francisella tularensis.*

38. The method of claim 36, wherein the bacteria or mycoplasma comprises *E. coli* H157:O7.

39. The method of claim 36, wherein the fungus comprises *Absidia, Piedraia hortae, Aspergillus, Prototheca, Candida, Paecilomyces, Cryptococcus neoformans, Cryptosporidium parvum, Phialaphora, Dermatophilus congolensis, Rhizopus, Epidermophyton, Scopulariopsis, Exophiala, Sporothrix schenkii, Fusarium, Trichophyton, Madurella mycetomi, Toxoplasma, Trichosporon, Microsporum, Microsporidia, Wangiella dermatitidis, Mucor, Blastomyces dermatitidis, Giardia lamblia, Entamoeba histolytica, Coccidioides immitis,* or *Histoplasma capsulatum.*

40. The method of claim 36, wherein the rickettsia or virus comprises a Coronavirus, a Hepatitis virus, Myxovirus, Paramyxovirus, Picornavirus, *Rickettsia akari, Rochalimaea Quintana, Rochalimaea vinsonii,* Norwalk Agent, an Adenovirus, an Arenavirus, a Herpesvirus, a Human Immunodeficiency Virus, a Parainfluenza virus, a Poxvirus, Papovaviruses, a Spongiform Encephalopathy Virus, a Rhabdoviruses, a Togavirus, *Coxiella burnetii, Rickettsia canada, Rickettsia prowazekii, Rickettsia rickettsii, Rickettsia Tsutsugamushi, Rickettsia typhi,* a Spotted Fever Group Agent, a Vesicular Stomatitis Virus, a Toga virus, an Arena virus, a Bunya virus, a Flaviruses, a Filovirus, a Nipah virus, a viral encephalitis agent, a LaCrosse virus, a Kyasanur Forest virus, a Yellow fever, and a West Nile virus.

41. The method of claim 36, wherein the rickettsia or virus comprises an Influenza virus, a Measles virus, a Mumps virus, a Newcastle disease virus, a Coxsackie virus, an Echoviruses, a Poliomyelitis virus, a *Herpesvirus hominis,* a Cytomegalovirus, an Epstein-Barr virus, a Caliciviruses, a Pseudo-rabies virus, a Varicella virus, a Respiratory syncytial virus, a Subsclerosing panencephalitis virus, a Variola virus, a Cowpox virus, a *Molluscum contagiosum* virus, a Monkeypox virus, an Orf virus, a Paravaccinia virus, a Tanapox virus, a Vaccinia virus, a Yabapox virus, an SV 40 virus, a B-K-virus, Creutzfeld-Jacob agent, Kuru agent, BSE, a Rabies virus, a Rubella virus, *R. mooseri,* a LCM virus, a Junin virus, a Lassa virus, a Marchupo virus, a Guanarito virus, a hantavirus, a Rift Valley Fever virus, a Dengue virus, an Ebola virus, or a Marburg virus.

42. The method of claim 34, wherein the microbe comprises a Variola Virus, a Congo-Crimean hemorrhagic fever virus, a Tick-borne encephalitis virus complex, a Marburg virus, an Ebola virus, a Junin virus, a Lassa virus, a Machupo virus, a Herpesvirus simiae, a Bluetongue virus, a Louping III virus, a Rift Valley fever virus, a Wesselsbron virus, a Foot and Mouth Disease virus, a Newcastle Disease virus, an African Swine Fever virus, a Vesicular exanthema virus, a Swine vesicular disease virus, a Rinderpest virus, an African horse sickness virus, an Avian influenza virus, a Sheep pox virus.

43. The method of claim 1, wherein the test ligand comprises drug of abuse, peptide, polypeptide, oligonucleotide, polynucleotide, microbe, or mixture thereof 44. The method of claim 1, wherein the test ligand comprises isomer, conformation of protein, or proteome.

45. The method of claim 1, wherein the test ligand comprises a cell.

46. The method of claim 45 wherein the cell comprises a hapatocyte.

47. The method of claim 1, wherein the test ligand comprises an oligosaccharide or polysaccharide.

48. The method of claim 1, wherein the support comprises a dish, a tube, a well, a bead, a chromatography support, or a microchannel.

49. A method of producing a working artificial receptor, the method comprising:

providing a plurality of candidate artificial receptors; the plurality of candidate artificial receptors independently comprising:

at least 6 structural characteristics selected from the group consisting of positive charge, negative charge, acid, base, electron acceptor, electron donor, hydrogen bond donor, hydrogen bond acceptor, free electron pair, π electrons, charge polarization, hydrophilicity, and hydrophobicity;

a region on a solid support comprising 2, 3, 4, 5, or 6 different building block molecules; each of the building block molecules being independently covalently coupled to the region; a plurality of adjacent building block molecules forming a binding site;

the region being a contiguous portion of the surface of the solid support with the different building block molecules distributed randomly throughout the contiguous region;

contacting one or more candidate artificial receptors with a test ligand;

identifying one or more artificial receptors that bind the test ligand as one or more working artificial receptors;

selecting one or more of the working artificial receptors for use on an affinity support for binding the test ligand;

wherein:

each of the building block molecules comprises a framework and n recognition elements and is independently of the formula:

framework-(recognition element)$_n$ in which:

n=1, 2, or 3; each recognition element is independently covalently coupled to the framework; and the framework comprises a functional group effective for covalent coupling to a support or a linker;

the framework is alkyl, substituted alkyl, cycloalkyl, heterocyclic, substituted heterocyclic, aryl alkyl, aryl, heteroaryl, or heteroaryl alkyl; substituted with 1 to 4 functional groups;

the functional groups independently being carboxyl, amine, hydroxyl, phenol, carbonyl, or thiol;

each recognition element is independently a 1-12 carbon alkyl, substituted alkyl, cycloalkyl, heterocyclic, substituted heterocyclic, aryl alkyl, aryl, heteroaryl, or heteroaryl alkyl moiety; substituted with a group with a property of positive charge, negative charge, acid, base, electron acceptor, electron donor, hydrogen bond donor, hydrogen bond acceptor, free electron pair, π electrons, charge polarization, hydrophilicity, or hydrophobicity; and when the building block molecule comprises an amino acid derivative, wherein amino acid derivatives are defined as a core feature having the chemical structure —NH—

C—C(O)—, the building block molecule comprises a single derivatized amino acid and the framework is the amino acid derivative.

50. The method of claim 49, further comprising producing the affinity support comprising the one or more selected working artificial receptors.

51. The method of claim 49, wherein the affinity support comprises a chromatography support, a filtration membrane, or an electrophoresis medium.

52. The method of claim 41, wherein the affinity support comprises a chromatography support.

53. The method of claim 49, wherein the support comprises a dish, a tube, a well, a bead, a chromatography support, or a microchannel.

* * * * *